US007408025B2

(12) United States Patent
Hill et al.

(10) Patent No.: US 7,408,025 B2
(45) Date of Patent: *Aug. 5, 2008

(54) LIPOPEPTIDES AS ANTIBACTERIAL AGENTS

(75) Inventors: Jason Hill, Auburndale, MA (US); Ian Parr, Medford, MA (US); Michael Morytko, Framingham, MA (US); Jim Siedlecki, Burlington, MA (US); Xiang Yang Yu, Billerica, MA (US); Jared Silverman, Brookline, MA (US); Dennis Keith, Arlington, MA (US); John Finn, Stow, MA (US); Dale Christensen, Apex, NC (US); Tsvetelina Lazarova, Brookline, MA (US); Alan D. Watson, Lexington, MA (US); Yan Zhang, Sharon, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 1220 days.

This patent is subject to a terminal disclaimer.

(21) Appl. No.: 09/737,908

(22) Filed: Dec. 15, 2000

(65) Prior Publication Data

US 2004/0067878 A1 Apr. 8, 2004

Related U.S. Application Data

(60) Provisional application No. 60/208,222, filed on Apr. 3, 2000, provisional application No. 60/170,946, filed on Dec. 15, 1999.

(51) Int. Cl.
C07K 7/50 (2006.01)

(52) U.S. Cl. .......................... 530/317; 530/327; 514/11; 514/14

(58) Field of Classification Search ................. 530/317, 530/327, 332; 514/11, 14
See application file for complete search history.

(56) References Cited

U.S. PATENT DOCUMENTS

| | | | | |
|---|---|---|---|---|
| 4,396,543 A | * | 8/1983 | Debono | 530/323 |
| 4,399,067 A | * | 8/1983 | Debono | 530/323 |
| 4,482,487 A | * | 11/1984 | Abbott et al. | 530/317 |
| 4,524,135 A | * | 6/1985 | Abbott et al. | 435/68.1 |
| 4,537,717 A | * | 8/1985 | Abbott et al. | 530/317 |
| RE32,310 E | | 12/1986 | Debono | 530/317 |
| RE32,311 E | | 12/1986 | Debono | 530/317 |
| 5,573,936 A | * | 11/1996 | Kreuzman et al. | 435/196 |
| 5,629,288 A | | 5/1997 | Lattrell et al. | 514/9 |
| 5,912,226 A | | 6/1999 | Baker et al. | 514/9 |

FOREIGN PATENT DOCUMENTS

| | | |
|---|---|---|
| EP | 095 295 A | 11/1983 |
| EP | 178 152 A | 4/1986 |
| EP | 0 885 957 A1 | 12/1998 |
| WO | WO 99/43700 | 8/1999 |

OTHER PUBLICATIONS

Tally, F.P. et al., "Daptomycin: a Novel Agent for Gram-positive Infections," *Exp. Opin. Invest. Drugs* 8: 1223-1238 (1999).

Alborn, W. E. Jr. et al., "Daptomycin Disrupts Membrane Potential in Growing *Staphylococcus aureus*," *Antimicrobial Agents and Chemotherapy* 35: 2282-2287 (1991).

Allen, N. E. et al. "Inhibition of Peptidoglycan Biosynthesis in Gram-Positive Bacteria by LY146032," *Antimicrobial Agents and Chemotherapy* 31: 1093-1099 (1987).

Allen, N. E. et al. "Inhibition of Membrane Potential-Dependent Amino Acid Transport by Daptomycin," *Antimicrobial Agents and Chemotherapy* 35: 2639-2642 (1991).

Baltz, R. H., "Lipopeptide Antibiotics Produced by *Streptomyces roseosporus* and *Streptomyces fradiae*," in *Biotechnology of Antibiotics*, 2d Ed., 415-435 (1997).

Bingen, E. et al. "Bactericidal Activity of Daptomycin Against Vancomycin-Resistant *Enterococcus faecium* in an in Vitro Pharmacokinetic Model," *Eur. J. Clin. Microbiol. Infect. Dis.* 10: 1062-1065 (1991).

Boeck, LaVerne D. et al. "Deacylation of A21978C, An Acidic Lipopeptide Antibiotic Complex, by *Actinoplanes utahensis*," *Journal of Antibiotics* XLI: 1085-1092 (1988).

Boeck, L. D. et al. "A54145, A New Lipopeptide Antibiotic Complex: Discovery, Taxonomy, Fermentation and HPLC," *Journal of Antibiotics* XLIII: 587-593 (1990).

Champlin, Franklin R. et al. "Cell Envelope Impermeability to Daptomycin in *Pseudomonas aeruginosa* and *Pasteurella multocida*," *Current Microbiology* 21: 367-372 (1990).

Chong, Pei Pei et al. "Physical Identification of a Chromosomal Locus Encoding Biosynthetic Genes for the Lipopeptide Calcium-Dependent Antibiotic (CDA) of *Streptomyces coelicolor* A3(2)," *Microbiology* 144: 193-199 (1998).

Debono, M. et al. "A21978C, A Complex of New Acidic Peptide Antibiotics: Isolation, Chemistry, and Mass Spectral Structure Elucidation," *Journal of Antibiotics* XL: 761-777 (1987).

Debono, M. et al. "Enzymatic and Chemical Modifications of Lipopeptide Antibiotic A21978C: The Synthesis and Evaluation of Daptomycin (LY146032)," *Journal of Antibiotics* XLI: 1093-1105 (1988).

(Continued)

*Primary Examiner*—David Lukton
(74) *Attorney, Agent, or Firm*—Timothy J. Douros; Jill M. N. Mandelblatt

(57) ABSTRACT

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

30 Claims, No Drawings

OTHER PUBLICATIONS

Debono, M. et al. "Synthesis of New Analogs of Echinocandin B by Enzymatic Deacylation and Chemical Reacylation of the Echinocandin B Peptide: Synthesis of the Antifungal Agent Cilofungin (LY121019)," *Journal of Antibiotics* XLII: 389-397 (1989).

Dong, Mei-Yan et al. "Treatment of *Clostridium difficile* Colitis in Hamsters with a Lipopeptide Antibiotic, LY146032," *Antimicrobial Agents and Chemotherapy* 31: 1135-1136 (1987).

Eid, Pascale et al. "Effect of Daptomycin on the Barotropic Behavior of Dioleoylphosphatidylglycerol: An Infrared Spectroscopic Investigation," *Chemistry and Physics of Lipids* 83: 131-140 (1996).

Eliopoulos, George M. et al. "In Vitro Activity and Mechanism of Action of A21978C$_1$, a Novel Cyclic Lipopeptide Antibiotic," *Antimicrobial Agents and Chemotherapy* 27: 357-362 (1985).

Huber, F. M. et al. "The Formation of Daptomycin by Supplying Decanoic Acid to *Streptomyces roseosporus* Cultures Producing the Antibiotic Complex A21978C," *Journal of Biotechnology* 7: 283-292 (1988).

Huber, F. M. et al. "The Synthesis of A21978C Analogs by *Streptomyces roseosporus* Cultivated Under Carbon Limitation and Fed Fatty Acids," *Biotechnology Letters* 12: 789-792 (1990).

Inokoshi, Junji et al. "Cloning and Sequencing of the Aculeacin A Acylase-Encoding Gene From *Actinoplanes utahensis* and Expression in *Streptomyces lividans*," *Gene* 119: 29-35 (1992).

Inokoshi, Junji et al. "Efficient Production of Aculeacin A Acylase in Recombinant *Streptomyces* strains," *Appl. Microbiol. Biotechnol.* 39: 532-536 (1993).

Kempter, Christoph et al. "CDA: Calcium-Dependent Peptide Antibiotics from *Streptomyces coelicolor* A3(2) Containing Unusual Residues," *Angew. Chem. Int. Ed. Engl.* 36: 498-501 (1997).

Kirsch, Lee E. et al. "Kinetics of the Aspartyl Transpeptidation of Daptomycin, a Novel Lipopeptide Antibiotic," *Pharmaceutical Research* 6: 387-393 (1989).

Lakey, Jeremy H. et al. "The Role of Acyl Chain Character and Other Determinants on the Bilayer Activity of A21978C An Acidic Lipopeptide Antibiotic," *Biochimica et Biophysica Acta* 859: 219-226 (1986).

Lakey, Jeremy H. et al. "Fluorescence Indicates a Calcium-Dependent Interaction Between the Lipopeptide Antibiotic LY146032 and Phospholipid Membranes," *Biochemistry* 27: 4639-4645 (1988).

Lakey, Jeremy H. et al. "The Lipopeptide Antibiotic A21978C Has a Specific Interaction With DMPC Only in the Presence of Calcium Ions," *Biochimica et Biophysica Acta* 985: 60-66 (1989).

Lee, Belle L. et al. "Effect of Protein Binding of Daptomycin on MIC and Antibacterial Activity," *Antimicrobial Agents and Chemotherapy* 35: 2505-2508 (1991).

Liebowitz, Lynne D. et al. "In Vitro Selection of Bacteria Resistant to LY146032, a New Cyclic Lipopeptide," *Antimicrobial Agents and Chemotherapy* 32: 24-26 (1988).

Maget-Dana, Régine et al. "A Comparative Monomolecular Film Study of Antibiotic A21978C Homologues of Various Lipid Chain Length," *Biochimica et Biophysica Acta* 962: 201-207 (1988).

Zambias, Robert A. et al. "Preparation and Structure-Activity Relationships of Simplified Analogues of the Antifungal Agent Cilofungin: A Total Synthesis Approach," *Journal of Medicinal Chemistry* 35: 2843-2855 (1992).

Zmijewski, M.J. et al. "Role of Branched Chain Fatty Acid Precursors in Regulating Factor Profile in the Biosynthesis of A21978 C Complex," *Journal of Antibiotics* XXXIX: 1483-1485 (1986).

Applicant's Oct. 5, 2005 response to Apr. 7, 2005 office action in U.S. Appl. No. 10/213,218.

* cited by examiner

LIPOPEPTIDES AS ANTIBACTERIAL AGENTS

FIELD OF THE INVENTION

The present invention relates to novel lipopeptide compounds. The invention also relates to pharmaceutical compositions of these compounds and methods of using these compounds as antibacterial compounds. The invention also relates to methods of producing these novel lipopeptide compounds and intermediates used in producing these compounds.

BACKGROUND OF THE INVENTION

The rapid increase in the incidence of gram-positive infections—including those caused by resistant bacteria—has sparked renewed interest in the development of novel classes of antibiotics. A class of compounds which have shown potential as useful antibiotics includes the A-21978C lipopeptides described in, for example, U.S. Pat. Nos. RE 32,333; RE 32,455; RE 32,311; RE 32,310; 4,482,487; 4,537,717; and 5,912,226. Daptomycin, a member of this class, has potent bactericidal activity in vitro and in vivo against clinically relevant gram-positive bacterial that cause serious and life-threatening diseases. These bacterial include resistant pathogens, such as vancomycin-resistant enterococci (VRE), methicillin-resistant *Staphylococcus aureus* (MRSA), glycopeptide intermediate susceptible *Staphylococcus aureus* (GISA), coagulase-negative staphylococci (CNS), and penicillin-resistant *Streptococcus pneumoniae* (PRSP), for which there are few therapeutic alternatives. See, e.g., Tally et al., 1999, *Exp. Opin. Invest. Drugs* 8: 1223-1238.

Despite the promise that antibacterial agents such as daptomycin offer, the need for novel antibiotics continues. Many pathogens have been repeatedly exposed to commonly-used antibiotics. This exposure has led to the selection of variant antibacterial strains resistant to a broad spectrum of antibiotics. The loss of potency and effectiveness of an antibiotic caused by resistant mechanisms renders the antibiotic ineffective and consequently can lead to life-threatening infections that are virtually untreatable. As new antibiotics come to market pathogens may develop resistance or intermediate resistance to these new drugs, effectively creating a need for a stream of new antibacterial agents to combat these emerging strains. In addition compounds that exhibit bacteriacidal activity would offer advantages over present bacteriastatic compounds. Thus, novel synthetic antibacterial agents would be expected to be useful to treat not only "natural" pathogens, but also intermediate drug resistant and drug resistant pathogens because the pathogen has never been exposed to the novel antibacterial agent. Additionally, new antibacterial agents may exhibit differential effectiveness against different types of pathogens.

SUMMARY OF THE INVENTION

The present invention addresses this problem by providing novel lipopeptide compounds which have antibacterial activity against a broad spectrum of bacteria, including drug-resistant bacteria. Further, the compounds of the present invention exhibit bacteriacidal activity.

The present invention comprises, in one aspect, antibacterial compounds of Formula I:

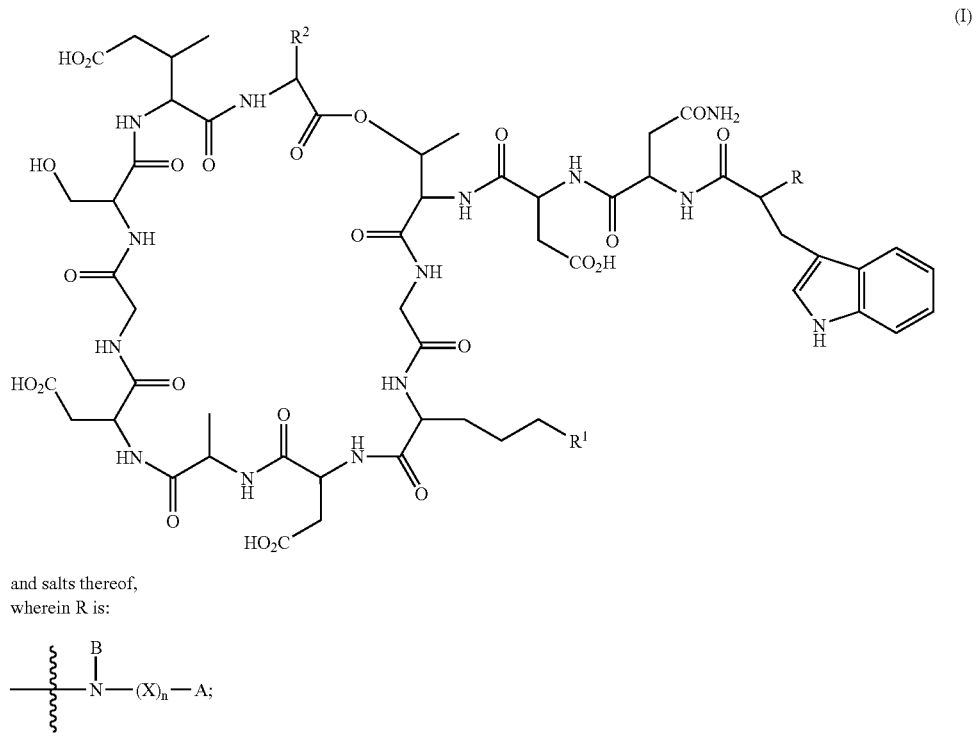

and salts thereof,
wherein R is:

$$-N(X)_n-A;$$
with B substituent on N wherein X and X" are independently selected from C=O, C=S, C=NH, C=NR$^X$, S=O or SO$_2$;

wherein n is 0 or 1;

wherein $R^X$ is selected from alkyl, alkenyl, alkynyl, aryl, heteroaryl, cycloalkyl, heterocyclyl, hydroxyl, alkoxy, carboxy or caboalkoxy;

wherein B is $X''R^Y$, H, alkyl, alkenyl, alkynyl, aryl, heteroaryl, cycloalkyl or heterocyclyl;

wherein $R^Y$ is selected from hydrido, alkyl, alkenyl, alkynyl, aryl, heteroaryl, cycloalkyl, hetercyclyl or hydroxyl;

wherein A is H, $NH_2$, $NHR^A$, $NR^AR^B$, alkyl, alkenyl, alkynyl, alkoxy, aryloxy, aryl, heteroaryl, cycloalkyl or heterocyclyl;

wherein $R^A$ and $R^B$ are independently selected from alkyl, alkenyl, alkynyl, aryl, heteroaryl, cycloalkyl, heterocyclyl or carboalkoxy;

wherein when n is 0, then A is additionally selected from:

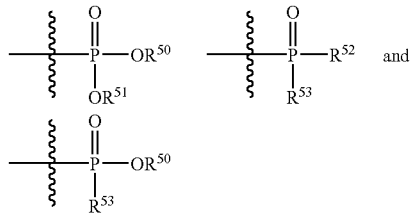

wherein each of $R^{50}$-$R^{53}$ is independently selected from $C_1$-$C_{15}$ alkyl;

alternatively, wherein B and A together form a 5-7 membered heterocyclic or heteroaryl ring.

Wherein $R^1$ is

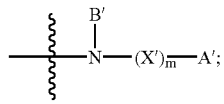

wherein $X^{40}$ and $X'''$ are independently selected from C═O, C═S, C═NH, C═$NR^{X'}$, S═O or $SO_2$;

where m is 0 or 1;

wherein $R^{X'}$ is selected from alkyl, alkenyl, alkynyl, aryl, heteroaryl, cycloalkyl, heterocyclyl, hydroxyl, alkoxy, carboxy or carboalkoxy;

wherein B' is $X'''R^{Y'}$, H, alkyl, alkenyl, alkynyl, aryl, heteroaryl, cycloalkyl or heterocyclyl; and wherein $R^{Y'}$ is selected from hydrido, alkyl, alkenyl, alkynyl, aryl, heteroaryl, cycloalkyl, heterocyclyl or hydroxyl.

In one aspect of the invention, A' is H, $NH_2$, $NHR^{A'}$, $NR^{A'}R^{B'}$, heteroaryl, cycloalkyl or heterocyclyl;

wherein $R^{A'}$ and $R^{B'}$ are independently selected from alkyl, alkenyl, alkynyl, aryl, heteroaryl, cycloalkyl, heterocyclyl or carboalkoxy;

wherein when m is 0, then A' is additionally selected from:

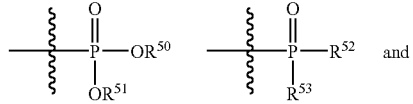

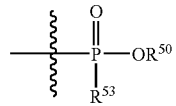

wherein each of $R^{50}$-$R^{53}$ is independently selected from $C_1$-$C_{15}$ alkyl;

provided that when B' is H and X' is C═O, then A' is other than (a) a pyridinyl ring substituted with one substituent $NHC(O)R^D$ or
(b) a $C_5$-$C_6$ saturated cycloalkyl ring substituted with one substituent $NHC(O)R^D$;

wherein $R^D$ is $C_1$-$C_{17}$ unsubstituted alkyl or $C_2$-$C_{17}$ unsubstituted alkenyl; and wherein B' is H and m=0, then A' is not H.

In another aspect of the invention, A' is aryl;

provided that when B' is H and X' is C═O, then A' is other than a phenyl ring substituted with substituent $NHC(O)R^D$, wherein $R^D$ is defined as above, which may be further optionally substituted on the phenyl ring with 1-2 substituents independently selected from amino, nitro, $C_1$-$C_3$ alkyl, hydroxyl, $C_1$-$C_3$ alkoxy, halo, mercapto, $C_1$-$C_3$ alkylthio, carbamyl or $C_1$-$C_3$ alkyl carbamyl.

In a third aspect of the invention, A' is alkyl, alkenyl, alkynyl, alkoxy or aryloxy;

provided that when B' is H and X' is C═O, then A' is other than (a) —($C_1$-$C_{16}$ unsubstituted alkyl)—$NH_2$;
(b) —($C_1$-$C_{10}$ unsubstituted alkyl)—$NHC(O)R^D$, wherein $R^D$ is defined as described above;
(c) —$C_1$-$C_{18}$ alkyl, optionally substituted with up to one hydroxyl, carboxyl or $C_1$-$C_3$ alkoxy, or one to three halo substituents;
(d) —$C_4$-$C_{18}$ unsubstituted alkenyl;

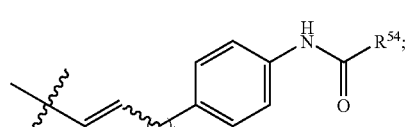
(e)

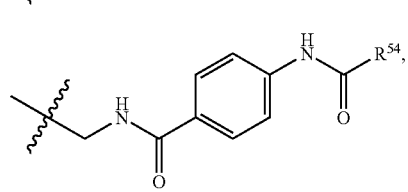
(f)

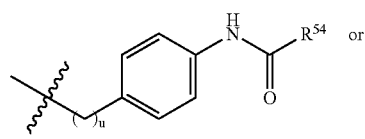
(g) or

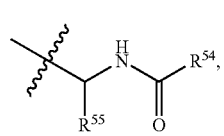
(h)

wherein $R^{54}$ is selected from $C_1$-$C_{17}$-unsubstituted alkyl or $C_2$-$C_{17}$-unsubstituted alkenyl; where $R^{55}$ is selected from hydroxyethyl, hydroxymethyl, mercaptomethyl, mercaptoethyl, methylthioethyl, 2-thienyl, 3-indolemethyl, phenyl optionally substituted with a group selected from halo, nitro, $C_1$-$C_3$-unsubstituted alkyl, hydroxy, $C_1$-$C_3$-unsubstituted alkoxy, $C_1$-$C_3$-unsubstituted alkylthio, carbamyl or $C_1$-$C_3$ unsubstituted alkylcarbamyl; or benzyl optionally substituted with a group selected from halo, nitro, $C_1$-$C_3$-unsubstituted alkyl, hydroxy, $C_1$-$C_3$-unsubstituted alkoxy, $C_1$-$C_3$-unsubstituted alkylthio, carbamyl or $C_1$-$C_3$ unsubstituted alkylcarbamyl; wherein t is 0 or 1 and wherein u is an integer from 1-3; and when B' is H and X' is C=O, then X', together with A', does not form a carbamate amino protecting group; and wherein B' is H and m is 0, then A' is other than $C_4$-$C_{14}$ unsubstituted alkyl.

In a fourth aspect of the invention, B' and A' together form a 5-7 membered heterocyclic or heteroaryl ring.

Wherein $R^2$ is

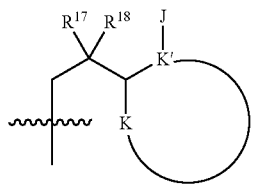

wherein K and K' together form a $C_3$-$C_7$ cycloalkyl or heterocyclyl ring or a $C_5$-$C_{10}$ aryl or heteroaryl ring;

wherein J is selected from the group consisting of hydrido, amino, $NHR^J$, $NR^J R^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

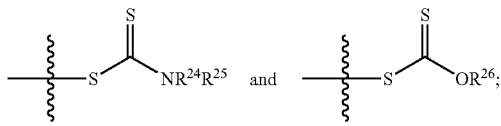

wherein each of $R^{24}$, $R^{25}$, and $R^{26}$ is independently selected from the group consisting of alkyl, cycloalkyl, heterocyclyl, aryl and heteroaryl; or $R^{24}$ and $R^{25}$ together form a 5-8 membered heterocyclyl ring;

wherein $R^J$ and $R^K$ are independently selected from alkyl, alkenyl, alkynyl, aryl, heteroaryl, cycloalkyl or heterocyclyl; or alternatively, wherein J, together with $R^{17}$, forms a 5-8 membered heterocyclyl or cycloalkyl ring; or alternatively, wherein J, together with both $R^{17}$ and $R^{18}$, forms a 5-8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and

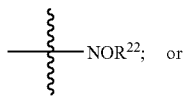

NOR$^{22}$; or where $R^{17}$ and $R^{18}$ taken together can form a group consisting of ketal, thioketal,

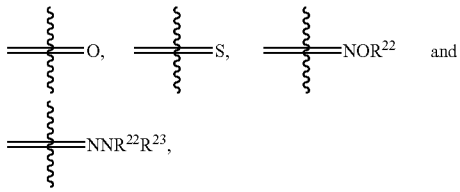

wherein each of $R^{22}$ and $R^{23}$ is independently selected from the group consisting of hydrido and alkyl.

In another embodiment, the invention also provides pharmaceutical compositions comprising compounds of Formula I and methods of use thereof.

In a further embodiment, the invention provides methods of making compounds of Formula I and pharmaceutical compositions thereof.

In a further embodiment, the invention provides compounds useful as intermediates for the preparation of compounds of Formula I.

In a still further embodiment, the invention provides methods of use of the compounds of Formula I to treat bacterial infections in humans.

DETAILED DESCRIPTION OF THE INVENTION

Definitions

Molecular terms, when used in this application, have their common meaning unless otherwise specified.

The term "hydrido" denotes a single hydrogen atom (H).

The term "acyl" is defined as a carbonyl radical attached to an alkyl, alkenyl, alkynyl, cycloalkyl, heterocycyl, aryl or heteroaryl group, examples including, without limitation, such radicals as acetyl and benzoyl.

The term "amino" denotes a nitrogen radical containing two substituents independently selected from the group consisting of hydrido, alkyl, cycloalkyl, carboalkoxy, heterocyclyl, aryl, heteroaryl and sulfonyl. Subsets of the term amino are (1) the term "unsubstituted amino" which denotes an $NH_2$ radical, (2) the term "mono substituted amino" which is defined as a nitrogen radical containing a hydrido group and a substituent group selected from alkyl, cycloalkyl, heterocyclyl, aryl, or heteroaryl, and (3) the term "disubstituted amino" which is defined as a nitrogen radical containing two substituent groups independently selected from, alkyl, cycloalkyl, heterocyclyl, aryl, and heteroaryl. Preferred mono substituted amino radicals are "lower mono substituted amino" radicals, whereby the substituent group is a lower alkyl group. Preferred disubstituted amino radicals are "lower disubstituted amino" radicals, whereby the substituent groups are lower alkyl.

The term "acyloxy" denotes an oxygen radical adjacent to an acyl group.

The term "acylamino" denotes a nitrogen radical adjacent to an acyl group.

The term "carboalkoxy" is defined as a carbonyl radical adjacent to an alkoxy or aryloxy group.

The term "carboxyamido" denotes a carbonyl radical adjacent to an amino group.

The term "halo" is defined as a bromo, chloro, fluoro or iodo radical.

The term "thio" denotes a radical containing a substituent group independently selected from hydrido, alkyl, cycloalkyl, heterocyclyl, aryl and heteroaryl, attached to a divalent sulfur atom, such as, methylthio and phenylthio.

The term "alkyl" is defined as a linear or branched, saturated radical having one to about twenty carbon atoms unless otherwise specified. Preferred alkyl radicals are "lower alkyl" radicals having one to about five carbon atoms. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino, formul and an amino acid side chain. Examples of alkyl groups include, without limitation, methyl, tert-butyl, isopropyl, and methyoxymethyl. Subsets of the term alkyl are (1) "unsubstituted alkyl" which is defined as an alkyl group that bears no substituent groups (2) "substituted alkyl" which denotes an alkyl radical in which (a) one or more hydrogen atoms is replaced by a substituent group selected from acyl, acyloxy, carboalkoxy, carboxy, carboxyamido, cyano, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, N-acylaminosulfonyl or (b) two or more hydrogen atoms are each replaced by a substituent group independently selected from hydroxyl, carboxy, $C_1$-$C_3$ alkoxy, amino, acylamino, oxo or guanidino; and (3) the term "selected substituted alkyl" which denotes an alkyl radical in which (a) one proton is replaced by a group selected from hydroxyl, carboxy $C_1$-$C_3$ alkoxy, unsubstituted amino, acylamino, or acylamino phenyl or (b) one to three protons is replaced by a halo substituent.

The term "alkenyl" is defined as linear or branched radicals having two to about twenty carbon atoms, preferably three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration. Examples of alkenyl groups include, without limitations, ethylenyl or phenyl ethylenyl.

The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cyclalkyl, heterocyclyl, aryl, heteroaryl, alkoxy, aryloxy, sulfinyl, sulfonyl, formyl, oxo and guanidino. An example of alkynyl group includes, without limitations, propynyl.

The term "aryl" or "aryl ring" denotes aromatic radicals in a single or fused carbocyclic ring system, having from five to fourteen ring members. In a preferred embodiment, the ring system has from six to ten ring members. One or more hydrogen atoms may also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of aryl groups include, without limitation, phenyl, naphthyl, biphenyl, terphenyl. Subsets of the term aryl are (1) the term "phenyl" which denotes a compound of the formula:

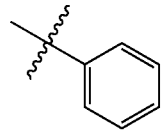

(2) the term "substituted phenyl" which is defined as a phenyl radical in which one or more protons are replaced by a substituent group selected from acyl, amino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino phenyl" denotes a phenyl radical in which one hydrogen atom is replaced by an acylamino group. One or more additional hydrogen atoms can also be replaced by a substituent group selected from acyl, amino, acylamino, acyloxy, azido, alkylthio, carboalkoxy, carboxy, carboxyamido, cyano, halo, hydroxyl nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

"Heteroaryl" or "heteroaryl ring" denotes an aromatic radical which contain one to four hetero atoms or hetero groups selected from O, N, S,

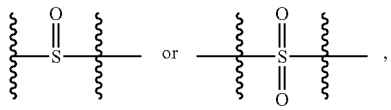

in a single or fused heterocyclic ring system, having from five to fifteen ring members. In a preferred embodiment, the heteroaryl ring system has from six to ten ring members. One or more hydrogen atoms may also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Subsets of the term heteroaryl are (1) the term "pyridinyl" which denotes compounds of the formula:

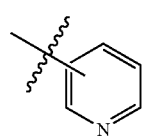

(2) the term "substituted pyridinyl" which is defined as a pyridinyl radical in which one or more protons is replaced by a substituent group selected from acyl, amino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino pyridinyl" which denotes a pyridinyl radical in which one hydrogen atom is replaced by an acylamino group, additionally, one or more additional hydrogen atoms can also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

The term "cycloalkyl" or "cycloalkyl ring" is defined as a saturated or partially unsaturated carbocyclic ring in a single or fused carbocyclic ring system having from three to twelve ring members. In a preferred embodiment, a cycloalkyl is a ring system having three to seven ring members. One or more hydrogen atoms may also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopropyl, cyclobutyl, cyclohexyl, and cycloheptyl.

The term "heterocyclyl," "heterocyclic" or "heterocyclyl ring" is defined as a saturated or partially unsaturated ring containing one to four hetero atoms or hetero groups selected from O, N, NH,

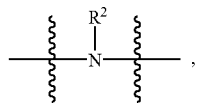

wherein $R^Z$ is defined for $R^X$.

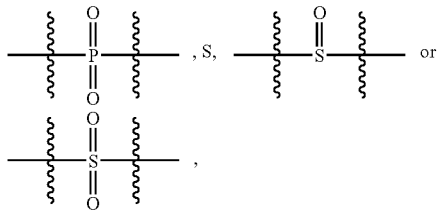

in a single or fused heterocyclic ring system having from three to twelve ring members. In a preferred embodiment, a heterocyclyl is a ring system having three to seven ring members. One or more hydrogen atoms may also be replaced by a substituent group selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkenyl, alkynyl, cycloalkyl, heterocyclyl, aryl, heteroaryl, alkoxy, aryloxy, sulfinyl, sulfonyl and formyl. Examples of a heterocyclyl group include, without limitation, morpholinyl, piperidinyl, and pyrrolidinyl.

The term "alkoxy" denotes oxy-containing radicals substituted with an alkyl, cycloalkyl or heterocyclyl group. Examples include, without limitation, methoxy, tert-butoxy, benzyloxy and cyclohexyloxy.

The term "aryloxy" denotes oxy-containing radicals substituted with an aryl or heteroaryl group. Examples include, without limitation, phenoxy.

The term "amino acid side chain" denotes any side chain (R group) from a naturally-occurring or a non-naturally occurring amino acid.

The term "sulfinyl" is defined as a tetravalent sulfur radical substituted with an oxo substituent and a second substituent selected from the group consisting of alkyl, cycloalkyl, heterocyclyl, aryl, or heteroaryl group.

The term "sulfonyl" is defined as a hexavalent sulfur radical substituted with two oxo substituents and a third substituent selected from alkyl, cycloalkyl, heterocyclyl aryl, or heteroaryl.

The term "carbamate amino protecting group" is defined as a recognized amino protecting group that when bound to an amino group forms a carbamate. Examples of carbamate amino protecting groups can be found in "Protective Groups in Organic Synthesis" by Theodora W. Greene, John Wiley and Sons, New York, 1981. Examples of carbamate amino protecting groups include benzyloxycarbonyl, t-butyloxycarbonyl, t-amyloxycarbonyl, isobornyloxycarbonyl, adamantyloxycarbonyl, chlorobenzyloxycarbonyl, nitrobenzyloxycarbonyl or the like.

The salts of the compounds of the invention (preferably a compound of Formula I) include acid addition salts and base addition salts. In a preferred embodiment, the salt is a pharmaceutically acceptable salt of the compound of Formula I. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention (preferably a compound of Formula I) may be prepared from an inorganic acid or an organic acid. Examples of such inorganic acids include, without limitation, hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, glactic, and galacturonic acid. Suitable pharmaceutically-acceptable base addition salts of compounds of the invention (preferably a compound of Formula I) include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention (preferably a compound of Formula I) by treating, for example, the compound of the invention (preferably a compound of Formula I) with the appropriate acid or base.

The compounds of the invention (preferably compounds of Formula I) can possess one or more asymmetric carbon atoms and are thus capable of existing in the form of optical isomers as well as in the form of racemic or non-racemic mixtures thereof. The compounds of the invention (preferably compounds of Formula I) can be utilized in the present invention as a single isomer or as a mixture of stereochemical isomeric forms. Diastereoisomers, i.e., nonsuperimposable stereochemical isomers, can be separated by conventional means such as chromatography, distillation, crystallization, or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention (preferably compounds of Formula I) with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention (preferably compounds of Formula I) can likewise be obtained by utilizing optically active starting materials. These isomers may be in the form of a free acid, a free base, an ester or a salt.

The invention also embraces isolated compounds. An isolated compound refers to a compound which represents at least 10%, preferably at least 20%, more preferably at least 50% and most preferably at least 80% of the compound present in the mixture. In a preferred embodiment, the compound, a pharmaceutically acceptable salt thereof, or a pharmaceutical composition comprising the compound exhibits a detectable (i.e. statistically significant) antimicrobial activity when tested in conventional biological assays such as those described herein.

Lipopeptide Compounds

A compound of the formula (I):

and salts thereof, wherein R is:

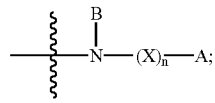

wherein X and X" are independently selected from C=O, C=S, C=NH, C=NR$^X$, S=O or SO$_2$;

wherein n is 0 or 1;

wherein R$^X$ is selected from alkyl, alkenyl, alkynyl, aryl, heteroaryl, cycloalkyl, heterocyclyl, hydroxyl, alkoxy, carboxy or carboalkoxy;

wherein B is X"R$^Y$, H, alkyl, alkenyl, alkynyl, aryl, heteroaryl, cycloalkyl or heterocyclyl;

wherein R$^Y$ is selected from hydrido, alkyl, alkenyl, alkynyl, aryl, heteroaryl, cycloalkyl, heterocyclyl or hydroxyl;

wherein A is H, NH$_2$, NHR$^A$, NR$^A$R$^B$, alkyl, alkenyl, alkynyl, alkoxy, aryloxy, aryl, heteroaryl, cycloalkyl or heterocyclyl;

wherein R$^A$ and R$^B$ are independently selected from alkyl, alkenyl, alkynyl, aryl, heteroaryl, cycloalkyl, heterocyclyl or carboalkoxy;

wherein when n is 0, then A is additionally selected from:

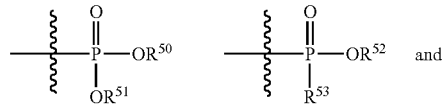

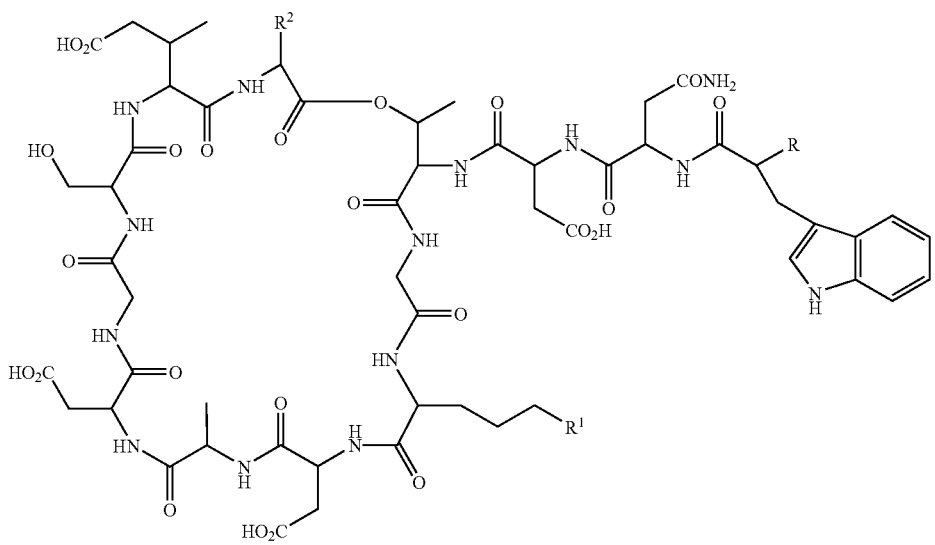

-continued

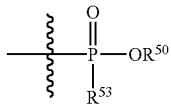

wherein each of $R^{50}$-$R^{53}$ is independently selected from $C_1$-$C_{15}$ alkyl;
alternatively, wherein B and A together form a 5-7 membered heterocyclic or heteroaryl ring.
Wherein $R^1$ is

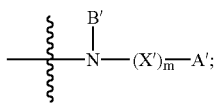

wherein X' and X''' are independently selected from C=O, C=S, C=NH, C=NR$^{X'}$, S=O or SO$_2$;
wherein m is 0 or 1;
wherein R$^{X'}$ is selected from alkyl, alkenyl, alkynyl, aryl, heteroaryl, cycloalkyl, heterocyclyl, hydroxyl, alkoxy, carboxy or carboalkoxy;
wherein B' is X'''R$^{Y'}$, H, alkyl, alkenyl, alkynyl, aryl, heteroaryl, cycloalkyl or heterocyclyl; and
wherein R$^{Y'}$ is selected from hydrido, alkyl, alkenyl, alkynyl, aryl, heteroaryl, cycloalkyl, heterocyclyl or hydroxyl.

In one aspect of the invention, A' is H, NH$_2$, NHR$^{A'}$, NR$^{A'}$R$^{B'}$, heteroaryl, cycloalkyl or heterocyclyl;
wherein R$^{A'}$ and R$^{B'}$ are independently selected from alkyl, alkenyl, alkynyl, aryl, heteroaryl, cycloalkyl, heterocyclyl or carboalkoxy;
wherein when m is 0, then A' is additionally selected from:

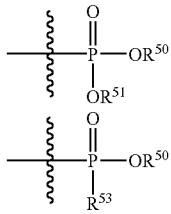 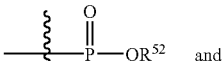

wherein each of $R^{50}$-$R^{53}$ is independently selected from $C_1$-$C_{15}$ alkyl;
provided that when B' is H and X' is C=O, then A' is other than
(a) pyridinyl ring substituted with one substituent NHC(O)R$^D$ or
(b) a $C_5$-$C_6$ saturated cycloalkyl ring substituted with one substituent NHC(O)R$^D$;
where R$^D$ is $C_1$-$C_{17}$ unsubstituted alkyl or $C_2$-$C_{17}$ unsubstituted alkenyl; and when B' is H and m=0, then A' is not H.

In another aspect of the invention, A' is aryl;
provided that when B' is H and X' is C=O, then A' is other than a phenyl ring substituted with substituent NHC(O)R$^D$, wherein R$^D$ is defined as above, which may be further optionally substituted on the phenyl ring with 1-2 substituents independently selected from amino, nitro, $C_1$-$C_3$ alkyl, hydroxyl, $C_1$-$C_3$ alkoxy, halo, mercapto, $C_1$-$C_3$ alkylthio, carbamyl or $C_1$-$C_3$ alkyl carbamyl.

In a third aspect of the invention, A' is alkyl, alkenyl, alkynyl, alkoxy or aryloxy;
provided that when B' is H and X' is C=O, then A' is other than
(a) —(C$_1$-C$_{16}$ unsubstituted alkyl)-NH$_2$;
(b) —(C$_1$-C$_{10}$ unsubstituted alkyl)-NHC(O)R$^D$, wherein R$^D$ is defined as described above;
(c) —C$_1$-C$_{18}$ alkyl, optionally substituted with up to one hydroxyl, carboxyl or C$_1$-C$_3$ alkoxy, or one to three halo substituents;
(d) —C$_4$-C$_{18}$ unsubstituted alkenyl;

(e)

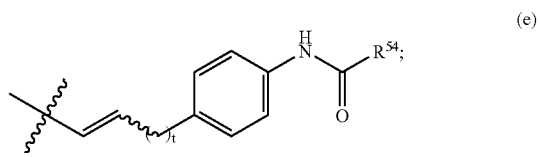

(f)

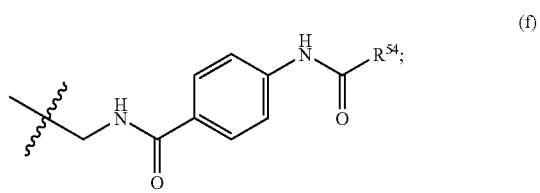

(g)

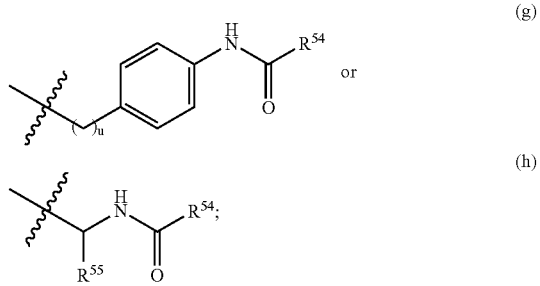

(h)

wherein R$^{54}$ is selected from C$_1$-C$_{17}$-unsubstituted alkyl or C$_2$-C$_{17}$-unsubstituted alkenyl; wherein R$^{55}$ is selected from hydroxyethyl, hydroxymethyl, mercaptomethyl, mercaptoethyl, methylthioethyl, 2-thienyl, 3-indolemethyl, phenyl optionally substituted with a group selected from halo, nitro, C$_1$-C$_3$-unsubstituted alkyl, hydroxy, C$_1$-C$_3$-unsubstituted alkoxy, C$_1$-C$_3$-unsubstituted alkylthio, carbamyl or C$_1$-C$_3$ unsubstituted alkylcarbamyl; or benzyl optionally substituted with a group selected from halo, nitro, C$_1$-C$_3$-unsubstituted alkyl, hydroxy, C$_1$-C$_3$-unsubstituted alkoxy, C$_1$-C$_3$-unsubstituted alkylthio, carbamyl or C$_1$-C$_3$ unsubstituted alkylcarbamyl; wherein t is 0 or 1 and wherein u is an integer from 1-3; and when B' is H and X' is C=O, then X', together with A', does not form a carbamate amino protecting group; and when B' is H and m is 0, then A' is other than C$_4$-C$_{14}$ unsubstituted alkyl.

In a fourth aspect of the invention, B' and A' together form a 5-7 membered heterocyclic or heteroaryl ring.
Wherein $R^2$ is

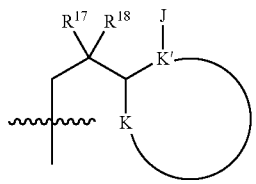

wherein K and K' together from a $C_3$-$C_7$ cycloalkyl or heterocyclyl ring or a $C_5$-$C_{10}$ aryl or heteroaryl ring;

wherein J is selected from the group consisting of hydrido, amino, $NHR^J$, $NR^J R^K$, alkyl, alkenyl, alkynyl, alkoxy, aryloxy, aryl, heteroaryl, cyclalkyl, heterocyclyl, alkylamino, hydroxyl, thio, alkylthio, alkenylthio, sulfinyl, sulfonyl, azido, cyano, halo,

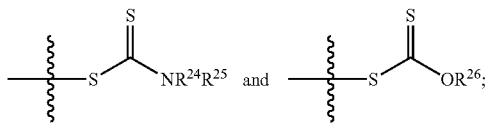

wherein each of $R^{24}$, $R^{25}$, and $R^{26}$ is independently selected from the group consisting of alkyl, cycloalkyl, heterocyclyl, aryl and heteroaryl, or $R^{24}$ and $R^{25}$ together form a 5-8 membered heterocyclyl ring;

wherein $R^J$ and $R^K$ are independently selected from alkyl, alkenyl, alkynyl, aryl, heteroaryl, cycloalkyl or heterocyclyl; or alternatively, wherein J, together with $R^{17}$, forms a 5-8 membered heterocyclyl or cycloalkyl ring; or alternatively, wherein J, together with both $R^{17}$ and $R^{18}$, forms a 5-8 membered aryl, cycloalkyl, heterocyclyl or heteroaryl ring; and wherein each of $R^{17}$ and $R^{18}$ is independently selected from the group consisting of hydrido, halo, hydroxyl, alkoxy, amino, thio, sulfinyl, sulfonyl and

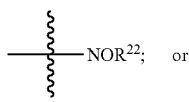

wherein $R^{17}$ and $R^{18}$ taken together can form a group consisting of ketal, thioketal,

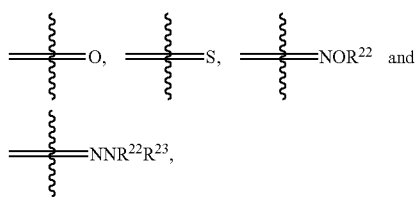

wherein each of $R^{22}$ and $R^{23}$ is independently selected from the group consisting of hydrido and alkyl.

In a preferred embodiment of the invention, R is selected from

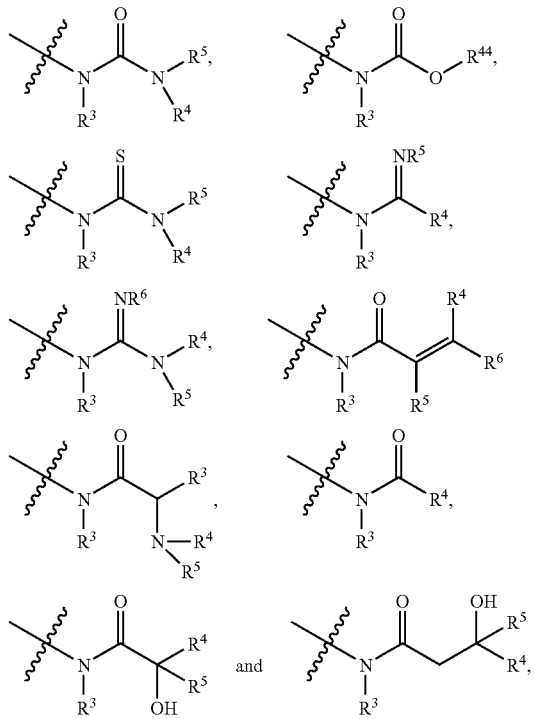

wherein each of $R^3$, $R^4$ $R^5$, and $R^6$ is independently selected from the group consisting of hydrido, alkyl, aryl, heterocyclyl and heteroaryl, and wherein $R^{44}$ is selected from the group consisting of alkyl, aryl, heterocyclyl and heteroaryl.

In a more preferred embodiment of the invention R is selected from

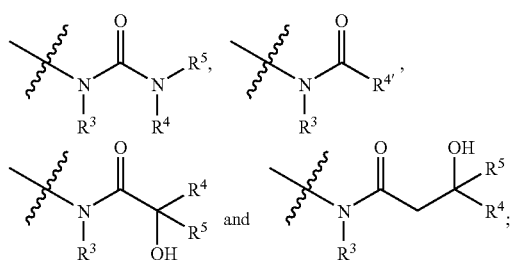

wherein $R^{4'}$ is selected from the group consisting of alkyl, aryl-substituted alkyl, substituted phenyl, heteroaryl, heterocyclyl, optionally substituted ($C_8$-$C_{14}$)-straight chain alkyl and

wherein $R^7$ is an alkyl group.

In an even more preferred embodiment, R is

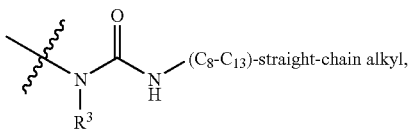

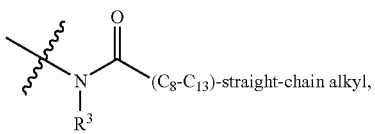

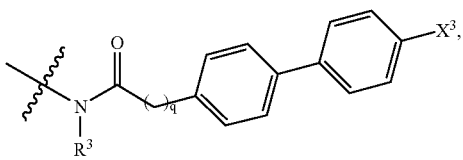

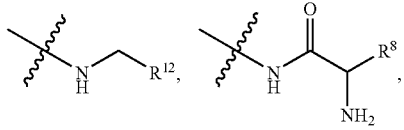

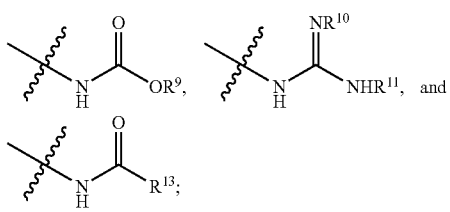

wherein $X^3$ is chloro or trifluoromethyl and wherein q is 0 or 1.

In a preferred embodiment of the invention, $R^1$ is selected from the group consisting of:

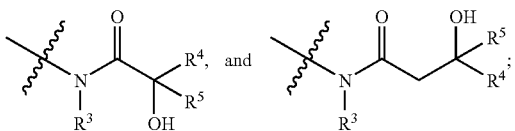

wherein $R^8$ is selected from an amino acid side chain, wherein said amino acid side chain may be one that is naturally occurring or one that is not naturally occurring, wherein each of $R^9$, $R^{10}$ and $R^{11}$ is selected from hydrido, alkyl, aryl, heterocyclyl and heteroaryl; wherein $R^{12}$ is selected from the group consisting of heterocyclyl, heteroaryl, aryl, and alkyl and wherein $R^{13}$ is selected from $(C_1$-$C_3)$-alkyl and aryl.

In a more preferred embodiment of the invention, $R^1$ is selected from the group consisting of:

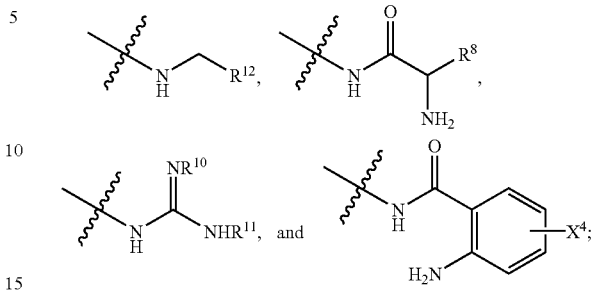

wherein $R^8$ is selected from tryptophan side chain and lysine side chain; wherein each of $R^{10}$ and $R^{11}$ is independently selected from hydrido and alkyl; wherein $R^{12}$ is selected from imidazolyl, N-methylimidazolyl, indolyl, quinolinyl, benzyloxybenzyl, and benzylpiperidenylbenzyl; and wherein $X^4$ is selected from fluoro and trifluoromethyl.

In a preferred embodiment of $R^2$, J is selected from the group consisting of hydrido, amino, azido and

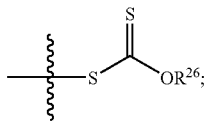

wherein $R^{17}$ and $R^{18}$ taken together form a group selected from the group consisting of ketal,

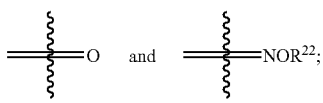

alternatively, $R^{17}$ is hydroxyl when $R^{18}$ is hydrido. Alternatively, wherein J, together with $R^{17}$, forms a heterocyclyl ring.

In a more preferred embodiment of the invention $R^2$ is selected from

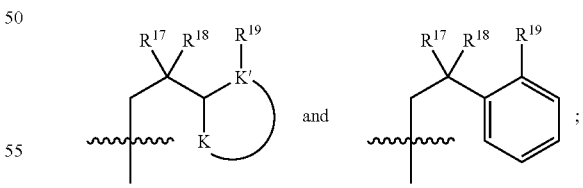

wherein $R^{17}$ and $R^{18}$ taken together form a group selected from

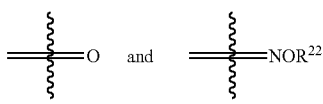

wherein $R^{22}$ is selected from the group consisting of H and alkyl; wherein $R^{19}$ is selected from the group consisting of hydrido, amino, azido and

[structure: -S-C(=S)-OR²⁶]

In an even more preferred embodiment of the invention $R^2$ is

[structure: 2-aminophenyl ketone group]

Another aspect of the present invention provides compounds of formula (I), wherein R is selected from NHCO—[(C$_6$-C$_{14}$)-alkyl]CH$_3$, and $R^1$ and $R^2$ are selected from Table A below. More preferably, R is selected from NHCO—[(CH$_2$)$_{6-14}$]-CH$_3$.

TABLE A

| $R^1$ | $R^2$ |
|---|---|
| [structure: -NH-C(=NCO₂tBu)-NHCO₂tBu] | [structure: 2-aminophenyl ketone] |
| [structure: -NH-C(=NH)-NH₂ guanidine] | [structure: 2-aminophenyl ketone] |
| NHSO₂Ph | [structure: 2-aminophenyl ketone] |
| [structure: HN=C(NH-)-NH-CH₂CH₂-piperidine] | [structure: 2-aminophenyl ketone] |
| [structure: HN-C(=S)-NH-CH₃ thiourea] | [structure: 2-aminophenyl ketone] |

TABLE A-continued

| R¹ | R² |
|---|---|
| HN-C(=S)-NH-CH(CH₃)₂ (isopropyl thiourea) | -C(=O)-C₆H₄-NH₂ (2-aminophenyl ketone) |
| HN-C(=S)-NH-CH₂-(tetrahydrofuran-2-yl) | -C(=O)-C₆H₄-NH₂ (2-aminophenyl ketone) |
| HN-C(=S)-NH-cyclopropyl | -C(=O)-C₆H₄-NH₂ (2-aminophenyl ketone) |
| HN-C(=O)-NH-(4-carboxy-1H-pyrazol-3-yl) | -C(=O)-C₆H₄-NH₂ (2-aminophenyl ketone) |
| HN-C(=O)-(2-aminophenyl) | -C(=O)-C₆H₄-NH₂ (2-aminophenyl ketone) |
| HN-C(=O)-(2-amino-5-chlorophenyl) | -C(=O)-C₆H₄-NH₂ (2-aminophenyl ketone) |
| HN-C(=O)-(2-amino-5-bromophenyl) | -C(=O)-C₆H₄-NH₂ (2-aminophenyl ketone) |
| HN-C(=O)-(2-amino-3-methylphenyl) | -C(=O)-C₆H₄-NH₂ (2-aminophenyl ketone) |

TABLE A-continued

| R¹ | R² |
|---|---|
| 2-amino-5-methylbenzamide (linked via NH) | 2-aminophenyl ketone (linked via CH₂) |
| 2-amino-5-methoxybenzamide (linked via NH) | 2-aminophenyl ketone (linked via CH₂) |
| 2-amino-3-methoxybenzamide (linked via NH) | 2-aminophenyl ketone (linked via CH₂) |
| 2-amino-3-chlorobenzamide (linked via NH) | 2-aminophenyl ketone (linked via CH₂) |
| 2-nitro-5-azidobenzamide (linked via NH) | 2-aminophenyl ketone (linked via CH₂) |
| 4-amino-3-carboxamido-benzoic acid (linked via NH) | 2-aminophenyl ketone (linked via CH₂) |
| 2-(methylamino)benzamide (linked via NH) | 2-aminophenyl ketone (linked via CH₂) |
| 2-methoxybenzamide (linked via NH) | 2-aminophenyl ketone (linked via CH₂) |

TABLE A-continued

| R¹ | R² |
|---|---|
| (2-amino-5-hydroxybenzamide linker) | (2-aminophenyl ketone linker) |
| (2-aminopyridine-3-carboxamide linker) | (2-aminophenyl ketone linker) |
| (2-amino-1-naphthamide linker) | (2-aminophenyl ketone linker) |
| (2-amino-6-fluorobenzamide linker) | (2-aminophenyl ketone linker) |
| (2-amino-5-fluorobenzamide linker) | (2-aminophenyl ketone linker) |
| (2-amino-4-fluorobenzamide linker) | (2-aminophenyl ketone linker) |
| (benzamide linker) | (2-aminophenyl ketone linker) |
| (pyrazine-2-carboxamide linker) | (2-aminophenyl ketone linker) |

TABLE A-continued

| R¹ | R² |
|---|---|
| (3-aminobenzamide, N-linked) | (2-aminophenyl ketone, propyl-linked) |
| (4-aminobenzamide, N-linked) | (2-aminophenyl ketone, propyl-linked) |
| (2-methylthiobenzamide, N-linked) | (2-aminophenyl ketone, propyl-linked) |
| (2-iodobenzamide, N-linked) | (2-aminophenyl ketone, propyl-linked) |
| (2-N,N-dimethylaminobenzamide, N-linked) | (2-aminophenyl ketone, propyl-linked) |
| (1,4-benzodioxane-2-carboxamide, N-linked) | (2-aminophenyl ketone, propyl-linked) |
| (2-(N-methylamino)benzamide, N-linked) | (2-azidophenyl ketone, propyl-linked) |
| (biotinamide, N-linked) | (2-azidophenyl ketone, propyl-linked) |

TABLE A-continued

| R¹ | R² |
|---|---|
| 4-fluorobenzylamine | 2-aminophenyl ketone |
| 2,3-diacetoxysuccinamide (OCOCH₃, CO₂H, OCOCH₃) | 2-aminophenyl ketone |
| 2-methoxybenzylamine | 2-aminophenyl ketone |
| 2,3-bis(NHBOC) propanamide | 2-aminophenyl ketone |
| 2-NHBOC, 4-CO₂CH₃ butanamide | 2-aminophenyl ketone |
| 2-NHBOC, 3-CO₂ᵗBu propanamide | 2-aminophenyl ketone |
| N-BOC tryptophan amide | 2-aminophenyl ketone |
| tryptophan amide (free NH₂) | 2-aminophenyl ketone |

TABLE A-continued

| R¹ | R² |
|---|---|
| (structure: -NH-CH(NH₂)-C(=O)- with -CH₂CH₂-CO₂CH₃ side chain) | (structure: -CH₂-C(=O)-C₆H₄-NH₂ (ortho)) |
| (structure: -NH-CH(NH₂)-C(=O)- with -CH₂CH₂-CONH₂ side chain) | (structure: -CH₂-C(=O)-C₆H₄-NH₂ (ortho)) |
| (structure: -NH-CH(NH₂)-C(=O)- with -CH₂-CONH₂ side chain) | (structure: -CH₂-C(=O)-C₆H₄-NH₂ (ortho)) |
| (structure: -NH-CH(NHBOC)-C(=O)- with -(CH₂)₄-NHTs side chain) | (structure: -CH₂-C(=O)-C₆H₄-NH₂ (ortho)) |
| (structure: -NH-CH₂-(2-pyridyl)) | (structure: -CH₂-C(=O)-C₆H₄-NH₂ (ortho)) |
| (structure: -CH₂-C(=O)-CH(NH₂)-(CH₂)₄-NHTs) | (structure: -CH₂-C(=O)-C₆H₄-NH₂ (ortho)) |
| (structure: -NH-CH₂-C₆H₄-CH₃ (para)) | (structure: -CH₂-C(=O)-C₆H₄-NH₂ (ortho)) |
| (structure: -NH-C(=O)-CH(NH₂)-(CH₂)₄-NH₂) | (structure: -CH₂-C(=O)-C₆H₄-NH₂ (ortho)) |

TABLE A-continued

| R¹ | R² |
|---|---|
| (structure: Tyr with NHBOC) | (structure: 2-aminophenyl ketone) |
| (structure: Tyr with NH₂) | (structure: 2-aminophenyl ketone) |
| (structure: Pro with N-Cbz) | (structure: 2-aminophenyl ketone) |
| (structure: biotin amide) | (structure: 2-aminophenyl ketone) |
| (structure: Arg with NH₂) | (structure: 2-aminophenyl ketone) |
| (structure: tryptamine-propanamide) | (structure: 2-aminophenyl ketone) |
| (structure: 4-fluoro-Trp with NH₂) | (structure: 2-aminophenyl ketone) |
| (structure: 5-fluoro-Trp with NH₂) | (structure: 2-aminophenyl ketone) |

TABLE A-continued

| R¹ | R² |
|---|---|

TABLE A-continued

| R¹ | R² |
|---|---|
| (histidine amide with free NH on imidazole) | 2-aminophenyl ketone |
| (histidine amide with NBOC on imidazole) | 2-aminophenyl ketone |
| (β-alanine amide with NHBOC) | 2-aminophenyl ketone |
| NH(CH₂)₂OH | 2-aminophenyl ketone |
| (aminomethyl-triazine with NHPh and NH₂ substituents) | 2-aminophenyl ketone |
| (tryptamine-like, indol-3-ylmethyl-NH) | 2-aminophenyl ketone |
| (5-methoxy-indol-3-ylmethyl-NH) | 2-aminophenyl ketone |
| (5-fluoro-indol-3-ylmethyl-NH) | 2-aminophenyl ketone |

TABLE A-continued

| R¹ | R² |
|---|---|
| (N-methylindol-3-yl)methylaminomethyl | 2-aminophenacyl |
| 4-(2-chloro-6-fluorophenoxymethyl)benzylaminomethyl | 2-aminophenacyl |
| (1-methylbenzimidazol-2-yl)methylaminomethyl | 2-aminophenacyl |
| (1-methylimidazol-2-yl)methylaminomethyl | 2-aminophenacyl |
| 4-(4-nitrobenzyloxy)benzylaminomethyl | 2-aminophenacyl |
| bis[4-(3,4-dichlorobenzyloxy)benzyl]aminomethyl | 2-aminophenacyl |
| 4-(3,4-dichlorobenzyloxy)benzylaminomethyl | 2-aminophenacyl |
| bis[3-(4-methoxyphenoxy)benzyl]aminomethyl | 2-aminophenacyl |

TABLE A-continued

| R¹ | R² |
|---|---|
| N(CH₂CH=CH-C₆H₄-NEt₂)₂ | 2-aminobenzoyl-CH₂- |
| HN-CH₂CH=CH-C₆H₄-NEt₂ | 2-aminobenzoyl-CH₂- |
| HN-CH₂-C₆H₄-OⁿBu | 2-aminobenzoyl-CH₂- |
| HN-CH₂-C₆H₄-OⁿPr | 2-aminobenzoyl-CH₂- |
| HN-CH₂-C₆H₄-O-CH₂-C₆H₄-F | 2-aminobenzoyl-CH₂- |
| HN-CH₂-(2-MeO-naphthyl) | 2-aminobenzoyl-CH₂- |
| HN-CH₂-(2-OMe-4-OBn-C₆H₃) | 2-aminobenzoyl-CH₂- |
| N(CH₂-C₆H₄-3-F)₂ | 2-aminobenzoyl-CH₂- |

TABLE A-continued

| R¹ | R² |
|---|---|
| N(CH₂-2-fluorophenyl)₂ | C(=O)-(2-aminophenyl) |
| HNCH₂-(4-benzyloxyphenyl) | C(=O)-(2-aminophenyl) |
| HNCH₂-[2-(4-benzylpiperazin-1-yl)phenyl] | C(=O)-(2-aminophenyl) |
| N{CH₂-[2-(4-benzylpiperazin-1-yl)phenyl]}₂ | C(=O)-(2-aminophenyl) |
| HNCH₂-(3-nitrophenyl) | C(=O)-(2-aminophenyl) |
| HNCH₂-(2-hydroxy-4-benzyloxyphenyl) | C(=O)-(2-aminophenyl) |
| HNCH₂-[3-(3-trifluoromethylphenoxy)phenyl] | C(=O)-(2-aminophenyl) |
| HNCH₂-[3-(3,5-dichlorophenoxy)phenyl] | C(=O)-(2-aminophenyl) |

TABLE A-continued
| R¹ | R² |
|---|---|
| 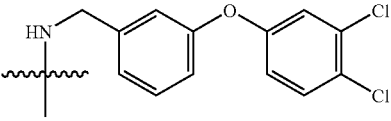 | 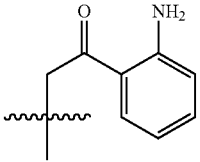 |
| 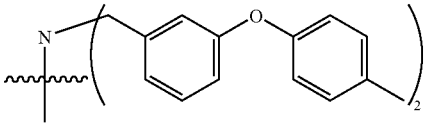 | 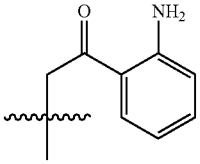 |
| 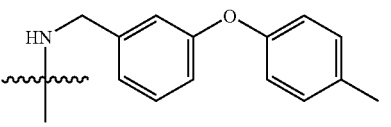 | 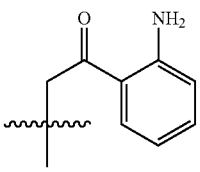 |
| 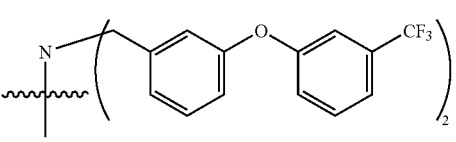 | 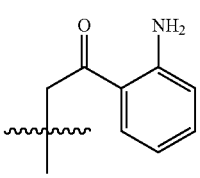 |
| 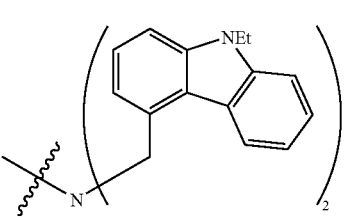 | 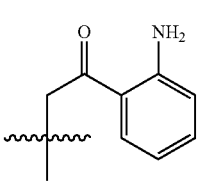 |
| 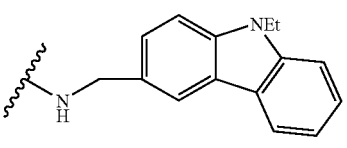 | 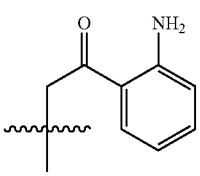 |
| 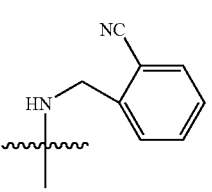 | 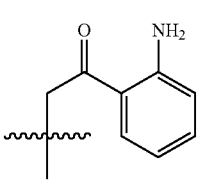 |
| 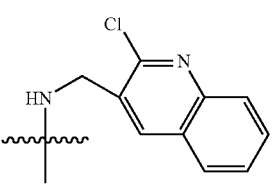 | 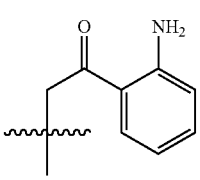 |

TABLE A-continued

| R¹ | R² |
|---|---|
| HN-CH2-(3-phenoxyphenyl with 4-tBu) | C(=O)-phenyl-2-NH2 |
| N(-CH2-(3-phenoxyphenyl with 4-Cl))2 | C(=O)-phenyl-2-NH2 |
| HN-CH2-(3-(4-chlorophenoxy)phenyl) | C(=O)-phenyl-2-NH2 |
| N(-CH2-(4-((4-nitrobenzyl)oxy)phenyl))2 | C(=O)-phenyl-2-NH2 |
| HN-CH2-(3-phenoxyphenyl) | C(=O)-phenyl-2-NH2 |
| HN-CH2-(4-CO2H-phenyl) | C(=O)-phenyl-2-NH2 |
| HN-CH2-(4-OnHex-phenyl) | C(=O)-phenyl-2-NH2 |
| N(-CH2-(4-OnHex-phenyl))2 | C(=O)-phenyl-2-NH2 |

TABLE A-continued

| R¹ | R² |
|---|---|
| (4-nBuO-benzyl)₂N- | 2-aminophenyl C(=O)CH₂- |
| (4-nPrO-benzyl)₂N- | 2-aminophenyl C(=O)CH₂- |
| 4-(phenylethynyl)benzyl-NH- | 2-aminophenyl C(=O)CH₂- |
| [4-((4-fluorobenzyl)oxy)benzyl]₂N- | 2-aminophenyl C(=O)CH₂- |
| 2-nitrobenzyl-NH- | 2-aminophenyl C(=O)CH₂- |
| quinolin-2-ylmethyl-NH- | 2-aminophenyl C(=O)CH₂- |
| (quinolin-2-ylmethyl)₂N- | 2-aminophenyl C(=O)CH₂- |
| [(1-methoxynaphthalen-8-yl)methyl]₂N- | 2-aminophenyl C(=O)CH₂- |

TABLE A-continued

| R¹ | R² |
|---|---|
| (2-aminobenzyl)amine group | 2'-aminophenyl ketone |
| bis(2-methoxy-4-benzyloxybenzyl)amine group | 2'-aminophenyl ketone |
| (3-fluorobenzyl)amine group | 2'-aminophenyl ketone |
| (2-fluorobenzyl)amine group | 2'-aminophenyl ketone |
| bis(4-benzyloxybenzyl)amine group | 2'-aminophenyl ketone |
| (quinolin-4-ylmethyl)amine group | 2'-aminophenyl ketone |
| (benzofuran-2-ylmethyl)amine group | 2'-aminophenyl ketone |
| bis(benzofuran-2-ylmethyl)amine group | 2'-aminophenyl ketone |

TABLE A-continued

| R¹ | R² |
|---|---|

TABLE A-continued

| R¹ | R² |
| --- | --- |
| 4-(3-dimethylaminopropoxy)benzylamino | 2-aminobenzoylmethyl |
| (3-phenyl-1H-pyrazol-4-yl)methylamino | 2-aminobenzoylmethyl |
| 4-benzyloxy-3-methoxybenzylamino | 2-aminobenzoylmethyl |
| bis(4-benzyloxy-3-methoxybenzyl)amino | 2-aminobenzoylmethyl |
| 4-n-dodecyloxybenzylamino | 2-aminobenzoylmethyl |
| 4-n-decyloxybenzylamino | 2-aminobenzoylmethyl |
| 4-n-octyloxybenzylamino | 2-aminobenzoylmethyl |
| 4-(2-carboxyvinyl)benzylamino | 2-aminobenzoylmethyl |

TABLE A-continued

| R¹ | R² |
|---|---|

TABLE A-continued

| R¹ | R² |
|---|---|
| N(-CH₂-C₆H₄-3-OCH₂Ph)₂ | 2-aminophenyl ketone |
| HN-CH₂-(2,4-difluorophenyl) | 2-aminophenyl ketone |
| N(-CH₂-CH=CH-Ph)₂ | 2-aminophenyl ketone |
| HN-CH₂-(quinolin-3-yl) | 2-aminophenyl ketone |
| N(-CH₂-CH₂-Ph)₂ | 2-aminophenyl ketone |
| N(-CH₂-C₆H₄-4-nBu)₂ | 2-aminophenyl ketone |
| HN-CH₂-C₆H₄-4-nBu | 2-aminophenyl ketone |
| HN-CH₂-C₆H₄-4-CN | 2-aminophenyl ketone |

TABLE A-continued
| R¹ | R² |
|---|---|
| 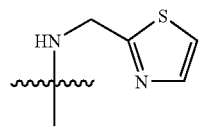 | 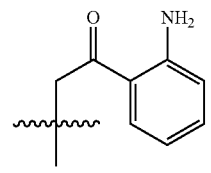 |
| 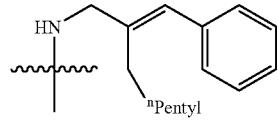 | 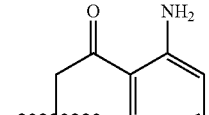 |
| 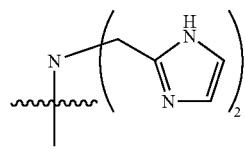 | 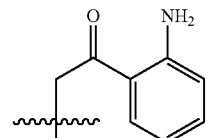 |
| 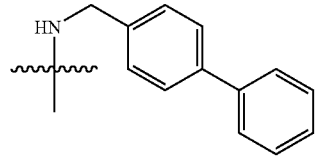 | 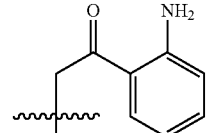 |
| 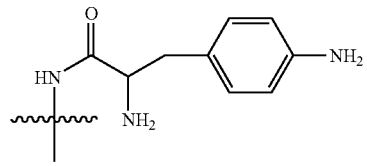 | 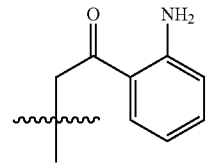 |
| 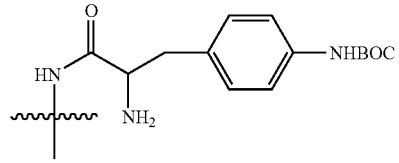 | 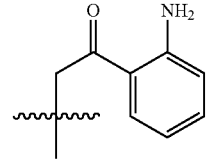 |
| 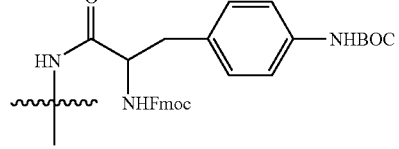 | 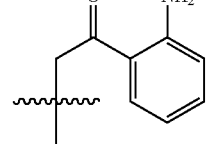 |
| 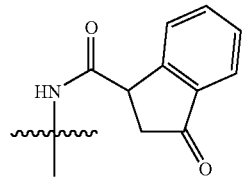 | 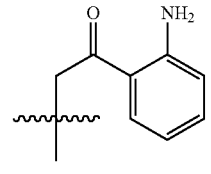 |

TABLE A-continued

| R¹ | R² |
|---|---|
| (structure: N with two 3-hydroxybenzyl groups) | (structure: 2-aminophenyl ketone) |
| (structure: HN-CH₂-(3-hydroxyphenyl)) | (structure: 2-aminophenyl ketone) |
| (structure: HN-CH₂-(2,3-dihydroxyphenyl)) | (structure: 2-aminophenyl ketone) |
| (structure: N with two benzo[1,3]dioxol-4-ylmethyl groups) | (structure: 2-aminophenyl ketone) |
| (structure: HN-CH₂-benzo[1,3]dioxol-4-yl) | (structure: 2-aminophenyl ketone) |
| (structure: 2,6-dioxopiperidin-1-yl / glutarimide) | (structure: 2-aminophenyl ketone) |
| (structure: HN-C(=O)-(2-sulfophenyl)) | (structure: 2-aminophenyl ketone) |
| (structure: HN-C(=O)-CH(NH₂)-CH₂-(4-hydroxyphenyl), tyrosine amide) | (structure: 2-azidophenyl ketone) |

TABLE A-continued

| R¹ | R² |
|---|---|
| (pyrrolidine with Boc, amide linker) | 2-aminophenyl ketone |
| 3-(trifluoromethoxy)benzylamino | 2-aminophenyl ketone |
| bis(3-(trifluoromethoxy)benzyl)amino | 2-aminophenyl ketone |
| 2,4-dichlorobenzylamino | 2-aminophenyl ketone |
| 4-chlorobenzylamino | 2-aminophenyl ketone |
| 4-(dimethylamino)benzylamino | 2-aminophenyl ketone |
| 2,6-dichlorobenzylamino | 2-aminophenyl ketone |
| tryptophan amide | phenyl ketone |

TABLE A-continued

| R¹ | R² |
|---|---|
| (structure: HN-CH(CH₃)-C(nHexyl)=CH-Ph) | (structure: 2-aminophenyl ketone) |
| (structure: HN-CH(CH₃)-CH₂-CH=CH-C₆H₄-NMe₂, ×2) | (structure: 2-aminophenyl ketone) |
| (structure: HN-CH₂-CH(NH₂)-CH₂-indol-3-yl) | (structure: 2-aminophenyl ketone) |
| (structure: HN-CH₂-CH(NHBoc)-CH₂-indol-3-yl) | (structure: 2-aminophenyl ketone) |
| (structure: HN-CH₂-CH(Ph)-S(O)₂-C₆H₄-CH₃) | (structure: 2-aminophenyl ketone) |
| (structure: HN-CH₂-[3-NO₂-4-(O-CH₂-C₆H₄-F)-phenyl]) | (structure: 2-aminophenyl ketone) |
| (structure: HN-CH₂-[3-Cl-4-OBn-phenyl]) | (structure: 2-aminophenyl ketone) |
| (structure: HN-CH₂-[3,4-di-OBn-phenyl]) | (structure: 2-aminophenyl ketone) |

TABLE A-continued
| R¹ | R² |
|---|---|
|  |  |
| 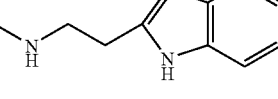 |  |
|  |  |
| 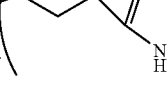 |  |
| 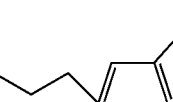 |  |
| 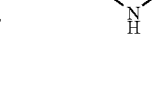 |  |
| 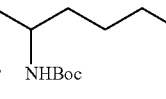 |  |
|  | 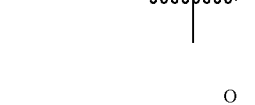 |

TABLE A-continued

| R¹ | R² |
|---|---|
| HN-CH₂-C₆H₄-C(O)-N(piperazine)N-C₆H₄-4-F | C(O)-C₆H₄-2-NH₂ |
| HN-CH₂-C₆H₄-C(O)-N(piperazine)N-CH₂-Ph | C(O)-C₆H₄-2-NH₂ |
| HN-CH₂-C₆H₄-C(O)-N(piperazine)N-C₆H₃-3,4-Cl₂ | C(O)-C₆H₄-2-NH₂ |
| HN-CH₂-C₆H₄-C(O)-N(piperazine)N-CH(Ph)₂ | C(O)-C₆H₄-2-NH₂ |
| HN-CH₂-C₆H₄-C(O)-N(piperazine)N-CH₂-CH=CH-Ph | C(O)-C₆H₄-2-NH₂ |
| HN-CH₂-C₆H₄-C(O)-N(piperazine)N-(2-pyrimidinyl) | C(O)-C₆H₄-2-NH₂ |
| HN-CH₂-C₆H₄-C(O)-N(piperazine)N-(2-pyridyl) | C(O)-C₆H₄-2-NH₂ |
| HN-CH₂-C₆H₄-C(O)-N(piperazine)N-C₆H₄-4-Cl | C(O)-C₆H₄-2-NH₂ |

TABLE A-continued

| R¹ | R² |
|---|---|

TABLE A-continued

| R¹ | R² |
|---|---|
| (structure: HN-CH2-phenyl-CH=CH-C(O)-N-piperazine-N-(4-chlorophenyl)) | (structure: C(O)-phenyl-NH2 (ortho)) |
| (structure: HN-C(O)-CH(NH2)-octyl) | (structure: C(O)-phenyl-NH2 (ortho)) |
| (structure: HN-C(O)-CH(NH2)-(CH2)4-NH2, lysine-like) | (structure: C(O)-phenyl-NH2 (ortho)) |
| (structure: HN-CH2-phenyl(3-NO2)-4-(N-piperazine-N-Bn)) | (structure: C(O)-phenyl-NH2 (ortho)) |
| (structure: HN-CH2-phenyl-4-(N-piperazine-N-Bn)) | (structure: C(O)-phenyl-NH2 (ortho)) |
| (structure: HN-C(=NBoc)-N(Boc)-propyl guanidine) | (structure: C(O)-phenyl-NH2 (ortho)) |
| (structure: HN-CH2-pyridyl-2-S-(2,4-dichlorophenyl)) | (structure: C(O)-phenyl-NH2 (ortho)) |
| (structure: HN-CH2-phenyl(3-NO2)-4-morpholino) | (structure: C(O)-phenyl-NH2 (ortho)) |

TABLE A-continued

| R¹ | R² |
|---|---|
| (4-(phenylsulfonylmethyl)-3-nitrobenzyl)amino | 2-aminobenzoyl methyl |
| (2-(4-(5-(trifluoromethyl)pyridin-2-yl)piperazin-1-yl)benzyl)amino | 2-aminobenzoyl methyl |
| N-propylguanidino | 2-aminobenzoyl methyl |
| (4-(bis(2-chloroethyl)amino)benzyl)amino | 2-aminobenzoyl methyl |
| bis(4-(bis(2-chloroethyl)amino)benzyl)amino | 2-aminobenzoyl methyl |
| bis((6-methoxyquinolin-2-yl)methyl)amino | 2-aminobenzoyl methyl |
| ((6-methoxyquinolin-2-yl)methyl)amino | 2-aminobenzoyl methyl |
| ((7-chloroquinolin-2-yl)methyl)amino | 2-aminobenzoyl methyl |

TABLE A-continued
| R¹ | R² |
|---|---|
| 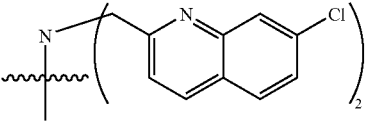 | 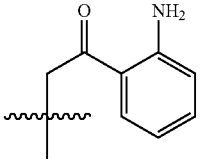 |
| 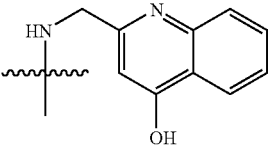 | 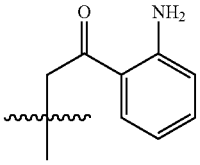 |
| 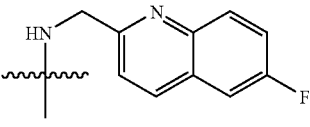 | 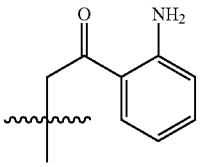 |
| 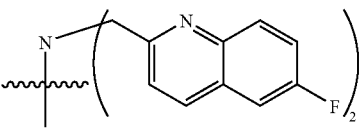 | 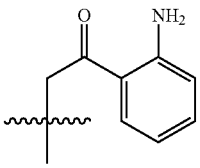 |
| 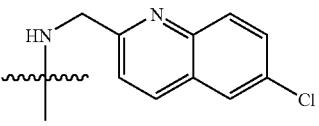 | 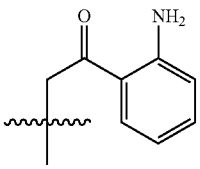 |
| 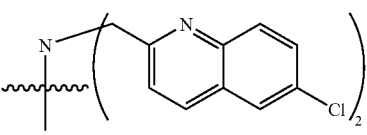 | 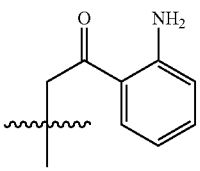 |
| 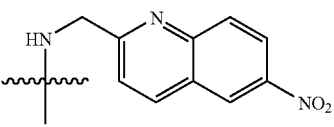 | 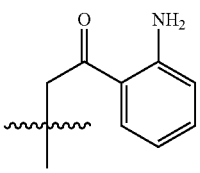 |
| 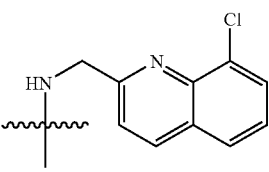 | 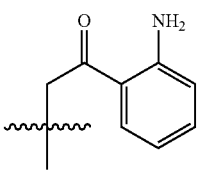 |

TABLE A-continued

| R¹ | R² |
|---|---|
| (quinolin-2-ylmethyl with 8-Cl, as bis substituent)₂N– | –CH₂–C(=O)–(2-aminophenyl) |
| HN–CH₂–(4-chloroquinolin-2-yl) | –CH₂–C(=O)–(2-aminophenyl) |
| HN–CH₂–(8-(phenylcarbamoyloxy)quinolin-2-yl) | –CH₂–C(=O)–(2-aminophenyl) |
| HN–CH₂–(4-carbamoylquinolin-2-yl) | –CH₂–C(=O)–(2-aminophenyl) |
| HN–CH₂–(6-chloro-4-hydroxyquinolin-2-yl) | –CH₂–C(=O)–(2-aminophenyl) |
| HN–CH₂–(6-dimethylaminoquinolin-2-yl) | –CH₂–C(=O)–(2-aminophenyl) |
| HN–CH₂–(8-nitroquinolin-2-yl) | –CH₂–C(=O)–(2-aminophenyl) |
| HN–CH₂–(5,7-dichloro-8-hydroxyquinolin-2-yl) | –CH₂–C(=O)–(2-aminophenyl) |

TABLE A-continued

| R¹ | R² |
|---|---|
| (S)-lysine derivative with NHBoc groups and amide linkage | 2-aminophenyl ketone |
| (5-methoxy-1H-indol-3-yl)methylamino | 2-aminophenyl ketone |
| (6-nitroquinolin-2-yl)methylamino | 2-aminophenyl ketone |
| {3-fluoro-4-[(4-trifluoromethylbenzyl)oxy]benzyl}amino | 2-aminophenyl ketone |
| {3-fluoro-4-[(2,4-bis(trifluoromethyl)benzyl)oxy]benzyl}amino | 2-aminophenyl ketone |
| {3-fluoro-4-[(4-fluorobenzyl)oxy]benzyl}amino | 2-aminophenyl ketone |
| {3-fluoro-4-[(2,4-difluorobenzyl)oxy]benzyl}amino | 2-aminophenyl ketone |
| {3-fluoro-4-(benzyloxy)benzyl}amino | 2-aminophenyl ketone |

TABLE A-continued

| R¹ | R² |
|---|---|
| (3-chloro-4-((4-(trifluoromethyl)benzyl)oxy)benzyl)amino group | 2-aminophenyl ketone group |
| (3-chloro-4-((2,4-bis(trifluoromethyl)benzyl)oxy)benzyl)amino group | 2-aminophenyl ketone group |
| (3-chloro-4-((4-fluorobenzyl)oxy)benzyl)amino group | 2-aminophenyl ketone group |
| (3-nitro-4-((2,4-bis(trifluoromethyl)benzyl)oxy)benzyl)amino group | 2-aminophenyl ketone group |
| (4-(N-phenethylsulfamoyl)benzyl)amino group | 2-aminophenyl ketone group |
| (4-(N-phenylsulfamoyl)benzyl)amino group | 2-aminophenyl ketone group |
| (4-((4-methylpiperazin-1-yl)sulfonyl)benzyl)amino group | 2-aminophenyl ketone group |
| (4-((4-acetylpiperazin-1-yl)sulfonyl)benzyl)amino group | 2-aminophenyl ketone group |

TABLE A-continued

| R¹ | R² |
|---|---|

TABLE A-continued

| R¹ | R² |
|---|---|
| HN-CH₂-C₆H₄-SO₂-N(piperazine)N-C₆H₄-F | -CH₂-C(=O)-C₆H₄-NH₂ |
| HN-CH₂-C₆H₄-SO₂-N(piperazine)N-CH₂-(benzo[1,3]dioxole) | -CH₂-C(=O)-C₆H₄-NH₂ |
| HN-CH₂-C₆H₄-SO₂-N(piperazine)N-CH₂-C₆H₄-CF₃ | -CH₂-C(=O)-C₆H₄-NH₂ |
| HN-CH₂-C₆H₄-SO₂-N(piperazine)N-C₆H₃-Cl₂ (3,4-diCl) | -CH₂-C(=O)-C₆H₄-NH₂ |
| HN-CH₂-C₆H₄-SO₂-N(piperazine)N-(pyrimidin-2-yl) | -CH₂-C(=O)-C₆H₄-NH₂ |
| HN-CH₂-C₆H₄-SO₂-NH-CH₂-C₆H₄-F (2-F) | -CH₂-C(=O)-C₆H₄-NH₂ |
| HN-CH₂-C₆H₄-SO₂-NH-CH₂-C₆H₄-F (3-F) | -CH₂-C(=O)-C₆H₄-NH₂ |
| HN-CH₂-C₆H₄-SO₂-NH-CH₂-C₆H₄-F (4-F) | -CH₂-C(=O)-C₆H₄-NH₂ |

TABLE A-continued

| R¹ | R² |
|---|---|
| (structure: -NH-CH₂-C₆H₄-SO₂-NH-CH₂CH₂CH₂-phenyl) | (structure: -CH₂-C(=O)-C₆H₄-2-NH₂) |
| (structure: -NH-CH₂-C₆H₄-SO₂-NH-CH₂-(3-Cl-phenyl)) | (structure: -CH₂-C(=O)-C₆H₄-2-NH₂) |
| (structure: -NH-CH₂-C₆H₄-SO₂-NH-CH₂-(4-Cl-phenyl)) | (structure: -CH₂-C(=O)-C₆H₄-2-NH₂) |
| (structure: -NH-CH₂-C₆H₄-SO₂-NH-CH₂-(2,4-diF-phenyl)) | (structure: -CH₂-C(=O)-C₆H₄-2-NH₂) |
| (structure: -NH-CH₂-C₆H₄-SO₂-NH-CH₂-(3,4-diF-phenyl)) | (structure: -CH₂-C(=O)-C₆H₄-2-NH₂) |
| (structure: -NH-CH₂-C₆H₄-SO₂-NH-CH₂CH₂-(2-Cl-phenyl)) | (structure: -CH₂-C(=O)-C₆H₄-2-NH₂) |
| (structure: -NH-CH₂-C₆H₄-SO₂-NH-CH₂CH₂-(4-Cl-phenyl)) | (structure: -CH₂-C(=O)-C₆H₄-2-NH₂) |
| (structure: -NH-CH₂-C₆H₄-SO₂-NH-CH₂-(2-CF₃-phenyl)) | (structure: -CH₂-C(=O)-C₆H₄-2-NH₂) |

TABLE A-continued

| R¹ | R² |
|---|---|
| HN-CH₂-C₆H₄-SO₂-NH-CH₂-C₆H₄(3-CF₃) | -CH₂-C(O)-C₆H₄(2-NH₂) |
| HN-CH₂-C₆H₄-SO₂-NH-CH₂-C₆H₄(4-CF₃) | -CH₂-C(O)-C₆H₄(2-NH₂) |
| HN-CH₂-C₆H₄-SO₂-NH-CH₂CH₂-C₆H₄(4-F) | -CH₂-C(O)-C₆H₄(2-NH₂) |
| HN-CH₂-C₆H₄-SO₂-NH-CH₂-C₆H₃(3,4-Cl₂) | -CH₂-C(O)-C₆H₄(2-NH₂) |
| HN-CH₂-C₆H₄-SO₂-NH-CH₂-C₆H₃(3,5-Cl₂) | -CH₂-C(O)-C₆H₄(2-NH₂) |
| HN-CH₂-C₆H₄-SO₂-NH-CH₂-C₆H₃(2,4-Cl₂) | -CH₂-C(O)-C₆H₄(2-NH₂) |
| HN-CH₂-C₆H₄-SO₂-NH-CH₂-C₆H₄(3-OCF₃) | -CH₂-C(O)-C₆H₄(2-NH₂) |
| HN-CH₂-C₆H₄-SO₂-NH-CH₂-C₆H₄(4-OCF₃) | -CH₂-C(O)-C₆H₄(2-NH₂) |

TABLE A-continued

| R¹ | R² |
|---|---|
| (structure: HN-CH₂-phenyl-SO₂-NH-CH₂-(4-methylphenyl)) | (structure: 2-aminophenyl ketone with CH₂ linker) |
| (structure: HN-CH₂-phenyl-SO₂-NH-CH₂-phenyl) | (structure: 2-aminophenyl ketone with CH₂ linker) |
| (structure: HN-CH₂-(6-fluoroquinolin-2-yl) with 4-O-C(=O)-(5-methyl-3-phenylisoxazol-4-yl) ester) | (structure: 2-aminophenyl ketone with CH₂ linker) |
| (structure: HN-CH₂-quinolin-2-yl with 4-(4-chlorophenoxy)) | (structure: 2-aminophenyl ketone with CH₂ linker) |
| (structure: HN-CH₂-quinolin-2-yl with 4-(piperazin-1-yl)) | (structure: 2-aminophenyl ketone with CH₂ linker) |
| (structure: HN-CH₂-quinolin-2-yl with 4-(N-tosylamino)) | (structure: 2-aminophenyl ketone with CH₂ linker) |

TABLE A-continued
| R¹ | R² |
|---|---|
| 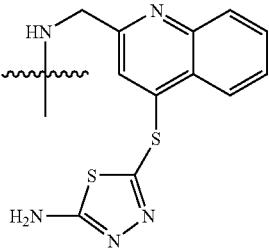 | 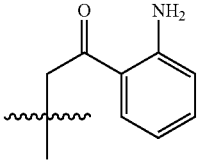 |
| 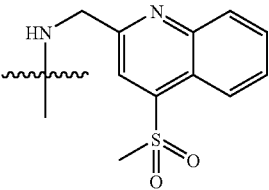 | 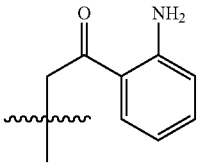 |
| 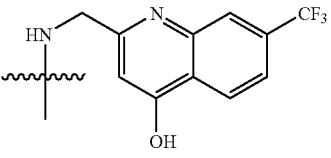 | 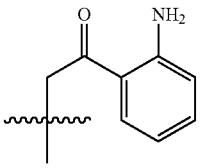 |
| 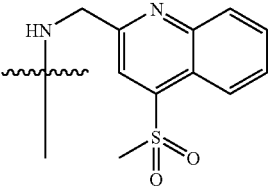 | 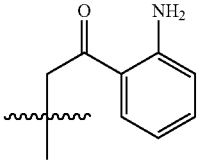 |
| 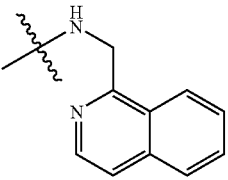 | 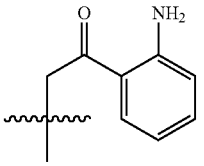 |
| 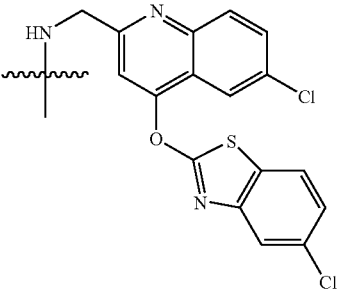 | 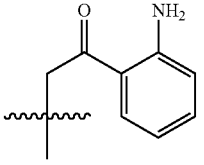 |

TABLE A-continued
| R¹ | R² |
|---|---|
| 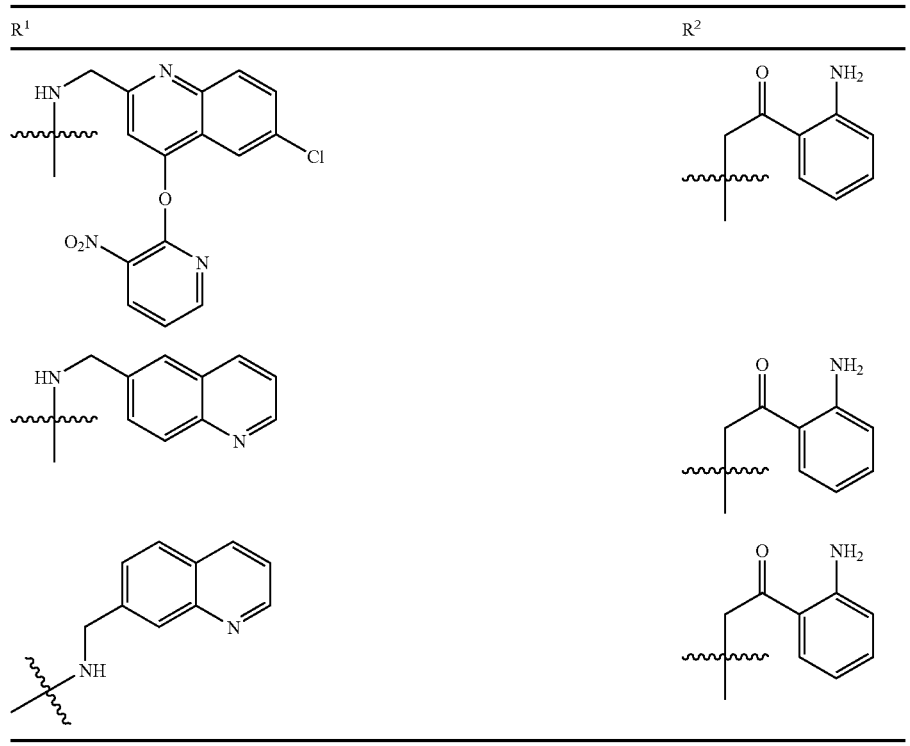 | |

TABLE I
Table I provides exemplary compounds of Formula I:
| Cpd # | R | R¹ | R² | Mass Spec | Synth Ex # |
|---|---|---|---|---|---|
| 1 | NHCO(CH₂)₈CH₃ | 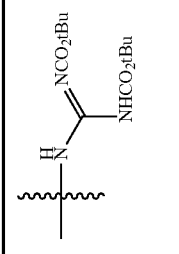 | 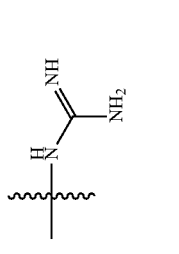 | 1863 | 6 |
| 2 | NHCO(CH₂)₈CH₃ | 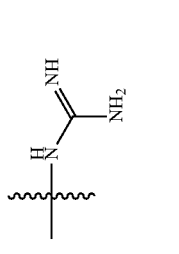 | 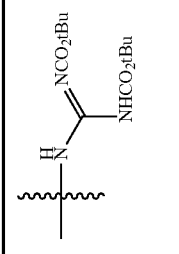 | 1663 | 6 |
| 3 | NHCO(CH₂)₈CH₃ | NHSO₂Ph | 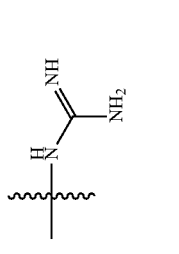 | 1762 | 5 |
| 4 | NHCO(CH₂)₈CH₃ | 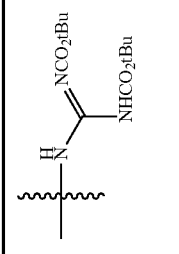 | 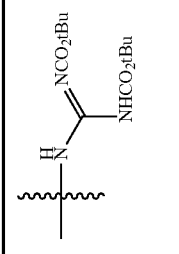 | 1792 | 4 |
| 5 | NHCO(CH₂)₈CH₃ | 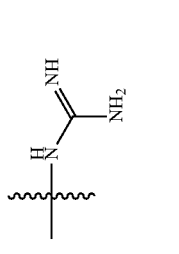 | 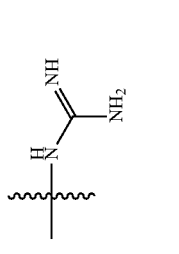 | 1694 | 4 |

TABLE I-continued

Table I provides exemplary compounds of Formula I:

| Cpd # | R | R¹ | R² | Mass Spec | Synth Ex # |
|---|---|---|---|---|---|
| 6 | NHCO(CH₂)₈CH₃ | isopropyl thiourea | 2-aminophenyl ketone | 1722 | 4 |
| 7 | NHCO(CH₂)₈CH₃ | tetrahydrofurfuryl thiourea | 2-aminophenyl ketone | 1764 | 4 |
| 8 | NHCO(CH₂)₈CH₃ | cyclopropyl thiourea | 2-aminophenyl ketone | 1720 | 4 |
| 9 | NHCO(CH₂)₈CH₃ | pyrazole-carboxylic acid urea | 2-aminophenyl ketone | 1775 | 4 |
| 10 | NHCO(CH₂)₈CH₃ | 2-aminobenzamide | 2-aminophenyl ketone | 1740 | 2 |

TABLE I-continued

Table I provides exemplary compounds of Formula I:

| Cpd # | R | R¹ | R² | Mass Spec | Synth Ex # |
|---|---|---|---|---|---|
| 11 | NHCO(CH$_2$)$_8$CH$_3$ | 2-amino-5-chlorobenzamide | 2-aminophenyl ketone | 1775 | 2 |
| 12 | NHCO(CH$_2$)$_8$CH$_3$ | 2-amino-5-bromobenzamide | 2-aminophenyl ketone | 1820 | 2 |
| 13 | NHCO(CH$_2$)$_8$CH$_3$ | 2-amino-3-methylbenzamide | 2-aminophenyl ketone | 1755 | 2 |
| 14 | NHCO(CH$_2$)$_8$CH$_3$ | 2-amino-5-methylbenzamide | 2-aminophenyl ketone | 1755 | 2 |
| 15 | NHCO(CH$_2$)$_8$CH$_3$ | 2-amino-5-methoxybenzamide | 2-aminophenyl ketone | 1771 | 2 |

TABLE I-continued

Table I provides exemplary compounds of Formula I:

| Cpd # | R | R¹ | R² | Mass Spec | Synth Ex # |
|---|---|---|---|---|---|
| 16 | NHCO(CH$_2$)$_8$CH$_3$ | 2-NH$_2$, 3-OCH$_3$ benzamide | 2-NH$_2$ phenacyl | 1771 | 2 |
| 17 | NHCO(CH$_2$)$_8$CH$_3$ | 2-NH$_2$, 3-Cl benzamide | 2-NH$_2$ phenacyl | 1775 | 2 |
| 18 | NHCO(CH$_2$)$_8$CH$_3$ | 2-NO$_2$, 5-N$_3$ benzamide | 2-NH$_2$ phenacyl | 1812 | 3b |
| 19 | NHCO(CH$_2$)$_8$CH$_3$ | 2-NH$_2$, 5-CO$_2$H benzamide | 2-NH$_2$ phenacyl | 1785 | 2 |
| 20 | NHCO(CH$_2$)$_8$CH$_3$ | 2-NHCH$_3$ benzamide | 2-NH$_2$ phenacyl | 1755 | 2 |

TABLE I-continued

Table I provides exemplary compounds of Formula I:

| Cpd # | R | R[1] | R[2] | Mass Spec | Synth Ex # |
|---|---|---|---|---|---|
| 21 | NHCO(CH$_2$)$_8$CH$_3$ | 2-OCH$_3$ benzamide | 2-NH$_2$ phenyl ketone | 1756 | 3b |
| 22 | NHCO(CH$_2$)$_8$CH$_3$ | 2-NH$_2$, 5-OH benzamide | 2-NH$_2$ phenyl ketone | 1757 | 2 |
| 23 | NHCO(CH$_2$)$_8$CH$_3$ | 2-NH$_2$ pyridine-3-carboxamide | 2-NH$_2$ phenyl ketone | 1742 | 2 |
| 24 | NHCO(CH$_2$)$_8$CH$_3$ | 2-NH$_2$ naphthalene-1-carboxamide | 2-NH$_2$ phenyl ketone | 1790 | 2 |
| 25 | NHCO(CH$_2$)$_8$CH$_3$ | 2-NH$_2$, 6-F benzamide | 2-NH$_2$ phenyl ketone | 1758 | 2 |

TABLE I-continued

Table I provides exemplary compounds of Formula I:

| Cpd # | R | R¹ | R² | Mass Spec | Synth Ex # |
|---|---|---|---|---|---|
| 26 | NHCO(CH$_2$)$_8$CH$_3$ | 2-amino-5-fluorobenzamide | 2'-aminophenyl ketone | 1758 | 2 |
| 27 | NHCO(CH$_2$)$_8$CH$_3$ | 2-amino-4-fluorobenzamide | 2'-aminophenyl ketone | 1758 | 2 |
| 28 | NHCO(CH$_2$)$_8$CH$_3$ | benzamide | 2'-aminophenyl ketone | 1726 | 3b |
| 29 | NHCO(CH$_2$)$_8$CH$_3$ | pyrazine-2-carboxamide | 2'-aminophenyl ketone | 1728 | 3b |
| 30 | NHCO(CH$_2$)$_8$CH$_3$ | 3-aminobenzamide | 2'-aminophenyl ketone | 1741 | 3b |

TABLE I-continued
Table I provides exemplary compounds of Formula I:
| Cpd # | R | R¹ | R² | Mass Spec | Synth Ex # |
|---|---|---|---|---|---|
| 31 | NHCO(CH$_2$)$_8$CH$_3$ | 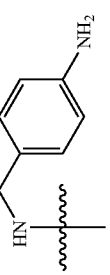 | 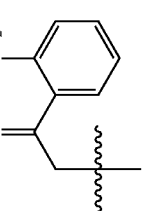 | 1741 | 3b |
| 32 | NHCO(CH$_2$)$_8$CH$_3$ |  | 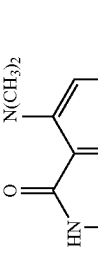 | 1771 | 3b |
| 33 | NHCO(CH$_2$)$_8$CH$_3$ |  | 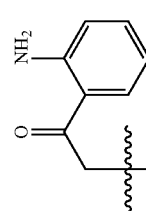 | 1851 | 3b |
| 34 | NHCO(CH$_2$)$_8$CH$_3$ | 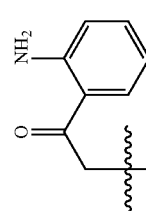 | 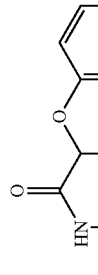 | 1767 | 3b |
| 35 | NHCO(CH$_2$)$_8$CH$_3$ | 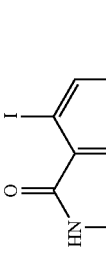 | 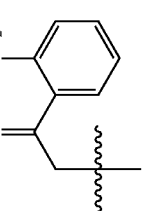 | 1782 | 3b |

TABLE I-continued

Table I provides exemplary compounds of Formula I:

| Cpd # | R | R¹ | R² | Mass Spec | Synth Ex # |
|---|---|---|---|---|---|
| 36 | NHCO(CH$_2$)$_8$CH$_3$ | 2-(NHCH$_3$)benzamide | 2'-azidophenacyl | 1780 | 8 |
| 37 | NHCO(CH$_2$)$_8$CH$_3$ | biotinyl | 2'-azidophenacyl | 1873 | 8 |
| 38 | NHCO(CH$_2$)$_8$CH$_3$ | 4-fluorobenzyl | 2'-aminophenacyl | 1729 | 1 |
| 39 | NHCO(CH$_2$)$_8$CH$_3$ | 2,3-di-O-acetyl-tartramide | 2'-aminophenacyl | 1838 | 3b |
| 40 | NHCO(CH$_2$)$_8$CH$_3$ | 2-methoxybenzyl | 2'-aminophenacyl | 1741 | 1 |

TABLE I-continued
Table I provides exemplary compounds of Formula I:
| Cpd # | R | R¹ | R² | Mass Spec | Synth Ex # |
|---|---|---|---|---|---|
| 41 | NHCO(CH$_2$)$_8$CH$_3$ | 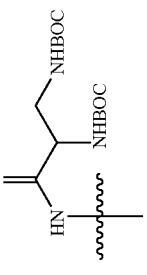 | 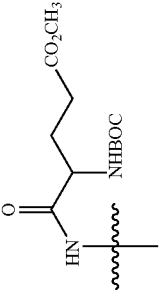 | 1908 | 3 |
| 42 | NHCO(CH$_2$)$_8$CH$_3$ | 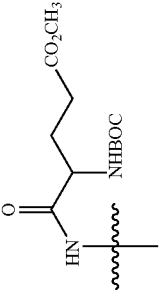 | 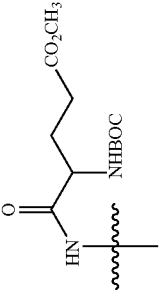 | 1865 | 3 |
| 43 | NHCO(CH$_2$)$_8$CH$_3$ | 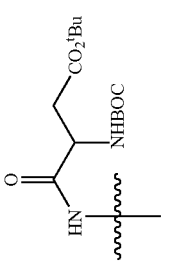 | 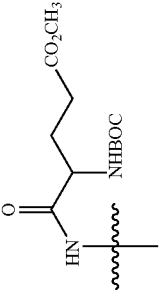 | 1893 | 3 |
| 44 | NHCO(CH$_2$)$_8$CH$_3$ | 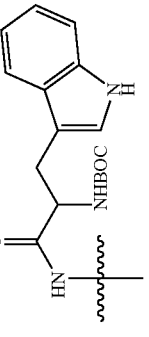 | 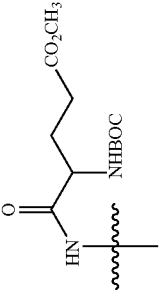 | 1908 | 3 |
| 45 | NHCO(CH$_2$)$_8$CH$_3$ | 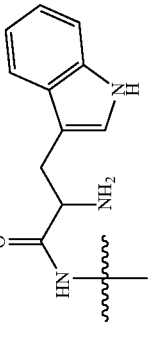 | 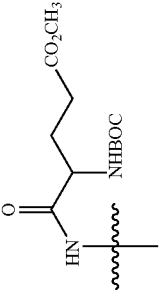 | 1808 | 3 |

TABLE I-continued
Table I provides exemplary compounds of Formula I:
| Cpd # | R | R¹ | R² | Mass Spec | Synth Ex # |
|---|---|---|---|---|---|
| 46 | NHCO(CH$_2$)$_8$CH$_3$ |  | 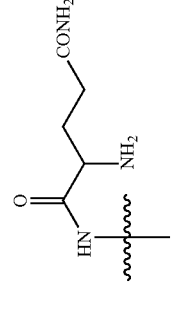 | 1764 | 3 |
| 47 | NHCO(CH$_2$)$_8$CH$_3$ |  |  | 1750 | 3 |
| 48 | NHCO(CH$_2$)$_8$CH$_3$ |  |  | 1736 | 3 |
| 49 | NHCO(CH$_2$)$_8$CH$_3$ |  |  | 2004 | 3a |
| 50 | NHCO(CH$_2$)$_8$CH$_3$ | 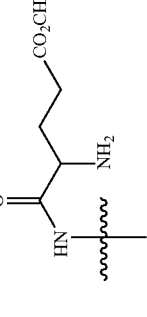 |  | 1712 | 1 |

TABLE I-continued

Table I provides exemplary compounds of Formula I:

| Cpd # | R | R$^1$ | R$^2$ | Mass Spec | Synth Ex # |
|---|---|---|---|---|---|
| 51 | NHCO(CH$_2$)$_8$CH$_3$ | (lysine-like sidechain with NH$_2$ and NHTs, ketone linker) | 2-aminophenyl ketone | 1904 | 3a |
| 52 | NHCO(CH$_2$)$_8$CH$_3$ | (4-methylbenzyl-NH linker) | 2-aminophenyl ketone | 1725 | 1 |
| 54 | NHCO(CH$_2$)$_8$CH$_3$ | (lysine sidechain with NH$_2$, amide linker) | 2-aminophenyl ketone | 1749 | 3a |
| 55 | NHCO(CH$_2$)$_8$CH$_3$ | (tyrosine-like with NHBOC, amide linker) | 2-aminophenyl ketone | 1884 | 3 |
| 56 | NHCO(CH$_2$)$_8$CH$_3$ | (tyrosine-like with NH$_2$, amide linker) | 2-aminophenyl ketone | 1785 | 3 |

TABLE I-continued

Table I provides exemplary compounds of Formula I:

| Cpd # | R | R¹ | R² | Mass Spec | Synth Ex # |
|---|---|---|---|---|---|
| 57 | NHCO(CH$_2$)$_8$CH$_3$ | proline-Cbz amide | 2-aminophenyl ketone | 1853 | 3 |
| 58 | NHCO(CH$_2$)$_8$CH$_3$ | biotinyl amide | 2-aminophenyl ketone | 1847 | 3 |
| 60 | NHCO(CH$_2$)$_8$CH$_3$ | arginyl amide | 2-aminophenyl ketone | 1778 | 3 |
| 61 | NHCO(CH$_2$)$_8$CH$_3$ | indolepropionyl amide | 2-aminophenyl ketone | 1792 | 3 |

TABLE I-continued

Table I provides exemplary compounds of Formula I:

| Cpd # | R | R¹ | R² | Mass Spec | Synth Ex # |
|---|---|---|---|---|---|
| 62 | NHCO(CH$_2$)$_8$CH$_3$ | 4-fluoro-tryptophan amide | 2-aminophenyl ketone | 1826 | 3 |
| 63 | NHCO(CH$_2$)$_8$CH$_3$ | 5-fluoro-tryptophan amide | 2-aminophenyl ketone | 1826 | 3 |
| 64 | NHCO(CH$_2$)$_8$CH$_3$ | 5-methoxy-tryptophan amide | 2-aminophenyl ketone | 1838 | 3 |
| 65 | NHCO(CH$_2$)$_8$CH$_3$ | 2-aminophenyl ketone amide | 2-aminophenyl ketone | 1812 | 3 |
| 66 | NHCO(CH$_2$)$_8$CH$_3$ | tryptophan amide | 2-aminophenyl ketone | 1808 | 3 |

TABLE I-continued

Table I provides exemplary compounds of Formula I:

| Cpd # | R | R¹ | R² | Mass Spec | Synth Ex # |
|---|---|---|---|---|---|
| 67 | NHCO(CH$_2$)$_8$CH$_3$ | phenylalanine-like (benzyl, α-NH$_2$, C(O)NH-) | 2-aminophenyl-C(O)-CH$_2$- | 1769 | 3 |
| 68 | NHCO(CH$_2$)$_8$CH$_3$ | benzothiophen-3-ylmethyl, α-NH$_2$, C(O)NH- | 2-aminophenyl-C(O)-CH$_2$- | 1824 | 3 |
| 69 | NHCO(CH$_2$)$_8$CH$_3$ | thiazol-4-ylmethyl, α-NH$_2$, C(O)NH- | 2-aminophenyl-C(O)-CH$_2$- | 1775 | 3 |
| 70 | NHCO(CH$_2$)$_8$CH$_3$ | tetrahydro-β-carboline-3-carboxamide | 2-aminophenyl-C(O)-CH$_2$- | 1820 | 3 |
| 72 | NHCO(CH$_2$)$_8$CH$_3$ | CH$_2$NH$_2$, α-NH$_2$, C(O)NH- (diaminopropanamide) | 2-aminophenyl-C(O)-CH$_2$- | 1707 | 3 |

TABLE I-continued

Table I provides exemplary compounds of Formula I:

| Cpd # | R | R¹ | R² | Mass Spec | Synth Ex # |
|---|---|---|---|---|---|
| 73 | NHCO(CH₂)₈CH₃ | histidine-amide linker | 2-aminophenyl ketone linker | 1758 | 3 |
| 74 | NHCO(CH₂)₈CH₃ | N-BOC histidine-amide linker | 2-aminophenyl ketone linker | 1959 | 3 |
| 75 | NHCO(CH₂)₈CH₃ | NHBOC-propanamide linker | 2-aminophenyl ketone linker | 1810 | 3 |
| 76 | NHCO(CH₂)₈CH₃ | 4-phenylbenzyl-amine linker | 2-aminophenyl ketone linker | 1787 | 1g |
| 77 | NHCO(CH₂)₈CH₃ | NH(CH₂)₂OH | 2-aminophenyl ketone linker | 1665 | 1 |

TABLE I-continued
Table I provides exemplary compounds of Formula I:
| Cpd # | R | R¹ | R² | Mass Spec | Synth Ex # |
|---|---|---|---|---|---|
| 78 | NHCO(CH$_2$)$_8$CH$_3$ | 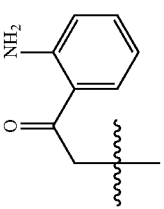 | 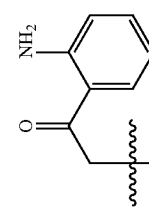 | 1820 | 1 |
| 79 | NHCO(CH$_2$)$_8$CH$_3$ | 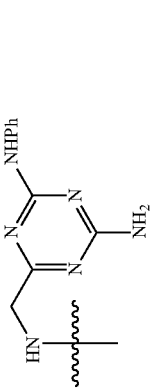 | 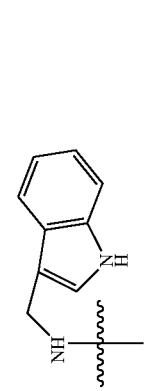 | 1750 | 1 |
| 80 | NHCO(CH$_2$)$_8$CH$_3$ |  |  | 1779 | 1 |
| 81 | NHCO(CH$_2$)$_8$CH$_3$ |  |  | 1767 | 1e |
| 82 | NHCO(CH$_2$)$_8$CH$_3$ |  |  | 1763 | 1 |

TABLE I-continued
Table I provides exemplary compounds of Formula I:
| Cpd # | R | R¹ | R² | Mass Spec | Synth Ex # |
|---|---|---|---|---|---|
| 83 | NHCO(CH$_2$)$_8$CH$_3$ | 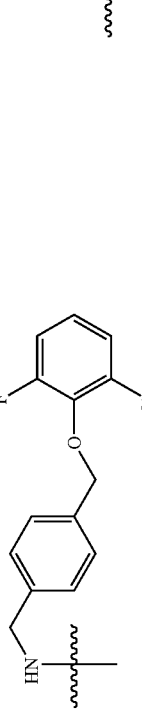 |  | 1869 | 1 |
| 84 | NHCO(CH$_2$)$_8$CH$_3$ |  |  | 1764 | 1 |
| 85 | NHCO(CH$_2$)$_8$CH$_3$ | 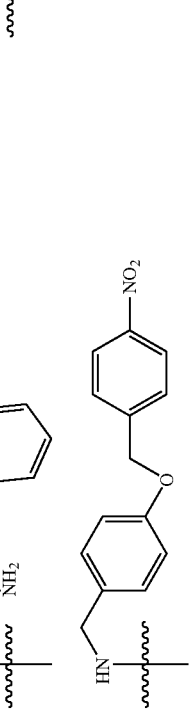 |  | 1714 | 1c |
| 86 |  |  | | 1935 | 9 |
| 87 | NHCO(CH$_2$)$_8$CH$_3$ | | | 1863 | 1 |

TABLE I-continued

Table I provides exemplary compounds of Formula I:

| Cpd # | R | R¹ | R² | Mass Spec | Synth Ex # |
|---|---|---|---|---|---|
| 88 | NHCO(CH$_2$)$_8$CH$_3$ | 3,4-dichlorobenzyl-O-(4-benzyl)-N (×2) | 2-aminophenyl-C(O)-CH$_2$- | 2151 | 1 |
| 89 | NHCO(CH$_2$)$_8$CH$_3$ | 3,4-dichlorobenzyl-O-(4-benzyl)-NH | 2-aminophenyl-C(O)-CH$_2$- | 1887 | 1 |
| 90 | NHCO(CH$_2$)$_8$CH$_3$ | 4-methoxyphenyl-O-(3-benzyl)-N (×2) | 2-aminophenyl-C(O)-CH$_2$- | 2046 | 1 |
| 91 | NHCO(CH$_2$)$_8$CH$_3$ | 4-(NEt$_2$)-cinnamyl-N (×2) | 2-aminophenyl-C(O)-CH$_2$- | 1996 | 1 |
| 92 | NHCO(CH$_2$)$_8$CH$_3$ | 4-(NEt$_2$)-cinnamyl-NH | 2-aminophenyl-C(O)-CH$_2$- | 1809 | 1 |

TABLE I-continued

Table I provides exemplary compounds of Formula I:

| Cpd # | R | R¹ | R² | Mass Spec | Synth Ex # |
|---|---|---|---|---|---|
| 93 | NHCO(CH$_2$)$_8$CH$_3$ | 4-(O$^n$Bu)-benzyl-NH- | 2-aminophenyl-C(O)-CH$_2$- | 1783 | 1 |
| 94 | NHCO(CH$_2$)$_8$CH$_3$ | 4-(O$^n$Pr)-benzyl-NH- | 2-aminophenyl-C(O)-CH$_2$- | 1770 | 1 |
| 95 | NHCO(CH$_2$)$_8$CH$_3$ | 4-(4-fluorobenzyloxy)-benzyl-NH- | 2-aminophenyl-C(O)-CH$_2$- | 1836 | 1 |
| 96 | NHCO(CH$_2$)$_8$CH$_3$ | 2-methoxy-naphthyl-methyl-NH- | 2-aminophenyl-C(O)-CH$_2$- | 1792 | 1 |
| 97 | NHCO(CH$_2$)$_8$CH$_3$ | 4-benzyloxy-2-methoxy-benzyl-NH- | 2-aminophenyl-C(O)-CH$_2$- | 1847 | 1 |

TABLE I-continued
Table I provides exemplary compounds of Formula I:
| Cpd # | R | R¹ | R² | Mass Spec | Synth Ex # |
|---|---|---|---|---|---|
| 98 | NHCO(CH₂)₈CH₃ | 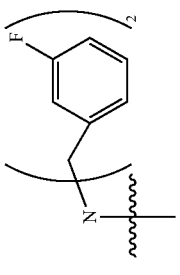 | 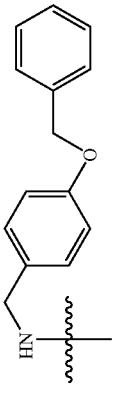 | 1838 | 1 |
| 99 | NHCO(CH₂)₈CH₃ | 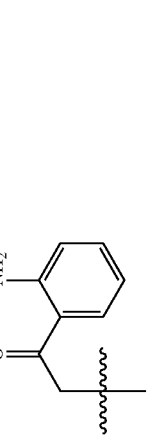 | 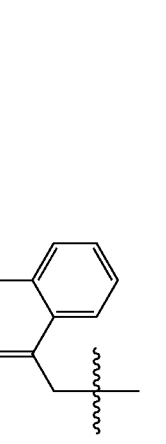 | 1837 | 1 |
| 100 | NHCO(CH₂)₈CH₃ | 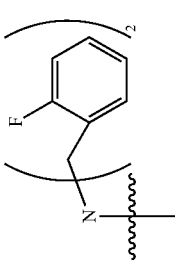 | 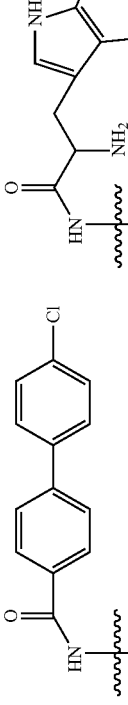 | 1817 | 1 |
| 101 | 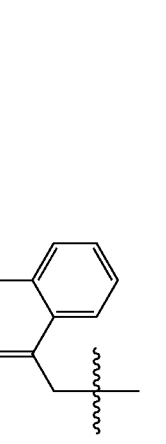 | 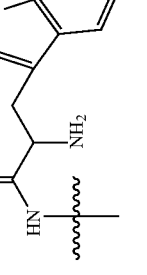 | 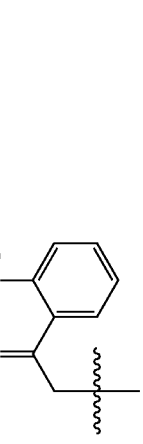 | 1867 | 9 |
| 102 | NHCO(CH₂)₁₁CH₃ | | | 1849 | 9 |

TABLE I-continued

Table I provides exemplary compounds of Formula I:

| Cpd # | R | R¹ | R² | Mass Spec | Synth Ex # |
|---|---|---|---|---|---|
| 103 | NHCO(CH$_2$)$_8$CH$_3$ | N-benzylpiperazinyl-phenyl-CH$_2$NH- | 2-aminophenyl-C(O)-CH$_2$- | 1885 | 1 |
| 104 | NHCO(CH$_2$)$_8$CH$_3$ | bis(N-benzylpiperazinyl-phenyl)-CH- | 2-aminophenyl-C(O)-CH$_2$- | 2150 | 1 |
| 105 | NHCO(CH$_2$)$_8$CH$_3$ | 3-nitrobenzyl-NH- | 2-aminophenyl-C(O)-CH$_2$- | 1756 | 1 |
| 106 | NHCO(CH$_2$)$_8$CH$_3$ | 2-hydroxy-4-benzyloxybenzyl-NH- | 2-aminophenyl-C(O)-CH$_2$- | 1833 | 1 |
| 107 | NHCO(CH$_2$)$_8$CH$_3$ | 3-(3-trifluoromethylphenoxy)benzyl-NH- | 2-aminophenyl-C(O)-CH$_2$- | 1871 | 1 |

TABLE I-continued
Table I provides exemplary compounds of Formula I:
| Cpd # | R | R¹ | R² | Mass Spec | Synth Ex # |
|---|---|---|---|---|---|
| 108 | NHCO(CH$_2$)$_8$CH$_3$ | 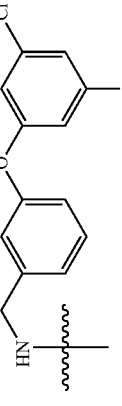 | 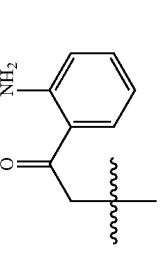 | 1873 | 1 |
| 109 | NHCO(CH$_2$)$_8$CH$_3$ | 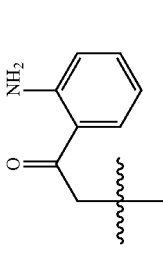 | 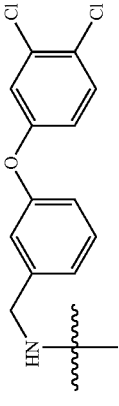 | 1872 | 1 |
| 110 | NHCO(CH$_2$)$_8$CH$_3$ | 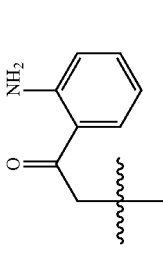 | 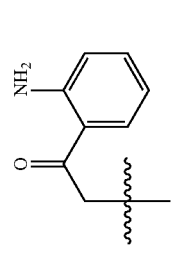 | 2014 | 1 |
| 111 | NHCO(CH$_2$)$_8$CH$_3$ | 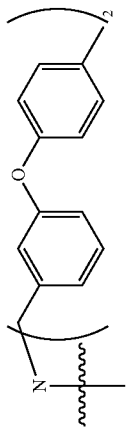 | 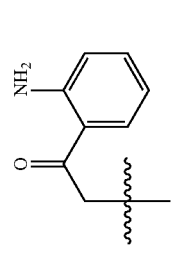 | 1817 | 1 |
| 112 | NHCO(CH$_2$)$_8$CH$_3$ | 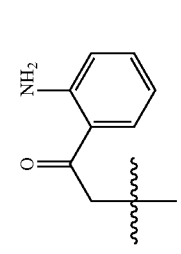 | 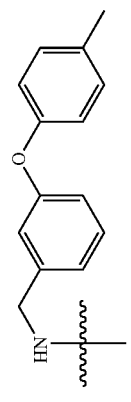 | 2121 | 1 |

TABLE I-continued

Table I provides exemplary compounds of Formula I:

| Cpd # | R | R¹ | R² | Mass Spec | Synth Ex # |
|---|---|---|---|---|---|
| 113 | NHCO(CH$_2$)$_8$CH$_3$ | (bis-N-ethylcarbazolylethyl)amine group | 2-aminophenyl ketone | 2036 | 1 |
| 114 | NHCO(CH$_2$)$_8$CH$_3$ | N-ethylcarbazolylmethylamine | 2-aminophenyl ketone | 1826 | 1 |
| 115 | NHCO(CH$_2$)$_8$CH$_3$ | 2-cyanobenzylamine | 2-aminophenyl ketone | 1736 | 1 |
| 116 | NHCO(CH$_2$)$_8$CH$_3$ | (2-chloroquinolin-3-yl)methylamine | 2-aminophenyl ketone | 1797 | 1 |
| 117 | NHCO(CH$_2$)$_8$CH$_3$ | 3-(4-tert-butylphenoxy)benzylamine | 2-aminophenyl ketone | 1860 | 1 |

TABLE I-continued

Table I provides exemplary compounds of Formula I:

| Cpd # | R | R¹ | R² | Mass Spec | Synth Ex # |
|---|---|---|---|---|---|
| 118 | NHCO(CH$_2$)$_8$CH$_3$ | (4-chlorophenoxy)phenyl-N, ×2 | 2-aminophenyl ketone | 2055 | 1 |
| 119 | NHCO(CH$_2$)$_8$CH$_3$ | (4-chlorophenoxy)phenyl-CH$_2$NH | 2-aminophenyl ketone | 1837 | 1 |
| 120 | NHCO(CH$_2$)$_8$CH$_3$ | (4-nitrobenzyloxy)phenyl-N, ×2 | 2-aminophenyl ketone | 2104 | 1 |
| 121 | NHCO(CH$_2$)$_8$CH$_3$ | (3-phenoxyphenyl)-CH$_2$NH | 2-aminophenyl ketone | 1803 | 1 |
| 122 | NHCO(CH$_2$)$_8$CH$_3$ | 4-carboxybenzyl-NH | 2-aminophenyl ketone | 1755 | 1 |

TABLE I-continued

Table I provides exemplary compounds of Formula I:

| Cpd # | R | R¹ | R² | Mass Spec | Synth Ex # |
|---|---|---|---|---|---|
| 123 | NHCO(CH$_2$)$_8$CH$_3$ | 4-(O-nHex)benzyl-NH- | 2-aminophenyl-CO-CH$_2$- | 1812 | 1 |
| 124 | NHCO(CH$_2$)$_8$CH$_3$ | bis(4-(O-nHex)benzyl)-N- | 2-aminophenyl-CO-CH$_2$- | 2002 | 1 |
| 125 | NHCO(CH$_2$)$_8$CH$_3$ | bis(4-(O-nBu)benzyl)-N- | 2-aminophenyl-CO-CH$_2$- | 1946 | 1 |
| 126 | NHCO(CH$_2$)$_8$CH$_3$ | bis(4-(O-nPr)benzyl)-N- | 2-aminophenyl-CO-CH$_2$- | 1918 | 1 |
| 127 | NHCO(CH$_2$)$_8$CH$_3$ | 4-(phenylethynyl)benzyl-NH- | | 1811 | 1 |

TABLE I-continued

Table I provides exemplary compounds of Formula I:

| Cpd # | R | R¹ | R² | Mass Spec | Synth Ex # |
|---|---|---|---|---|---|
| 128 | NHCO(CH₂)₈CH₃ | (4-fluorobenzyl-oxy-phenyl-methyl)₂-N— | 2-aminophenyl-C(O)-CH₂— | 2050 | 1 |
| 129 | NHCO(CH₂)₈CH₃ | 2-nitrobenzyl-NH— | 2-aminophenyl-C(O)-CH₂— | 1756 | 1 |
| 130 | NHCO(CH₂)₈CH₃ | quinolin-2-ylmethyl-NH— | 2-aminophenyl-C(O)-CH₂— | 1762 | 1 |
| 131 | NHCO(CH₂)₈CH₃ | (quinolin-2-ylmethyl)₂-N— | 2-aminophenyl-C(O)-CH₂— | 1904 | 1 |
| 132 | NHCO(CH₂)₈CH₃ | (2-methoxynaphth-1-ylmethyl)₂-N— | 2-aminophenyl-C(O)-CH₂— | 1962 | 1 |

TABLE I-continued

Table I provides exemplary compounds of Formula I:

| Cpd # | R | R¹ | R² | Mass Spec | Synth Ex # |
|---|---|---|---|---|---|
| 133 | NHCO(CH₂)₈CH₃ | 2-aminobenzyl-NH- | 2-aminophenyl-C(O)CH₂- | 1726 | 1 |
| 134 | NHCO(CH₂)₈CH₃ | 4-benzyloxy-2-methoxybenzyl-N(-)- (cyclic) | 2-aminophenyl-C(O)CH₂- | 2074 | 1 |
| 135 | NHCO(CH₂)₈CH₃ | 3-fluorobenzyl-NH- | 2-aminophenyl-C(O)CH₂- | 1729 | 1 |
| 136 | NHCO(CH₂)₈CH₃ | 2-fluorobenzyl-NH- | 2-aminophenyl-C(O)CH₂- | 1729 | 1 |
| 137 | NHCO(CH₂)₈CH₃ | 4-benzyloxybenzyl-N(-)- (cyclic) | 2-aminophenyl-C(O)CH₂- | 2014 | 1 |

TABLE I-continued

Table I provides exemplary compounds of Formula I:

| Cpd # | R | R¹ | R² | Mass Spec | Synth Ex # |
|---|---|---|---|---|---|
| 138 | NHCO(CH$_2$)$_8$CH$_3$ | quinoline-4-CH$_2$NH– | 2-aminophenyl-C(O)CH$_2$– | 1762 | 1 |
| 139 | NHCO(CH$_2$)$_8$CH$_3$ | benzofuran-2-CH$_2$NH– | 2-aminophenyl-C(O)CH$_2$– | 1751 | 1 |
| 140 | NHCO(CH$_2$)$_8$CH$_3$ | (benzofuran-2-CH$_2$)$_2$N– | 2-aminophenyl-C(O)CH$_2$– | 1881 | 1 |
| 141 | NHCO(CH$_2$)$_8$CH$_3$ | (4-(vinyloxy)benzyl)$_2$N– | 2-aminophenyl-C(O)CH$_2$– | 1914 | 1 |
| 142 | NHCO(CH$_2$)$_8$CH$_3$ | 4-(vinyloxy)benzyl-NH– | 2-aminophenyl-C(O)CH$_2$– | 1753 | 1 |

TABLE I-continued

Table I provides exemplary compounds of Formula I:

| Cpd # | R | R¹ | R² | Mass Spec | Synth Ex # |
|---|---|---|---|---|---|
| 143 | NHCO(CH$_2$)$_8$CH$_3$ | 4-phenoxybenzyl-NH- | 2-aminophenyl-C(O)-CH$_2$- | 1803 | 1 |
| 144 | NHCO(CH$_2$)$_8$CH$_3$ | (E)-4-styrylbenzyl-NH- | 2-aminophenyl-C(O)-CH$_2$- | 1813 | 1 |
| 145 | NHCO(CH$_2$)$_8$CH$_3$ | bis[(E)-4-styrylbenzyl]-N- | 2-aminophenyl-C(O)-CH$_2$- | 2006 | 1 |
| 146 | NHCO(CH$_2$)$_8$CH$_3$ | (1H-imidazol-4-yl)methyl-NH- | 2-aminophenyl-C(O)-CH$_2$- | 1701 | 1 |
| 147 | NHCO(CH$_2$)$_8$CH$_3$ | (9H-fluoren-2-yl)methyl-NH- | 2-aminophenyl-C(O)-CH$_2$- | 1799 | 1 |

TABLE I-continued
Table I provides exemplary compounds of Formula I:
| Cpd # | R | R¹ | R² | Mass Spec | Synth Ex # |
|---|---|---|---|---|---|
| 148 | NHCO(CH$_2$)$_8$CH$_3$ | 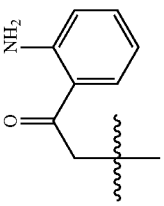 |  | 1978 | 1 |
| 149 | NHCO(CH$_2$)$_8$CH$_3$ | 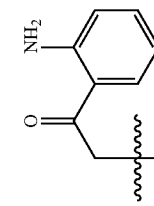 |  | 1834 | 1 |
| 150 | NHCO(CH$_2$)$_8$CH$_3$ | 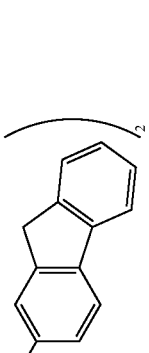 |  | 1777 | 1 |
| 151 | NHCO(CH$_2$)$_8$CH$_3$ | 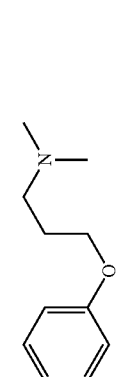 |  | 1847 | 1 |
| 152 | NHCO(CH$_2$)$_8$CH$_3$ |  |  | 2074 | 1 |

TABLE I-continued

Table I provides exemplary compounds of Formula I:

| Cpd # | R | R¹ | R² | Mass Spec | Synth Ex # |
|---|---|---|---|---|---|
| 153 | NHCO(CH$_2$)$_8$CH$_3$ | 4-(n-dodecyloxy)benzyl-NH- | 2-aminophenyl-C(O)-CH- | 1895 | 1 |
| 154 | NHCO(CH$_2$)$_8$CH$_3$ | 4-(n-decyloxy)benzyl-NH- | 2-aminophenyl-C(O)-CH- | 1867 | 1 |
| 155 | NHCO(CH$_2$)$_8$CH$_3$ | 4-(n-octyloxy)benzyl-NH- | 2-aminophenyl-C(O)-CH- | 1839 | 1 |
| 156 | NHCO(CH$_2$)$_8$CH$_3$ | 4-(2-carboxyvinyl)benzyl-NH- | 2-aminophenyl-C(O)-CH- | 1781 | 1 |
| 157 | NHCO(CH$_2$)$_8$CH$_3$ | 4-(dimethylamino)cinnamyl-NH- | 2-aminophenyl-C(O)-CH- | 1780 | 1 |

TABLE I-continued

Table I provides exemplary compounds of Formula I:

| Cpd # | R | R¹ | R² | Mass Spec | Synth Ex # |
|---|---|---|---|---|---|
| 158 | NHCO(CH$_2$)$_8$CH$_3$ | (3-methylbenzothiophen-2-yl)methyl-NH- | 2-aminophenyl ketone | 1781 | 1 |
| 159 | NHCO(CH$_2$)$_8$CH$_3$ | (1-Ph-3,5-dimethylpyrazol-4-yl)methyl-NH- | 2-aminophenyl ketone | 1805 | 1 |
| 160 | NHCO(CH$_2$)$_8$CH$_3$ | bis-(1-Ph-3,5-dimethylpyrazol-4-ylmethyl)-N- | 2-aminophenyl ketone | 1990 | 1 |
| 161 | NHCO(CH$_2$)$_8$CH$_3$ | 4-(carboxymethoxy)benzyl-NH- | 2-aminophenyl ketone | 1785 | 1 |
| 162 | NHCO(CH$_2$)$_8$CH$_3$ | bis-[5-(4-bromophenyl)furan-2-ylmethyl]-N- | 2-aminophenyl ketone | 2092 | 1 |

TABLE I-continued

Table I provides exemplary compounds of Formula I.

| Cpd # | R | R¹ | R² | Mass Spec | Synth Ex # |
|---|---|---|---|---|---|
| 163 | NHCO(CH$_2$)$_8$CH$_3$ | (4-NO$_2$-phenyl-CH=CH-CH$_2$)$_2$N- | 2-aminophenyl-C(O)-CH$_2$- | 1944 | 1 |
| 164 | NHCO(CH$_2$)$_8$CH$_3$ | 3-(benzyloxy)benzyl-NH- | 2-aminophenyl-C(O)-CH$_2$- | 1817 | 1 |
| 165 | NHCO(CH$_2$)$_8$CH$_3$ | (3-(benzyloxy)benzyl)$_2$N- | 2-aminophenyl-C(O)-CH$_2$- | 2014 | 1 |
| 166 | NHCO(CH$_2$)$_8$CH$_3$ | 2,4-difluorobenzyl-NH- | 2-aminophenyl-C(O)-CH$_2$- | 1747 | 1 |
| 167 | NHCO(CH$_2$)$_8$CH$_3$ | (phenyl-CH=CH-CH$_2$)$_2$N- | 2-aminophenyl-C(O)-CH$_2$- | 1853 | 1 |

TABLE I-continued

Table I provides exemplary compounds of Formula I:

| Cpd # | R | R¹ | R² | Mass Spec | Synth Ex # |
|---|---|---|---|---|---|
| 168 | NHCO(CH₂)₈CH₃ | 3-quinolinylmethyl-NH- | 2-aminophenyl-C(O)-CH₂- | 1762 | 1 |
| 169 | NHCO(CH₂)₈CH₃ | N,N-bis(phenethyl)amino- | 2-aminophenyl-C(O)-CH₂- | 1829 | 1 |
| 171 | NHCO(CH₂)₈CH₃ | N,N-bis(4-n-butylbenzyl)amino- | 2-aminophenyl-C(O)-CH₂- | 1914 | 1 |
| 172 | NHCO(CH₂)₈CH₃ | 4-n-butylbenzyl-NH- | 2-aminophenyl-C(O)-CH₂- | 1767 | 1 |
| 173 | NHCO(CH₂)₈CH₃ | 4-cyanobenzyl-NH- | 2-aminophenyl-C(O)-CH₂- | 1736 | 1 |

TABLE I-continued

Table I provides exemplary compounds of Formula I:

| Cpd # | R | R¹ | R² | Mass Spec | Synth Ex # |
|-------|---|----|----|-----------|------------|
| 174 | NHCO(CH$_2$)$_8$CH$_3$ | thiazol-2-ylmethylamino | 2-aminophenyl ketone | 1718 | 1 |
| 175 | NHCO(CH$_2$)$_8$CH$_3$ | 2-benzyl-heptylamino | 2-aminophenyl ketone | 1808 | 1 |
| 176 | NHCO(CH$_2$)$_8$CH$_3$ | bis(1H-imidazol-2-ylmethyl)amino | 2-aminophenyl ketone | 1781 | 1 |
| 177 | NH$_2$ | biphenyl-4-ylmethylamino | 2-aminophenyl ketone | 1632 | 1 |
| 178 | NHCO(CH$_2$)$_8$CH$_3$ | 4-amino-phenylalaninamido | 2-aminophenyl ketone | 1783 | 3 |

TABLE I-continued

Table I provides exemplary compounds of Formula I:

| Cpd # | R | R¹ | R² | Mass Spec | Synth Ex # |
|---|---|---|---|---|---|
| 179 | NHCO(CH$_2$)$_8$CH$_3$ | phenylalanine with para-NHBOC | 2'-aminophenyl ketone | 1884 | 3 |
| 180 | NHCO(CH$_2$)$_8$CH$_3$ | phenylalanine with para-NHBOC, α-NHFmoc | 2'-aminophenyl ketone | 1905 | 3 |
| 181 | NHCONH(CH$_2$)$_{10}$CH$_3$ | 3-(3-oxoindan-1-yl)alanine | 2'-aminophenyl ketone | 1851 | 9 |
| 182 | NHCO(CH$_2$)$_8$CH$_3$ | 3-oxoindan-1-carboxamide | 2'-aminophenyl ketone | 1801 | 3b |
| 183 | NHCO(CH$_2$)$_8$CH$_3$ | bis(3-hydroxybenzyl)amine | 2'-aminophenyl ketone | 1833 | 1 |

TABLE I-continued

Table I provides exemplary compounds of Formula I:

| Cpd # | R | R¹ | R² | Mass Spec | Synth Ex # |
|---|---|---|---|---|---|
| 184 | NHCO(CH$_2$)$_8$CH$_3$ | 3-hydroxybenzyl-NH- | 2-aminophenyl-C(O)-CH$_2$- | 1727 | 1 |
| 185 | NHCO(CH$_2$)$_8$CH$_3$ | 2,3-dihydroxybenzyl-NH- | 2-aminophenyl-C(O)-CH$_2$- | 1743 | 1 |
| 186 | NHCO(CH$_2$)$_8$CH$_3$ | bis(benzo[1,3]dioxol-4-ylmethyl)-N- | 2-aminophenyl-C(O)-CH$_2$- | 1890 | 1 |
| 187 | NHCO(CH$_2$)$_8$CH$_3$ | benzo[1,3]dioxol-4-ylmethyl-NH- | 2-aminophenyl-C(O)-CH$_2$- | 1756 | 1 |
| 189 | NHCO(CH$_2$)$_8$CH$_3$ | glutarimido-N- | 2-aminophenyl-C(O)-CH$_2$- | 1717 | 3b |

TABLE I-continued

Table I provides exemplary compounds of Formula I:

| Cpd # | R | R¹ | R² | Mass Spec | Synth Ex # |
|---|---|---|---|---|---|
| 190 | NHCO(CH₂)₈CH₃ | 2-SO₃H-benzoyl-NH- | 2-NH₂-phenyl-C(O)-CH₂- | 1805 | 2 |
| 192 | NHCO(CH₂)₈CH₃ | tyrosyl-NH- | 2-N₃-phenyl-C(O)-CH₂- | 1811 | 8 |
| 193 | NHCO(CH₂)₈CH₃ | N-Boc-prolyl-NH- | 2-NH₂-phenyl-C(O)-CH₂- | 1836 | 3 |
| 194 | NHCO(CH₂)₈CH₃ | 3-OCF₃-benzyl-NH- | 2-NH₂-phenyl-C(O)-CH₂- | 1795 | 1 |
| 195 | NHCO(CH₂)₈CH₃ | bis(3-OCF₃-benzyl)-N- | 2-NH₂-phenyl-C(O)-CH₂- | 1862 | 1 |

TABLE I-continued

Table I provides exemplary compounds of Formula I:

| Cpd # | R | R¹ | R² | Mass Spec | Synth Ex # |
|---|---|---|---|---|---|
| 196 | NHCO(CH$_2$)$_8$CH$_3$ | 2,4-dichlorobenzylamino | 2-aminophenyl ketone | 1780 | 1 |
| 197 | NHCO(CH$_2$)$_8$CH$_3$ | 4-chlorobenzylamino | 2-aminophenyl ketone | 1746 | 1 |
| 198 | NHCO(CH$_2$)$_8$CH$_3$ | 4-(N(CH$_3$)$_2$)benzylamino | 2-aminophenyl ketone | 1754 | 1 |
| 199 | NHCO(CH$_2$)$_8$CH$_3$ | 2,6-dichlorobenzylamino | 2-aminophenyl ketone | 1780 | 1 |
| 200 | NHCO(CH$_2$)$_8$CH$_3$ | tryptophan-amide | phenyl ketone | 1792 | 8a |

TABLE I-continued

Table I provides exemplary compounds of Formula I:

| Cpd # | R | R¹ | R² | Mass Spec | Synth Ex # |
|---|---|---|---|---|---|
| 201 | NHCO(CH$_2$)$_8$CH$_3$ | (cinnamyl-type, phenyl with nHexyl) | 2-aminophenyl ketone | 1821 | 1 |
| 202 | NHCO(CH$_2$)$_8$CH$_3$ | (4-NMe$_2$ cinnamyl-type) | 2-aminophenyl ketone | | 1 |
| 203 | NHCO(CH$_2$)$_8$CH$_3$ | (indolyl with NH$_2$) | 2-aminophenyl ketone | 1793 | 1 |
| 204 | NHCO(CH$_2$)$_8$CH$_3$ | (indolyl with NHBoc) | 2-aminophenyl ketone | 1893 | |
| 205 | NH(CH$_2$)$_8$CH$_3$ | (tryptophan amide) | 2-aminophenyl ketone | 1779 | 9a |

TABLE I-continued

Table I provides exemplary compounds of Formula I:

| Cpd # | R | R¹ | R² | Mass Spec | Synth Ex # |
|---|---|---|---|---|---|
| 206 | NHCO(CH$_2$)$_8$CO$_2$Me | tryptophan amide | 2-aminophenyl ketone | 1851 | 9 |
| 207 | NHCO(CH$_2$)$_6$CO$_2$Me | tryptophan amide | 2-aminophenyl ketone | 1823 | 9 |
| 208 | NHCO(CH$_2$)$_8$CH$_3$ | (p-tolylsulfonyl)-Ph-ethylamine | 2-aminophenyl ketone | 1878 | 1 |
| 209 | NHCO(CH$_2$)$_8$CH$_3$ | 4-((4-fluorobenzyloxy)-3-nitrobenzyl)amine | 2-aminophenyl ketone | 1880 | 1h |
| 210 | NHCO(CH$_2$)$_8$CH$_3$ | 4-(benzyloxy)-3-chlorobenzylamine | 2-aminophenyl ketone | 1851 | 1 |

TABLE I-continued

Table I provides exemplary compounds of Formula I:

| Cpd # | R | R¹ | R² | Mass Spec | Synth Ex # |
|---|---|---|---|---|---|
| 211 | NHCO(CH$_2$)$_8$CH$_3$ | (3,4-di-OBn-benzyl)NH- | 2-aminophenyl-CO-CH$_2$- | 1924 | 1 |
| 212 | NHCO(CH$_2$)$_8$CH$_3$ | (imidazol-2-yl-methyl)NH- | 2-aminophenyl-CO-CH$_2$- | 1701 | 1d |
| 213 | NHCO(CH$_2$)$_6$NHBoc | Trp(NHBoc)-NH- | 2-aminophenyl-CO-CH$_2$- | 1980 | 9 |
| 214 | NHCO(CH$_2$)$_7$NHBoc | Trp(NHBoc)-NH- | 2-aminophenyl-CO-CH$_2$- | 1994 | 9 |
| 215 | NHCO(CH$_2$)$_{10}$NHBoc | Trp(NHBoc)-NH- | 2-aminophenyl-CO-CH$_2$- | 2036 | 9 |

TABLE I-continued

Table I provides exemplary compounds of Formula I:

| Cpd # | R | R¹ | R² | Mass Spec | Synth Ex # |
|---|---|---|---|---|---|
| 216 | NHCO(CH$_2$)$_{11}$NHBoc | tryptophan-NHBoc amide | 2-aminophenyl ketone | 2050 | 9 |
| 217 | NHCO(CH$_2$)$_{10}$NH$_2$ | tryptophan-NH$_2$ amide | 2-aminophenyl ketone | 1836 | 9 |
| 218 | NHCO(CH$_2$)$_{11}$NH$_2$ | tryptophan-NH$_2$ amide | 2-aminophenyl ketone | 1850 | 9 |
| 219 | NHCO(CH$_2$)$_6$CH(CH$_3$)$_2$ | tryptophan-NH$_2$ amide | 2-aminophenyl ketone | 1807 | 9 |
| 220 | NHCONH(CH$_2$)$_{11}$CH$_3$ | tryptophan-NH$_2$ amide | 2-aminophenyl ketone | 1865 | 9 |

TABLE I-continued

Table I provides exemplary compounds of Formula I:

| Cpd # | R | R¹ | R² | Mass Spec | Synth Ex # |
|---|---|---|---|---|---|
| 221 | NHCO(CH$_2$)$_8$CH$_3$ | (indolyl-ethyl-guanidine group) | (2-aminophenyl ketone group) | 1807 | 6 |
| 222 | NHCO(CH$_2$)$_8$CH$_3$ | (bis-indolyl-alkyl-amine group) | (2-aminophenyl ketone group) | 1935 | 1 |
| 223 | NHCO(CH$_2$)$_8$CH$_3$ | (indolyl-propyl-amine group) | (2-aminophenyl ketone group) | 1779 | 1 |
| 224 | NHCO(CH$_2$)$_8$CH$_3$ | (di-NHBoc lysine-like group) | (2-aminophenyl ketone group) | 1936 | 1 |
| 225 | NHCO(CH$_2$)$_8$CH$_3$ | (di-NH$_2$ lysine-like group) | (2-aminophenyl ketone group) | 1735 | 1 |

TABLE I-continued

Table I provides exemplary compounds of Formula I:

| Cpd # | R | R¹ | R² | Mass Spec | Synth Ex # |
|---|---|---|---|---|---|
| 226 | NHCO(CH$_2$)$_8$CH$_3$ | 4-(benzo[1,3]dioxol-5-ylmethyl)piperazine-1-carbonyl-benzyl-NH– | 2-aminophenyl-C(O)-CH$_2$– | 1958 | 1 |
| 227 | NHCO(CH$_2$)$_8$CH$_3$ | 4-phenylpiperazine-1-carbonyl-benzyl-NH– | 2-aminophenyl-C(O)-CH$_2$– | 1899 | 1 |
| 228 | NHCO(CH$_2$)$_8$CH$_3$ | 4-(4-fluorophenyl)piperazine-1-carbonyl-benzyl-NH– | 2-aminophenyl-C(O)-CH$_2$– | 1917 | 1 |
| 229 | NHCO(CH$_2$)$_8$CH$_3$ | 4-benzylpiperazine-1-carbonyl-benzyl-NH– | 2-aminophenyl-C(O)-CH$_2$– | 1914 | 1 |
| 230 | NHCO(CH$_2$)$_8$CH$_3$ | 4-(3,4-dichlorophenyl)piperazine-1-carbonyl-benzyl-NH– | 2-aminophenyl-C(O)-CH$_2$– | 1969 | 1 |

TABLE I-continued

Table I provides exemplary compounds of Formula I:

| Cpd # | R | R¹ | R² | Mass Spec | Synth Ex # |
|---|---|---|---|---|---|
| 231 | NHCO(CH$_2$)$_8$CH$_3$ | 4-(piperazinylcarbonyl)benzyl-NH– with N-CHPh$_2$ | 2-aminophenyl C(O)CH$_2$– | 1990 | 1 |
| 232 | NHCO(CH$_2$)$_8$CH$_3$ | 4-(piperazinylcarbonyl)benzyl-NH– with N-cinnamyl | 2-aminophenyl C(O)CH$_2$– | 1940 | 1 |
| 233 | NHCO(CH$_2$)$_8$CH$_3$ | 4-(piperazinylcarbonyl)benzyl-NH– with N-(pyrimidin-2-yl) | 2-aminophenyl C(O)CH$_2$– | 1902 | 1 |
| 234 | NHCO(CH$_2$)$_8$CH$_3$ | 4-(piperazinylcarbonyl)benzyl-NH– with N-(pyridin-2-yl) | 2-aminophenyl C(O)CH$_2$– | 1901 | 1 |
| 235 | NHCO(CH$_2$)$_8$CH$_3$ | 4-(piperazinylcarbonyl)benzyl-NH– with N-(4-chlorophenyl) | 2-aminophenyl C(O)CH$_2$– | 1934 | 1 |

TABLE I-continued

Table I provides exemplary compounds of Formula I:

| Cpd # | R | R¹ | R² | Mass Spec | Synth Ex # |
|---|---|---|---|---|---|
| 236 | NHCO(CH$_2$)$_8$CH$_3$ | piperazine N-CH$_2$-(benzo[1,3]dioxol-5-yl), other N-CO-CH=CH-(4-CH$_2$NH-phenyl) | 2-aminophenyl-C(O)-CH$_2$- | 1984 | 1 |
| 237 | NHCO(CH$_2$)$_8$CH$_3$ | piperazine N-phenyl, other N-CO-CH=CH-(4-CH$_2$NH-phenyl) | 2-aminophenyl-C(O)-CH$_2$- | 1926 | 1 |
| 238 | NHCO(CH$_2$)$_8$CH$_3$ | piperazine N-(4-F-phenyl), other N-CO-CH=CH-(4-CH$_2$NH-phenyl) | 2-aminophenyl-C(O)-CH$_2$- | 1944 | 1 |
| 239 | NHCO(CH$_2$)$_8$CH$_3$ | piperazine N-Bn, other N-CO-CH=CH-(4-CH$_2$NH-phenyl) | 2-aminophenyl-C(O)-CH$_2$- | 1940 | 1 |
| 240 | NHCO(CH$_2$)$_8$CH$_3$ | piperazine N-(3,4-diCl-phenyl), other N-CO-CH=CH-(4-CH$_2$NH-phenyl) | 2-aminophenyl-C(O)-CH$_2$- | 1995 | 1 |

TABLE I-continued

Table I provides exemplary compounds of Formula I:

| Cpd # | R | R¹ | R² | Mass Spec | Synth Ex # |
|---|---|---|---|---|---|
| 241 | NHCO(CH$_2$)$_8$CH$_3$ | 4-(diphenylmethyl-piperazinyl-carbonyl-vinyl)-benzyl-amino | 2-aminophenyl ketone | 2016 | 1 |
| 242 | NHCO(CH$_2$)$_8$CH$_3$ | 4-(pyrimidin-2-yl-piperazinyl-carbonyl-vinyl)-benzyl-amino | 2-aminophenyl ketone | 1928 | 1 |
| 243 | NHCO(CH$_2$)$_8$CH$_3$ | 4-(pyridin-2-yl-piperazinyl-carbonyl-vinyl)-benzyl-amino | 2-aminophenyl ketone | 1927 | 1 |
| 244 | NHCO(CH$_2$)$_8$CH$_3$ | 4-(4-chlorophenyl-piperazinyl-carbonyl-vinyl)-benzyl-amino | 2-aminophenyl ketone | 1960 | 1 |
| 245 | NHCO(CH$_2$)$_8$CH$_3$ | 2-amino-decanoyl-amino | 2-aminophenyl ketone | 1790 | 3 |

TABLE I-continued

Table I provides exemplary compounds of Formula I:

| Cpd # | R | R¹ | R² | Mass Spec | Synth Ex # |
|---|---|---|---|---|---|
| 246 | 4-chlorobenzyl-C(O)NH- | Trp-NH- | 2-aminophenyl-C(O)CH₂- | 1807 | 9 |
| 247 | 4-chlorobenzyl-C(O)NH- | Trp-NH- | 2-aminophenyl-C(O)CH₂- | 1841 | 9 |
| 248 | 4-phenoxybenzyl-C(O)NH- | Trp-NH- | 2-aminophenyl-C(O)CH₂- | 1864 | 9 |
| 249 | 4-n-butoxybenzyl-C(O)NH- | Trp-NH- | 2-aminophenyl-C(O)CH₂- | 1843 | 9 |
| 250 | 4'-chlorobiphenyl-4-yl-methyl-C(O)NH- | Trp-NH- | 2-aminophenyl-C(O)CH₂- | 1882 | 9 |

TABLE I-continued

Table I provides exemplary compounds of Formula I:

| Cpd # | R | R¹ | R² | Mass Spec | Synth Ex # |
|---|---|---|---|---|---|
| 251 | 4'-Cl-biphenyl-CH₂-C(O)NH- | H₂N-(CH₂)₄-CH(NH₂)-C(O)NH- | 2-aminophenyl-C(O)-CH₂- | 1823 | 9 |
| 252 | NHCO(CH₂)₈CH₃ | 4-(4-Bn-piperazin-1-yl)-3-nitro-benzyl-NH- | 2-aminophenyl-C(O)-CH₂- | 1931 | 1 |
| 253 | NHCO(CH₂)₈CH₃ | 4-(4-Bn-piperazin-1-yl)-benzyl-NH- | 2-aminophenyl-C(O)-CH₂- | 1886 | 1f |
| 254 | NHCO(CH₂)₇CH₃ | (NBoc)(NHBoc)C= | 2-aminophenyl-C(O)-CH₂- | 1650 | 7 |
| 255 | NHCO(CH₂)₉CH₃ | (NBoc)(NHBoc)C= | 2-aminophenyl-C(O)-CH₂- | 1678 | 7 |

TABLE I-continued

Table I provides exemplary compounds of Formula I:

| Cpd # | R | R¹ | R² | Mass Spec | Synth Ex # |
|---|---|---|---|---|---|
| 256 | NHCO(CH$_2$)$_{10}$CH$_3$ | HN-C(=NBoc)-NHBoc | 2-aminophenyl-C(O)-CH$_2$- | 1692 | 7 |
| 257 | NHCO(CH$_2$)$_{11}$CH$_3$ | HN-C(=NBoc)-NHBoc | 2-aminophenyl-C(O)-CH$_2$- | 1706 | 7 |
| 258 | NHCO(CH$_2$)$_{12}$CH$_3$ | HN-C(=NBoc)-NHBoc | 2-aminophenyl-C(O)-CH$_2$- | 1720 | 7a |
| 259 | NHCO(CH$_2$)$_8$CH$_3$ | HN-C(=NBoc)-N(Boc)(n-Pr) | 2-aminophenyl-C(O)-CH$_2$- | 1706 | 6 |
| 260 | NHCO(CH$_2$)$_9$CH$_3$ | HN-C(=NH)-NH$_2$ | 2-aminophenyl-C(O)-CH$_2$- | 1678 | 7 |

TABLE I-continued

Table I provides exemplary compounds of Formula I:

| Cpd # | R | R¹ | R² | Mass Spec | Synth Ex # |
|---|---|---|---|---|---|
| 261 | NHCO(CH₂)₁₁CH₃ | guanidine group | 2-aminophenyl ketone | 1705 | 7 |
| 262 | NHCO(CH₂)₁₂CH₃ | guanidine group | 2-aminophenyl ketone | 1719 | 7a |
| 263 | | di-Boc guanidine group | 2-aminophenyl ketone | 1738 | 7 |
| 264 | | indanone-amino acid amide | 2-aminophenyl ketone | 1862 | 9 |
| 265 | NHCO(CH₂)₈CH₃ | (2,4-dichlorophenylthio)pyridylmethylamine | 2-aminophenyl ketone | 1890 | 1 |

TABLE I-continued

Table I provides exemplary compounds of Formula I:

| Cpd # | R | R¹ | R² | Mass Spec | Synth Ex # |
|---|---|---|---|---|---|
| 266 | NHCO(CH$_2$)$_8$CH$_3$ | morpholine-nitrobenzyl-NH- | 2-aminophenyl-C(O)-CH$_2$- | 1841 | 1 |
| 267 | NHCO(CH$_2$)$_8$CH$_3$ | phenylsulfonylmethyl-nitrobenzyl-NH- | 2-aminophenyl-C(O)-CH$_2$- | 1910 | 1 |
| 268 | NHCO(CH$_2$)$_8$CH$_3$ | 5-(trifluoromethyl)pyridin-2-yl-piperazinyl-phenyl-CH$_2$-NH- | 2-aminophenyl-C(O)-CH$_2$- | 1940 | 9 |
| 269 | | indolyl-CH$_2$-CH(NHBoc)-C(O)-NH- | 2-aminophenyl-C(O)-CH$_2$- | 1862 | 6 |
| 270 | NHCO(CH$_2$)$_8$CH$_3$ | propyl-guanidinyl- | 2-aminophenyl-C(O)-CH$_2$- | 1706 | 6 |

Additional structure at position 269 R: n-heptyl-triazolyl-CH$_2$-C(O)-NH-

TABLE I-continued

Table I provides exemplary compounds of Formula I:

| Cpd # | R | R¹ | R² | Mass Spec | Synth Ex # |
|---|---|---|---|---|---|
| 271 | NHCO(CH$_2$)$_8$CH$_3$ | bis(2-chloroethyl)amino-phenyl-CH$_2$NH- | 2-aminophenyl-C(O)-CH$_2$- | 1851 | 1 |
| 272 | NHCO(CH$_2$)$_8$CH$_3$ | bis(2-chloroethyl)amino-phenyl-CH$_2$N< (×2) | 2-aminophenyl-C(O)-CH$_2$- | 2081 | 1 |
| 273 | NHCO(CH$_2$)$_8$CH$_3$ | 6-OMe-quinolin-2-yl-CH$_2$N< (OMe ×2) | 2-aminophenyl-C(O)-CH$_2$- | 1964 | 1 |
| 274 | NHCO(CH$_2$)$_8$CH$_3$ | 6-OMe-quinolin-2-yl-CH$_2$NH- | 2-aminophenyl-C(O)-CH$_2$- | 1793 | 1 |
| 275 | NHCO(CH$_2$)$_8$CH$_3$ | 7-Cl-quinolin-2-yl-CH$_2$NH- | 2-aminophenyl-C(O)-CH$_2$- | 1797 | 1 |

TABLE I-continued

Table I provides exemplary compounds of Formula I:

| Cpd # | R | R¹ | R² | Mass Spec | Synth Ex # |
|---|---|---|---|---|---|
| 276 | NHCO(CH₂)₈CH₃ | 6-chloroquinolin-2-ylmethylamino (Cl)₂ | 2-aminophenyl ketone | 1973 | 1 |
| 277 | NHCO(CH₂)₈CH₃ | (4-hydroxyquinolin-2-yl)methylamino | 2-aminophenyl ketone | 1778 | 1 |
| 278 | NHCO(CH₂)₈CH₃ | (6-fluoroquinolin-2-yl)methylamino | 2-aminophenyl ketone | 1780 | 1 |
| 279 | NHCO(CH₂)₈CH₃ | 6-fluoroquinolin-2-ylmethylamino (F)₂ | 2-aminophenyl ketone | 1940 | 1 |
| 280 | NHCO(CH₂)₈CH₃ | (6-chloroquinolin-2-yl)methylamino | 2-aminophenyl ketone | 1797 | 1 |

TABLE I-continued

Table I provides exemplary compounds of Formula I:

| Cpd # | R | R¹ | R² | Mass Spec | Synth Ex # |
|---|---|---|---|---|---|
| 281 | NHCO(CH$_2$)$_8$CH$_3$ | quinoline-2-yl-CH$_2$, 6-Cl$_2$ substituted, N-linked | 2-aminophenyl C(O)CH$_2$– | 1974 | 1 |
| 282 | NHCO(CH$_2$)$_8$CH$_3$ | 6-NO$_2$-quinolin-2-yl-CH$_2$-NH– | 2-aminophenyl C(O)CH$_2$– | 1807 | 1a |
| 283 | NHCO(CH$_2$)$_8$CH$_3$ | 8-Cl-quinolin-2-yl-CH$_2$-NH– | 2-aminophenyl C(O)CH$_2$– | 1797 | 1 |
| 284 | NHCO(CH$_2$)$_8$CH$_3$ | 8-Cl-quinoline-2-yl-CH$_2$, 2 substituted, N-linked | 2-aminophenyl C(O)CH$_2$– | 1973 | 1 |
| 285 | NHCO(CH$_2$)$_8$CH$_3$ | 4-Cl-quinolin-2-yl-CH$_2$-NH– | 2-aminophenyl C(O)CH$_2$– | 1796 | 1b |

TABLE I-continued

Table I provides exemplary compounds of Formula I:

| Cpd # | R | R¹ | R² | Mass Spec | Synth Ex # |
|---|---|---|---|---|---|
| 286 | NHCO(CH$_2$)$_8$CH$_3$ | quinoline-8-yl O-C(O)NH-phenyl, 2-CH$_2$NH- | 2-aminophenyl C(O)CH$_2$- | 1898 | 1 |
| 287 | NHCO(CH$_2$)$_8$CH$_3$ | 4-CONH$_2$ quinoline, 2-CH$_2$NH- | 2-aminophenyl C(O)CH$_2$- | 1806 | 1 |
| 288 | NHCO(CH$_2$)$_8$CH$_3$ | 6-Cl, 4-OH quinoline, 2-CH$_2$NH- | 2-aminophenyl C(O)CH$_2$- | 1812 | 1 |
| 289 | NHCO(CH$_2$)$_8$CH$_3$ | 6-N(CH$_3$)$_2$ quinoline, 2-CH$_2$NH- | 2-aminophenyl C(O)CH$_2$- | 1806 | 1 |
| 290 | NHCO(CH$_2$)$_8$CH$_3$ | 8-NO$_2$ quinoline, 2-CH$_2$NH- | 2-aminophenyl C(O)CH$_2$- | 1806 | 1 |

TABLE I-continued

Table I provides exemplary compounds of Formula I:

| Cpd # | R | R¹ | R² | Mass Spec | Synth Ex # |
|---|---|---|---|---|---|
| 291 | NHCO(CH₂)₈CH₃ | 5,7-dichloro-8-hydroxyquinolin-2-ylmethylamino | 2-aminophenacyl | 1848 | 1 |
| 292 | | 4'-chlorobiphenyl-4-ylacetamido | 2-aminophenacyl | 1738 | 7 |
| 293 | NHCO(CH₂)₁₀CH₃ | guanidino | 2-aminophenacyl | 1692 | 7 |
| 294 | NHCO(CH₂)₇CH₃ | guanidino | 2-aminophenacyl | 1650 | 7 |
| 295 | NHCO(CH₂)₁₁CH₃ | N²,N⁶-di-Boc-lysyl amide | 2-aminophenacyl | 1991 | 10b |

TABLE I-continued

Table I provides exemplary compounds of Formula I:

| Cpd # | R | R¹ | R² | Mass Spec | Synth Ex # |
|---|---|---|---|---|---|
| 296 | NHCO(CH$_2$)$_{10}$CH$_3$ | lysine-NHBoc,NHBoc amide | 2-aminophenyl ketone | 1978 | 10b |
| 297 | NHCO(CH$_2$)$_9$CH$_3$ | lysine-NHBoc,NHBoc amide | 2-aminophenyl ketone | 1964 | 10b |
| 298 | NHCONH(CH$_2$)$_7$CH$_3$ | lysine-NHBoc,NHBoc amide | 2-aminophenyl ketone | 1950 | 10b |
| 299 | NHCONH(CH$_2$)$_{10}$CH$_3$ | lysine-NHBoc,NHBoc amide | 2-aminophenyl ketone | 1992 | 10b |
| 300 | NHCONH(CH$_2$)$_{11}$CH$_3$ | lysine-NHBoc,NHBoc amide | 2-aminophenyl ketone | 2006 | 10b |

TABLE I-continued

Table I provides exemplary compounds of Formula I:

| Cpd # | R | R¹ | R² | Mass Spec | Synth Ex # |
|---|---|---|---|---|---|
| 301 | NHCO(CH₂)₁₁CH₃ | lysinyl amide | 2-aminophenyl ketone | 1791 | 10b |
| 302 | NHCO(CH₂)₁₀CH₃ | lysinyl amide | 2-aminophenyl ketone | 1778 | 10b |
| 303 | NHCO(CH₂)₉CH₃ | lysinyl amide | 2-aminophenyl ketone | 1764 | 10b |
| 304 | NHCONH(CH₂)₇CH₃ | lysinyl amide | 2-aminophenyl ketone | 1750 | 10b |
| 305 | NHCONH(CH₂)₁₀CH₃ | lysinyl amide | 2-aminophenyl ketone | 1792 | 10b |

TABLE I-continued
Table I provides exemplary compounds of Formula I:
| Cpd # | R | R¹ | R² | Mass Spec | Synth Ex # |
|---|---|---|---|---|---|
| 306 | NHCONH(CH$_2$)$_{11}$CH$_3$ | 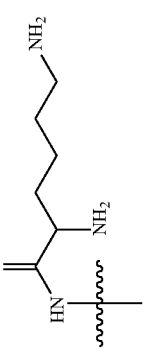 | 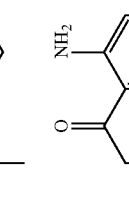 | 1806 | 10b |
| 307 | NHCO(CH$_2$)$_9$CH$_3$ | 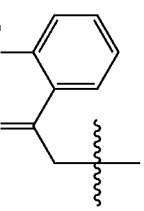 |  | 1922 | 10b |
| 308 | NHCO(CH$_2$)$_{10}$CH$_3$ | 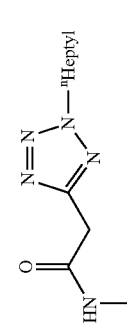 | 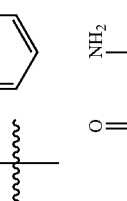 | 1936 | 10b |
| 309 | NHCO(CH$_2$)$_{10}$CH$_3$ | 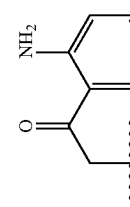 | 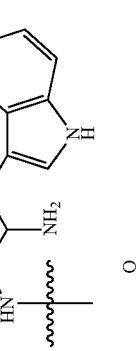 | 1836 | 10b |
| 310 | NHCO(CH$_2$)$_9$CH$_3$ | 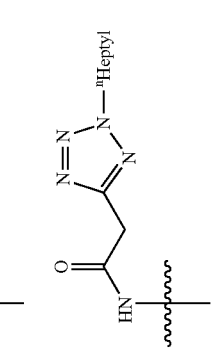 | 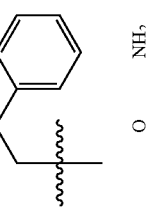 | 1821 | 10b |

TABLE I-continued

Table I provides exemplary compounds of Formula I:

| Cpd # | R | R¹ | R² | Mass Spec | Synth Ex # |
|---|---|---|---|---|---|
| 311 | NHCONH(CH$_2$)$_7$CH$_3$ | tryptophan-like (indole-CH$_2$-CH(NH$_2$)-C(O)-NH-) | 2-aminophenyl-C(O)-CH$_2$- | 1808 | 10b |
| 312 | NHCONH(CH$_2$)$_7$CH$_3$ | 2-amino-6-fluorobenzamide | 2-aminophenyl-C(O)-CH$_2$- | 1759 | 10b |
| 313 | NHCONH(CH$_2$)$_7$CH$_3$ | guanidino (HN=C(NH$_2$)-NH-) | 2-aminophenyl-C(O)-CH$_2$- | 1665 | 7 |
| 314 | NHCONH(CH$_2$)$_{10}$CH$_3$ | N,N'-di-Boc-guanidino | 2-aminophenyl-C(O)-CH$_2$- | 1707 | 7 |
| 315 | NHCONH(CH$_2$)$_7$CH$_3$ | (5-methoxyindol-3-yl)methylamino | 2-aminophenyl-C(O)-CH$_2$- | 1779 | 10a |

TABLE I-continued

Table I provides exemplary compounds of Formula I:

| Cpd # | R | R$^1$ | R$^2$ | Mass Spec | Synth Ex # |
|---|---|---|---|---|---|
| 316 | NHCONH(CH$_2$)$_7$CH$_3$ | tryptophan-NHBoc amide | 2-aminophenyl ketone | 1700 | 10a |
| 317 | NHCONH(CH$_2$)$_7$CH$_3$ | 6-nitroquinolin-2-ylmethyl | 2-aminophenyl ketone | 1806 | 10a |
| 318 | NHCO(CH$_2$)$_9$CH$_3$ | 5-methoxyindol-3-ylmethyl | 2-aminophenyl ketone | 1793 | 10a |
| 319 | NHCO(CH$_2$)$_9$CH$_3$ | tryptophan-NHBoc amide | 2-aminophenyl ketone | 1714 | 10a |
| 320 | NHCO(CH$_2$)$_{11}$CH$_3$ | 5-methoxyindol-3-ylmethyl | 2-aminophenyl ketone | 1821 | 10a |

TABLE I-continued

Table I provides exemplary compounds of Formula I:

| Cpd # | R | R¹ | R² | Mass Spec | Synth Ex # |
|---|---|---|---|---|---|
| 321 | NHCO(CH$_2$)$_{11}$CH$_3$ | 6-nitroquinolin-2-ylmethylamino | 2-aminophenyl ketone | 1848 | 10a |
| 322 | NHCO(CH$_2$)$_{11}$CH$_3$ | N-Boc-tryptophan amide | 2-aminophenyl ketone | 1742 | 10a |
| 323 | NHCO(CH$_2$)$_8$CH$_3$ | 3-fluoro-4-(3-trifluoromethylbenzyloxy)benzylamino | 2-aminophenyl ketone | 1943 | 1 |
| 324 | NHCO(CH$_2$)$_8$CH$_3$ | 3-fluoro-4-(3,5-bis(trifluoromethyl)benzyloxy)benzylamino | 2-aminophenyl ketone | 2010 | 1 |
| 325 | NHCO(CH$_2$)$_8$CH$_3$ | 3-fluoro-4-(4-fluorobenzyloxy)benzylamino | 2-aminophenyl ketone | 1893 | 1 |

TABLE I-continued
Table I provides exemplary compounds of Formula I:
| Cpd # | R | R¹ | R² | Mass Spec | Synth Ex # |
|---|---|---|---|---|---|
| 326 | NHCO(CH$_2$)$_8$CH$_3$ | 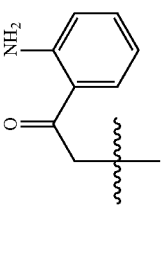 | 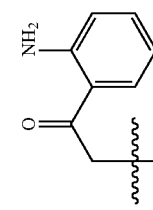 | 956 | 1 |
| 327 | NHCO(CH$_2$)$_8$CH$_3$ | 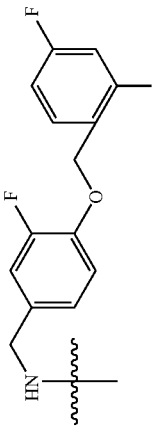 | 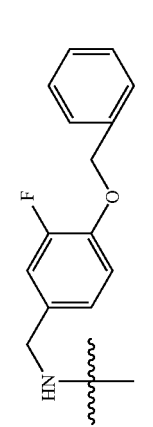 | 1875 | 1 |
| 328 | NHCO(CH$_2$)$_8$CH$_3$ |  |  | 1919 | 1 |
| 329 | NHCO(CH$_2$)$_8$CH$_3$ | 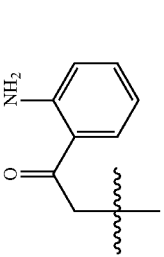 | 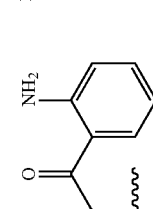 | 1987 | 1 |
| 330 | NHCO(CH$_2$)$_8$CH$_3$ | 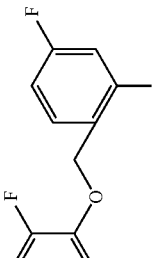 |  | 1909 | 1 |

TABLE I-continued

Table I provides exemplary compounds of Formula I:

| Cpd # | R | R¹ | R² | Mass Spec | Synth Ex # |
|---|---|---|---|---|---|
| 331 | NHCO(CH$_2$)$_8$CH$_3$ | 2-nitro-4-[(2,4-bis(trifluoromethyl)benzyloxy)]benzylamino | 2'-aminophenyl ketone | 1998 | 1 |
| 332 | NHCO(CH$_2$)$_{10}$CH$_3$ | (5-methoxy-1H-indol-3-yl)methylamino | 2'-aminophenyl ketone | 1807 | 10a |
| 333 | NHCO(CH$_2$)$_{10}$CH$_3$ | (6-nitroquinolin-2-yl)methylamino | 2'-aminophenyl ketone | 1834 | 10a |
| 334 | NHCO(CH$_2$)$_{10}$CH$_3$ | N-Boc-tryptophanamide | 2'-aminophenyl ketone | 1728 | 10a |
| 335 | NHCONH(CH$_2$)$_{11}$CH$_3$ | N-Boc-tryptophanamide | 2'-aminophenyl ketone | 1757 | 10a |

TABLE I-continued

Table I provides exemplary compounds of Formula I:

| Cpd # | R | R¹ | R² | Mass Spec | Synth Ex # |
|---|---|---|---|---|---|
| 336 | NHCONH(CH$_2$)$_{11}$CH$_3$ | 6-nitroquinolin-2-ylmethylamino | 2-aminophenyl ketone | 1864 | 10a |
| 337 | NHCONH(CH$_2$)$_{11}$CH$_3$ | 5-methoxy-1H-indol-3-ylmethylamino | 2-aminophenyl ketone | 1836 | 10a |
| 338 | NHCO(CH$_2$)$_{12}$CH$_3$ | 2-n-heptyl-2H-tetrazol-5-yl acetamide | 2-aminophenyl ketone | 1963 | 10b |
| 339 | NHCO(CH$_2$)$_{12}$CH$_3$ | tryptophan amide | 2-aminophenyl ketone | 1863 | 10b |
| 340 | NHCO(CH$_2$)$_{12}$CH$_3$ | N,N'-di-Boc-lysine amide | 2-aminophenyl ketone | 2006 | 10b |

TABLE I-continued

Table I provides exemplary compounds of Formula I:

| Cpd # | R | R¹ | R² | Mass Spec | Synth Ex # |
|---|---|---|---|---|---|
| 341 | NHCO(CH$_2$)$_{12}$CH$_3$ | lysinyl (H$_2$N-(CH$_2$)$_4$-CH(NH$_2$)-C(O)-NH-) | 2-aminophenyl ketone -C(O)-CH$_2$- linker | 1805 | 10b |
| 342 | NHCO(CH$_2$)$_9$CH$_3$ | 2-amino-6-fluorobenzamide | 2-aminophenyl ketone -C(O)-CH$_2$- linker | 1773 | 10b |
| 343 | NHCO(CH$_2$)$_{10}$CH$_3$ | 2-amino-6-fluorobenzamide | 2-aminophenyl ketone -C(O)-CH$_2$- linker | 1786 | 10b |
| 344 | NHCO(CH$_2$)$_{12}$CH$_3$ | 2-amino-6-fluorobenzamide | 2-aminophenyl ketone -C(O)-CH$_2$- linker | 1814 | 10b |
| 345 | NHCO(CH$_2$)$_{12}$CH$_3$ | N-Boc-tryptophanyl amide | 2-aminophenyl ketone -C(O)-CH$_2$- linker | 1756 | 10a |

TABLE I-continued

Table I provides exemplary compounds of Formula I:

| Cpd # | R | R¹ | R² | Mass Spec | Synth Ex # |
|---|---|---|---|---|---|
| 346 | NHCO(CH₂)₁₂CH₃ | 5-methoxy-indol-3-ylmethyl-NH- | 2-aminophenyl-C(O)CH₂- | 1836 | 10a |
| 347 | NHCO(CH₂)₇CH₃ | 5-methoxy-indol-3-ylmethyl-NH- | 2-aminophenyl-C(O)CH₂- | 1765 | 10a |
| 348 | NHCO(CH₂)₇CH₃ | N-Boc-tryptophanyl-NH- | 2-aminophenyl-C(O)CH₂- | 1686 | 10a |
| 349 | NHCO(CH₂)₇CH₃ | 6-nitro-quinolin-2-ylmethyl-NH- | 2-aminophenyl-C(O)CH₂- | 1792 | 10a |
| 350 | 4'-chlorobiphenyl-4-ylacetamido | 2-amino-6-fluorobenzamido | 2-aminophenyl-C(O)CH₂- | 1832 | 10b |

TABLE I-continued

Table I provides exemplary compounds of Formula I:

| Cpd # | R | R¹ | R² | Mass Spec | Synth Ex # |
|---|---|---|---|---|---|
| 351 | NHCO(CH$_2$)$_{11}$CH$_3$ | 2-amino-6-fluorobenzamide linker | 2'-aminophenyl ketone linker | 1801 | 10b |
| 352 | NHCONH(CH$_2$)$_{10}$CH$_3$ | 2-amino-6-fluorobenzamide linker | 2'-aminophenyl ketone linker | 1801 | 10b |
| 355 | NHCONH(CH$_2$)$_{10}$CH$_3$ | N-Boc-tryptophan amide linker | 2'-aminophenyl ketone linker | 1743 | 10a |
| 356 | NHCONH(CH$_2$)$_{10}$CH$_3$ | 5-methoxyindole-3-methylamine linker | 2'-aminophenyl ketone linker | 1822 | 10a |
| 358 | NHCO(CH$_2$)$_8$CH$_3$ | 4-(N-phenethylsulfamoyl)benzylamine linker | 2'-aminophenyl ketone linker | 1893 | 1 |

TABLE I-continued

Table I provides exemplary compounds of Formula I:

| Cpd # | R | R¹ | R² | Mass Spec | Synth Ex # |
|---|---|---|---|---|---|
| 359 | NHCO(CH$_2$)$_8$CH$_3$ | 4-(phenylaminosulfonyl)benzyl-NH- | 2-aminophenyl-C(O)-CH< | 948 | 1 |
| 360 | NHCO(CH$_2$)$_8$CH$_3$ | 4-(4-methylpiperazin-1-ylsulfonyl)benzyl-NH- | 2-aminophenyl-C(O)-CH< | 938 | 1 |
| 361 | NHCO(CH$_2$)$_8$CH$_3$ | 4-(4-acetylpiperazin-1-ylsulfonyl)benzyl-NH- | 2-aminophenyl-C(O)-CH< | 952 | 1 |
| 362 | NHCO(CH$_2$)$_8$CH$_3$ | 4-(4-phenylpiperazin-1-ylsulfonyl)benzyl-NH- | 2-aminophenyl-C(O)-CH< | 969 | 1 |
| 363 | NHCO(CH$_2$)$_8$CH$_3$ | 4-(4-(pyridin-2-yl)piperazin-1-ylsulfonyl)benzyl-NH- | 2-aminophenyl-C(O)-CH< | 970 | 1 |

TABLE I-continued

Table I provides exemplary compounds of Formula I:

| Cpd # | R | R¹ | R² | Mass Spec | Synth Ex # |
|---|---|---|---|---|---|
| 364 | NHCO(CH$_2$)$_8$CH$_3$ | (4-sulfonyl-benzyl-NH)-piperazine-N-(2-methylphenyl) | -CH$_2$-C(O)-(2-aminophenyl) | 976 | 1 |
| 365 | NHCO(CH$_2$)$_8$CH$_3$ | (4-sulfonyl-benzyl-NH)-piperidine-NBn | -CH$_2$-C(O)-(2-aminophenyl) | 976 | 1 |
| 366 | NHCO(CH$_2$)$_8$CH$_3$ | (4-methoxyphenyl)-piperazine-sulfonyl-phenyl-CH$_2$-NH | -CH$_2$-C(O)-(2-aminophenyl) | 984 | 1 |
| 367 | NHCO(CH$_2$)$_8$CH$_3$ | (4-sulfonyl-benzyl-NH)-piperazine-N-(2-methoxyphenyl) | -CH$_2$-C(O)-(2-aminophenyl) | 984 | 1 |
| 368 | NHCO(CH$_2$)$_8$CH$_3$ | (4-sulfonyl-benzyl-NH)-piperazine-N-(2-chlorophenyl) | -CH$_2$-C(O)-(2-aminophenyl) | 986 | 1 |

TABLE I-continued

Table I provides exemplary compounds of Formula I:

| Cpd # | R | R¹ | R² | Mass Spec | Synth Ex # |
|---|---|---|---|---|---|
| 369 | NHCO(CH$_2$)$_8$CH$_3$ | 4-(pyrrolidin-1-ylcarbonylmethyl)piperazin-1-ylsulfonylbenzyl-NH- | 2-aminophenyl-C(O)-CH$_2$- | 987 | 1 |
| 370 | NHCO(CH$_2$)$_8$CH$_3$ | 4-(4-fluorophenyl)piperazin-1-ylsulfonylbenzyl-NH- | 2-aminophenyl-C(O)-CH$_2$- | 978 | 1 |
| 371 | NHCO(CH$_2$)$_8$CH$_3$ | 4-(benzo[1,3]dioxol-5-ylmethyl)piperazin-1-ylsulfonylbenzyl-NH- | 2-aminophenyl-C(O)-CH$_2$- | 998 | 1 |
| 372 | NHCO(CH$_2$)$_8$CH$_3$ | 4-(3-trifluoromethylbenzyl)piperazin-1-ylsulfonylbenzyl-NH- | 2-aminophenyl-C(O)-CH$_2$- | 1003 | 1 |
| 373 | NHCO(CH$_2$)$_8$CH$_3$ | 4-(3,4-dichlorophenyl)piperazin-1-ylsulfonylbenzyl-NH- | 2-aminophenyl-C(O)-CH$_2$- | 1003 | 1 |

TABLE I-continued

Table I provides exemplary compounds of Formula I:

| Cpd # | R | R¹ | R² | Mass Spec | Synth Ex # |
|---|---|---|---|---|---|
| 374 | NHCO(CH$_2$)$_8$CH$_3$ | 4-(pyrimidin-2-yl)piperazin-1-ylsulfonyl-phenylmethylamino | 2-aminophenyl ketone | 970 | 1 |
| 375 | NHCO(CH$_2$)$_8$CH$_3$ | 2-fluorobenzylaminosulfonyl-phenylmethylamino | 2-aminophenyl ketone | 950 | 1 |
| 376 | NHCO(CH$_2$)$_8$CH$_3$ | 3-fluorobenzylaminosulfonyl-phenylmethylamino | 2-aminophenyl ketone | 950 | 1 |
| 377 | NHCO(CH$_2$)$_8$CH$_3$ | 4-fluorobenzylaminosulfonyl-phenylmethylamino | 2-aminophenyl ketone | 950 | 1 |
| 378 | NHCO(CH$_2$)$_8$CH$_3$ | 3-phenylpropylaminosulfonyl-phenylmethylamino | 2-aminophenyl ketone | 955 | 1 |

TABLE I-continued

Table I provides exemplary compounds of Formula I:

| Cpd # | R | R¹ | R² | Mass Spec | Synth Ex # |
|---|---|---|---|---|---|
| 379 | NHCO(CH$_2$)$_8$CH$_3$ | 3-chlorobenzyl-NH-SO$_2$-C$_6$H$_4$-CH$_2$-NH- | 2-aminophenyl-C(O)-CH$_2$- | 957 | 1 |
| 380 | NHCO(CH$_2$)$_8$CH$_3$ | 4-chlorobenzyl-NH-SO$_2$-C$_6$H$_4$-CH$_2$-NH- | 2-aminophenyl-C(O)-CH$_2$- | 958 | 1 |
| 381 | NHCO(CH$_2$)$_8$CH$_3$ | 2,4-difluorobenzyl-NH-SO$_2$-C$_6$H$_4$-CH$_2$-NH- | 2-aminophenyl-C(O)-CH$_2$- | 959 | 1 |
| 382 | NHCO(CH$_2$)$_8$CH$_3$ | 3,4-difluorobenzyl-NH-SO$_2$-C$_6$H$_4$-CH$_2$-NH- | 2-aminophenyl-C(O)-CH$_2$- | 959 | 1 |
| 383 | NHCO(CH$_2$)$_8$CH$_3$ | 2-chlorophenethyl-NH-SO$_2$-C$_6$H$_4$-CH$_2$-NH- | 2-aminophenyl-C(O)-CH$_2$- | 965 | 1 |

TABLE I-continued
Table I provides exemplary compounds of Formula I:
| Cpd # | R | R¹ | R² | Mass Spec | Synth Ex # |
|---|---|---|---|---|---|
| 384 | NHCO(CH$_2$)$_8$CH$_3$ | 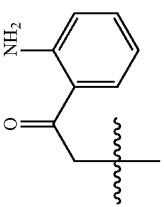 |  | 965 | 1 |
| 385 | NHCO(CH$_2$)$_8$CH$_3$ | 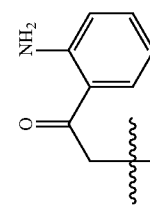 |  | 975 | 1 |
| 386 | NHCO(CH$_2$)$_8$CH$_3$ | 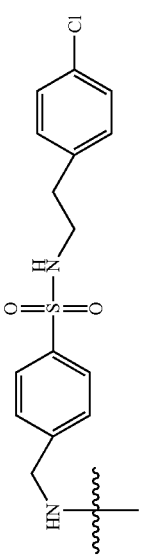 |  | 975 | 1 |
| 387 | NHCO(CH$_2$)$_8$CH$_3$ | 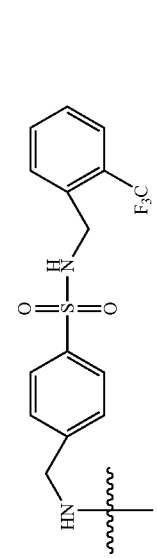 | 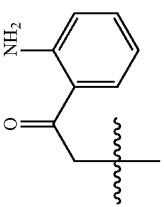 | 975 | 1 |
| 388 | NHCO(CH$_2$)$_8$CH$_3$ |  | 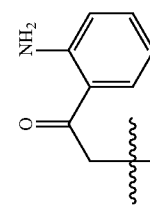 | 957 | 1 |

TABLE I-continued

Table I provides exemplary compounds of Formula I:

| Cpd # | R | R¹ | R² | Mass Spec | Synth Ex # |
|---|---|---|---|---|---|
| 389 | NHCO(CH$_2$)$_8$CH$_3$ | 3,4-dichlorobenzyl-NH-SO$_2$-C$_6$H$_4$-CH$_2$-NH- | 2-aminophenyl-CO-CH$_2$- | 976 | 1 |
| 390 | NHCO(CH$_2$)$_8$CH$_3$ | 3,5-dichlorobenzyl-NH-SO$_2$-C$_6$H$_4$-CH$_2$-NH- | 2-aminophenyl-CO-CH$_2$- | 976 | 1 |
| 391 | NHCO(CH$_2$)$_8$CH$_3$ | 2,4-dichlorobenzyl-NH-SO$_2$-C$_6$H$_4$-CH$_2$-NH- | 2-aminophenyl-CO-CH$_2$- | 976 | 1 |
| 392 | NHCO(CH$_2$)$_8$CH$_3$ | 3-OCF$_3$-benzyl-NH-SO$_2$-C$_6$H$_4$-CH$_2$-NH- | 2-aminophenyl-CO-CH$_2$- | 983 | 1 |
| 393 | NHCO(CH$_2$)$_8$CH$_3$ | 4-OCF$_3$-benzyl-NH-SO$_2$-C$_6$H$_4$-CH$_2$-NH- | 2-aminophenyl-CO-CH$_2$- | 983 | 1 |

TABLE I-continued
Table I provides exemplary compounds of Formula I:
| Cpd # | R | R¹ | R² | Mass Spec | Synth Ex # |
|---|---|---|---|---|---|
| 394 | NHCO(CH$_2$)$_8$CH$_3$ |  | 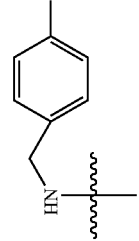 | 948 | 1 |
| 395 | NHCO(CH$_2$)$_8$CH$_3$ |  | 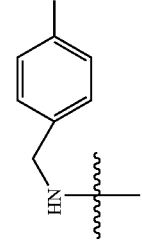 | 941 | 1 |
| 398 | NHCO(CH$_2$)$_8$CH$_3$ | 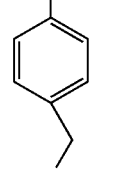 |  | | 1 |
| 399 | NHCO(CH$_2$)$_8$CH$_3$ | 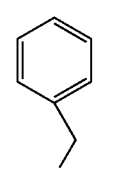 |  | | 1 |

TABLE I-continued

Table I provides exemplary compounds of Formula I:

| Cpd # | R | R¹ | R² | Mass Spec | Synth Ex # |
|---|---|---|---|---|---|
| 400 | NHCO(CH$_2$)$_8$CH$_3$ | quinoline-piperazine-CH$_2$NH- | 2-aminophenyl-C(O)-CH$_2$- | | 1 |
| 401 | NHCO(CH$_2$)$_8$CH$_3$ | quinoline-NHSO$_2$(4-methylphenyl), 2-CH$_2$NH- | 2-aminophenyl-C(O)-CH$_2$- | | 1 |
| 402 | NHCO(CH$_2$)$_8$CH$_3$ | quinoline-S-(5-amino-1,3,4-thiadiazol-2-yl), 2-CH$_2$NH- | 2-aminophenyl-C(O)-CH$_2$- | | 1 |
| 403 | NHCO(CH$_2$)$_8$CH$_3$ | quinoline-4-SO$_2$CH$_3$, 2-CH$_2$NH- | 2-aminophenyl-C(O)-CH$_2$- | | 1 |

TABLE I-continued

Table I provides exemplary compounds of Formula I:

| Cpd # | R | R¹ | R² | Mass Spec | Synth Ex # |
|---|---|---|---|---|---|
| 404 | NHCO(CH$_2$)$_8$CH$_3$ | 7-CF$_3$, 4-OH quinolin-2-ylmethylamino | 2-aminophenyl ketone | | 1 |
| 405 | NHCO(CH$_2$)$_8$CH$_3$ | 4-(methylsulfonyl)quinolin-2-ylmethylamino | 2-aminophenyl ketone | | 1 |
| 406 | NHCO(CH$_2$)$_8$CH$_3$ | isoquinolin-8-ylmethylamino | 2-aminophenyl ketone | | 1 |
| 407 | NHCO(CH$_2$)$_8$CH$_3$ | 6-chloro-4-(5-chlorobenzothiazol-2-yloxy)quinolin-2-ylmethylamino | 2-aminophenyl ketone | | 1 |

TABLE I-continued

Table I provides exemplary compounds of Formula I:

| Cpd # | R | R$^1$ | R$^2$ | Mass Spec | Synth Ex # |
|---|---|---|---|---|---|
| 408 | NHCO(CH$_2$)$_8$CH$_3$ | 6-chloro-2-[(aminomethyl)]-4-[(3-nitropyridin-2-yl)oxy]quinoline linker | 2-aminophenyl ketone linker | | 1 |
| 409 | NHCO(CH$_2$)$_8$CH$_3$ | quinolin-6-ylmethylamino linker | 2-aminophenyl ketone linker | | 1 |
| 410 | NHCO(CH$_2$)$_8$CH$_3$ | quinolin-7-ylmethyl-NH linker | 2-aminophenyl ketone linker | | 1 |

Preferred compounds of the present invention are compounds 45, 54, 76, 81, 85, 102, 209, 212, 253, 260, 262, 282, 285, 319, 322, 333, 334, 335, 336, 344 and 355.

According to a preferred embodiment, the present invention provides one or more crystalline forms of compounds of formula (I) and salts thereof.

Lipopeptide Intermediates

The present invention also provides compounds that are particularly useful as intermediates for the preparation of the compounds of Formula I. These compounds may also have antibacterial properties, as discussed above. In one aspect of the invention, compounds of Formula II are provided:

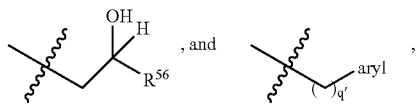

wherein $R^{56}$ is an optionally substituted straight-chain $C_8$-$C_{14}$ alkyl group and wherein q' is 0-3.

In another aspect of the invention, compounds of Formula III are provided as useful intermediates for the preparation of compounds of Formula I and/or as antibacterial compounds:

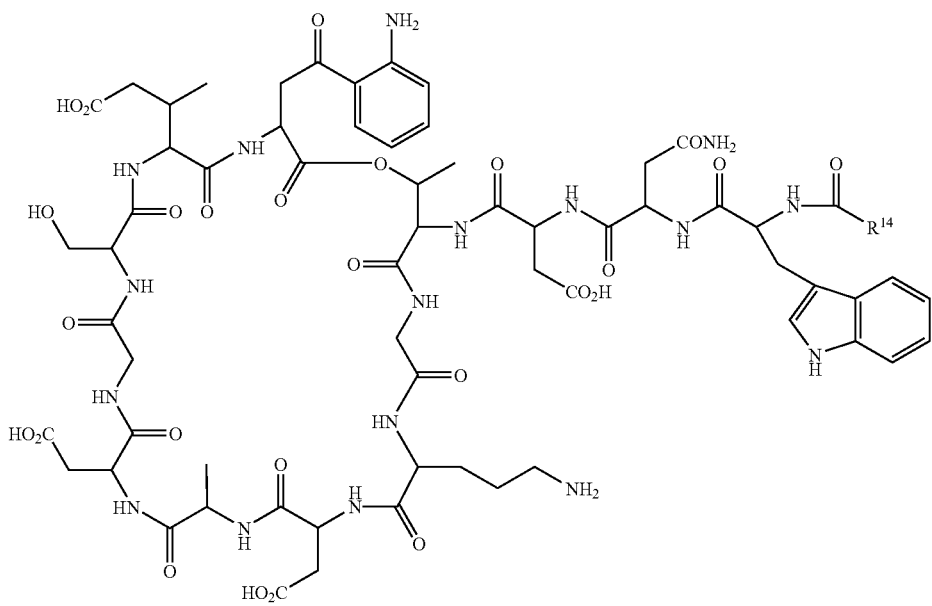

(II)

wherein $R^{14}$ is selected from the group consisting of

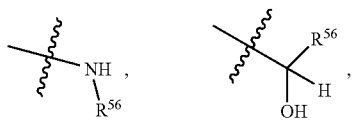

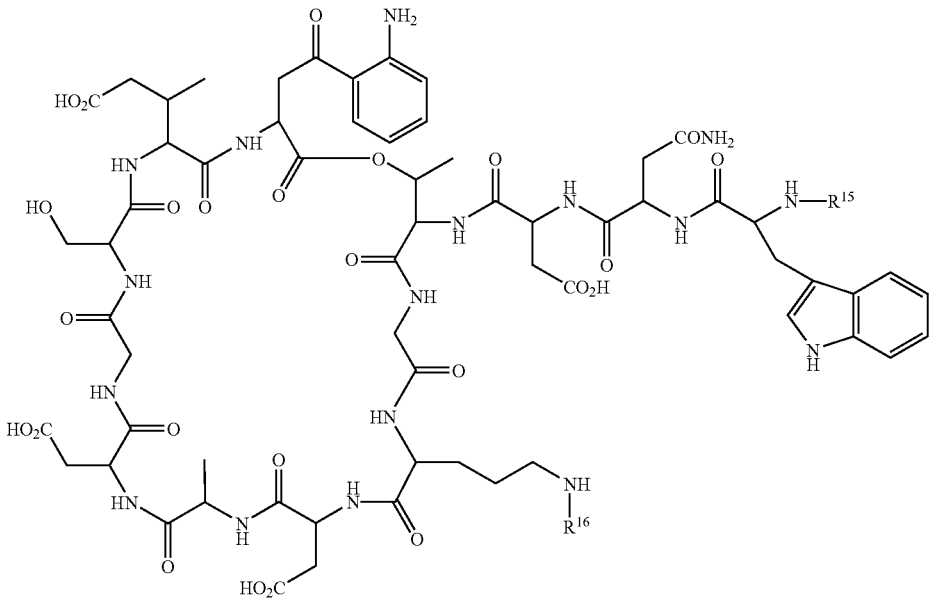

(III)

wherein $R^{15}$ is selected from hydrido and a carbamate amino protecting group, preferably a tert-butoxycarbonyl group; wherein $R^{16}$ is selected from the group consisting of

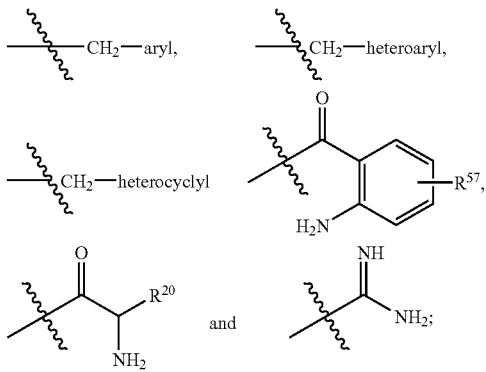

wherein $R^{57}$ is a halo or halo substituted alkyl group, preferably a fluoro or trifluoromethyl group; wherein, $R^{20}$ is an amino acid side chain, preferably a lysine or tryptophan side chain.

Compounds 2, 10, 25, 38, 45, 50, 54, 76, 78, 79, 80, 81, 82, 84, 85, 103, 105, 107, 111, 115, 130, 138, 139, 146, 147, 150, 158, 164, 168, 174, 210, 212, 227, 253, 274, 275, 280, 283, 285, 317, 372 and 386 are useful both as antibacterial compounds and as intermediates in the synthesis of compounds of this invention.

Lipopeptide Compound Pharmaceutical Compositions And Methods Of Use Thereof

Another object of the instant invention is to provide lipopeptide compounds or salts thereof, as well as pharmaceutical compositions or formulations comprising lipopeptide compounds or its salts.

Lipopeptide compounds, or pharmaceutically acceptable salts thereof, can be formulated for oral, intravenous, intramuscular, subcutaneous or parenteral administration for the therapeutic or prophylactic treatment of diseases, particularly bacterial infections. For oral or parenteral administration, lipopeptide compounds of this invention can be mixed with conventional pharmaceutical carriers and excipients and used in the form of tablets, capsules, elixers, suspensions, syrups, wafers and the like. The compositions comprising a compound of this invention will contain from about 0.1 to about 99% by weight of the active compound, and more generally from about 10 to about 30%.

The pharmaceutical preparations disclosed herein are prepared in accordance with standard procedures and are administered at dosages that are selected to reduce, prevent or eliminate the infection (see, e.g., Remington's Pharmaceutical Sciences, Mack Publishing Company, Easton, Pa. and Goodman and Gilman's The Pharmaceutical Basis of Therapeutics, Pergamon Press, New York, N.Y., the contents of which are incorporated herein by reference, for a general description of the methods for administering various antimicrobial agents for human therapy). The compositions of the invention (preferably of Formula I) can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. Nos. 4,452,775 (issued to Kent), 5,239,660 (issued to Leonard), 3,854,480 (issued to Zaffaroni).

The pharmaceutically-acceptable compositions of the present invention comprise one or more compounds of the invention (preferably compounds of Formula I) in association with one or more nontoxic, pharmaceutically-acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose, lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixers may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl parahydroxybenzoate, propylene glycol, sorbitol, or sorbic acid.

For intravenous (IV) use, a lipopeptide compound according to the invention can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of a lipopeptide compound or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular or parenteral formulation of a lipopeptide compound may be administered as a bolus or by slow infusion. A bolus is a dose that is administered in less than 30 minutes. In a preferred embodiment, a bolus is administered in less than 15 or less than 10 minutes. In a more preferred embodiment, a bolus is administered in less than 5 minutes. In an even more preferred embodiment, a bolus is administered in one minute or less. An infusion is a dose that is administered at a rate of 30 minutes or greater. In a preferred embodiment, the infusion is one hour or greater. In another embodiment, the infusion is substantially constant.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery. In another embodiment, the unit dosage form of the compound can be a solution of the compound or preferably a salt thereof in a suitable diluent in sterile, hermetically sealed ampoules or sterile syringes. The concentration of the compound in the unit dosage may vary, e.g. from about 1 percent to about 50 percent, depending on the compounds used and its solubility and the dose desired by the physician. If the compositions contain dosage units, each dosage unit preferably contains from 1-500 mg of the active material. For adult human treatment, the dosage employed preferably ranges from 5 mg to 10 g, per day, depending on the route and frequency of administration.

In another aspect, the invention provides a method for inhibiting the growth of microorganisms, preferably bacteria, comprising contacting said organisms with a compound of the invention, preferably a compound of Formula I, under conditions which permit entry of the compound into said organism and into said microorganism. Such conditions are known to one skilled in the art and are exemplified in the Examples. This method involves contacting a microbial cell with a therapeutically-effective amount of compound(s) of the invention, preferably compound(s) of Formula I, in vivo or in vitro.

According to this aspect of the invention, the novel compositions disclosed herein are placed in a pharmaceutically acceptable carrier and are delivered to a recipient subject (preferably a human) in accordance with known methods of drug delivery. In general, the methods of the invention for delivering the compositions of the invention in vivo utilize art-recognized protocols for delivering the agent with the only substantial procedural modification being the substitution of the compounds of the invention (preferably compounds of Formula I) for the drugs in the art-recognized protocols. Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the invention (preferably compounds of Formula I) for the agents used in the art-recognized protocols.

In one embodiment, the invention provides a method for treating an infection, especially those caused by gram-positive bacteria, in a subject with a therapeutically-effective amount of a lipopeptide compound according to Formula I. Exemplary procedures for delivering an antibacterial agent are described in U.S. Pat. Nos. 5,041,567, issued to Rogers and in PCT patent application number EP94/02552 (publication no. WO95/05384), the entire contents of which documents are incorporated in their entirety herein by reference. As used herein the phrase "therapeutically-effective amount" means an amount of a compound of the present invention that prevents the onset, alleviates the symptoms, or stops the progression of a bacterial infection. The term "treating" is defined as administering, to a subject, a therapeutically-effective amount of a compound of the invention (preferably a compound of Formula I) both to prevent the occurrence of an infection and to control or eliminate an infection. The term "subject", as described herein, is defined as a mammal, a plant or a cell culture. In a preferred embodiment, a subject is a human or other animal patient in need of lipopeptide compound treatment.

The method comprises administering to the subject an effective dose of a compound of this invention. An effective dose is generally between about 0.1 and about 100 mg/kg of a lipopeptide compound of Formula I or a pharmaceutically acceptable salt thereof. A preferred dose is from about 0.1 to about 50 mg/kg of a lipopeptide compound of Formula I or a pharmaceutically acceptable salt thereof. A more preferred dose is from about 1 to 25 mg/kg of a lipopeptide compound of Formula I or a pharmaceutically acceptable salt thereof. An effective dose for cell culture is usually between 0.1 and 1000 µg/mL, more preferably between 0.1 and 200 µg/mL.

The compound of Formula I can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. A method of administration to a patient of daptomycin, another member of the lipopeptide compound class, is disclosed in U.S. Ser. No. 09/406,568, filed Sep. 24, 1999, which claims the benefit of U.S. Provisional Application Nos. 60/101,828, filed Sep. 25, 1998, and 60/125,750, filed Mar. 24, 1999.

A lipopeptide compound according to this invention may also be administered in the diet or feed of a patient or animal. If administered as part of a total dietary intake, the amount of compound employed can be less than 1% by weight of the diet and preferably no more than 0.5% by weight. The diet for animals can be normal foodstuffs to which the compound can be added or it can be added to a premix.

The methods of the present invention comprise administering a lipopeptide compounds of Formula I or a pharmaceutical composition thereof to a subject in need thereof in an amount that is efficacious in reducing or eliminating the bacterial infection. The compound may be administered orally, parenterally, by inhalation, topically, rectally, nasally, buccally, vaginally, or by an implanted reservoir, external pump or catheter. The compound may be prepared for opthalmic or aerosolized uses. The compounds of the present invention can be administered as an aerosol for the treatment of pneumonia or other lung-based infections. A preferred aerosol delivery vehicle is an anhydrous or dry powder inhaler. Lipopeptide compounds of Formula I or a pharmaceutical composition thereof also may be directly injected or administered into an abscess, vertical or joint. Parenteral administration includes subcutaneous, intravenous, intramuscular, intra-articular, intra-synovial, cisternal, intrathecal, intrahepatic, intralesional and intracranial injection or infusion. In a preferred embodiment, lipopeptide compounds are administered intravenously, subcutaneously or orally. In a preferred embodiment for administering a lipopeptide compound according to Formula I to a cell culture, the compound may be administered in a nutrient medium.

The method of the instant invention may be used to treat a subject having a bacterial infection in which the infection is caused or exacerbated by any type of bacteria, particularly gram-positive bacteria. In one embodiment, a lipopeptide compound or a pharmaceutical composition thereof is administered to a patient according to the methods of this invention. In a preferred embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus,* and coagulase-negative staphylococci), glycopeptide intermediary-susceptible *S. aureus* (GISA), penicillin-susceptible and penicillin-resistant streptococci (including *Streptococcus pneumoniae, S. pyogenes, S. agalactiae, S. avium, S. bovis, S. lactis, S. sangius* and *Streptococci* Group C, *Streptococci* Group G and viridans streptococci), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Haemophilus influenzae, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus, Peptostreptococcus anaerobius, P. asaccarolyticus, P. magnus, P. micros, P. prevotti, P. productus, Propionibacterium acnes, actinomyces* spp., *Moraxella* spp. (including *M. catarrhalis*) and *Escherichia* spp. (including *E. coli*).

In a preferred embodiment, the antibacterial activity of lipopeptide compounds of Formula I against classically "resistant" strains is comparable to that against classically "susceptible" strains in in vitro experiments. In another preferred embodiment, the minimum inhibitory concentration (MIC) value for lipopeptide compounds according to this invention against susceptible strains is typically the same or lower than that of vancomycin. Thus, in a preferred embodiment, a lipopeptide compound of this invention or a pharmaceutical composition thereof is administered according to the methods of this invention to a patient who exhibits a bacterial infection that is resistant to other compounds, including vancomycin or daptomycin. In addition, unlike glycopeptide antibiotics, lipopeptide compounds exhibits rapid, concentration-dependent bactericidal activity against gram-positive organisms. Thus, in a preferred embodiment, a lipopeptide compound according to this invention or a pharmaceutical composition thereof is administered according to the methods of this invention to a patient in need of rapidly acting antibiotic therapy.

The method of the instant invention may be used for any bacterial infection of any organ or tissue in the body. In a preferred embodiment, the bacterial infection is caused by gram-positive bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *S. pneumoniae* or *H. influenzae*. The method of the invention also may be used to treat mixed infections that comprise different types of gram-positive bacteria, or which comprise both gram-positive and gram-negative bacteria. These types of infections include intra-abdominal infections and obstetrical/gynecological infections. The method of the invention also may be used to treat an infection including, without limitation, endocarditis, nephritis, septic arthritis, intra-abdominal sepsis, bone and joint infections and osteomyelitis. In a preferred embodiment, any of the above-described diseases may be treated using lipopeptide compounds according to this invention or pharmaceutical compositions thereof.

The method of the instant invention may also be practiced while concurrently administering one or more other antimicrobial agents, such as antibacterial agents (antibiotics) or antifungal agents. In one aspect, the method may be practiced by administering more than one lipopeptide compounds according to this invention. In another embodiment, the method may be practiced by administering a lipopeptide compound according to this invention with another lipopeptide compound, such as daptomycin.

Antibacterial agents and classes thereof that may be co-administered with a compound of the present invention include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, evernimicin, glycopeptide, glycylcycline, ketolides, oxazolidinone; impienen, amikacin, netilmicin, fosfomycin, gentamicin, cefriazone, ZIRACIN, LY 333328, CL 331002, linezolid, SYNERCID, aztreonam, metronidazole, epiroprim, OCA-983, GV-143253, sanfetrinem sodium, CS-834, biapenem, A-99058.1, A-165600, A-179796, KA 159, dynemicin A, DX8739, DU 6681; ccfluprenam, ER 35786, cefoselis, sanfetrinem celexetil, HGP-31, cefpirome, HMR-3647, RU-59863, mersacidin, KP 736, rifalazil; kosan, AM 1732, MEN 10700, lenapenem, BO 2502A, NE-1530, K130, OPC 20000, OPC 2045, veneprim, PD 138312, PD 140248, CP 111905, sulopenem, ritipenam acoxyl, RO-65-5788, cyclothialidine, Sch-40832, SEP-132613, micacocidin A, SB-275833, SR-15402, SUN A0026, TOC 39, carumonam, cefozopran, cefetamet pivoxil, and T 3811.

In a preferred embodiment, antibacterial agents that may be co-administered with a compound according to this invention include, without limitation, imipenen, amikacin, netilimicin, fosfomycin, gentamicin, ceftriaxone, teicoplanin, Ziracin, LY 333328, CL 331002, HMR 3647, Linezolid, Synercid, Aztreonam, and Metronidazole.

Antifungal agents that may be co-administered with a compound according to this invention include, without limitation, Caspofungen, Voriconazole, Sertaconazole, IB-367, FK-463, LY-303366, Sch-56592, Sitafloxacin, DB-289 polyenes, such as Amphotericin, Nystatin, Primaricin; azoles, such as Fluconazole, Itraconazole, and Ketoconazole, allylamines, such as Naftifine and Terbinafine, and anti-metabolites such as Flucytosine. Other antifungal agents include without limitation, those disclosed in Fostel et al., Drug Discovery Today 5:25-32 (2000), herein incorporated by reference. Fostel et al. disclose antifungal compounds including Corynecandin, Mer-WF3010, Fusacandins, Artrichitin/LL 15G256γ, Sordarins, Cispentacin, Azoxybacillin, Aureobasidin and Khafrefungin.

Lipopeptide compounds may be administered according to this method until the bacterial infection is eradicated or reduced. In one embodiment, a lipopeptide compound is administered for a period of time from 3 days to 6 months. In a preferred embodiment, a lipopeptide compound is administered for 7 to 56 days. In a more preferred embodiment, a lipopeptide compounds is administered for 7 to 28 days. In an even more preferred embodiment, a lipopeptide compound is administered for 7 to 14 days. Lipopeptide compounds may be administered for a longer or shorter time period if it is so desired.

General Procedures For Lipopeptide Compound Synthesis

Lipopeptide compounds of Formula I may be produced as described below. The lipopeptide compounds of the instant invention may be produced semi-synthetically using daptomycin as a starting point or may be produced by a total synthesis approach.

For the semi-synthetic approach according to the present invention, daptomycin may be prepared by any method known in the art. See, e.g., U.S. Pat. Nos. 4,885,243 and 4,874,843. Daptomycin may be used in its acylated state or it may be deacylated prior to its use as described herein. Daptomycin may be deacylated using *Actinoplanes utahensis* as described in U.S. Pat. Nos. 4,482,487. Alternatively, daptomycin may be deacylated as follows:

Daptomycin (5.0 g) was dissolved in water (25 ml) and adjusted to pH 9 with 5M sodium hydroxide. Ditert-butyldicarbonate (1.5 g) was added and the mixture was adjusted to maintain pH 9 with 5 M sodium hydroxide until the reaction was complete (4 hours). The pH was adjusted to 7 and the mixture was loaded onto a Bondesil 40 μ C8 resin column. The column was washed with water and the product was eluted from the column with methanol. Evaporation of the methanol gave BOC-protected daptomycin as a yellow powder.

A preparation of deacylase enzyme was produced from recombinant *Streptomyces lividans*, which expresses the *Actinoplanes utahensis* deacylase enzyme. The enzyme is ethylene glycol (400 μl) was added to BOC-protected daptomycin (1 g) in water (100 ml) at pH7-8. After incubation for 72 hours, the mixture was loaded on a Bondesil 40 μ C8 resin column. The column was washed with water and the product was eluted from the column with 10% acetonitrile in water. The product was evaporated to give deacylated BOC-protected daptomycin as a yellow powder.

Kymurenine Derivatives

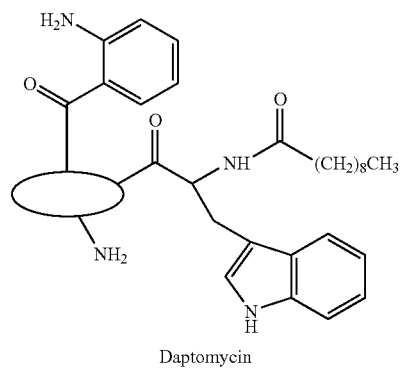

Scheme 1

Daptomycin

I

II

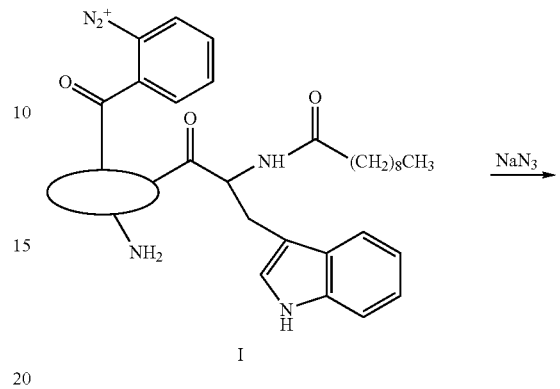

Scheme 2

I

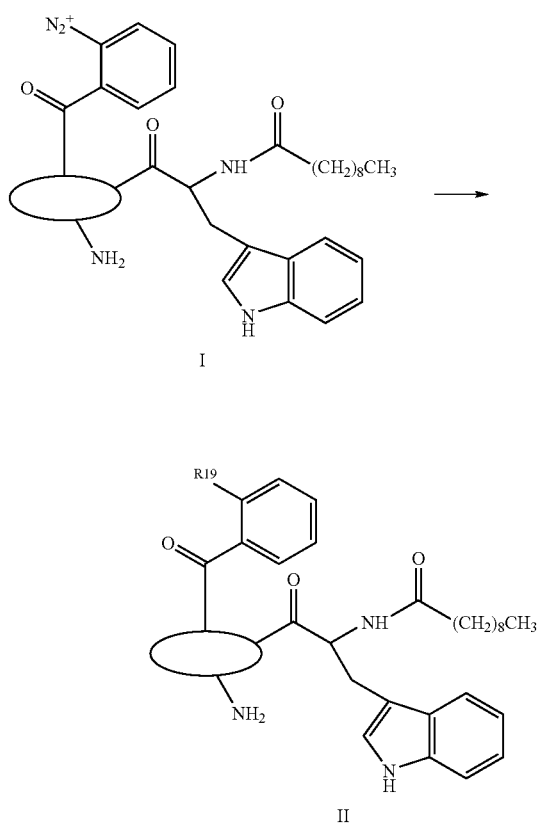

III

IV

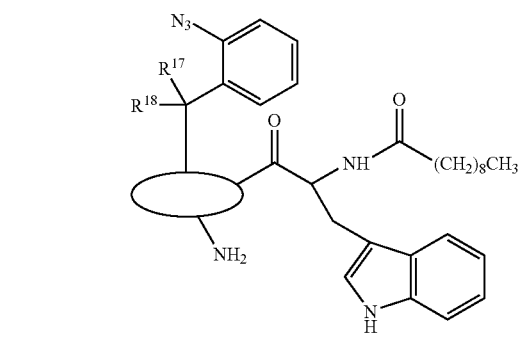

Daptomycin can be converted into analogs bearing modifications at the $R^2$ position by converting the aromatic amino group to the diazonium salt compound I with reagents such as sodium nitrite/hydrochloric acid or isoamylnitrite. Using chemistry known to those skilled in the art and following the teachings of the disclosure, the diazonium group can then be displaced by reagents such as sodium azide, potassium ethylxanthate or copper chloride to yield derivative compounds II, wherein $R^{19}$ is as previously defined.

Additionally, compound I can be converted to the azide compound III by reaction with an azide source, typically sodium azide. Modifications to the ketone group can then be undertaken using chemistry known to those having ordinary skill in the art, such as reduction, oxime formation, ketalization conversion to a leaving group and displacement to give compounds of formula IV, wherein $R^{17}$ and $R^{18}$ are as previously defined Scheme 3

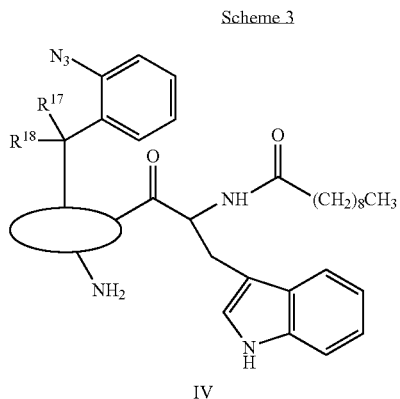

IV

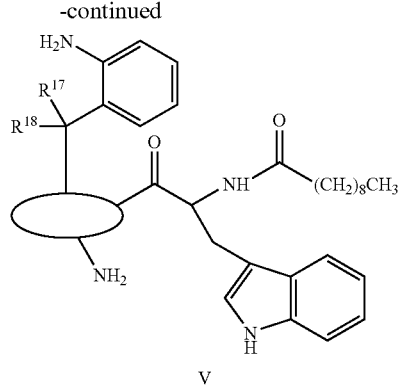

V

Compound IV may also be converted to compound V by reducing the azide group to the amine using chemistry known to those having ordinary skill in the art, and following the teachings of the disclosure, such as reaction with triphenyl phosphine and water, or reducing agents such as sodium borohydride wherein $R^{17}$ and $R^{18}$ are as previously defined.

Scheme 4

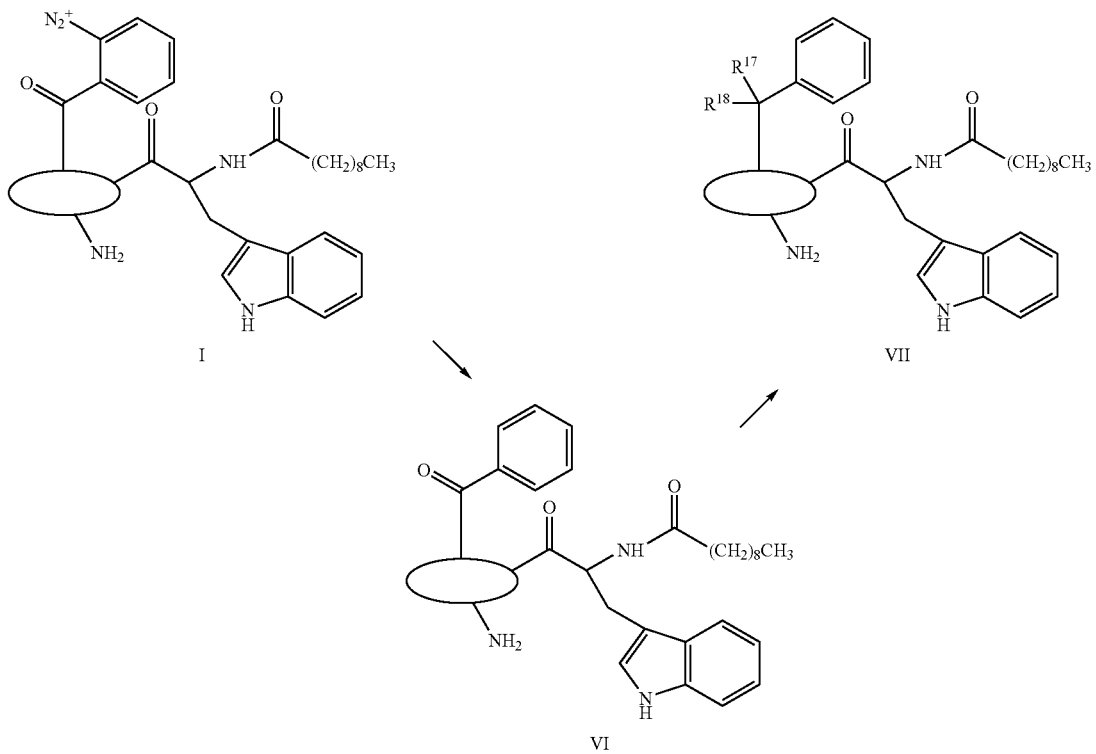

Additionally, compound I can be converted into compound VI by reduction with hypophosphorus acid. Modifications to the ketone group can then be undertaken using chemistry known to those having ordinary skill in the art similar to those used in scheme 2, wherein $R^{17}$ and $R^{18}$ are as previously defined.

Ornithine Derivatives

Scheme 1

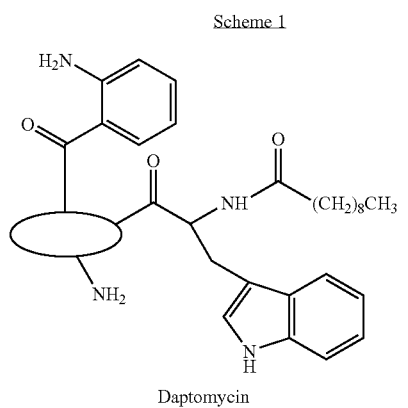

Daptomycin

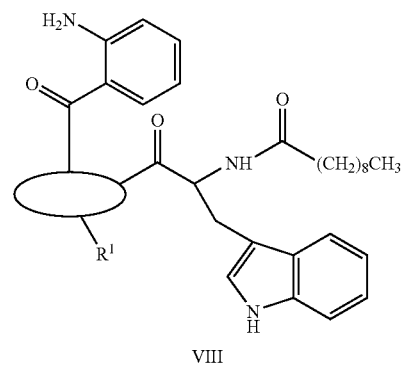

VIII

Daptomycin can be converted into analogs bearing modifications at the $R^1$ position by treating the aromatic amino group of the ornithine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound VIII, wherein $R^1$ is as previously defined.

Tryptophan Amine Derivatives

Scheme 1

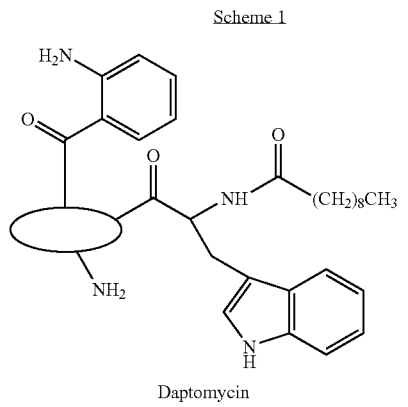

Daptomycin

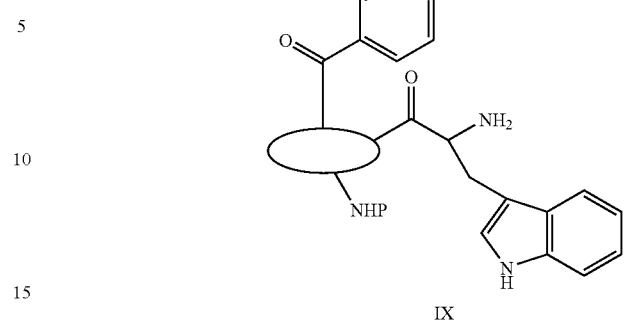

IX

Daptomycin can be converted into compound IX by first protecting the ornithine amine with an appropriate amino protecting group (P) known to those skilled in the art and following the teachings of the disclosure. The decyl side chain on the tryptophan is then removed using an enzyme capable of deacylating daptomycin, such as that described above.

Scheme 2

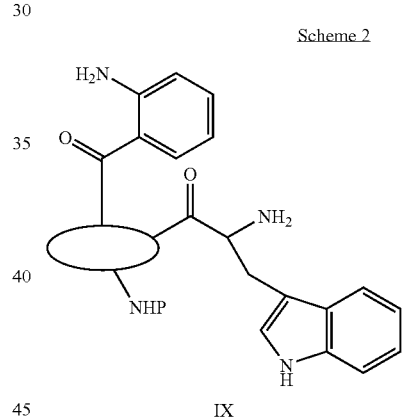

IX

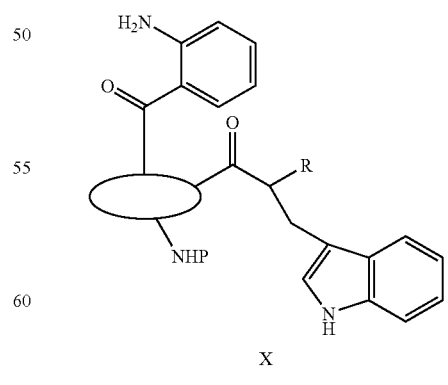

X

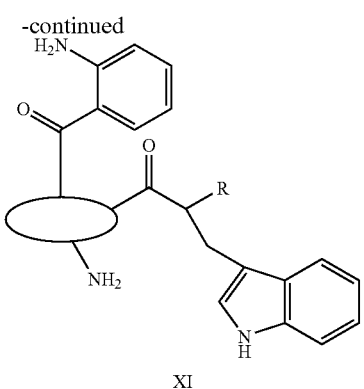

XI

Compound IX can be modified at the tryptophan amine with reagents such as isocyanates, isothiocyanates, activated esters, acid chlorides, sulfonylchlorides or activated sulfonamides, heterocycles bearing readily displaceable groups, imidates, lactones or reductively with aldehydes to yield compound X. Compound X can be deprotected to give compound XI according to procedures known to those skilled in the art following the disclosure of this invention, wherein R is as previously defined.

The above modifications to the ornithine amine $R^1$, tryptophan amine R or kynurenine side chain $R^2$ may be independently combined to yield additional compounds that are modified at up to all three sites. In order to achieve these modifications, it may be necessary to protect certain functionalities in the molecule. Protecting these functionalities should be within the expertise of one skilled in the art following the disclosure of this invention. See, e.g., Greene, supra.

Solid Support Synthesis Of Lipopeptide Compounds

In an alternative embodiment of the invention, the lipopeptide compounds of Formula I may be synthesized on a solid support as outlined below. In step 1, a suitably-N-protected-βMeGlu(OH)-OAllyl ester is coupled to a suitable resin to give Compound XII. Deprotection of the amino group of Compound XII, followed by coupling of the amino group with a suitably protected seryl derivative (A1) gives Compound XIII, wherein P is a suitable protecting group. This peptide coupling process, i.e., deprotection of the alpha-amino group, followed by coupling to a suitably protected amino acid, is repeated until the desired number of amino acids have been coupled to the resin. In the scheme shown below, eleven amino acids have been coupled to give Compound XIV. Addition of an activated R group, R*, is added to Compound XIV to give Compound XV. In step 4, Compound XV is cyclized to give Compound XVI. Subsequently, in step 5, Compound XVI is removed from the resin to give the lipopeptide Compound XVII.

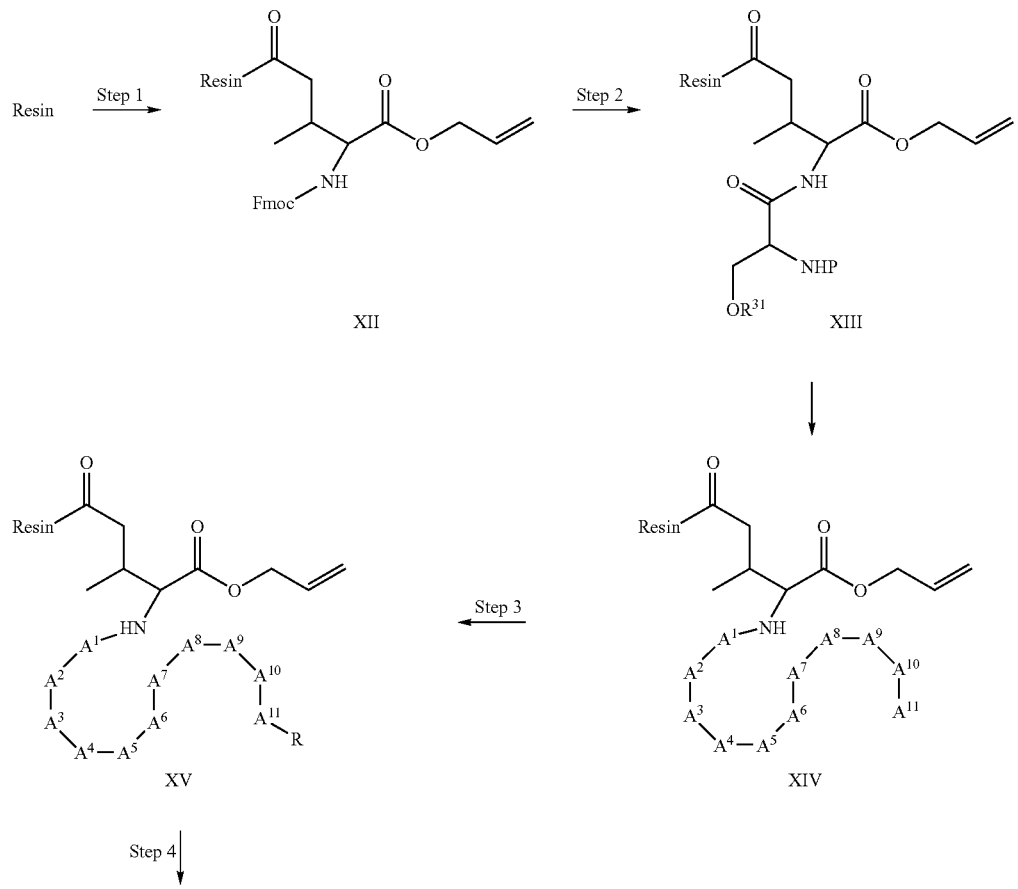

-continued

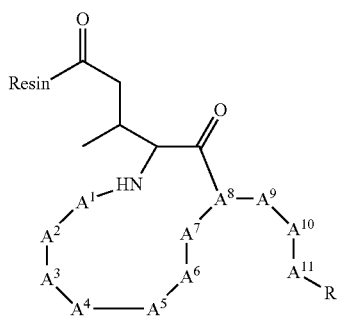

XVI

Step 5 →

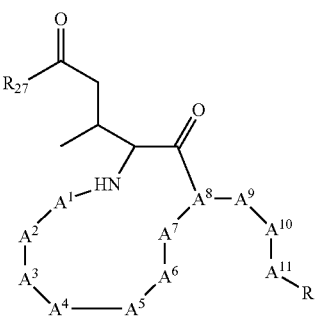

XVII

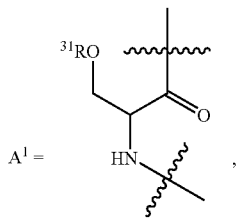

wherein $A^1$, is a suitably protected serine derivative, wherein $R^{31}$ is a suitable, cleavable hydroxyl protecting group as outlined below.

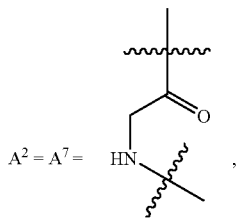

wherein $A^2$ and $A^7$, are suitably protected glycine derivatives as outlined below.

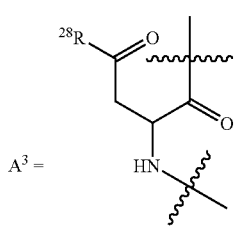 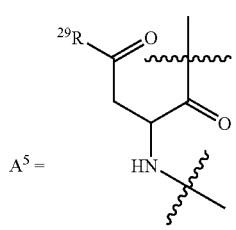

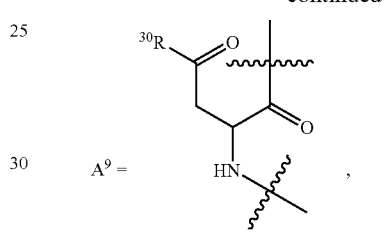

wherein $A^3$, $A^5$ and $A^9$ are suitably protected aspartic acid derivatives as outlined below, wherein $^{28}R$, $^{29}R$ and $^{30}R$ are cleavable protecting groups, preferably t-butyl groups.

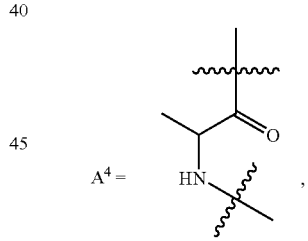

wherein $A^4$ is a suitably protected alanine derivative as outlined. below.

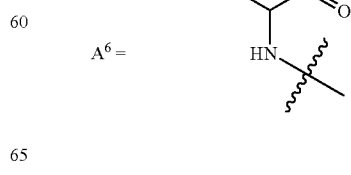

wherein $A^6$ is a suitably protected ornithinine derivative as outlined below, or derivatized ornithine wherein $*R^1$ is $R^1$ as previously described or alternatively a protected form of $R^1$ that would yield $R^1$ upon subsequent deprotection.

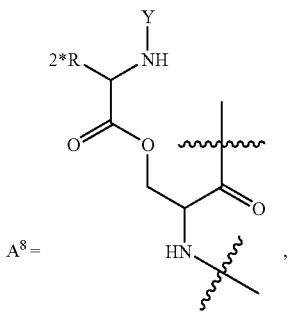

wherein $A^8$ is a suitably protected depsipeptide as outlined below, Y is a protecting group that is cleavable under conditions that leave other protecting groups intact to the others used, i.e., Alloc; and wherein $*R^2$ is $R^2$ as previously described or alternatively a protected form of $R^2$ that would yield $R^2$ upon subsequent deprotection. Preferably $^{2*}R$ is a kynurenine, or substituted kynurenine side chain, most preferably

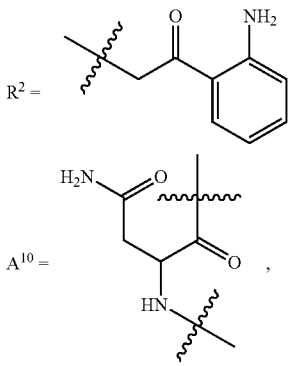

wherein $A^{10}$ is a suitably protected asparagine derivative as outlined below.

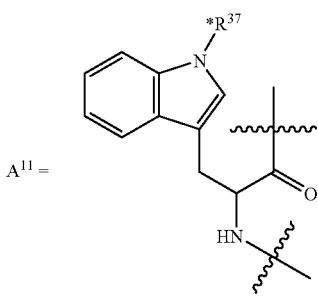

wherein $A^{11}$ is a suitably protected tryptophan derivative as outlined below, wherein $R^{*37}$ is hydrido or a suitable protecting group, preferably t-butoxy carbonyl.

It will be understood by those skilled in the art that both the amino and the side chain functional groups must be suitably protected prior to attaching them to the growing peptide chain. Suitable protecting groups can be any group known in the art to be useful in peptide synthesis. Such pairings of protecting groups are well known. See, e.g., "Synthesis Notes" in the Novabiochem Catalog and Peptide Synthesis Handbook (1999), pages S1-S93 and references cited therein. Following the disclosure of the present application, the selection of protecting groups and method of use thereof will be known to one skilled in the art.

It will also be understood by those skilled in the art that the choice of protecting group on the side chain functional groups will either result or not result in the protecting group being cleaved concomitantly with the peptide's final cleavage from the resin, which will give the natural amino acid functionality or a protected derivative thereof, respectively.

The following general procedures serve to exemplify the solid support synthesis of compounds of Formula I.

Step 1: Coupling Suitably-N-Protected-β
MeGlu(OH)—OAllyl Ester To A Resin

Five molar equivalents each, with respect to the resin, of a suitably-N-protected-βMeGlu(OH)—OAllyl ester, 1,3-Di-isopropylcarbodiimide (DIC) and 1-Hydroxy-7-azabenzotriazole (HOAt) are stirred for 30 mins in dimethylformamide (DMF; 5 ml/g resin). A suitably functionalised resin or solid support, such as, but not limited to, Wang, Safety Catch, Rink, Knorr, PAL, or PAM resin, is added and the resulting suspension is stirred for 16 hrs. The resin-N-protected-βMeGlu (OH)—OAllyl ester is then filtered, dried and the coupling is repeated. The N-protecting group is then removed using the appropriate conditions given in the coupling steps below.

Step 2: (A) General Coupling Cycle For Amino
Acids With An N-9-Fluorenylmethoxycarbonyl
(Fmoc) Protecting Group Five molar equivalents each, with respect to the resin-AA (wherein resin-AA is defined as the resin attached the growing amino acid chain), of a suitably protected Fmoc amino acid, DIC, and HOAt (0.5 molar solution in DMF) are added to the resin-AA, along with sufficient DMF to give a working volume. The mixture is shaken for one hour, filtered, and the coupling is repeated. After the second coupling the resin is washed twice with DMF, twice with methanol, and twice again with DMF. The Fmoc group of the newly coupled amino acid $A^{1-11}$ is deprotected by stirring the resin product in one working volume of a solution of 20% piperdine in N-methyl pyrolidine for five minutes, filtering the resin, and stirring the resin in 20% piperidine in N-methyl pyrolidine again for 20 minutes. The resin is washed twice with DMF, twice with methanol, and twice again with DMF.

Step 2 (B): General Coupling Cycle Of Amino Acids
With An N-tert-Butoxy-carbonyl (N-Boc) Protecting
Group Five molar equivalents each, with respect to the resin-AA, of a suitably protected N-Boc amino acid, DIC, and HOAt (0.5 molar solution in DMF) are added to the resin-AA, along with sufficient DMF to give a working volume. The mixture is shaken for one hour, filtered, and the coupling is repeated. After the repeated coupling the resin is washed twice with DMF, twice with methanol, and twice again with DMF. The Boc group of the newly coupled amino acid $A^{1-11}$, is then deprotected by stirring the resin in one working volume of $CH_2$-$Cl_2$-trifluoroacetic acid (TFA) 1:1 for 15 minutes, filtering, and stirring in one working volume of $CH_2-Cl_2$:TFA 1:1 for another 15 minutes. The resin is neutralized by washing with excess diisopropylethylamine (DIPEA) in $CH_2Cl_2$ and then washed twice with DMF, twice with methanol, and twice again with DMF.

Step 3: Terminal Amine Capping Reaction

Ten molar equivalents, with respect to the resin XV, of a suitable reagent containing R* such as an activated ester, isocyanate, thioisocyanate, anhydride, acid chloride, chloroformate, or reactive salt thereof, in one working volume of DMF is added to the resin XIV and agitated for 25 hours. The resulting resin XV is washed twice with DMF, twice with methanol, and twice again with DMF.

Step 4: Cyclization

The dried resin XV is placed under an argon atmosphere, and treated with a solution of $Pd(PPh_3)_4$ 125 mgs/0.1 mmol peptide substrate, in $CH_2Cl_2$: Acetic acid, N-Methylmorpholine, 40:2:1, 1 ml/0.1 mmol peptide substrate. The mixture is stirred for 3 hours at ambient temperature, filtered, and washed twice with DMF, twice with methanol, and twice again with DMF. Five molar equivalents each, with respect to the resin, of DIC, and HOAt (0.5 molar solution in DMF) are added to the resin, along with sufficient DMF to give a working volume. The reaction is shaken for 17 hours, filtered, and washed twice with DMF, twice with methanol, and twice again with DMF to give resin XVI.

Step 5: Cleavage And Isolation Of The Lipopeptide

The desired lipopeptide is cleaved from resin XVI and isolated, resulting in a compound in which $R^{27}$ is OH or $NH_2$. If Fmoc chemistry is used, the dried resin is suspended in 1 ml/0.1 mmol peptide substrate of $CH_2Cl_2$:TFA:Ethanedithiol (EDT):Trisopropylsilane (TIS), 16:22:1:1, and stirred for 6-8 hours at ambient temperature. The resin is filtered, washed with 1 equal volume of cold TFA, and the combined filtrates are evaporated under reduced pressure. Crude product XVII is then precipitated by the addition of diethyl ether, and isolated by centrifugation. This product may be further purified by preparative reverse phase HPLC.

If N-Boc chemistry is used, the dried resin is suspended in hydrogen fluoride (HF):amisole:dimethylsulfide (DMS), 10:1:1, and stirred for 2 hours at 0° C. The volatiles are evaporated under a stream of nitrogen. The resin is then extracted with TFA, filtered and washed twice with TFA, and the combined TFA filtrates evaporated under reduced pressure. Crude product is then precipitated by the addition of diethyl ether, and isolated by centrifugation. This product may be further purified by preparative reverse phase HPLC.

If the resin is a Safety Catch resin, then $R^{27}$=OR or NRH. The dried resin XVI is suspended in N-methylpyrolidine (NMP) or dimethylsulphoxide (DMSO) (8 ml/g resin), Five equivalents of DIPEA (with respect to resin substitution) and 24 equivalents of iodo or bromoacetonitrile (with respect to resin substitution) are added. The suspension is stirred for 24 hours at ambient temperature under inert atmosphere. The resin is filtered, washed with tetrahydrofuran (THF) and DMSO. For an ester, the resin is then treated with an alcohol, hydroxide or alkoxide (20 equivalents with respect to resin substitution) in THF for 20 hours. The resin is filtered, washed with THF and water, and the combined filtrates are evaporated under reduced pressure. Crude product is precipitated by the addition of diethyl ether, and isolated by centrifugation. The product may be further purified by preparative reverse phase HPLC. For amides the resin is then treated with a primary or secondary amine (20 equivalents with respect to resin substitution) in THF for 12-40 hours, at a gentle reflux under inert atmosphere. The resin is filtered, washed with THF and water, and the combined filtrates are evaporated under reduced pressure. Crude product is then precipitated by the addition of diethyl ether, and isolated by centrifugation. This product may be further purified by preparative reverse phase HPLC.

In order that this invention may be more fully understood, the following examples are set forth. These examples are for the purpose of illustration only and are not to be construed as limiting the scope of the invention in any way.

EXAMPLE 1

Preparation Of Compounds 38, 40, 50, 52, 77-80, 82-84, 87-100, 103-169, 171-176, 183-187, 194-199, 201-204, 208, 210-211, 222-244, 252, 265-267, 271-281, 283-284, 286-291, 323-331, 358-395 and 398-410

A suspension of daptomycin in dry dimethylformamide (0.6 ml) was treated with a solution of 4-Fluorobenzaldehyde (0.2 ml) and a suspension of sodium triacetoxyborohydride (0.2 ml, 1.5M in dry dimethylformamide). After 24 hours, the reaction mixture was diluted with water/acetonitrile (1:1, 0.4 ml) and purified by preparative HPLC. The reaction mixture was loaded onto an IBSIL-C8 5µ 250×20.2 mm column and eluted at 20 ml/min with 30-60% acetonitrile in 5 mM ammonium phosphate buffer. Fractions containing product were collected and freeze-dried. The freeze-dried residue was dissolved in water (5 ml) and applied to a Bondesil 40µ C8 resin column. The column was washed with water and eluted with methanol. Evaporation of the methanol gave compound 38 as a pale yellow solid (23 mg).

In an analogous manner, compounds 40, 50, 52, 77-80, 82-84, 87-100, 103-169, 171-176, 183-187, 194-199, 201-204, 208, 210-211, 222-244, 252, 265-267, 271-281, 283-284, 286-291, 323-331, 358-395 and 398-410 can be prepared as detailed in the above example by appropriate substitutions of reagents obvious to those skilled in the art following the teachings of the disclosure.

EXAMPLE 1a

Preparation Of Compound 282

2-Methyl-6-nitroquinoline (0.4 ml, 0.5M solution in dioxane) was treated with selenium dioxide 90.2 ml, 0.9M solution in 9/1 dioxane/water) and heated to 90° C. overnight. The mixture was cooled to room temperature and diluted with water (1 ml). The mixture was then extracted with ethyl acetate (3×2 ml). The organic extract was then dried in vacuo to give 6-nitro-2-quinolinecarboxaldehyde which was carried forward without further purification. Daptomycin (1 ml, 0.1 M in dry dimethylformamide) was treated successively with 6-nitro-2-quinolinecarboxaldehyde prepared above in dry dimethylformamide (0.2 ml) and sodium triacetoxyborohydride (0.4 ml, 1.5M solution in dry dimethylformamide). The mixture was capped and shaken briefly. After 24 h, the mixture was treated with water (0.2 ml) and loaded onto an IBSIL-C87 5µ 250×20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected and the acetonitrile was removed by evaporation. The residue was applied to a Bondesil 40μ C8 resin column, washed with water and the product was eluted with methanol. Evaporation of the methanol gave compound 282 as a pale yellow solid.

EXAMPLE 1b

Preparation of Compound 285

4-Chloro-2-methylquinoline (0.4 ml, 0.5M solution in dioxane) was treated with selenium dioxide (0.2 ml, 0.9M solution in 9/1 dioxane/water) and heated to 90° C. overnight. The mixture was cooled to room temperature and diluted with water (1 ml). The mixture was then extracted with ethyl acetate (3×2 ml). The organic extract was then dried in vacuo to give 4-chloro-2-quinolinecarboxaldehyde which was carried forward without further purification. Daptomycin (1 ml, 0.1 M in dry dimethylformamide) was treated successively with 4-chloro-2-quinolinecarboxaldehyde prepared above and diluted in dry dimethylformamide (0.2 ml) and sodium triacetoxyborohydride (0.4 ml, 1.5M in dry dimethylformamide). The mixture was capped and shaken briefly. After 24 h the mixture was treated with water (0.2 ml) and loaded on an IBSIL-C8 5μ 250×20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected and the acetonitrile was removed by evaporation. The residue was applied to a Bondesil 40μ C8 resin column, washed with water and the product eluted off with methanol. Evaporation of the methanol gave compound 285 as a yellow solid.

EXAMPLE 1c

Preparation Of Compound 85

Daptomycin (1 ml, 0.1M in dry dimethylformamide) was treated successively with 1-methyl-2-imidazolecarboxaldehyde (0.2 ml, 0.5M solution in dry dimethylformamide) and sodium triacetoxyborohydride (0.4 ml, 1.5M solution in dry dimethylformamide). The mixture was capped and shaken briefly. After 24 h the mixture was treated with water (0.2 ml) and loaded onto an IBSIL-C8 5μ 250×20.2 mm column. The column was eluted at 30 ml/min under the gradient conditions of 35-40% acetonitrile in 5 mM ammonium phosphate buffer over 30 min. The desired fractions were collected and the acetonitrile was removed by evaporation. The residue was applied to a Bondesil 40μ C8 resin column, washed with water and eluted with methanol. This mixture was then loaded on a Prodigy ODS 10μ 250×21.2 mm column eluted at 50 ml/min at 33% acetonitrile in 5 mM ammonium phosphate buffer adjusted to pH 3.2. The desired fractions were collected and the acetonitrile was removed by evaporation. The residue was applied to a Bondesil 40μ C8 resin column, washed with water and the product was eluted with methanol. Evaporation of the methanol gave compound 85 as a pale yellow solid.

EXAMPLE 1d

Preparation Of Compound 212

Daptomycin (1, 0.1 M in dry dimethylformamide) was treated successively with 2-imidazolecarboxaldehyde (0.2 ml, 0.5M solution in dry dimethylformamide) and sodium triacetoxyborohydride (0.4 ml, 1.5M solution in dry dimethylformamide). The mixture was capped and shaken briefly. After 24 h, the mixture was treated with water (0.2 ml) and the mixture was loaded on an IBSIL-C8 5μ 250×20.2 mm column. The column was eluted at 30 ml/min under the gradient conditions of 35-40% acetonitrile in 5 mM ammonium phosphate buffer over 30 min. The desired fractions were collected and the acetonitrile was removed by evaporation. The residue was applied to a Bondesil 40μ C8 resin column, washed with water and eluted with methanol. This mixture was then loaded on a Prodigy ODS 10μ 250×21.2 mm column and eluted at 50 ml/min at 33% acetonitrile in 5 mM ammonium phosphate buffer adjusted to pH 3.2. The desired fractions were collected and the acetonitrile was removed by evaporation. The residue was applied to a Bondesil 40μ C8 resin column, washed with water and the product eluted with methanol. Evaporation of the methanol gave compound 212 as a yellow solid.

EXAMPLE 1e

Preparation Of Compound 81

Daptomycin (1 ml, 0.1M in dry dimethylformamide) was treated successively with 5-fluoroindole-3-carboxaldehyde (0.2 ml, 0.5M solution in dry dimethylformamide) and sodium triacetoxyborohydride (0.4 ml, 1.5M solution in dry dimethylformamide). The mixture was capped and shaken briefly. After 24 h the mixture was treated with water (0.2 ml) and loaded on an IBSIL-C8 5μ250×20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected, the acetonitrile was removed by evaporation and the residue applied to a Bondesil 40μ C8 resin column. The column was washed with water and the product was eluted with methanol. Evaporation of the methanol gave compound 81 as a pale yellow solid.

EXAMPLE 1f

Preparation Of Compound 253 p-N,N-Bis(2-chloroethyl)aminobenzaldehyde (0.3 g) was dissolved in acetone (2.5 ml) and treated with sodium iodide (0.4 g). The mixture was warmed to 40° C. for 3 h then treated with benzylamine (0.2 ml) and triethylamine (0.4 ml). The mixture was diluted to 7 ml with acetonitrile and then heated to 60° C. After 24 h, the mixture was cooled to room temperature and the solvent was removed by evaporation. 4-(4-Benzylpiperazino)benzaldehyde was purified by silica gel chromatography eluting with (10% triethylamine/methanol/dichloromethane).

Daptomycin (1 ml, 0.1 M in dry dimethylformamide) was treated successively with the 4-(4-benzylpiperazino)benzaldehyde prepared above diluted in dry dimethylformamide (0.2 ml), and sodium triacetoxyborohydride (0.4 ml, 1.5M solution in dry dimethylformamide). The mixture was capped and shaken briefly. After 24 h the mixture was treated with water (0.2 ml) and loaded on an IBSIL-C8 5μ 250×20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected, the acetonitrile

EXAMPLE 1g

Preparation Of Compound 76 and 177

Daptomycin (1 ml, 0.1 M in dry dimethylformamide) was treated successively with 4-phenylbenzaldehyde (0.2 ml, 0.5M in dry dimethylformamide) and sodium triacetoxyborohydride (0.4 ml, 1.5M in dry dimethylformamide). The reaction mixture was capped and shaken briefly to mix the solution. After 24 h the mixture was treated with water (0.2 ml) and loaded on an IBSIL-C8 5µ 250×20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected, the acetonitrile was removed by evaporation and the residue was applied to a Bondesil 40µ C8 resin column. The column was washed with water and the product was eluted with methanol. Evaporation of the methanol gave compound 76 as a pale yellow solid. Compound 177 was obtained by deacylation of compound 76 according to Example 7.

EXAMPLE 1h

Preparation Of Compound 209

4-Hydroxy-3-nitrobenzaldehyde (0.4 ml, 0.2M in acetone) was successively treated with potassium hydroxide (0.1 m, 1M in water) and 4-fluorobenzylbromide (0.4 ml, 0.2M in acetone). After 24 h the mixture was dried in vacuo to give 4-(4-fluorobenzyloxy)-3-nitro-banzaldehyde which was carried forward without further purification.

Daptomycin (1 ml, 0.1 M in dry dimethylformamide) was treated successively with, 4-(4-fluorobenzyloxy)-3-nitro-benzaldehyde previously prepared above diluted in dry dimethylformamide (0.2 ml), and sodium triacetoxyborohydride (0.4 ml, 1.5M in dry dimethylformamide). The mixture was capped and shaken briefly. After 24 h the mixture was treated with water (0.2 ml) and loaded onto an IBSIL-C8 5µ 250× 20.2 mm column. The column was eluted at 25 ml/min under the gradient conditions of 30-60% acetonitrile in 5 mM ammonium phosphate buffer over 25 min followed by holding at 60% acetonitrile in 5 mM ammonium phosphate buffer for another 10 min. The desired fractions were collected, the acetonitrile was removed by evaporation and the residue was applied to a Bondesil 40µ C8 resin column. The column was washed with water and the product was eluted with methanol. Evaporation of the methanol gave compound 209 as a pale yellow solid.

EXAMPLE 2

Preparation Of Compound 10, 11-17, 19-20, 22-27 And 190

Daptomycin (972 mg) was dissolved in dry dimethylformamide (20 ml), and isatoic anhydride (979 mg) was added. The mixture was stirred at ambient temperature for 10 days, then quenched by the addition of water (20 ml). The mixture was loaded onto a Bondesil 40µ C8 resin column (25 g), which had been previously washed with methanol (50 ml) and water (100 ml). The column was then eluted with water (200 ml), 15% methanol/water (1200 ml), 20% methanol/water (200 ml), 30% methanol/water (200 ml) and 40% methanol/water (200 ml). The product bearing fractions were combined and freeze dried to give compound 10 as a white solid (870 mg).

In an analogous manner, compounds 11-17, 19-20, 22-27 and 190 can be prepared as detailed in the above example by appropriate substitutions of reagents obvious to those skilled in the art following the teachings of the disclosure.

EXAMPLE 3

Preparation Of Compound 44, 45, 41-43, 46-48, 55-58, 60-75, 178-180, 193 And 245

Daptomycin (500 mg) and Boc-tryptophan-p-nitrophenyl ester (157.5 mg) were stirred at room temperature in dry dimethyldormamide (30 ml) for 3 days. Water (30 ml) was added and the mixture was purified on a Bondesil 40µ C8 resin column (25 g). The column was eluted with 20% acetonitrile in water (200 ml), 40% acetonitrile in water (200 ml) and finally with methanol. Evaporation of the solvent from the product-containing fractions gave compound 44 as a pale yellow solid (450 mg).

Compound 44 (200 mg) was cooled to 0° C. and a 0° C. solution of 5% thioanisole in trifluoroacetic acid (10 ml) was added. After 3 hours at 0° C. The mixture was evaporated to dryness and the residue was purified by preparative HPLC on an IBSIL-C8 5µ250×20.2 mm column. The column was eluted at 20 ml/min with 38% acetonitrile in 5 mM ammonium phosphate buffer. The product containing fractions were freeze-dried. The freeze-dried residue was dissolved in water (5 ml) and applied to a Bondesil 40µ C8 resin column. The column was washed with water and eluted with methanol. Evaporation of the methanol gave compound 45 as a pale yellow solid.

In an analogous manner, compounds 41-43, 46-48, 55-58, 60-75, 178-180, 193 and 245 can be prepared as detailed in the above example by appropriate substitutions of reagents obvious to those skilled in the art following the teachings of the disclosure.

EXAMPLE 3a

Preparation Of Compounds 54, 49 And 51

Daptomycin (400 mg) and N,N-bis(tert-butoxycarbonyl)-L-lysine-4-nitrophenyl ester (173 mg) were stirred in dry dimethylformamide (5 ml) at room temperature for two days. The mixture was loaded onto an IBSIL-C8 5µ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 µ C8 resin column, washed with water and eluted with methanol. Evaporation of the methanol gave the Boc protected intermediate as a pale yellow solid (370 mg).

Boc protected intermediate (200 mg) was stirred in trifluoroacetic acid (5 ml) and anisole (0.25 ml) at room temperature for 2 hours. Removal of the solvents under reduced pressure gave a residue which was loaded on an IBSIL-C8 5 µ 250× 20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 µ C8 resin column, washed with

--- was removed by evaporation and the residue was applied to a Bondesil 40µ C8 resin column. The column was washed with water and the product was eluted with methanol. Evaporation of the methanol gave compound 253 as a pale yellow solid.

water and eluted with methanol. Evaporation of the methanol gave compound 54 as a pale yellow solid (100 mg).

In an analogous manner, compounds 49 and 51 can be prepared as detailed in the above example by appropriate substitutions of reagents obvious to those skilled in the art following the teachings of the disclosure.

EXAMPLE 3b

Preparation Of Compounds 32, 18, 21, 28-31, 33-35, 39, 182 and 189

Daptomycin (162 mg) and 2-methylthiobenzoic acid pentafluorophenol ester (37 mg) were stirred at room temperature in dry dimethylformamide (10 ml) for 5 days. The dimethylformamide was evaporated under reduced pressure and the residue was purified by preparative HPLC on an IBSIL-C8 5μ 250×20.2 mm column. The column was eluted at 20 ml/min with 36% acetonitrile in 5 mM ammonium phosphate buffer. Fractions collected at 7.3 minutes were freeze-dried. The freeze-dried residue was dissolved in water (5 ml) and applied to a Bondesil 40μ C8 resin column. The column was washed with water and eluted with methanol. Evaporation of the methanol gave compound 32 as a pale yellow solid (47 mg).

In an analogous manner, compounds 18, 21, 28-31, 33-35, 39, 182 and 189 can be prepared as detailed in the above example by appropriate substitutions of reagents by one having ordinary skill in the art following the teachings of the disclosure.

EXAMPLE 4

Preparation Of Compound 5, 4, 6-8 And 9

Daptomycin (16 mg) was dissolved in dry dimethylformamide (0.5 ml) and methyl isothiocyanate (37 mg) was added. The mixture was stirred at ambient temperature for 24 hours, then quenched by the addition of 5% ammonium phosphate buffer (1 ml). The mixture was purified by preparative HPLC on an IBSIL-C8 5μ 250×20.2 mm column. The column was eluted at 20 ml/min with 36% acetonitrile in 5 mM ammonium phosphate buffer. The product bearing fractions were combined and freeze dried. The freeze-dried residue was dissolved in water (1.5 ml) and applied to a Bondesil 40μ C8 resin column. The column was washed with water and eluted with methanol. Evaporation of the methanol gave compound 5 as a pale yellow solid (5.2 mg).

In an analogous manner, compounds 4,6-8 and 9 can be prepared as detailed in the above example by appropriate substitutions of reagents obvious to those having ordinary skill in the art.

EXAMPLE 5

Preparation Of Compound 3

Daptomycin (16 mg) and N-benzotriazole phenylsulfonamide (2.6 mg) were stirred at room temperature in dry pyridine for 6 days. The solvent was evaporated and the residue was purified by preparative HPLC using an IBSIL-C8 5μ 250×20.2 mm column. The column was eluted at 20 ml/min with 36% acetonitrile in 5 mM ammonium phosphate buffer and product containing fractions were freeze-dried. The freeze dried residue was dissolved in water (5 ml) and applied to a Bondesil 40μ C8 resin column. The column was washed with water and eluted with methanol. Evaporation of the methanol gave compound 3 as a pale yellow solid (4 mg).

EXAMPLE 6

Preparation Of Compounds 1, 2, 221, 259 And 270

Daptomycin (32 mg) was dissolved in dry dimethylformamide (20 ml), and N,N'-bis-Boc-1-guanidinylpyrazole (31 mg) was added. The mixture was stirred at ambient temperature for 5 days, then quenched by the addition of water (3 ml). The resultant mixture was loaded onto a Bondesil 40μ C8 resin (900 mg) that had been previously washed with methanol and water. The column was eluted with water (30 ml) followed by methanol. The product-bearing fractions were combined and evaporated to give compound 1 as a white solid.

Compound 1 (30 mg) was dissolved in trifluoroacetic acid/dichloromethane/tri-isopropyl/silane/ethane dithiol (11/8/0.5/0.5, 3 ml) and stirred at ambient temperature for 90 minutes. The mixture was evaporated to dryness and the residue was precipitated by the addition of diethyl ether (10 ml). The residue was purified by preparative HPLC on an IBSIL-C8 5μ 250×20.2 mm column. The column was eluted at 20 ml/min with 38% acetonitrile in 5 mM ammonium phosphate buffer. The product-bearing fractions were combined and freeze dried. The freeze-dried residue was dissolved in water (1.5 ml) and applied to a Bondesil 40μ C8 resin column. The column was washed with water and eluted with methanol. Evaporation of the methanol gave compound 2 as a white solid (6.4 mg).

In an analogous manner, compounds 221, 259 and 270 can be prepared as detailed in the above example by appropriate substitutions of reagents obvious to those having ordinary skill in the art following the teachings of the disclosure.

EXAMPLE 7

Preparation Of Compounds 255, 260, 254, 256-257, 261, 263, 292-294 and 313-314

Daptomycin (10 g) was dissolved in dry dimethylformamide (100 ml). N,N'-bis-Boc-guanidinylpyrazole (2.3 g) in dry dimethylformamide (5 ml) was added. The mixture was stirred under nitrogen at room temperature overnight. The mixture was purified on a Bondesi 40μ C8 resin column. The product containing fractions were freeze-dried to give compound 1 (7.4 g) as pale yellow fluffy solid.

Compound 1 (2.6 g) was added to a preparation of deacylase enzyme produced from recombinant *Streptomyces lividans*, which expresses the *Actinoplanes utahensis* deacylase enzyme in ethylene glycol (1.2 ml) and water (25 ml). The pH of the solution was adjusted to 9 with 1.0M sodium hydroxide solution and stirred at room temperature. After 24 hours the mixture was purified on a Bondesi 40μ C8 resin column by eluting with 10% acetonitrile/water, then 40% acetonitrile/water. The product-containing fractions were freeze dried to give deacylated bis-Boc-guanidinylated daptomycin (0.69 g) as a pale yellow solid.

Undecanoyl pentafluorophenol ester (40.3 mg) was added to deacylated bis-Boc-guanidinylated daptomycin (171.5 mg) in dry dimethylformamide (2 ml). The mixture was stirred overnight at room temperature before being concentrated to give compound 255 (105 mg) as a yellow solid.

Compound 255 was dissolved in trifluoroacetic acid (5.5 ml), dichloromethane (4 ml), ethane dithiol (0.25 ml) and triisopropylsilane (0.25 ml). The mixture was stirred for 4 hours at room temperature before being concentrated and purified by preparative HPLC on an IB-SIL 5μ 250×20.2 mm column. The column was eluted at 25 ml/min with acetonitrile and ammonium phosphate buffer 30%-60% gradient for 40 min. The desired fractions were collected at 21 minutes and freeze dried. The freeze-dried residue was dissolved in water and applied to a Bondesil C8 resin column. The column was washed with water and eluted with methanol. Evaporation of the methanol gave compound 260 (27.8 mg) as a pale yellow solid.

In an analogous manner, compounds 254, 256-257, 261, 263, 292-294 and 313-314 can be prepared as detailed in the above example by appropriate substitutions of reagents obvious to those having ordinary skill in the art following the disclosure of the invention.

EXAMPLE 7a

Preparation Of Compounds 258 And 262

Tetradecanoyl pentafluorophenol ester (35.5 mg) and deacylated bis-Boc-guanidinylated daptomycin (102.5 mg) in dry dimethylformamide (2 ml). The mixture was stirred overnight at room temperature before being concentrated to give compound 258 (38.8 mg) as a yellow solid.

Compound 258 (38.8 mg) was dissolved in trifluoroacetic acid (5.5 ml), dichloromethane (4 ml), ethane dithiol (0.25 ml) and triisopropylsilane (0.25 ml). The mixture was stirred for 4 hours at room temperature before being concentrated and purified by preparative HPLC on an IB-SIL 5μ 250×20.2 mm column. The column was eluted at 25 ml/min with acetonitrile and ammonium phosphate buffer 30%-60% gradient for 40 min. The desired fractions were collected at 21 minutes and freeze dried. The freeze-dried residue was dissolved in water and applied to a Bondesil C8 resin column. The column was washed with water and eluted with methanol. Evaporation of the methanol gave compound 262 (2.1 mg) as a pale yellow solid.

EXAMPLE 8

Preparation Of Compound 37, 36 and 192

Daptomycin (162 mg) was stirred in 0.1 M hydrochloric acid (5 ml) at 0° C. for 10 minutes before sodium nitrite (8 mg) in water (0.2 ml) was added dropwise. Sulfamic acid (11 mg) was added after 15 minutes, followed by sodium azide (8 mg) 10 minutes later. The mixture was maintained at 0° C. for 4 hours and then neutralized with a saturated sodium bicarbonate solution and purified by preparative HPLC. An IBSIL-C8 5μ 250×20.2 mm column was loaded with the mixture and eluted at 20 ml/min with 37% acetonitrile in 5 mM ammonium phosphate buffer. Fractions were collected at 6.9 minutes and freeze dried. The freeze-dried residue was dissolved in water (5 ml) and applied to a Bondesil 40μ C8 resin column. The column was washed with water and eluted with methanol. Evaporation of the methanol gave the azido daptomycin as a pale yellow solid (60 mg).

The azido daptomycin (69 mg) was dissolved in dry dimethylformamide (4 ml) and iminobiotin-N-hydroxysuccinimide ester (53 mg) was added. The mixture was covered to exclude light and stirred at ambient temperature for 3 days. The mixture was quenched by the addition of water (20 ml). The resultant mixture was loaded onto a Bondesil 40μ C8 resin (25 g) column, which had been previously washed with methanol and water, and the column was eluted with water. The product-bearing fractions were combined and freeze dried to give Compound 37 as a white solid (49 mg).

In an analogous manner, compounds 36 and 192 can be prepared as detailed in the above example by appropriate substitutions of reagents obvious to those having ordinary skill in the art by following the disclosure of the invention.

EXAMPLE 8a

Preparation Of Compound 200

Daptomycin (1.62 g) in 50% wt aqueous solution of hypophosphorus acid (10 ml) was stirred at 0° C. for 30 minutes before adding dropwise a solution of sodium nitrite (76 mg) in water (0.5 ml). The mixture was allowed to come to room temperature and stirred for 24 hours. The mixture was purified by preparative HPLC by loading the mixture on an IBSIL-C8 5μ 250×20.2 mm column and eluting the column at 20 ml/min with 32% acetonitrile in 5 mM ammonium phosphate buffer. The desired fractions were collected at 30 minutes and freeze dried. The freeze-dried residue was dissolved in water (5 ml) and applied to a Bondesil 40μ C8 resin column. The column was washed with water and eluted with methanol. Evaporation of the methanol gave desamino daptomycin as a pale yellow solid (200 mg).

To desamino daptomycin (80 mg) in dry dimethylformamide (2 ml) was added N-t-butyoxycarbonyl-L-tryptophan-p-nitrophenyl ester (32 mg). The mixture was stirred at room temperature for 24 hours before being purified by preparative HPLC. The mixture was loaded on an IBSIL-C8 5μ 250×20.2 mm column and eluted at 20 ml/min with 40% acetonitrile in 5 mM ammonium phosphate buffer. The desired fractions were collected at 19 minutes and freeze-dried. The freeze-dried residue was dissolved in water (2 ml) and applied to a plug of Bondesil 40μ C8 resin (500 mg). The Bondesil resin was washed with water (10 ml) and then the product was eluted with methanol (10 ml). Evaporation of the methanol gave Boc protected compound 200 as a pale yellow solid (20 mg).

To Boc protected compound 200 (20 mg) in 60% trifluoroacetic acid in dichloromethane (0.5 ml) was added anisole (10 μL). The mixture was stirred at room temperature for 6 hours before being evaporated to dryness. Preparative HPLC purification of the residue was done on an IBSIL-C8 5μ 250×20.2 mm column and eluted at 20 ml/min with 38% acetonitrile in 5 mM ammonium phosphate buffer. The desired fractions were collected at 15 minutes and freeze-dried. The freeze-dried residue was dissolved in water (2 ml) and applied to a plug of Bondesil 40μ C8 resin (500 mg). The Bondesil resin was washed with water (10 ml) and the product was eluted with methanol (10 ml). Evaporation of the methanol gave compound 200 as a pale yellow solid (4 mg).

EXAMPLE 9

Preparation Of Compound 181, 86, 101-102, 206-207, 213-220, 246-251, 264 and 269

Daptomycin (250 mg) and N-tBoc-L-tryptophan-p-nitrophenyl ester (144 mg) were stirred in dry dimethylformamide (3 ml) at room temperature for two days. The mixture was loaded on an IBSIL-C8 5 μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave N-Boc tryptophan daptomycin as a pale yellow solid (130 mg).

A preparation of deacylase enzyme was produced from recombinant *Streptomyces lividans*, which expresses the

*Actinoplanes utahensis* deacylase enzyme. The enzyme in ethylene glycol (400 μl) was added to the solution of N-Boc tryptophan daptomycin (100 mg) in HPLC grade water (20 ml). The solution was adjusted to pH 8.5 with sodium hydroxide (1 M). The mixture was stirred for 24 hours. The mixture was loaded on a C8 resin plug column, washed with water and eluted with methanol. Evaporation of the methanol gave a residue which was applied to an IBSIL-C8 5 μ 250×20.3 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave deactylated N-Boc tryptophan daptomycin as a pale yellow solid (42 mg).

Deacylated N-Boc tryptophan daptomycin (20 mg) was stirred in dry dimethylformamide (2 ml) at room temperature. Undecyl isocyanate (2.25 mg) was added to the solution. After stirring at ambient temperature for 24 hours, the mixture was diluted with water (10 ml) and applied to a Bondesil 40 μ C8 resin column, washed with water and eluted with methanol. Evaporation of the methanol gave the undecyl urea of N-Boc tryptophan daptomycin as a pale yellow solid (21 mg).

N-Boc tryptophan daptomycin undecyl urea (21 mg) was stirred in trifluoroacetic acid (2 ml) and anisole (0.1 ml) at room temperature for 2 hours. Removal of the solvents under reduced pressure gave a residue which was loaded on an IBSIL-C8 5 μ150×20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave compound 181 as a pale yellow solid (0.8 mg).

In an analogous manner, compounds 86, 101-102, 206-207, 213-220, 246-251, 264 and 269 can be prepared as detailed in the above example by appropriate substitutions of reagents obvious to those having ordinary skill in the art following the disclosure of the invention.

EXAMPLE 9a

Preparation Of Compound 205

Deacylated N-Boc tryptophan daptomycin (50 mg) and nonaldehyde (4.1 mg) were stirred in dry dimethylformamide (2 ml) at room temperature. Sodium triacetoxy borohydride (3.6 mg) was added to the solution. The mixture was stirred for 24 hours, then loaded on an IBSIL-C8 5 μ 250×20.2 mm column and eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave nonyl amino N-Boc tryptphan daptomycin as a pale yellow solid (14 mg).

Nonyl amino N-Boc tryptphan daptomycin (14 mg) was stirred in trifluoroacetic acid (2 ml) and anisole (0.1 ml) at room temperature for 2 hours. Removal of the solvents under reduced pressure gave a residue which was loaded on an IBSIL-C8 5 μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave compound 7 as a pale yellow solid (5 mg).

EXAMPLE 10

Preparation Of Compounds 356, 315-322, 332-337, 345-349 And 355

Daptomycin (5.0 g) was dissolved in water (25 ml) and adjusted to pH 9 with 5M sodium hydroxide. Di-tert-butyl-dicarbonate (1.5 g) was added and the mixture was adjusted to maintain pH 9 with 5 M sodium hydroxide until the reaction was complete (4 hours). The pH was adjusted to 7 and the mixture was loaded onto a Bondesil 40μ C8 resin column. The column was washed with water and the product was eluted from the column with methanol. Evaporation of the methanol gave Boc-protected daptomycin (5.08 g) as a yellow powder.

A preparation of deacylase enzyme was produced from recombinant *Streptomyces lividans*, which expresses the *Actinoplanes utahensis* deacylase enzyme. The enzyme is ethylene glycol (400 μl) was added to Boc-protected daptomycin (1 g) in water (100 ml) at pH 7-8. After incubation for 72 hours, the mixture was loaded on a Bondesil 40μ C8 resin column. The column was washed with water and the product was eluted from the column with 10% acetonitrile in water. The solvent was removed by evaporation to give deacylated Boc-protected daptomycin (440 mg) as a yellow powder.

Daptomycin undecyl urea synthesized from deacylated Boc protected daptomycin above using undecyl isocyanate instead of undecanoyl pentafluorophenol ester according to example 7 (100 mg) and 5-methoxyindole-3-carboxaldehyde (11 mg) in dry dimethylformamide (0.6 ml) was added sodium triacetoxyborohydride (76 mg). The mixture was stirred at room temperature for 24 hours before purification by preparative HPLC. The mixture was loaded on an IBSIL-C8 5μ250×20.2 mm column and eluted at 25 ml/min with 30-60% acetonitrile in 5 mM ammonium phosphate gradient over 30 minutes. The desired fractions were collected at 21 minutes and freeze-dried. The freeze-dried residue was dissolved in water (2 ml) and applied to a plug of Bondesil 40μ C8 resin (500 mg). The Bondesil resin was washed with water (10 ml) and then the product was eluted with methanol (10 ml). Evaporation of the methanol gave compound 114 as a pale yellow solid (10 mg).

In an analogous manner, compounds 315-322, 332-337, 345-349 and 355 can be prepared as detailed in the above example by appropriate substitutions of reagents obvious to those skilled in the art.

EXAMPLE 10a

Preparation Of Compounds 307, 310, 295-306, 308-309, 311-312, 338-344 And 350-352

Daptomycin undecanoyl amide synthesized from deacylated Boc protected daptomycin by using undecanoyl pentafluorophenol ester according to examples 10 and 7 (60 mg) was stirred in dry dimethylformamode (2 ml) at room temperature. N-tBoc-L-tryptophan-p-nitrophenyl ester (31 mg) was added to the solution. The mixture was stirred for 24 hours. The mixture was loaded onto an IBSIL-C8 5 μ 250× 20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave compound 307 as a pale yellow solid (25 mg).

Compound 307 (20 mg) was stirred in trifluoroacetic acid (2 ml) and anisole (0.1 ml) at room temperature for 2 hours. Removal of the solvents under reduced pressure gave a residue which was loaded on an IBSIL-C8 5 μ 250×20.2 mm column and was eluted at 20 ml/min with 37% acetonitrile in 5 mM ammonium phosphate buffer. Fractions containing the desired compound were collected and freeze-dried. The freeze-dried residue was dissolved in water (5 ml) and applied to a Bondesil 40 μ C8 resin column, washed with water and eluted with methanol. Evaporation of the methanol gave compound 310 as a pale yellow solid (4 mg).

In an analogous manner, compounds 295-306, 308-309, 311-312, 338-344 and 350-352 can be prepared as detailed in the above example by appropriate substitutions of reagents obvious to those skilled in the art.

EXAMPLE 11

Compounds according to Formula I were tested for antimicrobial activity against a panel of organisms according to standard procedures described by the National Committee for Clinical Laboratory Standards (NCCLS document M7-A5, Vol. 20, Nov. 2, 2000) except that all testing was performed at 37° C. Compounds were dissolved in 100% dimethyl sulfoxide and were diluted to the final reaction concentration (0.1 μg/mL-100 μg/mL) in microbial growth media. In all cases the final concentration of dimethyl sulfoxide incubated with cells is less than or equal to 1%. For minimum inhibitory concentration (MIC) calculations, 2-fold dilutions of compounds were added to wells of a microtiter plate containing $5 \times 10^4$ bacterial cells in a final volume of 100 μL of media (Mueller-Hinton Broth supplemented with 50 mg/L $Ca^{2+}$). The optical densities (OD) of the bacterial cells, which measures bacterial cell growth and proliferation, were measured using a commercial plate reader. The MIC value is defined as the lowest compound concentration inhibiting growth of the test organism. The MIC (in μg/ml) values of representative compounds of the present invention are listed in Table III.

EXAMPLE 12

The mouse protection test is an industry standard for measuring the efficacy of a test compound in vivo [for examples of this model see J. J. Clement, et al., *Antimicrobial Agents and Chemotherapy*, 38 (5), 1071-1078, (1994)]. As exemplified below, this test is used to demonstrate the in vivo efficacy of the compounds of the present invention against bacteria.

The in vivo antibacterial activity was established by infecting female CD-1 mice (Charles River Lab, Mass.) weighing 19-23 g intraperitoneally with from Methicillin Resistant *S. aureus* (MRSA) inoculum. The inoculum was prepared from Methicillin Resistant *S. aureus* (ATCC 43300). The MRSA inoculum was cultured in Mueller-Hinton (MH) broth at 37° C. for 18 hours. The optical density at 600 nm ($OD_{600}$) was determined for a 1:10 dilution of the overnight culture. Bacteria ($8 \times 10^8$ cfu) was added to 20 ml of phosphate buffered saline (Sigma P-0261) containing 5% hog gastric mucin (Sigma M-2378). All animals were injected with 0.5 ml of the inoculum, equivalent to $2 \times 10^7$ cfu/mouse, which is the dose causing ~100% death of the animals without treatment.

The test compound was dissolved in 10.0 ml of 50 mM phosphate buffer to give a solution of 1 mg/ml (pH=7.0). This solution was serially diluted with vehicle by 4-fold (1.5 ml to 6.0 ml) to give 0.25, 0.063 and 0.016 mg/ml solutions. All the solutions were filtered with 0.2 m Nalgene syringe filter. Immediately after the bacterial inoculation, group 1 animals were subcutaneously (sc) injected with buffer (no test compound) and groups 2 to 5 were given test compound sc at 10.0, 2.5, 0.63, and 0.16 mg/kg, respectively. Group 6 animals received test compound sc at 10 mg/kg (or the highest therapeutic dose of a given compound) only for monitoring acute toxicity. These injections were repeated once at 4 hours after the inoculation for the respective groups. The injection volume at each time was 10 ml per kilogram of body weight. The results of the in vivo efficacy test are summarized in Table II, which provides a representative example of the results obtained for Compound 70. The 50% effective dose ($ED_{50}$) is calculated on the basis of the number of mice surviving 7 days after inoculation. The ED50 was determined for other compounds of this invention in a similar manner. The $ED_{50}$ in mg/kg of other representative compounds of the present invention are listed in Table III.

TABLE II

| Group | # of mice | Inoculated with | Treatment | Survival (7 days) |
|---|---|---|---|---|
| 1 | 5 | MRSA #43300 $2 \times 10^7$ cfu/mouse | Phosphate buffer 10 ml/kg, s.c. × 2 | 0/5 |
| 2 | 5 | MRSA #43300 $2 \times 10^7$ cfu/mouse | Compound 70 10 mg/kg, s.c. × 2 | 5/5 |
| 3 | 5 | MRSA #43300 $2 \times 10^7$ cfu/mouse | Compound 70 2.5 mg/kg, s.c. × 2 | 3/5 |
| 4 | 5 | MRSA #43300 $2 \times 10^7$ cfu/mouse | Compound 70 0.63 mg/kg, s.c. × 2 | 1/5 |
| 5 | 5 | MRSA #43300 $2 \times 10^7$ cfu/mouse | Compound 70 0.16 mg/kg, s.c. × 2 | 0/5 |
| 6 | 5 | No | Compound 70 10 mg/kg, s.c. × 2 | 5/5 |

The $ED_{50}$ of compound 70 is calculated to be 1.51 mg/kg

TABLE III

| Compound # | MIC (μg/ml) S. aureus | MIC (μg/ml) E. faecalis | $ED_{50}$ mg/kg S. aureus |
|---|---|---|---|
| 1 | ++ | + | ++ |
| 2 | +++ | + | +++ |
| 3 | ++ | + | |
| 4 | + | + | |
| 5 | ++ | ++ | |
| 6 | ++ | ++ | |
| 7 | ++ | ++ | |
| 8 | ++ | ++ | |
| 9 | +++ | ++ | |
| 10 | +++ | + | ++ |
| 11 | ++ | + | |
| 12 | +++ | ++ | |
| 13 | +++ | ++ | |
| 14 | ++ | ++ | |
| 15 | ++ | ++ | |
| 16 | +++ | ++ | |
| 17 | ++ | ++ | |
| 18 | ++ | + | |
| 19 | ++ | ++ | |
| 20 | +++ | ++ | |
| 21 | ++ | + | |
| 22 | ++ | ++ | |
| 23 | +++ | ++ | |
| 24 | +++ | ++ | ++ |
| 25 | +++ | ++ | |
| 26 | +++ | ++ | |
| 27 | ++ | + | |
| 28 | ++ | + | |
| 29 | + | | |
| 30 | ++ | + | |

TABLE III-continued

| Compound # | MIC (µg/ml) S. aureus | MIC (µg/ml) E. faecalis | ED$_{50}$ mg/kg S. aureus |
|---|---|---|---|
| 31 | ++ | + | |
| 32 | ++ | + | |
| 33 | ++ | + | |
| 34 | ++ | + | |
| 35 | ++ | + | |
| 36 | ++ | + | |
| 37 | ++ | + | |
| 38 | +++ | + | |
| 39 | + | + | |
| 40 | ++ | + | |
| 41 | + | + | |
| 42 | ++ | + | |
| 43 | ++ | + | |
| 44 | ++ | ++ | |
| 45 | +++ | ++ | +++ |
| 46 | ++ | ++ | |
| 47 | ++ | ++ | |
| 48 | +++ | ++ | |
| 49 | ++ | ++ | |
| 50 | ++ | + | |
| 51 | ++ | ++ | |
| 52 | +++ | + | |
| 53 | ++ | + | |
| 54 | ++ | ++ | ++ |
| 55 | +++ | + | |
| 56 | +++ | ++ | |
| 57 | ++ | + | |
| 58 | +++ | + | |
| 60 | ++ | + | |
| 61 | ++ | + | |
| 62 | ++ | + | |
| 63 | ++ | + | |
| 64 | ++ | + | |
| 65 | ++ | + | |
| 66 | ++ | + | |
| 67 | ++ | + | |
| 68 | ++ | + | |
| 69 | ++ | + | |
| 70 | +++ | + | ++ |
| 71 | ++ | + | |
| 72 | ++ | + | |
| 73 | ++ | + | |
| 74 | ++ | | |
| 75 | ++ | + | |
| 76 | +++ | ++ | ++ |
| 77 | ++ | ++ | |
| 78 | + | + | |
| 79 | +++ | ++ | |
| 80 | +++ | ++ | |
| 81 | +++ | ++ | +++ |
| 82 | +++ | ++ | |
| 83 | +++ | ++ | |
| 84 | +++ | ++ | |
| 85 | +++ | ++ | +++ |
| 86 | + | + | |
| 87 | +++ | ++ | |
| 88 | ++ | + | |
| 89 | +++ | ++ | |
| 90 | ++ | ++ | |
| 91 | ++ | + | |
| 92 | ++ | + | |
| 93 | ++ | ++ | |
| 94 | +++ | ++ | |
| 95 | +++ | ++ | |
| 96 | +++ | ++ | |
| 97 | +++ | ++ | |
| 98 | +++ | ++ | |
| 99 | +++ | ++ | |
| 100 | +++ | ++ | |
| 101 | ++ | ++ | |
| 102 | +++ | +++ | |
| 103 | +++ | + | |
| 104 | ++ | ++ | |
| 105 | +++ | ++ | |
| 106 | +++ | ++ | |
| 107 | ++ | ++ | |
| 108 | ++ | ++ | |
| 109 | ++ | ++ | |
| 110 | ++ | ++ | |
| 111 | +++ | ++ | |
| 112 | ++ | + | |
| 113 | ++ | ++ | |
| 114 | ++ | + | |
| 115 | +++ | + | |
| 116 | +++ | ++ | |
| 117 | ++ | ++ | |
| 118 | ++ | ++ | |
| 119 | +++ | ++ | |
| 120 | ++ | ++ | |
| 121 | +++ | ++ | |
| 122 | +++ | + | |
| 123 | ++ | + | |
| 124 | ++ | + | |
| 125 | ++ | ++ | |
| 126 | ++ | ++ | |
| 127 | +++ | ++ | |
| 128 | ++ | ++ | |
| 129 | +++ | + | |
| 130 | +++ | ++ | |
| 131 | +++ | + | |
| 132 | ++ | ++ | |
| 133 | +++ | ++ | |
| 134 | ++ | + | |
| 135 | +++ | + | |
| 136 | +++ | ++ | |
| 137 | ++ | + | |
| 138 | +++ | + | |
| 139 | +++ | ++ | |
| 140 | +++ | ++ | |
| 141 | ++ | + | |
| 142 | +++ | + | |
| 143 | ++ | + | |
| 144 | +++ | ++ | |
| 145 | ++ | ++ | |
| 146 | +++ | + | |
| 147 | +++ | ++ | |
| 148 | ++ | ++ | |
| 149 | ++ | + | |
| 150 | +++ | ++ | |
| 151 | +++ | ++ | |
| 152 | ++ | ++ | |
| 153 | ++ | + | |
| 154 | ++ | ++ | |
| 155 | ++ | ++ | |
| 156 | +++ | + | |
| 157 | ++ | + | |
| 158 | ++ | + | |
| 159 | +++ | + | |
| 160 | ++ | + | |
| 161 | +++ | + | |
| 162 | ++ | ++ | |
| 163 | +++ | ++ | |
| 164 | +++ | ++ | |
| 165 | ++ | ++ | |
| 166 | +++ | ++ | |
| 167 | +++ | ++ | |
| 168 | +++ | ++ | |
| 169 | +++ | + | |
| 170 | ++ | ++ | |
| 171 | ++ | ++ | |
| 172 | +++ | ++ | |
| 173 | +++ | ++ | |
| 174 | +++ | ++ | |
| 175 | ++ | ++ | |
| 176 | +++ | ++ | |
| 177 | + | + | |
| 178 | ++ | + | |
| 179 | ++ | + | |
| 180 | ++ | ++ | |
| 181 | +++ | +++ | +++ |

TABLE III-continued

| Compound # | MIC (µg/ml) S. aureus | MIC (µg/ml) E. faecalis | ED$_{50}$ mg/kg S. aureus |
|---|---|---|---|
| 182 | ++ | + | |
| 183 | +++ | + | |
| 184 | +++ | + | |
| 185 | ++ | + | |
| 186 | ++ | + | |
| 187 | +++ | + | |
| 189 | | | |
| 190 | | | |
| 192 | ++ | + | |
| 193 | ++ | + | |
| 194 | ++ | + | |
| 195 | ++ | + | |
| 196 | +++ | + | |
| 197 | ++ | + | |
| 198 | ++ | + | |
| 199 | +++ | + | |
| 200 | + | | |
| 201 | ++ | ++ | |
| 202 | | | |
| 203 | ++ | + | |
| 204 | +++ | ++ | |
| 205 | ++ | + | |
| 206 | | | |
| 207 | | | |
| 208 | ++ | ++ | |
| 209 | +++ | ++ | |
| 210 | +++ | ++ | |
| 211 | | ++ | |
| 212 | +++ | ++ | +++ |
| 213 | | | |
| 214 | | | |
| 215 | | | |
| 216 | ++ | + | |
| 217 | | | |
| 218 | + | | |
| 219 | +++ | ++ | |
| 220 | +++ | +++ | |
| 221 | + | + | |
| 222 | ++ | ++ | |
| 223 | +++ | ++ | |
| 224 | ++ | + | |
| 225 | ++ | + | |
| 226 | ++ | + | |
| 227 | +++ | ++ | |
| 228 | +++ | ++ | |
| 229 | +++ | ++ | |
| 230 | +++ | +++ | |
| 231 | +++ | ++ | |
| 232 | +++ | ++ | |
| 233 | ++ | + | |
| 234 | ++ | + | |
| 235 | +++ | ++ | |
| 236 | ++ | + | |
| 237 | +++ | ++ | |
| 238 | +++ | ++ | |
| 239 | +++ | + | |
| 240 | +++ | ++ | |
| 241 | ++ | ++ | |
| 242 | ++ | + | |
| 243 | ++ | + | |
| 244 | +++ | ++ | |
| 245 | | | |
| 246 | + | | |
| 247 | + | | |
| 248 | + | | |
| 249 | + | | |
| 250 | +++ | + | |
| 251 | ++ | + | |
| 252 | ++ | ++ | |
| 253 | +++ | ++ | |
| 254 | ++ | + | |
| 255 | +++ | ++ | |
| 256 | +++ | +++ | |
| 257 | ++ | + | |
| 258 | +++ | ++ | |
| 259 | +++ | +++ | |
| 260 | +++ | ++ | |
| 261 | ++ | ++ | |
| 262 | ++ | ++ | |
| 263 | +++ | ++ | |
| 264 | ++ | + | |
| 265 | ++ | ++ | |
| 266 | +++ | + | |
| 267 | ++ | + | |
| 268 | ++ | ++ | |
| 269 | + | | |
| 270 | +++ | + | |
| 271 | +++ | +++ | |
| 272 | ++ | + | |
| 273 | +++ | ++ | |
| 274 | +++ | +++ | |
| 275 | +++ | ++ | |
| 276 | +++ | +++ | |
| 277 | +++ | +++ | |
| 278 | +++ | +++ | |
| 279 | +++ | ++ | |
| 280 | +++ | ++ | |
| 281 | +++ | ++ | |
| 282 | +++ | +++ | +++ |
| 283 | +++ | ++ | |
| 284 | +++ | +++ | |
| 285 | +++ | +++ | +++ |
| 286 | +++ | +++ | |
| 287 | +++ | +++ | |
| 288 | +++ | +++ | |
| 289 | +++ | ++ | |
| 290 | ++ | ++ | |
| 291 | +++ | +++ | |
| 292 | +++ | ++ | |
| 293 | +++ | ++ | |
| 294 | ++ | + | |
| 295 | | ++ | |
| 296 | | | |
| 297 | | ++ | |
| 298 | | | |
| 299 | | ++ | |
| 300 | | ++ | |
| 301 | +++ | ++ | |
| 302 | +++ | ++ | |
| 303 | +++ | ++ | |
| 304 | | | |
| 305 | +++ | ++ | |
| 306 | +++ | ++ | |
| 307 | +++ | ++ | |
| 308 | +++ | ++ | |
| 309 | +++ | ++ | |
| 310 | +++ | ++ | |
| 311 | +++ | | |
| 312 | | | |
| 313 | +++ | | |
| 314 | +++ | ++ | |
| 315 | ++ | + | |
| 316 | +++ | | |
| 317 | | | |
| 318 | +++ | +++ | |
| 319 | +++ | ++ | |
| 320 | +++ | ++ | |
| 321 | +++ | ++ | |
| 322 | +++ | ++ | |
| 323 | +++ | ++ | |
| 324 | | ++ | |
| 325 | +++ | ++ | |
| 326 | +++ | ++ | |
| 327 | +++ | ++ | |
| 328 | | ++ | |
| 329 | | | |
| 330 | +++ | ++ | |
| 331 | | ++ | |
| 332 | +++ | ++ | |
| 333 | | ++ | |

TABLE III-continued

| Compound # | MIC (µg/ml) S. aureus | MIC (µg/ml) E. faecalis | ED$_{50}$ mg/kg S. aureus |
|---|---|---|---|
| 334 | +++ | +++ | |
| 335 | +++ | ++ | |
| 336 | +++ | ++ | |
| 337 | +++ | +++ | |
| 338 | ++ | ++ | |
| 339 | +++ | ++ | |
| 340 | + | + | |
| 341 | ++ | ++ | |
| 342 | +++ | ++ | |
| 343 | +++ | ++ | |
| 344 | +++ | ++ | |
| 345 | ++ | +++ | |
| 346 | +++ | +++ | |
| 347 | ++ | + | |
| 348 | ++ | + | |
| 349 | ++ | + | |
| 350 | ++ | + | |
| 351 | ++ | ++ | |
| 352 | ++ | ++ | |
| 355 | ++ | ++ | |
| 356 | +++ | +++ | |
| 358 | ++ | ++ | |
| 359 | +++ | | |
| 360 | +++ | ++ | |
| 361 | +++ | | |
| 362 | +++ | ++ | |
| 363 | +++ | | |
| 364 | +++ | ++ | |
| 365 | +++ | | |
| 366 | +++ | ++ | |
| 367 | +++ | ++ | |
| 368 | +++ | ++ | |
| 369 | +++ | | |
| 370 | +++ | ++ | |
| 371 | +++ | ++ | |
| 372 | +++ | ++ | |
| 373 | +++ | ++ | |
| 374 | +++ | ++ | |
| 375 | +++ | | |
| 376 | +++ | ++ | |
| 377 | +++ | ++ | |
| 378 | +++ | ++ | |
| 379 | +++ | ++ | |
| 380 | +++ | ++ | |
| 381 | +++ | ++ | |
| 382 | +++ | ++ | |
| 383 | +++ | ++ | |
| 384 | +++ | ++ | |
| 385 | +++ | ++ | |
| 386 | +++ | ++ | |
| 387 | +++ | +++ | |
| 388 | ++ | ++ | |
| 389 | +++ | ++ | |
| 390 | +++ | ++ | |
| 391 | +++ | ++ | |
| 392 | +++ | ++ | |
| 393 | +++ | ++ | |
| 394 | +++ | ++ | |
| 395 | +++ | ++ | |

Wherein "+++" indicates that the compound has an MIC (µg/ml) of 1 µg/ml or less or an ED$_{50}$ of 1 mg/kg or less;
"++" indicates that the compound has an MIC (µg/ml) or ED$_{50}$ of greater than 1 µg/ml or 1 mg/kg, respectively but less than or equal to 10 µg/ml or ED$_{50}$ of 10 mg/kg, respectively; and
"+" indicates that the compound has an MIC (µg/ml) of greater than 10 µg/ml or an ED$_{50}$ of greater than 10 mg/kg.

All publications and patent applications cited in this specification are herein incorporated by reference as if each individual publication or patent application were specifically and individually indicated to be incorporated by reference. Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

We claim:
1. A compound having the formula (I):

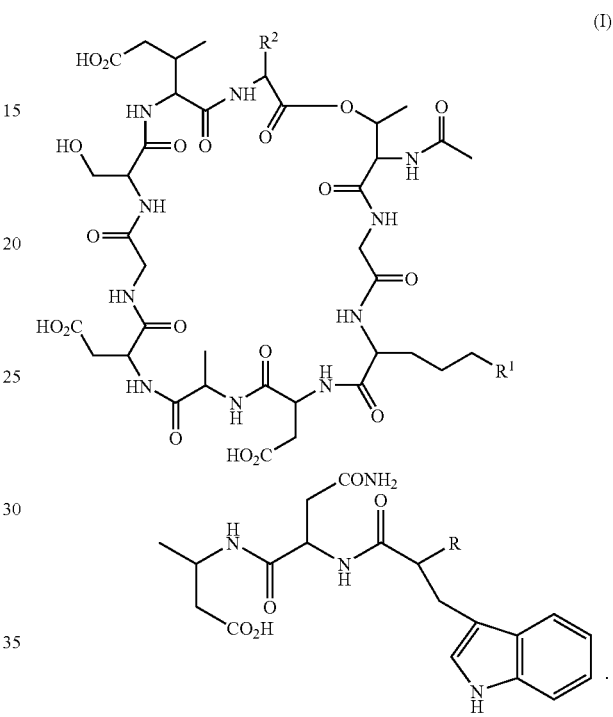

and salts thereof;
wherein R is:

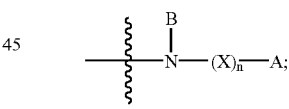

wherein X' and X" are independently C=O, C=S, C=NH, C=NR$^X$, S=O or SO$_2$;
wherein n is 0 or 1;
wherein R$^X$ is alkyl, alkenyl, alkynyl, aryl, heteroaryl, cycloalkyl, heterocyclyl, hydroxyl, alkoxy, carboxy or carboalkoxy;
wherein B is X"R$^Y$, H, alkyl, alkenyl, alkynyl, aryl, heteroaryl, cycloalkyl or heterocyclyl;
wherein R$^Y$ is hydrido, alkyl, alkenyl, alkynyl, aryl, heteroaryl, cycloalkyl, heterocyclyl or hydroxyl;
wherein A is H, NH$_2$, NHR$^A$, NR$^A$R$^B$, alkyl, alkenyl, alkynyl, alkoxy, aryloxy, aryl, heteroaryl, cycloalkyl or heterocyclyl;
wherein R$^A$ and R$^B$ are independently alkyl, alkenyl, alkynyl, aryl, heteroaryl, cycloalkyl, heterocyclyl or carboalkoxy;
wherein when n is 0, then A is additionally:

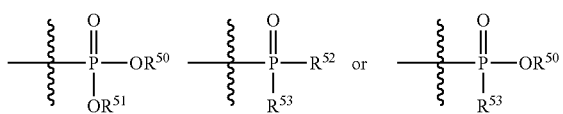

wherein each of $R^{50}$-$R^{53}$ is independently $C_1$-$C_{15}$ alkyl;
alternatively, wherein B and A together form a 5-7 membered heterocyclic or heteroaryl ring;
wherein $R^1$ is

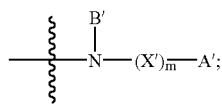

wherein X' and X''' are independently C=O, C=S, C=NH, C=NR$^{X'}$, S=O or SO$_2$;
wherein m is 0 or 1;
wherein $R^{X'}$ is alkyl, alkenyl, alkynyl, aryl, heteroaryl, cycloalkyl, heteorcyclyl, hydroxyl, alkoxy, carboxy or carboalkoxy;
wherein B' is X'''R$^{Y'}$, H, alkyl, alkenyl, alkynyl, aryl, heteroaryl, cycloalkyl or heterocyclyl;
wherein $R^{Y'}$ is hydrido, alkyl, alkenyl, alkynyl, aryl, heteroaryl, cycloalkyl, heterocyclyl or hydroxyl;
wherein A' is unsubstituted alkyl, alkenyl, alkynyl, alkoxy, aryloxy; or alkyl wherein one or more hydrogen atoms is replaced by a substituent group selected from acyl, amino, acylamino, acyloxy, carboalkoxy, carboxy, carboxyamido, cyano, halo, hydroxyl, nitro, thio, alkenyl, alkynyl, cycloalkyl, heterocyclyl, aryl, heteroaryl, alkoxy, aryloxy, sulfinyl, sulfonyl, oxo, guanidino, and formyl;
provided that when B' is H then (X')$_m$-A' is other than
 (a) —C(O)(C$_1$-C$_{16}$ unsubstituted alkyl)-NH$_2$;
 (b) —C(O)(C$_1$-C$_{10}$ unsubstituted alkyl)-NHC(O)R$^D$, wherein R$^D$ is —C$_1$-C$_{18}$ unsubstituted alkyl, or —C$_1$-C$_{18}$ selected substituted alkyl wherein one proton is replaced by a hydroxyl, carboxyl or C$_1$-C$_3$ alkoxy, or one to three protons is replaced by a halo substituent;
 (c) —C(O)C$_1$-C$_{18}$ unsubstituted alkyl;
 (d) —C(O)C$_4$-C$_{18}$ unsubstituted alkenyl;

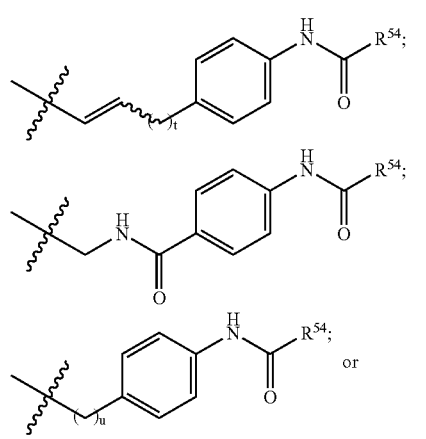

wherein R$^{54}$ is selected from C$_1$-C$_{17}$-unsubstituted alkyl or C$_2$-C$_{17}$-unsubstituted alkenyl; wherein R$^{55}$ is selected from hyroxyethyl, hydroxymethyl, mercaptomethyl, mercaptoethyl, methylthioethyl, 2-thienyl, 3-indolemthyl, phenyl optionally substituted with a group selected from halo, nitro, C$_1$-C$_3$-unsubstituted alkyl, hydroxy, C$_1$-C$_3$-unsubstituted alkoxy, C$_1$-C$_3$-unsubstituted alkylthio, carbamyl or C$_1$-C$_3$ unsubstituted alkylcarbamyl; or benzyl optionally substituted with a group selected from halo, nitro, C$_1$-C$_3$-unsubstituted alkyl, hydroxy, C$_1$-C$_3$-unsubstituted alkoxy, C$_1$-C$_3$-unsubstituted alkylthio, carbamyl or C$_1$-C$_3$ unsubstituted alkylcarbamyl; wherein t is 0 or 1 and wherein u is an integer from 1-3;
 (f) —C(O)C$_1$-C$_{18}$ selected unsubstituted alkyl wherein one proton is replaced by a hydroxyl, carboxyl or C$_1$-C$_3$ alkoxy, or one to three protons is replaced by a halo substituent; and
 (g) an amino protecting group; and
wherein when B' is H and m is 0, then A' is other than C$_4$-C$_{14}$ unsubstituted alkyl;
wherein R$^2$ is

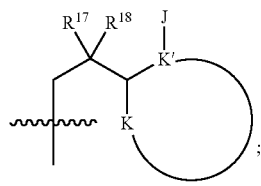

wherein K and K' together form a C$_3$-C$_7$ cycloalkyl or heterocyclyl ring or a C$_5$-C$_{10}$ aryl or heteroaryl ring;
wherein J is hydrido, amino, NHR$^J$, NR$^J$R$^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

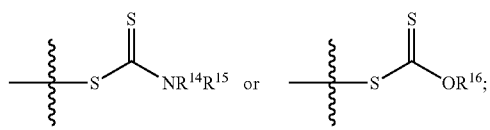

wherein each of R$^{24}$, R$^{25}$, and R$^{26}$ is independently alkyl, cycloalkyl, heterocyclyl, aryl or heteroaryl; or R$^{24}$ and R$^{25}$ together form a 5-8 membered heterocyclyl ring;
wherein R$^J$ and R$^K$ are independently alkyl, alkenyl, alkynyl, aryl, heteroaryl, cycloalkyl or heterocyclyl;
alternatively, wherein J together with R$^{17}$, forms a 5-8 membered heterocyclyl or cycloalkyl ring; or
alternatively, wherein J, together with both R$^{17}$ and R$^{18}$, forms a 5-8 membered aryl, cycloalkyl, heterocyclyl or heteroaryl ring; and
wherein each of R$^{17}$ and R$^{18}$ is independently hydrido, halo, hydroxyl, alkoxy, amino, thio, sulfinyl, sulfonyl or

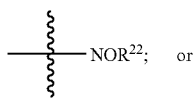

wherein $R^{17}$ and $R^{18}$ taken together can form a ketal, thioketal,

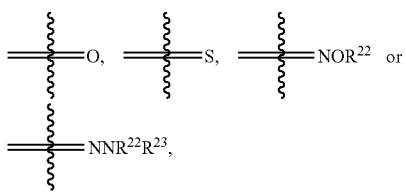

wherein each of $R^{22}$ and $R^{23}$ is independently hydrido or alkyl.

2. A compound having the formula (I):

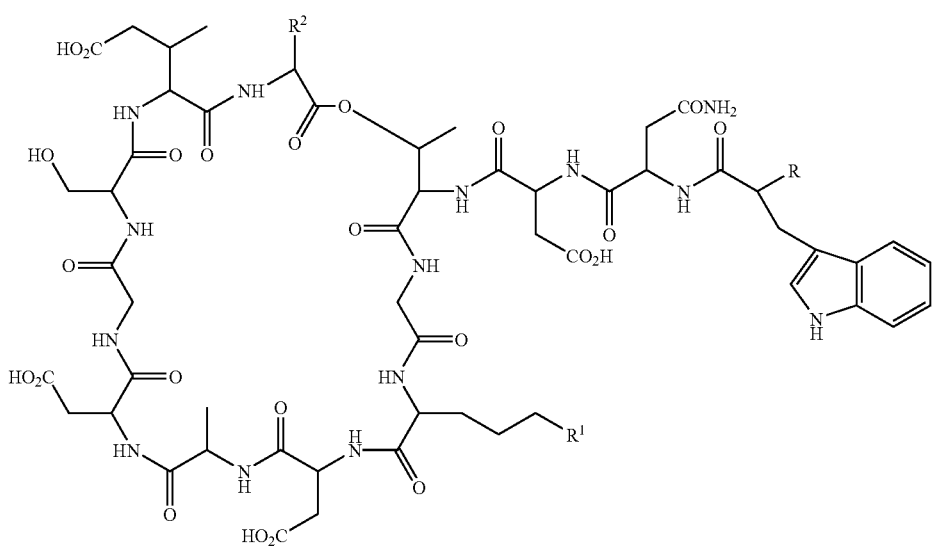

and salts thereof;
wherein R is:

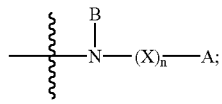

wherein X and X' are independently C=O, C=S, C=NH, C=NR$^X$, S=O or SO$_2$;
wherein n is 0 or 1;
wherein $R^X$ is alkyl, alkenyl, alkynyl, aryl, heteroaryl, cycloalkyl, heterocyclyl, hydroxyl, alkoxy, carboxy or carboalkoxy;
wherein B is X"R$^Y$, H, alkyl, alkenyl, alkynyl, aryl, heteroaryl, cycloalkyl or heterocyclyl;

wherein R$^Y$ is hydrido, alkyl, alkenyl, alkynyl, aryl, heteroaryl, cycloalkyl, heterocyclyl or hydroxyl;
wherein A is H, NH$_2$, NHR$^A$, NR$^A$R$^B$, alkyl, alkenyl, alkynyl, alkoxy, aryloxy, aryl, heteroaryl, cycloalkyl or heterocyclyl;
wherein R$^A$ and R$^B$ are independently alkyl, alkenyl, alkynyl, aryl, heteroaryl, cycloalkyl, heterocyclyl or carboalkoxy;
wherein when n is 0, then A is additionally:

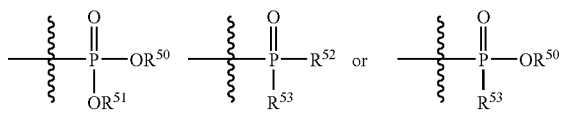

wherein each of $R^{50}$-$R^{53}$ is independently $C_1$-$C_{15}$ alkyl;
alternatively, wherein B and A together form a 5-7 membered heterocyclic or heteroaryl ring;
wherein $R^1$ is

wherein X' and X'" are independently C=O, C=S, C=NH, C=NR$^{X'}$ S=O or SO$_2$;
wherein m is 0 or 1;
wherein $R^{X'}$ is alkyl, alkenyl, alkynyl, aryl, heteroaryl, cycloalkyl, heterocyclyl, hydroxyl, alkoxy, carboxy or carboalkoxy;
wherein B' and A' together form a 5-7 membered heterocyclic or heteroaryl ring;
wherein $R^{A'}$ and $R^{B'}$ are independently alkyl, alkenyl, alkynyl, aryl, heteroaryl, cycloalkyl, heterocyclyl or carboalkoxy;

wherein $R^2$ is

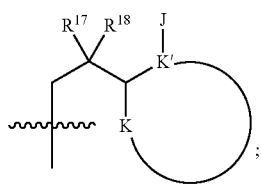

wherein K and K' together form a $C_3$-$C_7$ cycloalkyl or heterocyclyl ring or a $C_5$-$C_{10}$ aryl or heteroaryl ring;
wherein J is hydrido, amino, $NHR^J$, $NR^JR^K$, alkyl, alkenyl, alkynyl, alkoxy, aryloxy, aryl, heteroaryl, cycloalkyl, heterocyclyl, alkylamino, hydroxyl, thio, alkylthio, alkenylthio, sulfinyl, sulfonyl, azido, cyano, halo,

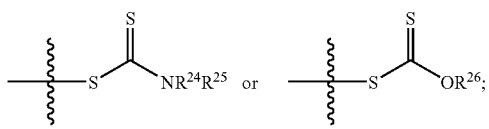

wherein each of $R^{24}$, $R^{25}$, and $R^{26}$ is independently alkyl, cycloalkyl, heterocyclyl, aryl and heteroaryl; or $R^{24}$ and $R^{25}$ together form a 5-8 membered heterocyclyl ring;
wherein $R^J$ and $R^K$ are independently alkyl, alkenyl, alkynyl, aryl, heteroaryl, cycloalkyl or heterocyclyl; or
alternatively, wherein J, together with $R^{17}$, forms a 5-8 membered heterocyclyl or cycloalkyl ring; or
alternatively, wherein J, together with both $R^{17}$ and $R^{18}$, forms a 5-8 membered aryl, cycloalkyl, heterocyclyl or heteroaryl ring; and
wherein each of $R^{17}$ and $R^{18}$ is of hydrido, halo, hydroxyl, alkoxy, amino, thio, sulfinyl, sulfonyl or

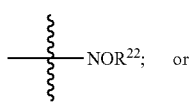

wherein $R^{17}$ and $R^{18}$ taken together can form a ketal, thioketal,

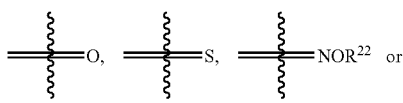

-continued

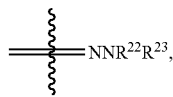

wherein each of $R^{22}$ and $R^{23}$ is independently hydrido or alkyl.

3. The compound according to either of claims 1 or 2, wherein R is

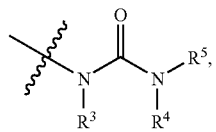 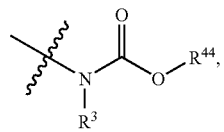

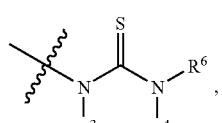 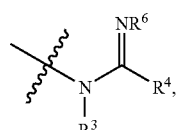

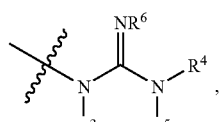 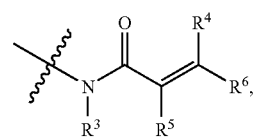

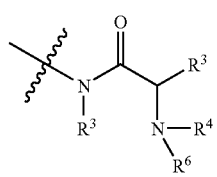 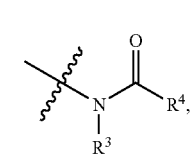

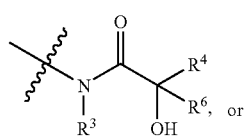 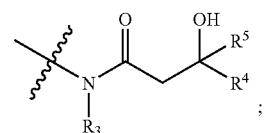

wherein each of $R^3$, $R^4$ $R^5$, and $R^6$ is independently hydrido, alkyl, aryl, heterocyclyl or heteroaryl, and wherein $R^{44}$ alkyl, aryl, heterocyclyl or heteroaryl.

4. The compound according to claim 3, wherein R is

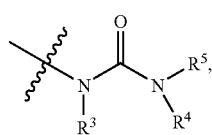 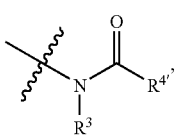

-continued

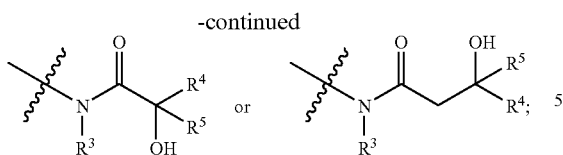

wherein R⁴ is alkyl, aryl-substituted alkyl, substituted phenyl, heteroaryl, heterocyclyl, optionally substituted ($C_8$-$C_{14}$)-straight chain alkyl or

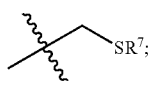

wherein $R^7$ is an alkyl group.

5. The compound according to claim 4, wherein R is

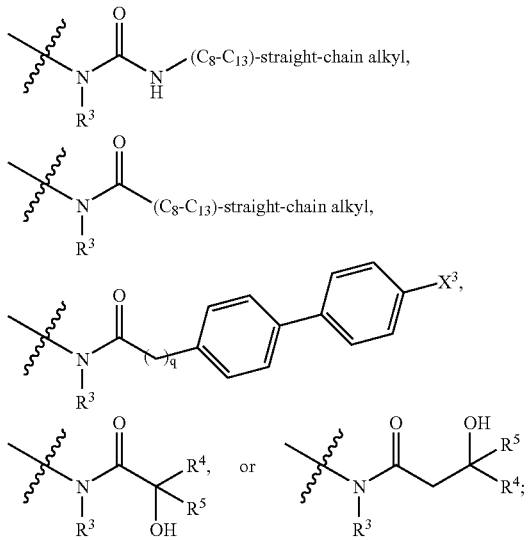

wherein $X^3$ is chloro or trifluoromethyl and wherein q is 0 or 1.

6. The compound according to claim 1, wherein $R^1$ is:

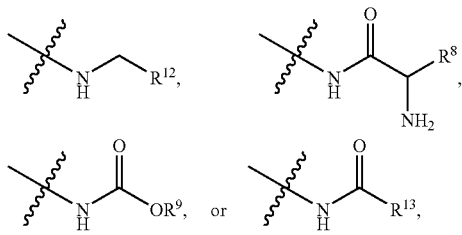

wherein $R^8$ is a natural amino acid side chain or an amino acid side chain that is not naturally occurring;

wherein $R^9$ is hydrido, alkyl, aryl, heterocyclyl or heteroaryl;

wherein $R^{12}$ is heterocyclyl, heteroaryl, aryl, or alkyl provided that $R^{12}$ is other than $C_3$-$C_{13}$ unsubstituted alkyl; and wherein $R^{13}$ is ($C_1$-$C_3$-alkyl) wherein one or more hydrogen atoms is replaced by a substituent group selected from acyl, amino, acylamino, acyloxy, carboalkoxy, carboxy, carboxyamido, cyano, halo, hydroxyl, nitro, thio, alkenyl, alkynyl, cycloalkyl, heterocyclyl, aryl, heteroaryl, alkoxy, aryloxy, sulfinyl, sulfonyl, oxo guanidino, and formyl.

7. The compound according to claim 6, wherein $R^J$ is:

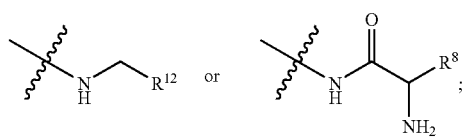

wherein $R^8$ is tryptophan side chain or lysine side chain;
wherein $R^{12}$ is imidazolyl, N-methylimidazolyl, indolyl, quinolinyl, benzyloxybenzyl, or benzylpiperidenylbenzyl.

8. The compound according to either of claims 1 or 4, wherein J is hydrido, amino, azido or

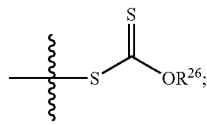

wherein $R^{17}$ and $R^{18}$ taken together form a ketal,

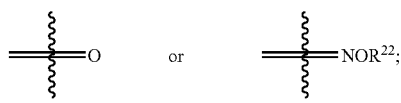

or wherein $R^{17}$ is hydroxyl when $R^{18}$ is hydrido;
or wherein J, together with $R^{17}$, forms a heterocyclyl ring.

9. The compound according to claim 8, wherein

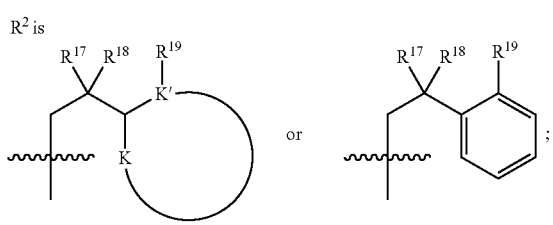

wherein $R^{17}$ and $R^{18}$ taken together form a

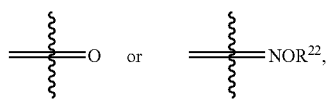

wherein $R^{22}$ is H or alkyl; and wherein $R^{19}$ is hydrido, amino, azido or

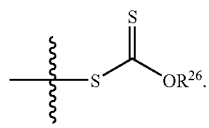
10. The compound according to claim 9, wherein $R^2$ is
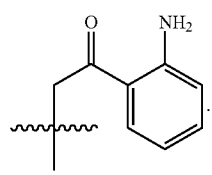
11. The compound according to claim 1 wherein said compound is

| Cpd # | R | R$^1$ | R$^2$ |
|---|---|---|---|
| 37 | NHCO(CH$_2$)$_8$CH$_3$ | biotin-CONH- | 2-azidophenyl-C(O)CH$_2$- |
| 38 | NHCO(CH$_2$)$_8$CH$_3$ | 4-fluorobenzyl-NH- | 2-aminophenyl-C(O)CH$_2$- |
| 39 | NHCO(CH$_2$)$_8$CH$_3$ | (2,3-diacetoxy-3-carboxy-propanoyl)NH- | 2-aminophenyl-C(O)CH$_2$- |
| 40 | NHCO(CH$_2$)$_8$CH$_3$ | 2-methoxybenzyl-NH- | 2-aminophenyl-C(O)CH$_2$- |
| 41 | NHCO(CH$_2$)$_8$CH$_3$ | (2,3-di-NHBOC-propanoyl)NH- | 2-aminophenyl-C(O)CH$_2$- |

-continued

| Cpd # | R | R¹ | R² |
|---|---|---|---|
| 42 | NHCO(CH$_2$)$_8$CH$_3$ | CH(CH$_2$CH$_2$CO$_2$CH$_3$)(NHBOC)C(O)NH–⁓ | 2-NH$_2$-C$_6$H$_4$-C(O)CH$_2$–⁓ |
| 43 | NHCO(CH$_2$)$_8$CH$_3$ | CH(CH$_2$CO$_2$ᵗBu)(NHBOC)C(O)NH–⁓ | 2-NH$_2$-C$_6$H$_4$-C(O)CH$_2$–⁓ |
| 44 | NHCO(CH$_2$)$_8$CH$_3$ | CH(CH$_2$-indol-3-yl)(NHBOC)C(O)NH–⁓ | 2-NH$_2$-C$_6$H$_4$-C(O)CH$_2$–⁓ |
| 45 | NHCO(CH$_2$)$_8$CH$_3$ | CH(CH$_2$-indol-3-yl)(NH$_2$)C(O)NH–⁓ | 2-NH$_2$-C$_6$H$_4$-C(O)CH$_2$–⁓ |
| 46 | NHCO(CH$_2$)$_8$CH$_3$ | CH(CH$_2$CH$_2$CO$_2$CH$_3$)(NH$_2$)C(O)NH–⁓ | 2-NH$_2$-C$_6$H$_4$-C(O)CH$_2$–⁓ |

-continued
| Cpd # | R | R¹ | R² |
|---|---|---|---|
| 47 | NHCO(CH$_2$)$_8$CH$_3$ |  |  |
| 48 | NHCO(CH$_2$)$_8$CH$_3$ |  |  |
| 49 | NHCO(CH$_2$)$_8$CH$_3$ | 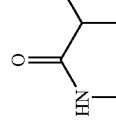 | 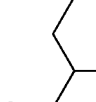 |
| 50 | NHCO(CH$_2$)$_8$CH$_3$ |  |  |
| 51 | NHCO(CH$_2$)$_8$CH$_3$ |  |  |

| Cpd # | R | R¹ | R² |
|---|---|---|---|
| 52 | NHCO(CH₂)₈CH₃ | 4-methylbenzylaminomethyl | 2-aminophenyl ketone |
| 54 | NHCO(CH₂)₈CH₃ | lysine amide | 2-aminophenyl ketone |
| 55 | NHCO(CH₂)₈CH₃ | N-Boc-tyrosine amide | 2-aminophenyl ketone |
| 56 | NHCO(CH₂)₈CH₃ | tyrosine amide | 2-aminophenyl ketone |
| 58 | NHCO(CH₂)₈CH₃ | biotinyl amide | 2-aminophenyl ketone |

-continued

| Cpd # | R | R¹ | R² |
|---|---|---|---|
| 60 | NHCO(CH₂)₈CH₃ | arginine side chain with -C(O)NH- linker | 2-aminophenyl ketone |
| 61 | NHCO(CH₂)₈CH₃ | tryptophan -C(O)NH- linker | 2-aminophenyl ketone |
| 62 | NHCO(CH₂)₈CH₃ | 4-fluoro-tryptophan -C(O)NH- linker | 2-aminophenyl ketone |
| 63 | NHCO(CH₂)₈CH₃ | 5-fluoro-tryptophan -C(O)NH- linker | 2-aminophenyl ketone |
| 64 | NHCO(CH₂)₈CH₃ | 5-methoxy-tryptophan -C(O)NH- linker | 2-aminophenyl ketone |

| Cpd # | R | R¹ | R² |
|---|---|---|---|
| 65 | NHCO(CH₂)₈CH₃ | (2-aminophenyl)-C(O)-CH(NH₂)-C(O)NH-~ | 2-aminophenyl-C(O)-CH₂-~ |
| 66 | NHCO(CH₂)₈CH₃ | (1H-indol-3-yl)-CH₂-CH(NH₂)-C(O)NH-~ | 2-aminophenyl-C(O)-CH₂-~ |
| 67 | NHCO(CH₂)₈CH₃ | phenyl-CH₂-CH(NH₂)-C(O)NH-~ | 2-aminophenyl-C(O)-CH₂-~ |
| 68 | NHCO(CH₂)₈CH₃ | (benzothiophen-3-yl)-CH₂-CH(NH₂)-C(O)NH-~ | 2-aminophenyl-C(O)-CH₂-~ |
| 69 | NHCO(CH₂)₈CH₃ | (thiazol-4-yl)-CH₂-CH(NH₂)-C(O)NH-~ | 2-aminophenyl-C(O)-CH₂-~ |

-continued

| Cpd # | R | R¹ | R² |
|---|---|---|---|
| 72 | NHCO(CH₂)₈CH₃ | (H₂N-CH(CH₂NH₂)-C(O)-NH-) | (2-aminophenyl-C(O)-CH₂-) |
| 73 | NHCO(CH₂)₈CH₃ | (imidazol-4-yl-CH₂-CH(NH₂)-C(O)-NH-) | (2-aminophenyl-C(O)-CH₂-) |
| 74 | NHCO(CH₂)₈CH₃ | (N-Boc-imidazol-4-yl-CH₂-CH(NH₂)-C(O)-NH-) | (2-aminophenyl-C(O)-CH₂-) |
| 75 | NHCO(CH₂)₈CH₃ | (BocHN-CH₂CH₂-C(O)-NH-) | (2-aminophenyl-C(O)-CH₂-) |
| 76 | NHCO(CH₂)₈CH₃ | (biphenyl-4-yl-CH₂-NH-) | (2-aminophenyl-C(O)-CH₂-) |

-continued

| Cpd # | R | R¹ | R² |
|---|---|---|---|
| 77 | NHCO(CH₂)₈CH₃ | NH(CH₂)₂OH | 2-aminophenyl-C(O)-CH₂- |
| 78 | NHCO(CH₂)₈CH₃ | 6-NHPh, 2-NH₂-triazin-4-yl-CH₂-NH- | 2-aminophenyl-C(O)-CH₂- |
| 79 | NHCO(CH₂)₈CH₃ | (1H-indol-3-yl)-CH₂-NH- | 2-aminophenyl-C(O)-CH₂- |
| 80 | NHGO(CH₂)₈CH₃ | (5-OCH₃-1H-indol-3-yl)-CH₂-NH- | 2-aminophenyl-C(O)-CH₂- |
| 81 | NHCO(CH₂)₈CH₃ | (5-F-1H-indol-3-yl)-CH₂-NH- | 2-aminophenyl-C(O)-CH₂- |

-continued

| Cpd # | R | R¹ | R² |
|---|---|---|---|
| 82 | NHCO(CH₂)₈CH₃ | (1-methyl-indol-3-yl)methylamino- | 2-aminophenacyl |
| 83 | NHCO(CH₂)₈CH₃ | (2-fluoro-6-chlorophenoxy)-p-xylyl-amino- | 2-aminophenacyl |
| 84 | NHCO(CH₂)₈CH₃ | (1-methyl-benzimidazol-2-yl)methylamino- | 2-aminophenacyl |
| 85 | NHCO(CH₂)₈CH₃ | (1-methyl-imidazol-2-yl)methylamino- | 2-aminophenacyl |
| 86 | N-Ts-lysinamide | tryptophanamide | 2-aminophenacyl |

-continued

| Cpd # | R | R¹ | R² |
|---|---|---|---|
| 87 | NHCO(CH₂)₈CH₃ | 4-NO₂-C₆H₄-CH₂-O-C₆H₄-CH₂-NH- | 2-NH₂-C₆H₄-CO-CH₂- |
| 88 | NHCO(CH₂)₈CH₃ | (3,4-Cl₂-C₆H₃-CH₂-O-C₆H₄-CH₂-)₂N- | 2-NH₂-C₆H₄-CO-CH₂- |
| 89 | NHCO(CH₂)₈CH₃ | 3,4-Cl₂-C₆H₃-CH₂-O-C₆H₄-CH₂-NH- | 2-NH₂-C₆H₄-CO-CH₂- |
| 90 | NHCO(CH₂)₈CH₃ | (4-MeO-C₆H₄-O-C₆H₄-CH₂-)₂N- | 2-NH₂-C₆H₄-CO-CH₂- |
| 91 | NHCO(CH₂)₈CH₃ | (4-NEt₂-C₆H₄-CH=CH-CH₂-)₂N- | 2-NH₂-C₆H₄-CO-CH₂- |

-continued

| Cpd # | R | R¹ | R² |
|---|---|---|---|
| 92 | NHCO(CH₂)₈CH₃ | 4-NEt₂-phenyl-CH=CH-CH₂-NH- | 2-aminophenyl-C(O)-CH₂- |
| 93 | NHCO(CH₂)₈CH₃ | 4-O^nBu-phenyl-CH₂-NH- | 2-aminophenyl-C(O)-CH₂- |
| 94 | NHCO(CH₂)₈CH₃ | 4-O^nPr-phenyl-CH₂-NH- | 2-aminophenyl-C(O)-CH₂- |
| 95 | NHCO(CH₂)₈CH₃ | 4-(4-F-benzyloxy)-phenyl-CH₂-NH- | 2-aminophenyl-C(O)-CH₂- |
| 96 | NHCO(CH₂)₈CH₃ | 2-MeO-3-(naphthyl)-CH₂-NH- | 2-aminophenyl-C(O)-CH₂- |

| Cpd # | R | R¹ | R² |
|---|---|---|---|
| 97 | NHCO(CH₂)₈CH₃ | 2-OMe, 4-benzyloxy benzylamine | 2-aminophenyl ketone |
| 98 | NHCO(CH₂)₈CH₃ | bis(3-fluorobenzyl)amine | 2-aminophenyl ketone |
| 99 | NHCO(CH₂)₈CH₃ | bis(2-fluorobenzyl)amine | 2-aminophenyl ketone |
| 100 | NHCO(CH₂)₈CH₃ | 4-benzyloxy benzylamine | 2-aminophenyl ketone |
| 101 | 4'-chloro-biphenyl-4-carboxamide | tryptophan amide | 2-aminophenyl ketone |

| Cpd # | R | R¹ | R² |
|---|---|---|---|
| 102 | NHCO(CH₂)₁₁CH₃ | tryptophan-derived (indole, NH₂, C(O)NH-) | 2-aminophenyl ketone |
| 103 | NHCO(CH₂)₈CH₃ | 1-benzyl-4-(2-(aminomethyl)phenyl)piperazine | 2-aminophenyl ketone |
| 104 | NHCO(CH₂)₈CH₃ | bis[1-benzyl-4-(2-(methyl)phenyl)piperazine]-N | 2-aminophenyl ketone |
| 105 | NHCO(CH₂)₈CH₃ | 3-nitrobenzylamino | 2-aminophenyl ketone |
| 106 | NHCO(CH₂)₈CH₃ | 2-hydroxy-4-(benzyloxy)benzylamino | 2-aminophenyl ketone |

| Cpd # | R | R¹ | R² |
|---|---|---|---|
| 107 | NHCO(CH₂)₈CH₃ | 3-(3-CF₃-phenoxy)benzyl-NH- | 2-aminophenyl-C(O)-CH₂- |
| 108 | NHCO(CH₂)₈CH₃ | 3-(3,5-dichlorophenoxy)benzyl-NH- | 2-aminophenyl-C(O)-CH₂- |
| 109 | NHCO(CH₂)₈CH₃ | 3-(3,4-dichlorophenoxy)benzyl-NH- | 2-aminophenyl-C(O)-CH₂- |
| 110 | NHCO(CH₂)₈CH₃ | 3-(4-phenoxy)benzyl-piperidinyl | 2-aminophenyl-C(O)-CH₂- |
| 111 | NHCO(CH₂)₈CH₃ | 3-(4-methylphenoxy)benzyl-NH- | 2-aminophenyl-C(O)-CH₂- |

-continued

| Cpd # | R | R¹ | R² |
|---|---|---|---|
| 112 | NHCO(CH₂)₈CH₃ | 3-(3-trifluoromethylphenoxy)benzyl-amino | 2-aminophenacyl |
| 113 | NHCO(CH₂)₈CH₃ | (N-ethylcarbazol-4-yl)methyl-amino | 2-aminophenacyl |
| 114 | NHCO(CH₂)₈CH₃ | (N-ethylcarbazol-3-yl)methyl-amino | 2-aminophenacyl |
| 115 | NHCO(CH₂)₈CH₃ | 2-cyanobenzyl-amino | 2-aminophenacyl |
| 116 | NHCO(CH₂)₈CH₃ | (2-chloroquinolin-3-yl)methyl-amino | 2-aminophenacyl |

-continued

| Cpd # | R | R¹ | R² |
|---|---|---|---|
| 117 | NHCO(CH$_2$)$_8$CH$_3$ | 4-tBu-phenoxy-phenyl-CH$_2$-NH- | 2-aminophenyl-C(O)-CH$_2$- |
| 118 | NHCO(CH$_2$)$_8$CH$_3$ | (4-Cl-phenoxy-phenyl-CH$_2$-)$_2$N- | 2-aminophenyl-C(O)-CH$_2$- |
| 119 | NHCO(CH$_2$)$_8$CH$_3$ | 4-Cl-phenoxy-phenyl-CH$_2$-NH- | 2-aminophenyl-C(O)-CH$_2$- |
| 120 | NHCO(CH$_2$)$_8$CH$_3$ | (4-NO$_2$-phenyl-CH$_2$-O-phenyl-CH$_2$-)$_2$N- | 2-aminophenyl-C(O)-CH$_2$- |
| 121 | NHCO(CH$_2$)$_8$CH$_3$ | 3-phenoxy-phenyl-CH$_2$-NH- | 2-aminophenyl-C(O)-CH$_2$- |

-continued
| Cpd # | R | R¹ | R² |
|---|---|---|---|
| 122 | NHCO(CH$_2$)$_8$CH$_3$ | 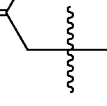 | 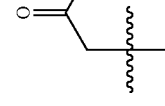 |
| 123 | NHCO(CH$_2$)$_8$CH$_3$ | 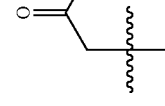 | 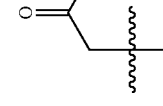 |
| 124 | NHCO(CH$_2$)$_8$CH$_3$ | 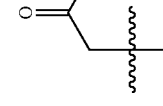 | 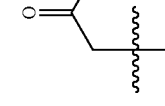 |
| 125 | NHCO(CH$_2$)$_8$CH$_3$ | 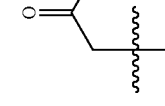 | 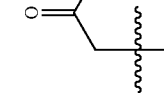 |
| 126 | NHCO(CH$_2$)$_8$CH$_3$ | 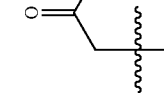 | 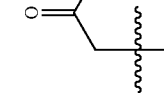 |

-continued

| Cpd # | R | R¹ | R² |
|---|---|---|---|
| 127 | NHCO(CH₂)₈CH₃ | phenylacetylene-phenyl-CH₂-NH- | 2-aminophenyl-C(O)-CH₂- |
| 128 | NHCO(CH₂)₈CH₃ | (4-fluorophenyl)-CH₂-O-(phenyl)-CH₂-N< | 2-aminophenyl-C(O)-CH₂- |
| 129 | NHCO(CH₂)₈CH₃ | 2-nitrobenzyl-NH- | 2-aminophenyl-C(O)-CH₂- |
| 130 | NHCO(CH₂)₈CH₃ | quinolin-2-yl-CH₂-NH- | 2-aminophenyl-C(O)-CH₂- |
| 131 | NHCO(CH₂)₈CH₃ | quinolin-2-yl-CH₂-N< | 2-aminophenyl-C(O)-CH₂- |

| Cpd # | R | R¹ | R² |
|---|---|---|---|
| 132 | NHCO(CH₂)₈CH₃ | (1-methoxynaphthalen-2-yl)methyl-N, cyclic dimer ()₂ | 2-aminophenyl-C(O)-CH₂- |
| 133 | NHCO(CH₂)₈CH₃ | (2-aminophenyl)methyl-HN- | 2-aminophenyl-C(O)-CH₂- |
| 134 | NHCO(CH₂)₈CH₃ | 4-benzyloxy-2-methoxybenzyl-N, cyclic dimer ()₂ | 2-aminophenyl-C(O)-CH₂- |
| 135 | NHCO(CH₂)₈CH₃ | (3-fluorophenyl)methyl-HN- | 2-aminophenyl-C(O)-CH₂- |
| 136 | NHCO(CH₂)₈CH₃ | (2-fluorophenyl)methyl-HN- | 2-aminophenyl-C(O)-CH₂- |

| Cpd # | R | R¹ | R² |
|---|---|---|---|
| 137 | NHCO(CH₂)₈CH₃ | benzyloxy-phenyl-CH₂-N< (×2) | 2-aminophenyl-C(O)-CH₂- |
| 138 | NHCO(CH₂)₈CH₃ | quinolin-4-yl-CH₂-NH- | 2-aminophenyl-C(O)-CH₂- |
| 139 | NHCO(CH₂)₈CH₃ | benzofuran-2-yl-CH₂-NH- | 2-aminophenyl-C(O)-CH₂- |
| 140 | NHCO(CH₂)₈CH₃ | benzofuran-2-yl-CH₂-N< (×2) | 2-aminophenyl-C(O)-CH₂- |
| 141 | NHCO(CH₂)₈CH₃ | (4-vinyloxy-phenyl)-CH₂-N< (×2) | 2-aminophenyl-C(O)-CH₂- |

-continued

| Cpd # | R | R¹ | R² |
|---|---|---|---|
| 142 | NHCO(CH$_2$)$_8$CH$_3$ | 4-(vinyloxy)benzyl-NH- | 2-aminophenyl-C(O)-CH$_2$- |
| 143 | NHCO(CH$_2$)$_8$CH$_3$ | 4-phenoxybenzyl-NH- | 2-aminophenyl-C(O)-CH$_2$- |
| 144 | NHCO(CH$_2$)$_8$CH$_3$ | 4-(2-phenylvinyl)benzyl-NH- | 2-aminophenyl-C(O)-CH$_2$- |
| 145 | NHCO(CH$_2$)$_8$CH$_3$ | 4-(2,2-diphenylvinyl)benzyl-N- | 2-aminophenyl-C(O)-CH$_2$- |
| 146 | NHCO(CH$_2$)$_8$CH$_3$ | (1H-imidazol-4-yl)methyl-NH- | 2-aminophenyl-C(O)-CH$_2$- |

-continued

| Cpd # | R | R¹ | R² |
|---|---|---|---|
| 147 | NHCO(CH₂)₈CH₃ | fluorenyl-CH₂-NH- | 2-aminophenyl-C(O)-CH₂- |
| 148 | NHCO(CH₂)₈CH₃ | (fluorenyl-CH₂)₂-N- | 2-aminophenyl-C(O)-CH₂- |
| 149 | NHCO(CH₂)₈CH₃ | Me₂N-(CH₂)₃-O-C₆H₄-CH₂-NH- | 2-aminophenyl-C(O)-CH₂- |
| 150 | NHCO(CH₂)₈CH₃ | 3-Ph-pyrazol-4-yl-CH₂-NH- | 2-aminophenyl-C(O)-CH₂- |
| 151 | NHCO(CH₂)₈CH₃ | 3-OMe-4-OBn-C₆H₃-CH₂-NH- | 2-aminophenyl-C(O)-CH₂- |

| Cpd # | R | R¹ | R² |
|---|---|---|---|
| 152 | NHCO(CH₂)₈CH₃ | 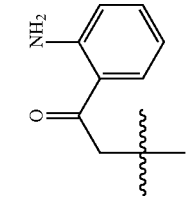 3,4-bis(benzyloxy)... with OMe | 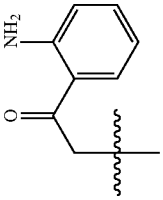 2-aminophenyl ketone |
| 153 | NHCO(CH₂)₈CH₃ | 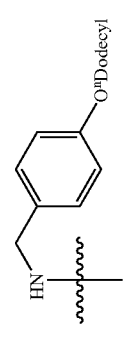 4-(O-n-dodecyl)benzyl-NH- | 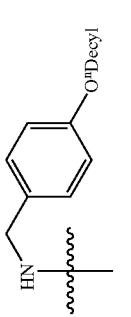 2-aminophenyl ketone |
| 154 | NHCO(CH₂)₈CH₃ | 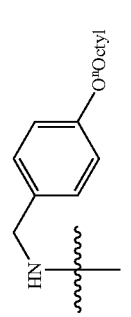 4-(O-n-decyl)benzyl-NH- | 2-aminophenyl ketone |
| 155 | NHCO(CH₂)₈CH₃ | 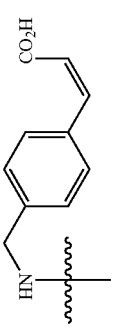 4-(O-n-octyl)benzyl-NH- | 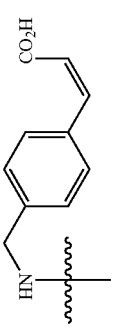 2-aminophenyl ketone |
| 156 | NHCO(CH₂)₈CH₃ | 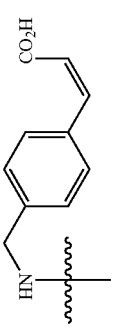 4-(CO₂H-vinyl)benzyl-NH- | 2-aminophenyl ketone |

-continued

| Cpd # | R | R¹ | R² |
|---|---|---|---|
| 157 | NHCO(CH₂)₈CH₃ | 4-NMe₂-styryl-CH₂-NH- | 2-aminophenyl-C(O)-CH₂- |
| 158 | NHCO(CH₂)₈CH₃ | (3-methylbenzothiophen-2-yl)-CH₂-NH- | 2-aminophenyl-C(O)-CH₂- |
| 159 | NHCO(CH₂)₈CH₃ | (1-phenyl-3,5-dimethylpyrazol-4-yl)-CH₂-NH- | 2-aminophenyl-C(O)-CH₂- |
| 160 | NHCO(CH₂)₈CH₃ | [(1-phenyl-3,5-dimethylpyrazol-4-yl)-CH₂-]₂N- | 2-aminophenyl-C(O)-CH₂- |
| 161 | NHCO(CH₂)₈CH₃ | 4-(CO₂H-CH₂-O)-benzyl-NH- | 2-aminophenyl-C(O)-CH₂- |

-continued

| Cpd # | R | R¹ | R² |
|---|---|---|---|
| 162 | NHCO(CH₂)₈CH₃ | (4-bromophenyl-furan-CH₂-N), subscript 2 | 2-aminophenyl-C(O)-CH₂- |
| 163 | NHCO(CH₂)₈CH₃ | (4-nitrophenyl-CH=CH-CH₂-N), subscript 2 | 2-aminophenyl-C(O)-CH₂- |
| 164 | NHCO(CH₂)₈CH₃ | 3-(benzyloxy)benzyl-NH- | 2-aminophenyl-C(O)-CH₂- |
| 165 | NHCO(CH₂)₈CH₃ | (3-(benzyloxy)benzyl-N), subscript 2 | 2-aminophenyl-C(O)-CH₂- |
| 166 | NHCO(CH₂)₈CH₃ | 2,4-difluorobenzyl-NH- | 2-aminophenyl-C(O)-CH₂- |

-continued

| Cpd # | R | R¹ | R² |
|---|---|---|---|
| 167 | NHCO(CH$_2$)$_8$CH$_3$ | cinnamyl-N(–)$_2$ | 2-aminophenyl-C(O)CH$_2$– |
| 168 | NHCO(CH$_2$)$_8$CH$_3$ | quinolin-3-ylmethyl-NH– | 2-aminophenyl-C(O)CH$_2$– |
| 169 | NHCO(CH$_2$)$_8$CH$_3$ | (phenethyl)$_2$N– | 2-aminophenyl-C(O)CH$_2$– |
| 171 | NHCO(CH$_2$)$_8$CH$_3$ | (4-n-butylbenzyl)$_2$N– | 2-aminophenyl-C(O)CH$_2$– |
| 172 | NHCO(CH$_2$)$_8$CH$_3$ | 4-n-butylbenzyl-NH– | 2-aminophenyl-C(O)CH$_2$– |

| Cpd # | R | R¹ | R² |
|---|---|---|---|
| 173 | NHCO(CH₂)₈CH₃ | 4-cyanobenzyl-NH- | 2-aminophenyl-CO-CH₂- |
| 174 | NHCO(CH₂)₈CH₃ | thiazol-2-ylmethyl-NH- | 2-aminophenyl-CO-CH₂- |
| 175 | NHCO(CH₂)₈CH₃ | 2-benzyl-heptyl-NH- | 2-aminophenyl-CO-CH₂- |
| 176 | NHCO(CH₂)₈CH₃ | bis(imidazol-2-ylmethyl)N- | 2-aminophenyl-CO-CH₂- |
| 177 | NH₂ | 4-phenylbenzyl-NH- | 2-aminophenyl-CO-CH₂- |

-continued

| Cpd # | R | R¹ | R² |
|---|---|---|---|
| 178 | NHCO(CH$_2$)$_8$CH$_3$ | 4-aminophenylalanine amide | 2-aminophenacyl |
| 179 | NHCO(CH$_2$)$_8$CH$_3$ | 4-NHBoc-phenylalanine amide | 2-aminophenacyl |
| 180 | NHCO(CH$_2$)$_8$CH$_3$ | 4-NHBoc-phenylalanine-NHFmoc amide | 2-aminophenacyl |
| 181 | NHCONH(CH$_2$)$_{10}$CH$_3$ | tryptophan amide | 2-aminophenacyl |
| 182 | NHCO(CH$_2$)$_8$CH$_3$ | 3-oxo-indan-1-carboxamide | 2-aminophenacyl |

-continued
| Cpd # | R | R¹ | R² |
|---|---|---|---|
| 183 | NHCO(CH₂)₈CH₃ | 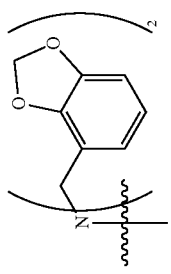 | 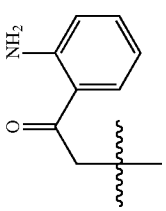 |
| 184 | NHCO(CH₂)₈CH₃ | 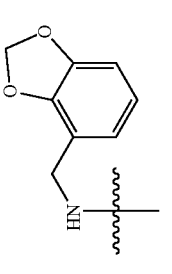 | 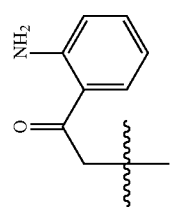 |
| 185 | NHCO(CH₂)₈CH₃ | 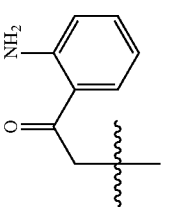 | 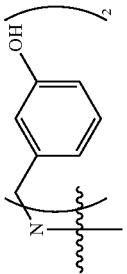 |
| 186 | NHCO(CH₂)₈CH₃ | 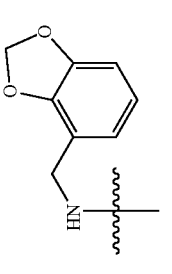 | 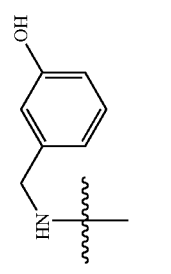 |
| 187 | NHCO(CH₂)₈CH₃ | 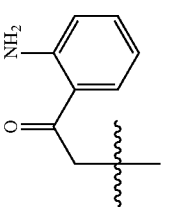 | 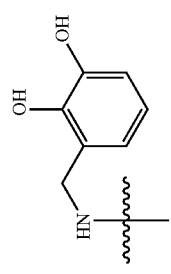 |

-continued

| Cpd # | R | R¹ | R² |
|---|---|---|---|
| 192 | NHCO(CH₂)₈CH₃ | tyrosine-like (4-hydroxyphenyl, α-NH₂, C(O)NH-) | 2-azidophenyl C(O)CH₂- |
| 193 | NHCO(CH₂)₈CH₃ | N-Boc-prolinamide | 2-aminophenyl C(O)CH₂- |
| 194 | NHCO(CH₂)₈CH₃ | 3-(trifluoromethoxy)benzylamino- | 2-aminophenyl C(O)CH₂- |
| 195 | NHCO(CH₂)₈CH₃ | bis[3-(trifluoromethoxy)benzyl]amino- | 2-aminophenyl C(O)CH₂- |
| 196 | NHCO(CH₂)₈CH₃ | 2,4-dichlorobenzylamino- | 2-aminophenyl C(O)CH₂- |

-continued

| Cpd # | R | R¹ | R² |
|---|---|---|---|
| 197 | NHCO(CH$_2$)$_8$CH$_3$ | 4-chlorobenzylamino | 2'-aminophenacyl |
| 198 | NHCO(CH$_2$)$_8$CH$_3$ | 4-(dimethylamino)benzylamino | 2'-aminophenacyl |
| 199 | NHCO(CH$_2$)$_8$CH$_3$ | 2,6-dichlorobenzylamino | 2'-aminophenacyl |
| 200 | NHCO(CH$_2$)$_8$CH$_3$ | tryptophanamido | phenacyl |
| 201 | NHCO(CH$_2$)$_8$CH$_3$ | 2-(n-hexyl)cinnamoylamino | 2'-aminophenacyl |

| Cpd # | R | R¹ | R² |
|---|---|---|---|
| 202 | NHCO(CH₂)₈CH₃ | (4-NMe₂-styryl-CH₂-NH-) | 2-aminophenyl-C(O)-CH₂- |
| 203 | NHCO(CH₂)₈CH₃ | indol-3-yl-CH₂-CH(NH₂)-CH₂-NH- | 2-aminophenyl-C(O)-CH₂- |
| 204 | NHCO(CH₂)₈CH₃ | indol-3-yl-CH₂-CH(NHBoc)-CH₂-NH- | 2-aminophenyl-C(O)-CH₂- |
| 205 | NH(CH₂)₈CH₃ | indol-3-yl-CH₂-CH(NH₂)-C(O)-NH- | 2-aminophenyl-C(O)-CH₂- |
| 206 | NHCO(CH₂)₈CO₂Me | indol-3-yl-CH₂-CH(NH₂)-C(O)-NH- | 2-aminophenyl-C(O)-CH₂- |

-continued

| Cpd # | R | R¹ | R² |
|---|---|---|---|
| 207 | NHCO(CH$_2$)$_6$CO$_2$Me | tryptophan-derived (indole-CH$_2$-CH(NH$_2$)-C(O)-NH-) | 2-aminophenyl-C(O)-CH$_2$- |
| 208 | NHCO(CH$_2$)$_8$CH$_3$ | 4-MeC$_6$H$_4$-SO$_2$-CH(Ph)-CH$_2$-NH- | 2-aminophenyl-C(O)-CH$_2$- |
| 209 | NHCO(CH$_2$)$_8$CH$_3$ | 4-(4-fluorophenoxy)-3-nitrobenzyl-NH- | 2-aminophenyl-C(O)-CH$_2$- |
| 210 | NHCO(CH$_2$)$_8$CH$_3$ | 4-benzyloxy-3-chlorobenzyl-NH- | 2-aminophenyl-C(O)-CH$_2$- |
| 211 | NHCO(CH$_2$)$_8$CH$_3$ | 3,4-bis(benzyloxy)benzyl-NH- | 2-aminophenyl-C(O)-CH$_2$- |

-continued

| Cpd # | R | R¹ | R² |
|---|---|---|---|
| 212 | NHCO(CH$_2$)$_8$CH$_3$ | imidazolylmethyl | 2-aminophenyl ketone |
| 213 | NHCO(CH$_2$)$_6$NHBoc | Trp(NHBoc) | 2-aminophenyl ketone |
| 214 | NHCO(CH$_2$)$_7$NHBoc | Trp(NHBoc) | 2-aminophenyl ketone |
| 215 | NHCO(CH$_2$)$_{10}$NHBoc | Trp(NHBoc) | 2-aminophenyl ketone |
| 216 | NHCO(CH$_2$)$_{11}$NHBoc | Trp(NHBoc) | 2-aminophenyl ketone |

-continued

| Cpd # | R | R¹ | R² |
|---|---|---|---|
| 217 | NHCO(CH$_2$)$_{10}$NH$_2$ | (tryptophan-like, amide-linked) | (2-aminophenyl ketone) |
| 218 | NHCO(CH$_2$)$_{11}$NH$_2$ | (tryptophan-like, amide-linked) | (2-aminophenyl ketone) |
| 219 | NHCO(CH$_2$)$_6$CH(CH$_3$)$_2$ | (tryptophan-like, amide-linked) | (2-aminophenyl ketone) |
| 220 | NHCONH(CH$_2$)$_{11}$CH$_3$ | (tryptophan-like, amide-linked) | (2-aminophenyl ketone) |
| 221 | NHCO(CH$_2$)$_8$CH$_3$ | (indolyl-ethyl guanidine) | (2-aminophenyl ketone) |

| Cpd # | R | R¹ | R² |
|---|---|---|---|
| 222 | NHCO(CH₂)₈CH₃ | (indol-2-yl-butyl)₂-N- | 2-aminophenyl-C(O)-CH₂- |
| 223 | NHCO(CH₂)₈CH₃ | indol-2-yl-ethyl-NH- | 2-aminophenyl-C(O)-CH₂- |
| 224 | NHCO(CH₂)₈CH₃ | bis-NHBoc lysine-like chain -NH- | 2-aminophenyl-C(O)-CH₂- |
| 225 | NHCO(CH₂)₈CH₃ | bis-NH₂ lysine-like chain -NH- | 2-aminophenyl-C(O)-CH₂- |
| 226 | NHCO(CH₂)₈CH₃ | 4-[(benzo[1,3]dioxol-5-ylmethyl)piperazine-1-carbonyl]benzyl-NH- | 2-aminophenyl-C(O)-CH₂- |

-continued

| Cpd # | R | R¹ | R² |
|---|---|---|---|
| 227 | NHCO(CH₂)₈CH₃ | 4-(4-phenylpiperazine-1-carbonyl)benzylamino | 2'-aminophenacyl |
| 228 | NHCO(CH₂)₈CH₃ | 4-[4-(4-fluorophenyl)piperazin-1-yl]benzoyl-aminomethyl | 2'-aminophenacyl |
| 229 | NHCO(CH₂)₈CH₃ | 4-(4-benzylpiperazin-1-yl)benzoylaminomethyl | 2'-aminophenacyl |
| 230 | NHCO(CH₂)₈CH₃ | 4-[4-(3,4-dichlorophenyl)piperazin-1-yl]benzoyl-aminomethyl | 2'-aminophenacyl |
| 231 | NHCO(CH₂)₈CH₃ | 4-(4-benzhydrylpiperazine-1-carbonyl)benzylamino | 2'-aminophenacyl |

-continued

| Cpd # | R | R¹ | R² |
|---|---|---|---|
| 232 | NHCO(CH$_2$)$_8$CH$_3$ | cinnamyl-piperazine-C(O)-C$_6$H$_4$-CH$_2$NH- | 2-aminophenyl-C(O)-CH$_2$- |
| 233 | NHCO(CH$_2$)$_8$CH$_3$ | (2-pyrimidinyl)-piperazine-C(O)-C$_6$H$_4$-CH$_2$NH- | 2-aminophenyl-C(O)-CH$_2$- |
| 234 | NHCO(CH$_2$)$_8$CH$_3$ | (2-pyridyl)-piperazine-C(O)-C$_6$H$_4$-CH$_2$NH- | 2-aminophenyl-C(O)-CH$_2$- |
| 235 | NHCO(CH$_2$)$_8$CH$_3$ | (4-chlorophenyl)-piperazine-C(O)-C$_6$H$_4$-CH$_2$NH- | 2-aminophenyl-C(O)-CH$_2$- |
| 236 | NHCO(CH$_2$)$_8$CH$_3$ | (benzo[1,3]dioxol-5-ylmethyl)-piperazine-C(O)-CH=CH-C$_6$H$_4$-CH$_2$NH- | 2-aminophenyl-C(O)-CH$_2$- |

| Cpd # | R | R¹ | R² |
|---|---|---|---|
| 237 | NHCO(CH₂)₈CH₃ | cinnamoyl-4-phenylpiperazine linked via benzyl-NH | 2-aminophenyl-C(O)-CH₂- |
| 238 | NHCO(CH₂)₈CH₃ | cinnamoyl-4-(4-fluorophenyl)piperazine linked via benzyl-NH | 2-aminophenyl-C(O)-CH₂- |
| 239 | NHCO(CH₂)₈CH₃ | cinnamoyl-4-benzylpiperazine linked via benzyl-NH | 2-aminophenyl-C(O)-CH₂- |
| 240 | NHCO(CH₂)₈CH₃ | cinnamoyl-4-(3,4-dichlorophenyl)piperazine linked via benzyl-NH | 2-aminophenyl-C(O)-CH₂- |
| 241 | NHCO(CH₂)₈CH₃ | cinnamoyl-4-(diphenylmethyl)piperazine linked via benzyl-NH | 2-aminophenyl-C(O)-CH₂- |

-continued

| Cpd # | R | R¹ | R² |
|---|---|---|---|
| 242 | NHCO(CH₂)₈CH₃ | (4-(pyrimidin-2-yl)piperazine cinnamoyl benzylamine) | (2-aminophenyl ketone) |
| 243 | NHCO(CH₂)₈CH₃ | (4-(pyridin-2-yl)piperazine cinnamoyl benzylamine) | (2-aminophenyl ketone) |
| 244 | NHCO(CH₂)₈CH₃ | (4-(4-chlorophenyl)piperazine cinnamoyl benzylamine) | (2-aminophenyl ketone) |
| 245 | NHCO(CH₂)₈CH₃ | (2-aminooctanoyl amide) | (2-aminophenyl ketone) |
| 246 | (4-chlorophenylacetamide) | (tryptophan amide) | (2-aminophenyl ketone) |

-continued

| Cpd # | R | R$^1$ | R$^2$ |
|---|---|---|---|
| 247 | 2,4-dichlorophenylacetamide | tryptophan-derived | 2-aminophenyl ketone |
| 248 | 4-phenoxyphenylacetamide | tryptophan-derived | 2-aminophenyl ketone |
| 249 | 4-n-butoxyphenylacetamide | tryptophan-derived | 2-aminophenyl ketone |
| 250 | 4'-chlorobiphenylacetamide | tryptophan-derived | 2-aminophenyl ketone |
| 251 | 4'-chlorobiphenylacetamide | lysine-derived | 2-aminophenyl ketone |

| Cpd # | R | R¹ | R² |
|---|---|---|---|
| 252 | NHCO(CH₂)₈CH₃ | 4-(4-benzylpiperazin-1-yl)-3-nitrobenzyl-NH- | 2-aminophenacyl |
| 253 | NHCO(CH₂)₈CH₃ | 4-(4-benzylpiperazin-1-yl)benzyl-NH- | 2-aminophenacyl |
| 264 | (2-n-heptyl-2H-tetrazol-5-yl)acetamido | tryptophan-amide | 2-aminophenacyl |
| 265 | NHCO(CH₂)₈CH₃ | [3-[(2,4-dichlorophenylthio)]pyridin-2-yl]methyl-NH- | 2-aminophenacyl |
| 266 | NHCO(CH₂)₈CH₃ | 4-morpholino-3-nitrobenzyl-NH- | 2-aminophenacyl |

-continued

| Cpd # | R | R¹ | R² |
|---|---|---|---|
| 267 | NHCO(CH₂)₈CH₃ | (benzenesulfonylmethyl-nitrophenyl)methylamino | 2-aminophenyl-C(O)CH₂- |
| 268 | NHCO(CH₂)₈CH₃ | {2-[4-(5-trifluoromethylpyridin-2-yl)piperazin-1-yl]phenyl}methylamino | 2-aminophenyl-C(O)CH₂- |
| 269 | (2-n-heptyl-2H-1,2,3-triazol-4-yl)acetamido | N-Boc-tryptophanamido | 2-aminophenyl-C(O)CH₂- |
| 270 | NHCO(CH₂)₈CH₃ | N-propylguanidino | 2-aminophenyl-C(O)CH₂- |
| 271 | NHCO(CH₂)₈CH₃ | {4-[bis(2-chloroethyl)amino]phenyl}methylamino | 2-aminophenyl-C(O)CH₂- |

-continued

| Cpd # | R | R¹ | R² |
|---|---|---|---|
| 272 | NHCO(CH₂)₈CH₃ | (4-[(3,5-dichloro-1,4-oxazepan-4-yl)]phenyl)methyl-N- | 2-aminophenyl-C(O)-CH₂- |
| 273 | NHCO(CH₂)₈CH₃ | 6,7-dimethoxyquinolin-2-ylmethyl-N- | 2-aminophenyl-C(O)-CH₂- |
| 274 | NHCO(CH₂)₈CH₃ | (6-methoxyquinolin-2-yl)methyl-NH- | 2-aminophenyl-C(O)-CH₂- |
| 275 | NHCO(CH₂)₈CH₃ | (7-chloroquinolin-2-yl)methyl-NH- | 2-aminophenyl-C(O)-CH₂- |
| 276 | NHCO(CH₂)₈CH₃ | (6,7-dichloroquinolin-2-yl)methyl-N- | 2-aminophenyl-C(O)-CH₂- |

-continued

| Cpd # | R | R¹ | R² |
|---|---|---|---|
| 277 | NHCO(CH₂)₈CH₃ | 2-(aminomethyl)quinolin-4-ol | 2'-aminophenacyl |
| 278 | NHCO(CH₂)₈CH₃ | (6-fluoroquinolin-2-yl)methylamino | 2'-aminophenacyl |
| 279 | NHCO(CH₂)₈CH₃ | (6-fluoroquinolin-2-yl)methyl-N-cyclo | 2'-aminophenacyl |
| 280 | NHCO(CH₂)₈CH₃ | (6-chloroquinolin-2-yl)methylamino | 2'-aminophenacyl |
| 281 | NHCO(CH₂)₈CH₃ | (6-chloroquinolin-2-yl)methyl-N-cyclo | 2'-aminophenacyl |

| Cpd # | R | R¹ | R² |
|---|---|---|---|
| 282 | NHCO(CH₂)₈CH₃ | 6-nitroquinolin-2-ylmethyl-NH- | 2-aminophenyl-C(O)-CH₂- |
| 283 | NHCO(CH₂)₈CH₃ | 8-chloroquinolin-2-ylmethyl-NH- | 2-aminophenyl-C(O)-CH₂- |
| 284 | NHCO(CH₂)₈CH₃ | (8-chloroquinolin-2-ylmethyl)₂-N- | 2-aminophenyl-C(O)-CH₂- |
| 285 | NHCO(CH₂)₈CH₃ | 4-chloroquinolin-2-ylmethyl-NH- | 2-aminophenyl-C(O)-CH₂- |
| 286 | NHCO(CH₂)₈CH₃ | 8-(phenylcarbamoyloxy)quinolin-2-ylmethyl-NH- | 2-aminophenyl-C(O)-CH₂- |

-continued

| Cpd # | R | R¹ | R² |
|---|---|---|---|
| 287 | NHCO(CH₂)₈CH₃ | quinoline-2-CH₂NH- with 4-CONH₂ | 2-aminophenyl-C(O)-CH₂- |
| 288 | NHCO(CH₂)₈CH₃ | 6-chloro-4-hydroxyquinolin-2-yl-CH₂NH- | 2-aminophenyl-C(O)-CH₂- |
| 289 | NHCO(CH₂)₈CH₃ | 6-N(CH₃)₂-quinolin-2-yl-CH₂NH- | 2-aminophenyl-C(O)-CH₂- |
| 290 | NHCO(CH₂)₈CH₃ | 8-nitroquinolin-2-yl-CH₂NH- | 2-aminophenyl-C(O)-CH₂- |
| 291 | NHCO(CH₂)₈CH₃ | 5,7-dichloro-8-hydroxyquinolin-2-yl-CH₂NH- | 2-aminophenyl-C(O)-CH₂- |

-continued

| Cpd # | R | R¹ | R² |
|---|---|---|---|
| 295 | NHCO(CH₂)₁₁CH₃ | (lysine with two NHBoc groups, amide linker) | 2-aminophenyl ketone |
| 296 | NHCO(CH₂)₁₀CH₃ | (lysine with two NHBoc groups, amide linker) | 2-aminophenyl ketone |
| 297 | NHCO(CH₂)₉CH₃ | (lysine with two NHBoc groups, amide linker) | 2-aminophenyl ketone |
| 298 | NHCONH(CH₂)₇CH₃ | (lysine with two NHBoc groups, amide linker) | 2-aminophenyl ketone |
| 299 | NHCONH(CH₂)₁₀CH₃ | (lysine with two NHBoc groups, amide linker) | 2-aminophenyl ketone |

| Cpd # | R | R¹ | R² |
|---|---|---|---|
| 300 | NHCONH(CH₂)₁₁CH₃ | Lysine with two NHBoc groups, amide linkage | 2-aminophenyl ketone |
| 301 | NHCO(CH₂)₁₁CH₃ | Lysine with NH₂ groups, amide linkage | 2-aminophenyl ketone |
| 302 | NHCO(CH₂)₁₀CH₃ | Lysine with NH₂ groups, amide linkage | 2-aminophenyl ketone |
| 303 | NHCO(CH₂)₉CH₃ | Lysine with NH₂ groups, amide linkage | 2-aminophenyl ketone |
| 304 | NHCONH(CH₂)₇CH₃ | Lysine with NH₂ groups, amide linkage | 2-aminophenyl ketone |

-continued

| Cpd # | R | R¹ | R² |
|---|---|---|---|
| 305 | NHCONH(CH₂)₁₀CH₃ | Lys-derived (NH₂ side chain, α-NH₂, C(O)NH-) | 2-aminophenyl-C(O)-CH₂- |
| 306 | NHCONH(CH₂)₁₁CH₃ | Lys-derived (NH₂ side chain, α-NH₂, C(O)NH-) | 2-aminophenyl-C(O)-CH₂- |
| 307 | NHCO(CH₂)₉CH₃ | Trp-derived (indole side chain, α-NHBoc, C(O)NH-) | 2-aminophenyl-C(O)-CH₂- |
| 308 | NHCO(CH₂)₁₀CH₃ | Trp-derived (indole side chain, α-NHBoc, C(O)NH-) | 2-aminophenyl-C(O)-CH₂- |
| 309 | NHCO(CH₂)₁₀CH₃ | Trp-derived (indole side chain, α-NH₂, C(O)NH-) | 2-aminophenyl-C(O)-CH₂- |

| Cpd # | R | R¹ | R² |
|---|---|---|---|
| 310 | NHCO(CH₂)₉CH₃ | tryptophan-amide | 2-aminophenyl ketone |
| 311 | NHCONH(CH₂)₇CH₃ | tryptophan-amide | 2-aminophenyl ketone |
| 315 | NHCONH(CH₂)₇CH₃ | 5-methoxy-indol-3-yl-methylamino | 2-aminophenyl ketone |
| 316 | NHCONH(CH₂)₇CH₃ | imidazol-2-yl-methylamino | 2-aminophenyl ketone |
| 317 | NHCONH(CH₂)₇CH₃ | (6-nitroquinolin-2-yl)methylamino | 2-aminophenyl ketone |

-continued

| Cpd # | R | R¹ | R² |
|---|---|---|---|
| 318 | NHCO(CH₂)₉CH₃ | 5-methoxy-1H-indol-3-ylmethylamino | 2-aminophenyl ketomethyl |
| 319 | NHCO(CH₂)₉CH₃ | 1H-imidazol-2-ylmethylamino | 2-aminophenyl ketomethyl |
| 320 | NHCO(CH₂)₁₁CH₃ | 5-methoxy-1H-indol-3-ylmethylamino | 2-aminophenyl ketomethyl |
| 321 | NHCO(CH₂)₁₁CH₃ | 6-nitroquinolin-2-ylmethylamino | 2-aminophenyl ketomethyl |
| 322 | NHCO(CH₂)₁₁CH₃ | 1H-imidazol-2-ylmethylamino | 2-aminophenyl ketomethyl |

-continued
| Cpd # | R | R¹ | R² |
|---|---|---|---|
| 323 | NHCO(CH$_2$)$_8$CH$_3$ | 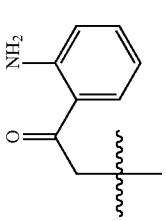 | 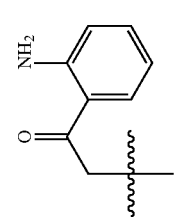 |
| 324 | NHCO(CH$_2$)$_8$CH$_3$ | 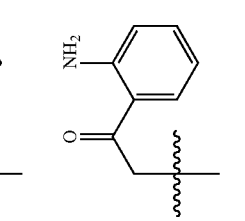 | 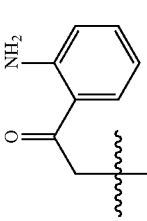 |
| 325 | NHCO(CH$_2$)$_8$CH$_3$ | 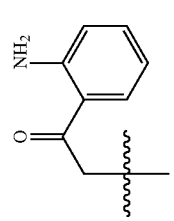 | 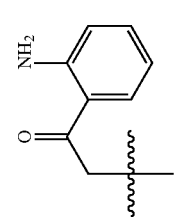 |
| 326 | NHCO(CH$_2$)$_8$CH$_3$ | 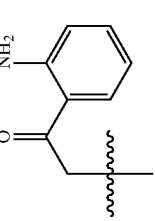 | 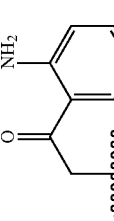 |
| 327 | NHCO(CH$_2$)$_8$CH$_3$ | 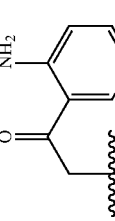 |  |

| Cpd # | R | R¹ | R² |
|---|---|---|---|
| 328 | NHCO(CH₂)₈CH₃ | 3-chloro-4-(3-trifluoromethylbenzyloxy)benzylamino | 2-aminophenacyl |
| 329 | NHCO(CH₂)₈CH₃ | 3-chloro-4-(3,5-bis(trifluoromethyl)benzyloxy)benzylamino | 2-aminophenacyl |
| 330 | NHCO(CH₂)₈CH₃ | 3-chloro-4-(3-fluorobenzyloxy)benzylamino | 2-aminophenacyl |
| 331 | NHCO(CH₂)₈CH₃ | 3-nitro-4-(3,5-bis(trifluoromethyl)benzyloxy)benzylamino | 2-aminophenacyl |
| 332 | NHCO(CH₂)₁₀CH₃ | (5-methoxyindol-3-yl)methylamino | 2-aminophenacyl |

-continued

| Cpd # | R | R¹ | R² |
|---|---|---|---|
| 333 | NHCO(CH$_2$)$_{10}$CH$_3$ | 6-nitroquinolin-2-ylmethylamino | 2-aminophenacyl |
| 334 | NHCO(CH$_2$)$_{10}$CH$_3$ | (1H-imidazol-2-yl)methylamino | 2-aminophenacyl |
| 335 | NHCONH(CH$_2$)$_{11}$CH$_3$ | (1H-imidazol-2-yl)methylamino | 2-aminophenacyl |
| 336 | NHCONH(CH$_2$)$_{11}$CH$_3$ | 6-nitroquinolin-2-ylmethylamino | 2-aminophenacyl |
| 337 | NHCONH(CH$_2$)$_{11}$CH$_3$ | (5-methoxy-1H-indol-3-yl)methylamino | 2-aminophenacyl |

-continued

| Cpd # | R | R¹ | R² |
|---|---|---|---|
| 338 | NHCO(CH₂)₁₂CH₃ | Tryptophan with NHBoc | 2-aminophenyl ketone |
| 339 | NHCO(CH₂)₁₂CH₃ | Tryptophan with NH₂ | 2-aminophenyl ketone |
| 340 | NHCO(CH₂)₁₂CH₃ | Lysine with NHBoc and NHBoc | 2-aminophenyl ketone |
| 341 | NHCO(CH₂)₁₂CH₃ | Lysine with NH₂ and NH₂ | 2-aminophenyl ketone |
| 345 | NHCO(CH₂)₁₂CH₃ | Imidazolylmethylamine | |

-continued
| Cpd # | R | R¹ | R² |
|---|---|---|---|
| 346 | NHCO(CH₂)₁₂CH₃ | 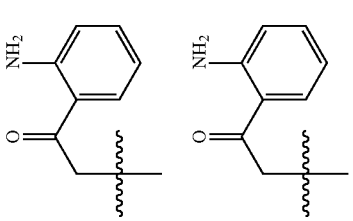 | 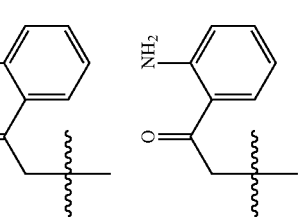 |
| 347 | NHCO(CH₂)₇CH₃ | 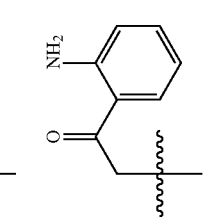 | 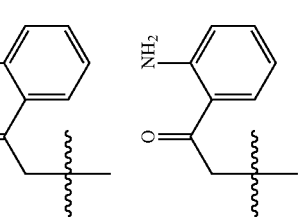 |
| 348 | NHCO(CH₂)₇CH₃ | 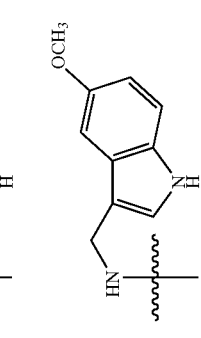 | 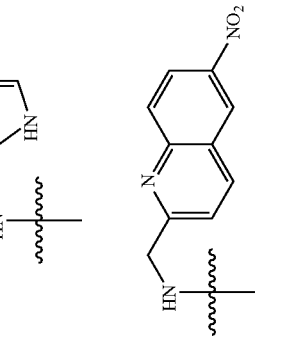 |
| 349 | NHCO(CH₂)₇CH₃ |  |  |
| 350 | 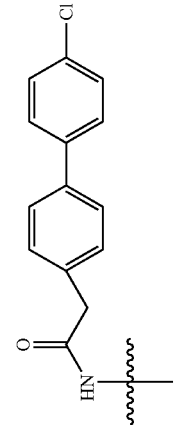 | | |

| Cpd # | R | R¹ | R² |
|---|---|---|---|
| 351 | NHCO(CH₂)₁₁CH₃ | 2-amino-6-fluorobenzamide (HN-linked) | 2′-aminophenacyl (ArC(O)CH₂–) |
| 352 | NHCONH(CH₂)₁₀CH₃ | 2-amino-6-fluorobenzamide (HN-linked) | 2′-aminophenacyl |
| 355 | NHCONH(CH₂)₁₀CH₃ | (1H-imidazol-2-yl)methyl-NH– | 2′-aminophenacyl |
| 356 | NHCONH(CH₂)₁₀CH₃ | (5-methoxy-1H-indol-3-yl)methyl-NH– | 2′-aminophenacyl |
| 358 | NHCO(CH₂)₈CH₃ | 4-[(phenethylsulfamoyl)]benzyl-NH– | 2′-aminophenacyl |

-continued

| Cpd # | R | R¹ | R² |
|---|---|---|---|
| 359 | NHCO(CH₂)₈CH₃ | phenylsulfonamide-benzyl-NH- | 2-aminophenyl-CO-CH₂- |
| 360 | NHCO(CH₂)₈CH₃ | 4-methylpiperazinyl-sulfonyl-benzyl-NH- | 2-aminophenyl-CO-CH₂- |
| 361 | NHCO(CH₂)₈CH₃ | 4-acetylpiperazinyl-sulfonyl-benzyl-NH- | 2-aminophenyl-CO-CH₂- |
| 362 | NHCO(CH₂)₈CH₃ | 4-phenylpiperazinyl-sulfonyl-benzyl-NH- | 2-aminophenyl-CO-CH₂- |
| 363 | NHCO(CH₂)₈CH₃ | 4-(2-pyridyl)piperazinyl-sulfonyl-benzyl-NH- | 2-aminophenyl-CO-CH₂- |

| Cpd # | R | R¹ | R² |
|---|---|---|---|
| 364 | NHCO(CH₂)₈CH₃ | 4-(4-phenylpiperazin-1-ylsulfonyl)benzyl-NH- | 2-aminophenyl-C(O)-CH₂- |
| 365 | NHCO(CH₂)₈CH₃ | 4-(4-benzylpiperazin-1-ylsulfonyl)benzyl-NH- | 2-aminophenyl-C(O)-CH₂- |
| 366 | NHCO(CH₂)₈CH₃ | 4-[4-(4-methoxyphenyl)piperazin-1-ylsulfonyl]benzyl-NH- | 2-aminophenyl-C(O)-CH₂- |
| 367 | NHCO(CH₂)₈CH₃ | 4-[4-(2-methoxyphenyl)piperazin-1-ylsulfonyl]benzyl-NH- | 2-aminophenyl-C(O)-CH₂- |
| 368 | NHCO(CH₂)₈CH₃ | 4-[4-(2-chlorophenyl)piperazin-1-ylsulfonyl]benzyl-NH- | 2-aminophenyl-C(O)-CH₂- |

| Cpd # | R | R¹ | R² |
|---|---|---|---|
| 369 | NHCO(CH₂)₈CH₃ | pyrrolidine-C(O)-CH₂-piperazine-SO₂-C₆H₄-CH₂-NH- | 2-aminophenyl-C(O)-CH₂- |
| 370 | NHCO(CH₂)₈CH₃ | 4-F-C₆H₄-piperazine-SO₂-C₆H₄-CH₂-NH- | 2-aminophenyl-C(O)-CH₂- |
| 371 | NHCO(CH₂)₈CH₃ | benzo[1,3]dioxol-5-yl-CH₂-piperazine-SO₂-C₆H₄-CH₂-NH- | 2-aminophenyl-C(O)-CH₂- |
| 372 | NHCO(CH₂)₈CH₃ | 3-CF₃-C₆H₄-piperazine-SO₂-C₆H₄-CH₂-NH- | 2-aminophenyl-C(O)-CH₂- |
| 373 | NHCO(CH₂)₈CH₃ | 3,4-diCl-C₆H₃-piperazine-SO₂-C₆H₄-CH₂-NH- | 2-aminophenyl-C(O)-CH₂- |

| Cpd # | R | R¹ | R² |
|---|---|---|---|
| 374 | NHCO(CH₂)₈CH₃ | 4-((pyrimidin-2-yl)piperazin-1-ylsulfonyl)benzyl-NH- | 2-aminophenyl-C(O)CH₂- |
| 375 | NHCO(CH₂)₈CH₃ | 4-((2-fluorophenyl)sulfamoyl)benzyl-NH- | 2-aminophenyl-C(O)CH₂- |
| 376 | NHCO(CH₂)₈CH₃ | 4-((3-fluorophenyl)sulfamoyl)benzyl-NH- | 2-aminophenyl-C(O)CH₂- |
| 377 | NHCO(CH₂)₈CH₃ | 4-((4-fluorophenyl)sulfamoyl)benzyl-NH- | 2-aminophenyl-C(O)CH₂- |
| 378 | NHCO(CH₂)₈CH₃ | 4-((phenylpropyl)sulfamoyl)benzyl-NH- | 2-aminophenyl-C(O)CH₂- |

-continued

| Cpd # | R | R¹ | R² |
|---|---|---|---|
| 379 | NHCO(CH$_2$)$_8$CH$_3$ | 3-chlorobenzyl sulfonamide | 2-aminophenyl ketone |
| 380 | NHCO(CH$_2$)$_8$CH$_3$ | 4-chlorobenzyl sulfonamide | 2-aminophenyl ketone |
| 381 | NHCO(CH$_2$)$_8$CH$_3$ | 2,4-difluorobenzyl sulfonamide | 2-aminophenyl ketone |
| 382 | NHCO(CH$_2$)$_8$CH$_3$ | 3,4-difluorobenzyl sulfonamide | 2-aminophenyl ketone |
| 383 | NHCO(CH$_2$)$_8$CH$_3$ | 2-chlorophenethyl sulfonamide | 2-aminophenyl ketone |

-continued

| Cpd # | R | R¹ | R² |
|---|---|---|---|
| 384 | NHCO(CH₂)₈CH₃ | 4-chlorophenethyl-sulfonamide-benzyl | 2-aminophenyl ketone |
| 385 | NHCO(CH₂)₈CH₃ | 2-(trifluoromethyl)benzyl-sulfonamide-benzyl | 2-aminophenyl ketone |
| 386 | NHCO(CH₂)₈CH₃ | 3-(trifluoromethyl)benzyl-sulfonamide-benzyl | 2-aminophenyl ketone |
| 387 | NHCO(CH₂)₈CH₃ | 4-(trifluoromethyl)benzyl-sulfonamide-benzyl | 2-aminophenyl ketone |
| 388 | NHCO(CH₂)₈CH₃ | 4-fluorophenethyl-sulfonamide-benzyl | 2-aminophenyl ketone |

-continued

| Cpd # | R | R¹ | R² |
|---|---|---|---|
| 389 | NHCO(CH₂)₈CH₃ | 3,4-dichlorobenzyl-NHSO₂-C₆H₄-CH₂-NH-~ | 2-aminophenyl-C(O)-CH₂-~ |
| 390 | NHCO(CH₂)₈CH₃ | 3,5-dichlorobenzyl-NHSO₂-C₆H₄-CH₂-NH-~ | 2-aminophenyl-C(O)-CH₂-~ |
| 391 | NHCO(CH₂)₈CH₃ | 2,4-dichlorobenzyl-NHSO₂-C₆H₄-CH₂-NH-~ | 2-aminophenyl-C(O)-CH₂-~ |
| 392 | NHCO(CH₂)₈CH₃ | 3-OCF₃-benzyl-NHSO₂-C₆H₄-CH₂-NH-~ | 2-aminophenyl-C(O)-CH₂-~ |
| 393 | NHCO(CH₂)₈CH₃ | 4-OCF₃-benzyl-NHSO₂-C₆H₄-CH₂-NH-~ | 2-aminophenyl-C(O)-CH₂-~ |

-continued

| Cpd # | R | R¹ | R² |
|---|---|---|---|
| 394 | NHCO(CH₂)₈CH₃ | (4-methylphenyl-sulfonamide-CH₂-NH-) | 2-aminophenyl-CO-CH₂- |
| 395 | NHCO(CH₂)₈CH₃ | (phenyl-sulfonamide-CH₂-NH-) | 2-aminophenyl-CO-CH₂- |
| 398 | NHCO(CH₂)₈CH₃ | (6-fluoroquinolin-4-yl 5-methyl-3-phenylisoxazole-4-carboxylate, 2-CH₂NH-) | 2-aminophenyl-CO-CH₂- |
| 399 | NHCO(CH₂)₈CH₃ | (4-(3-chlorophenoxy)quinolin-2-yl-CH₂-NH-) | 2-aminophenyl-CO-CH₂- |

-continued

| Cpd # | R | R¹ | R² |
|---|---|---|---|
| 400 | NHCO(CH₂)₈CH₃ | quinoline-4-piperazine-CH₂-NH- | 2-aminophenyl-C(O)CH₂- |
| 401 | NHCO(CH₂)₈CH₃ | quinolin-4-yl-N(SO₂-4-tolyl)-, 2-CH₂NH- | 2-aminophenyl-C(O)CH₂- |
| 402 | NHCO(CH₂)₈CH₃ | quinolin-4-yl-S-(5-amino-1,3,4-thiadiazol-2-yl), 2-CH₂NH- | 2-aminophenyl-C(O)CH₂- |
| 403 | NHCO(CH₂)₈CH₃ | quinolin-4-yl-SO₂CH₃, 2-CH₂NH- | 2-aminophenyl-C(O)CH₂- |

-continued

| Cpd # | R | R¹ | R² |
|---|---|---|---|
| 404 | NHCO(CH₂)₈CH₃ | 7-CF₃, 4-OH quinolin-2-ylmethylaminomethyl | 2-aminophenyl-C(O)-CH₂- |
| 405 | NHCO(CH₂)₈CH₃ | 4-(methylsulfonyl)quinolin-2-ylmethylaminomethyl | 2-aminophenyl-C(O)-CH₂- |
| 406 | NHCO(CH₂)₈CH₃ | quinolin-8-ylmethylaminomethyl | 2-aminophenyl-C(O)-CH₂- |
| 407 | NHCO(CH₂)₈CH₃ | 7-chloro-4-[(5-chlorobenzothiazol-2-yl)oxy]naphthalen-2-ylmethylaminomethyl | 2-aminophenyl-C(O)-CH₂- |

| Cpd # | R | R¹ | R² |
|---|---|---|---|
| 408 | NHCO(CH₂)₈CH₃ | 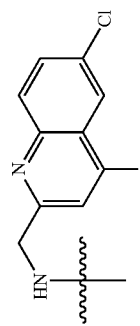 | 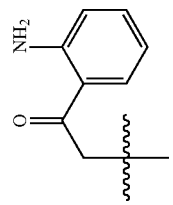 |
| 409 | NHCO(CH₂)₈CH₃ | 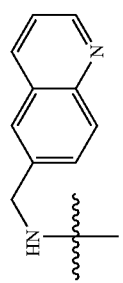 | 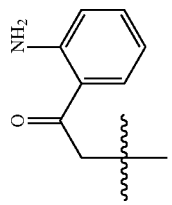 |
| 410 | NHCO(CH₂)₈CH₃ | 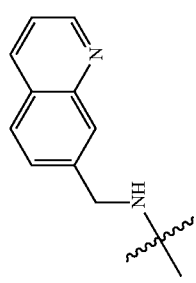 | 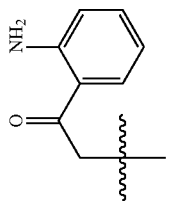 |

12. The compound according to claim 11 wherein the compound is

| Cpd # | R | R¹ | R² |
|---|---|---|---|
| 45 | NHCO(CH$_2$)$_8$CH$_3$ | tryptophan amide (α-NH$_2$, indole side chain) linked via NH | 2-aminophenyl ketone (–CH$_2$C(O)-C$_6$H$_4$-2-NH$_2$) |
| 54 | NHCO(CH$_2$)$_8$CH$_3$ | lysine amide (α-NH$_2$, ε-NH$_2$ side chain) linked via NH | 2-aminophenyl ketone |
| 76 | NHCO(CH$_2$)$_8$CH$_3$ | 4-biphenylmethyl-NH– | 2-aminophenyl ketone |
| 81 | NHCO(CH$_2$)$_8$CH$_3$ | (5-fluoro-1H-indol-3-yl)methyl-NH– | 2-aminophenyl ketone |
| 85 | NHCO(CH$_2$)$_8$CH$_3$ | (1-methyl-1H-imidazol-2-yl)methyl-NH– | 2-aminophenyl ketone |
| 102 | NHCO(CH$_2$)$_{11}$CH$_3$ | tryptophan amide (α-NH$_2$, indole side chain) linked via NH | 2-aminophenyl ketone |
| 209 | NHCO(CH$_2$)$_8$CH$_3$ | [4-(4-fluorobenzyloxy)-3-nitrophenyl]methyl-NH– | 2-aminophenyl ketone |
| 212 | NHCO(CH$_2$)$_8$CH$_3$ | (1H-imidazol-2-yl)methyl-NH– | 2-aminophenyl ketone |

-continued
| Cpd # | R | R¹ | R² |
|---|---|---|---|
| 253 | NHCO(CH$_2$)$_8$CH$_3$ | 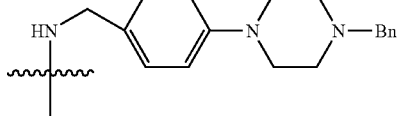 | 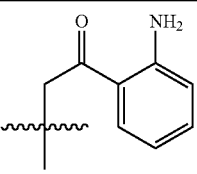 |
| 282 | NHCO(CH$_2$)$_8$CH$_3$ | 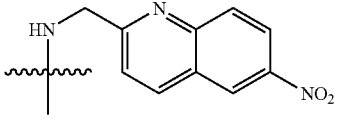 | 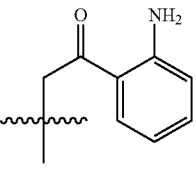 |
| 285 | NHCO(CH$_2$)$_8$CH$_3$ | 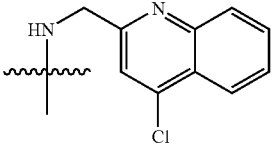 | 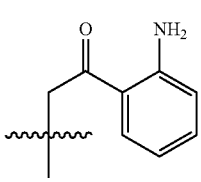 |
| 319 | NHCO(CH$_2$)$_9$CH$_3$ | 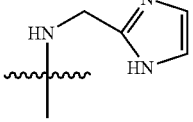 | 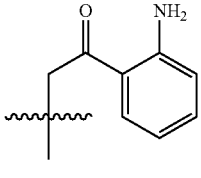 |
| 322 | NHCO(CH$_2$)$_{11}$CH$_3$ | 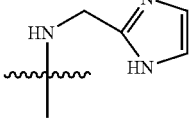 | 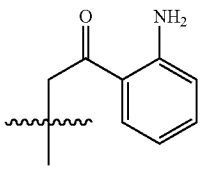 |
| 333 | NHCO(CH$_2$)$_{10}$CH$_3$ | 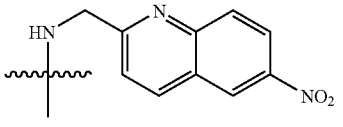 | 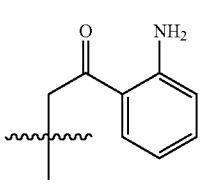 |
| 334 | NHCO(CH$_2$)$_{10}$CH$_3$ | 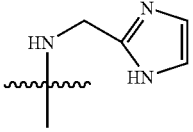 | 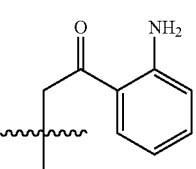 |
| 335 | NHCOKH(CH$_2$)$_{11}$CH$_3$ | 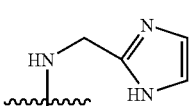 | 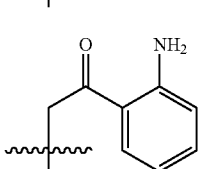 |
| 336 | NHCONH(CH$_2$)$_{11}$CH$_3$ | 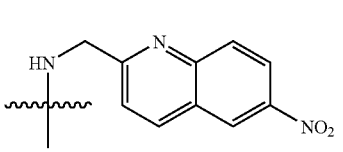 | 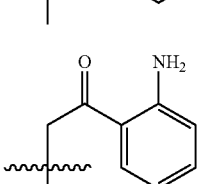 |

-continued
| Cpd # | R | R¹ | R² |
|---|---|---|---|
| 355 | NHCOKH(CH₂)₁₀CH₃ | 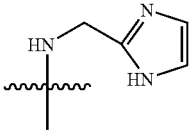 | 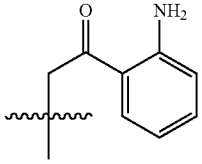 |
13. A compound of formula (I) according to claim 1, wherein R is NHCO-[(C₆-C₁₄)-alkyl]-CH₃, and R¹ and R² are selected from:
| R¹ | R² |
|---|---|
| 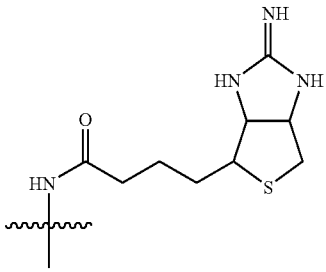 | 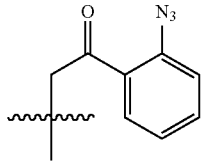 |
| 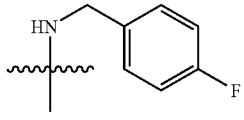 | 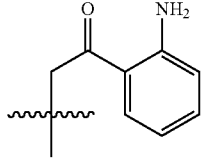 |
| 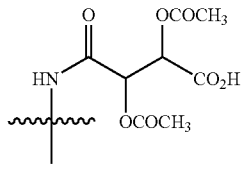 | 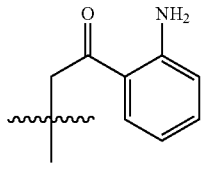 |
| 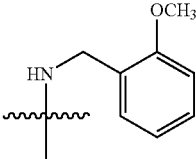 | 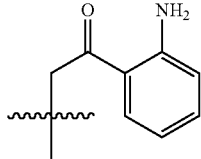 |
| 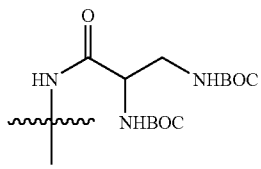 | 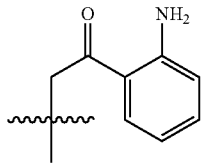 |

| R¹ | R² |
|---|---|
| (structure: HN-C(=O)-CH(NHBOC)-CH₂CH₂-CO₂CH₃) | (structure: 2-aminophenyl ketone) |
| (structure: HN-C(=O)-CH(NHBOC)-CH₂-CO₂ᵗBu) | (structure: 2-aminophenyl ketone) |
| (structure: HN-C(=O)-CH(NHBOC)-CH₂-indol-3-yl) | (structure: 2-aminophenyl ketone) |
| (structure: HN-C(=O)-CH(NH₂)-CH₂-indol-3-yl) | (structure: 2-aminophenyl ketone) |
| (structure: HN-C(=O)-CH(NH₂)-CH₂CH₂-CO₂CH₃) | (structure: 2-aminophenyl ketone) |
| (structure: HN-C(=O)-CH(NH₂)-CH₂CH₂-CONH₂) | (structure: 2-aminophenyl ketone) |
| (structure: HN-C(=O)-CH(NH₂)-CH₂-CONH₂) | (structure: 2-aminophenyl ketone) |
| (structure: HN-C(=O)-CH(NHBOC)-(CH₂)₄-NHTs) | (structure: 2-aminophenyl ketone) |

| R¹ | R² |
|---|---|
| 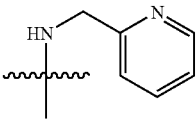 | 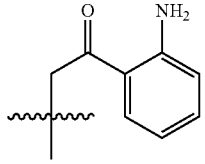 |
| 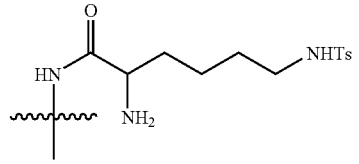 | 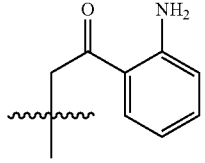 |
| 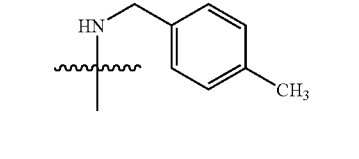 | 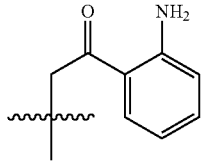 |
| 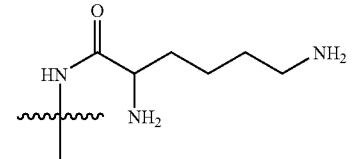 | 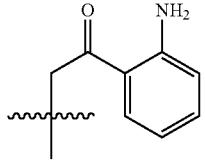 |
| 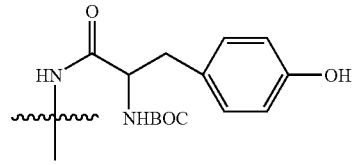 | 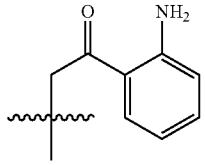 |
| 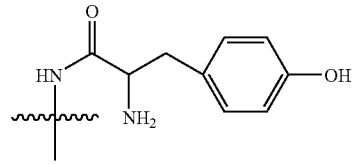 | 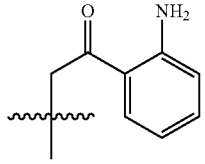 |
| 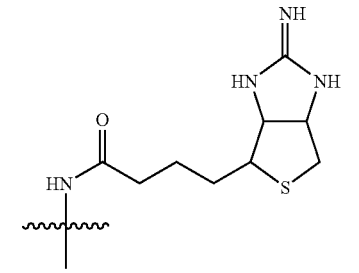 | 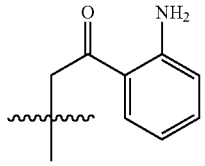 |
| 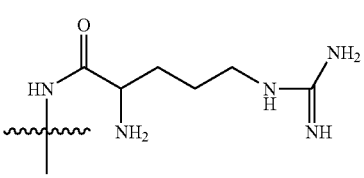 | 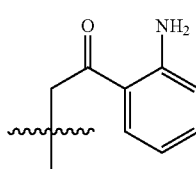 |

-continued
| R¹ | R² |
|---|---|
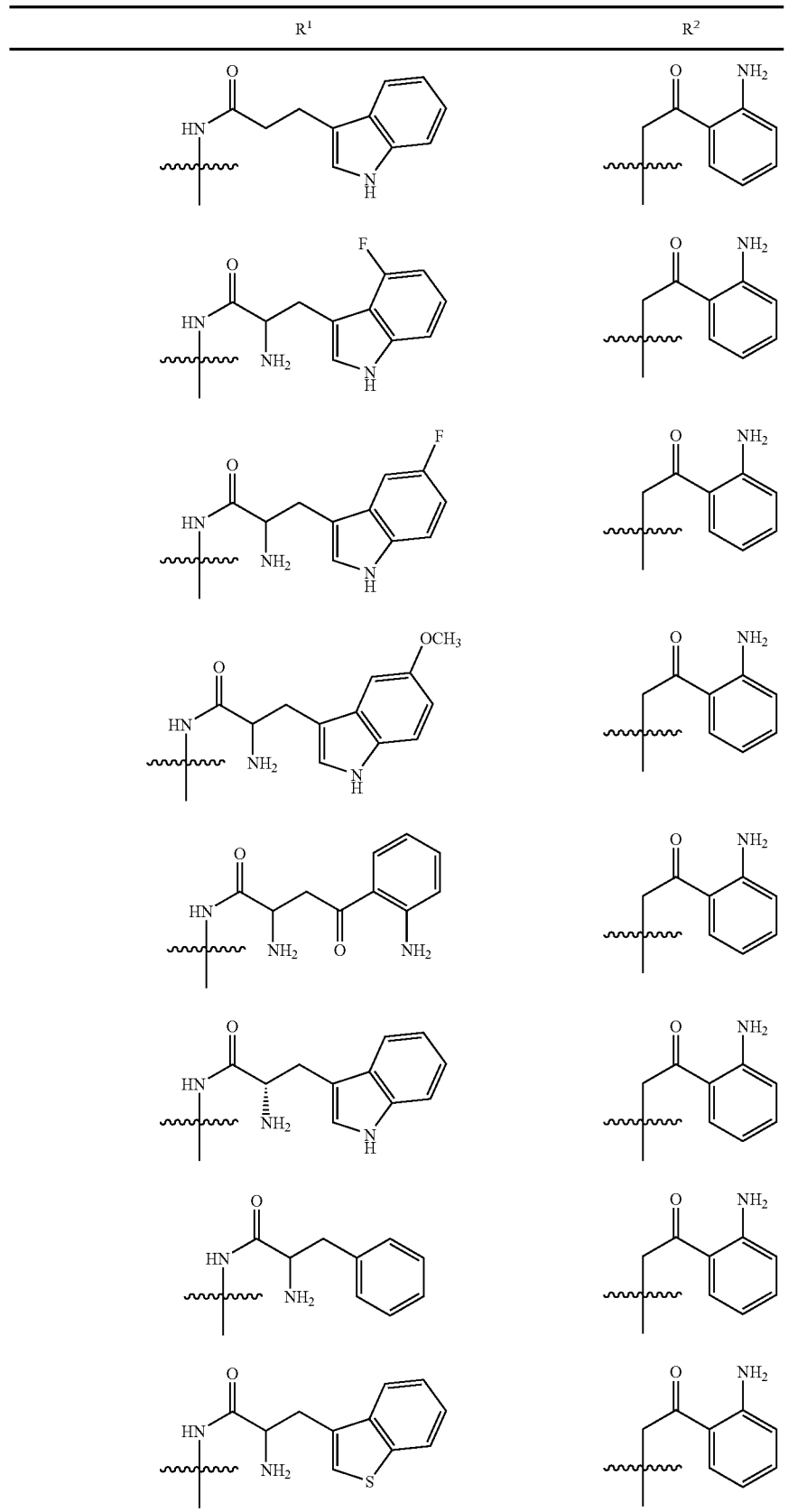

| R¹ | R² |
|---|---|
| (structure: α-amino amide with thiazol-4-ylmethyl side chain) | (structure: 2-aminophenyl ketone, –CH₂–C(=O)–C₆H₄–NH₂) |
| (structure: α-amino amide with –CH₂NH₂ side chain, 2,3-diaminopropanamide) | (structure: 2-aminophenyl ketone) |
| (structure: α-amino amide with imidazol-4-ylmethyl side chain, histidine-like) | (structure: 2-aminophenyl ketone) |
| (structure: α-amino amide with N-BOC imidazol-4-ylmethyl side chain) | (structure: 2-aminophenyl ketone) |
| (structure: β-alanine amide with NHBOC) | (structure: 2-aminophenyl ketone) |
| NH(CH₂)₂OH | (structure: 2-aminophenyl ketone) |
| (structure: 2-amino-4-(anilino)-1,3,5-triazin-6-ylmethylamino group) | (structure: 2-aminophenyl ketone) |
| (structure: (1H-indol-3-yl)methylamino group) | (structure: 2-aminophenyl ketone) |

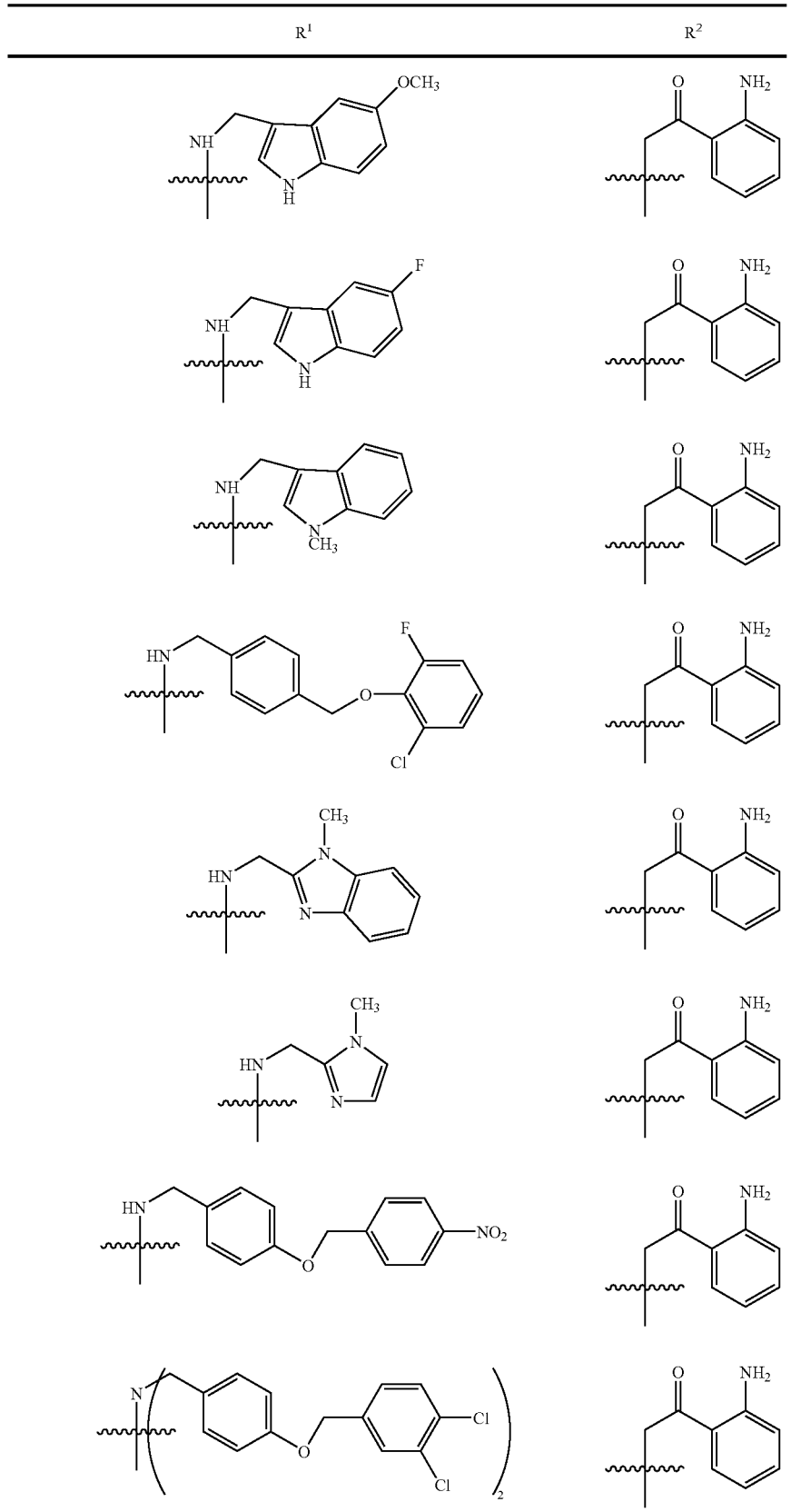

-continued

| R¹ | R² |
|---|---|
| (structure: HN-CH2-C6H4-O-CH2-C6H3(Cl)2) | (structure: C(=O)-CH2- on 2-aminophenyl) |
| (structure: N(-CH2-C6H4-O-C6H4-OMe)2) | (structure: C(=O)-CH2- on 2-aminophenyl) |
| (structure: N(-CH2-CH=CH-C6H4-NEt2)2) | (structure: C(=O)-CH2- on 2-aminophenyl) |
| (structure: HN-CH2-CH=CH-C6H4-NEt2) | (structure: C(=O)-CH2- on 2-aminophenyl) |
| (structure: HN-CH2-C6H4-OⁿBu) | (structure: C(=O)-CH2- on 2-aminophenyl) |
| (structure: HN-CH2-C6H4-OⁿPr) | (structure: C(=O)-CH2- on 2-aminophenyl) |
| (structure: HN-CH2-C6H4-O-CH2-C6H4-F) | (structure: C(=O)-CH2- on 2-aminophenyl) |
| (structure: HN-CH2-(2-methoxynaphthalen-1-yl)) | (structure: C(=O)-CH2- on 2-aminophenyl) |

-continued

| R¹ | R² |
|---|---|
| (structure: HN-CH2-phenyl with OMe and OBn substituents) | (structure: 2-aminophenyl ketone) |
| (structure: N(CH2-3-fluorophenyl)2) | (structure: 2-aminophenyl ketone) |
| (structure: N(CH2-2-fluorophenyl)2) | (structure: 2-aminophenyl ketone) |
| (structure: HN-CH2-4-(benzyloxy)phenyl) | (structure: 2-aminophenyl ketone) |
| (structure: HN-CH2-2-(4-benzylpiperazin-1-yl)phenyl) | (structure: 2-aminophenyl ketone) |
| (structure: N(CH2-2-(4-benzylpiperazin-1-yl)phenyl)2) | (structure: 2-aminophenyl ketone) |
| (structure: HN-CH2-3-nitrophenyl) | (structure: 2-aminophenyl ketone) |
| (structure: HN-CH2-2-hydroxy-4-(benzyloxy)phenyl) | (structure: 2-aminophenyl ketone) |

-continued
| R¹ | R² |
|---|---|
| 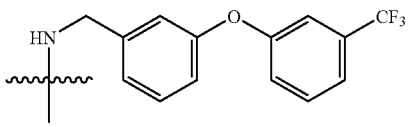 | 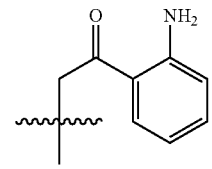 |
| 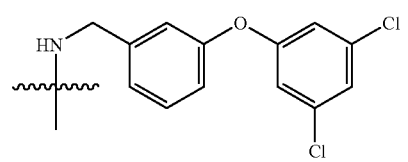 | 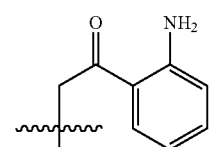 |
| 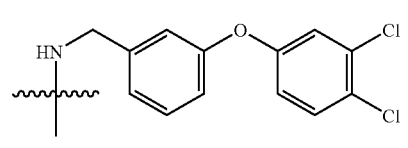 | 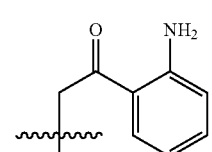 |
| 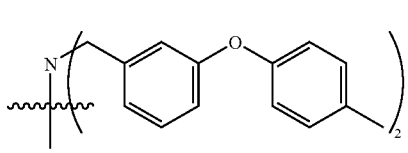 | 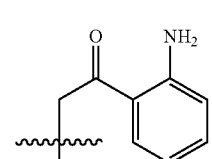 |
| 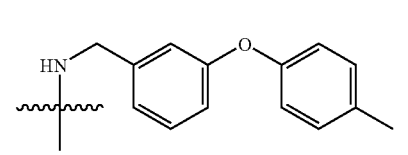 | 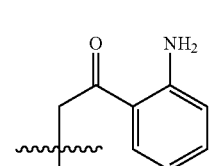 |
| 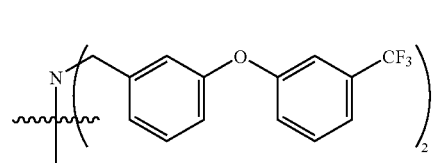 | 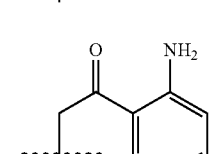 |
| 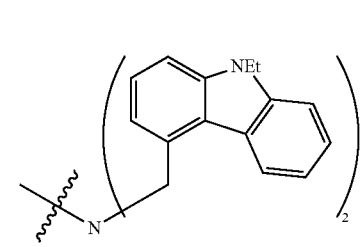 | 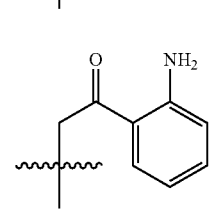 |
| 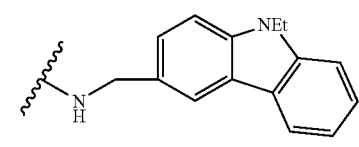 | 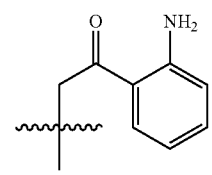 |

-continued
| R¹ | R² |
|---|---|
| 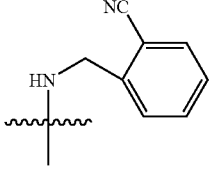 | 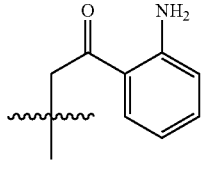 |
| 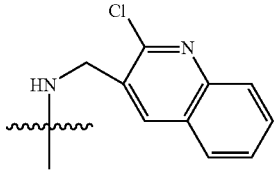 | 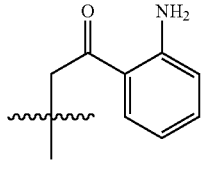 |
| 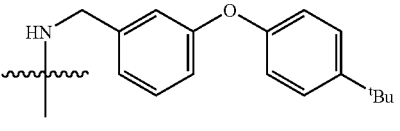 | 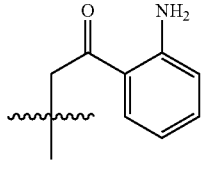 |
| 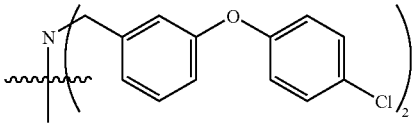 | 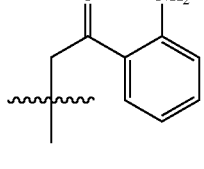 |
| 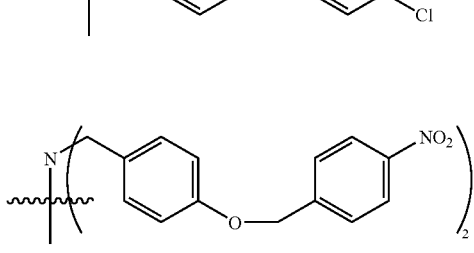 | 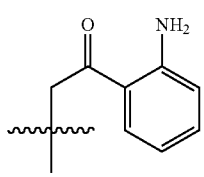 |
| 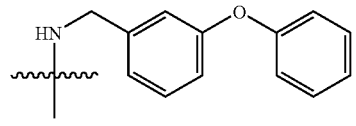 | 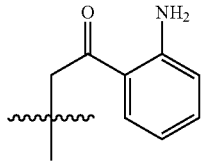 |
| 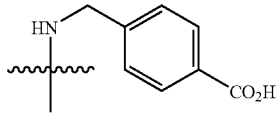 | 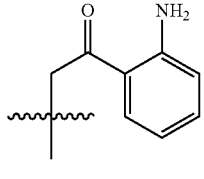 |

| R¹ | R² |
|---|---|
| 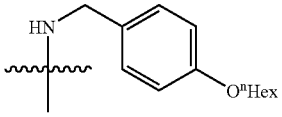 | 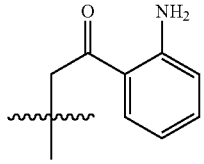 |
| 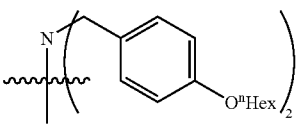 | 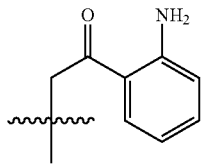 |
| 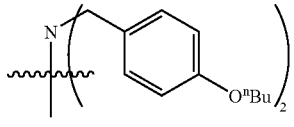 | 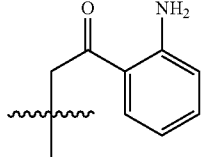 |
| 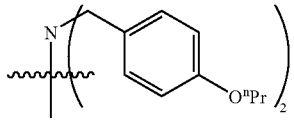 | 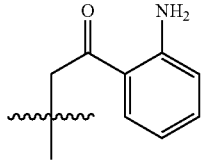 |
| 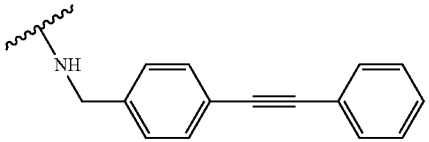 | 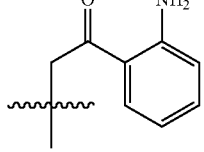 |
| 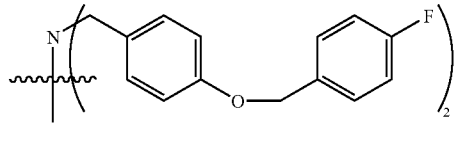 | 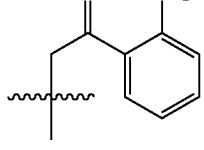 |
| 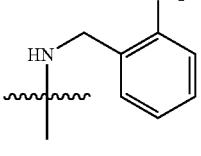 | 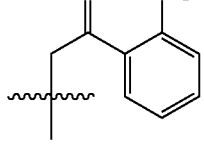 |
| 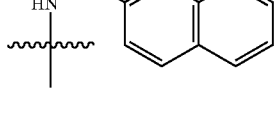 | 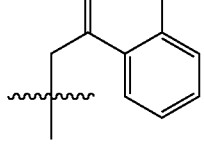 |
| 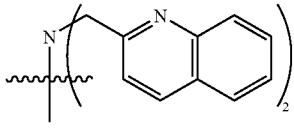 | 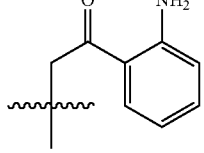 |

| R¹ | R² |
|---|---|
| 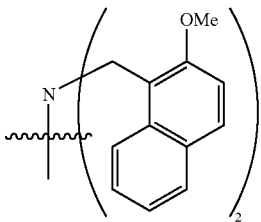 | 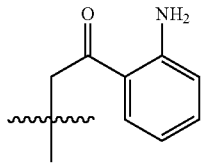 |
| 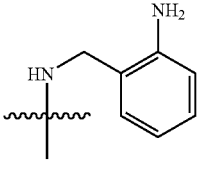 | 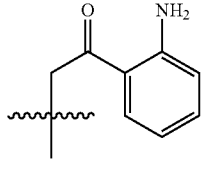 |
| 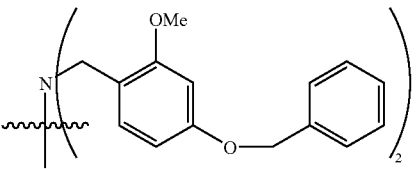 | 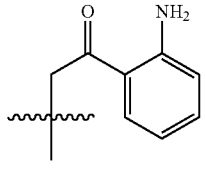 |
| 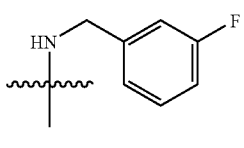 | 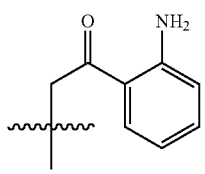 |
| 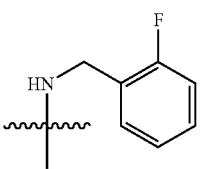 | 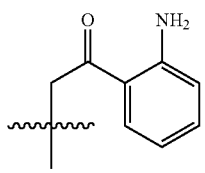 |
| 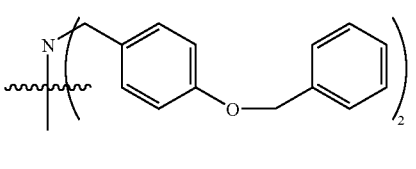 | 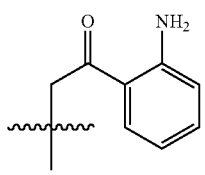 |
| 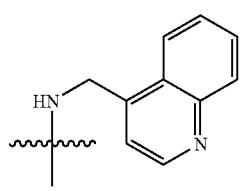 | 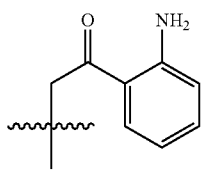 |
| 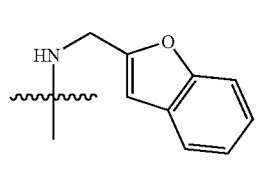 | 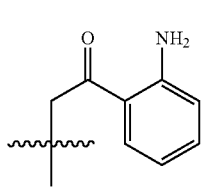 |

-continued

| R¹ | R² |
|---|---|

-continued

| R¹ | R² |
|---|---|

-continued

| R¹ | R² |
|---|---|
| (HN-CH₂-CH=CH-C₆H₄-NMe₂, para) | (2-aminophenyl ketone, -CH₂-C(O)-C₆H₄-NH₂) |
| (HN-CH₂-(3-methylbenzothiophen-2-yl)) | (2-aminophenyl ketone) |
| (HN-CH₂-(1-phenyl-3,5-dimethylpyrazol-4-yl)) | (2-aminophenyl ketone) |
| (N(-CH₂-(1-phenyl-3,5-dimethylpyrazol-4-yl))₂) | (2-aminophenyl ketone) |
| (HN-CH₂-C₆H₄-O-CH₂-CO₂H, para) | (2-aminophenyl ketone) |
| (N(-CH₂-(5-(4-bromophenyl)furan-2-yl))₂) | (2-aminophenyl ketone) |
| (N(-CH₂-CH=CH-C₆H₄-NO₂, para)₂) | (2-aminophenyl ketone) |
| (HN-CH₂-C₆H₄-O-CH₂-C₆H₅, meta) | (2-aminophenyl ketone) |

-continued

| R¹ | R² |
|---|---|
| N(CH₂-C₆H₄-O-CH₂-Ph)₂ (3-position) | C(=O)CH₂- (2-aminophenyl ketone) |
| HN-CH₂-(2,4-difluorophenyl) | C(=O)CH₂- (2-aminophenyl ketone) |
| N(CH₂-CH=CH-Ph)₂ | C(=O)CH₂- (2-aminophenyl ketone) |
| HN-CH₂-(quinolin-3-yl) | C(=O)CH₂- (2-aminophenyl ketone) |
| N(CH₂CH₂-Ph)₂ | C(=O)CH₂- (2-aminophenyl ketone) |
| N(CH₂-C₆H₄-ⁿButyl)₂ (4-position) | C(=O)CH₂- (2-aminophenyl ketone) |
| HN-CH₂-(4-ⁿButyl-phenyl) | C(=O)CH₂- (2-aminophenyl ketone) |
| HN-CH₂-(4-CN-phenyl) | C(=O)CH₂- (2-aminophenyl ketone) |

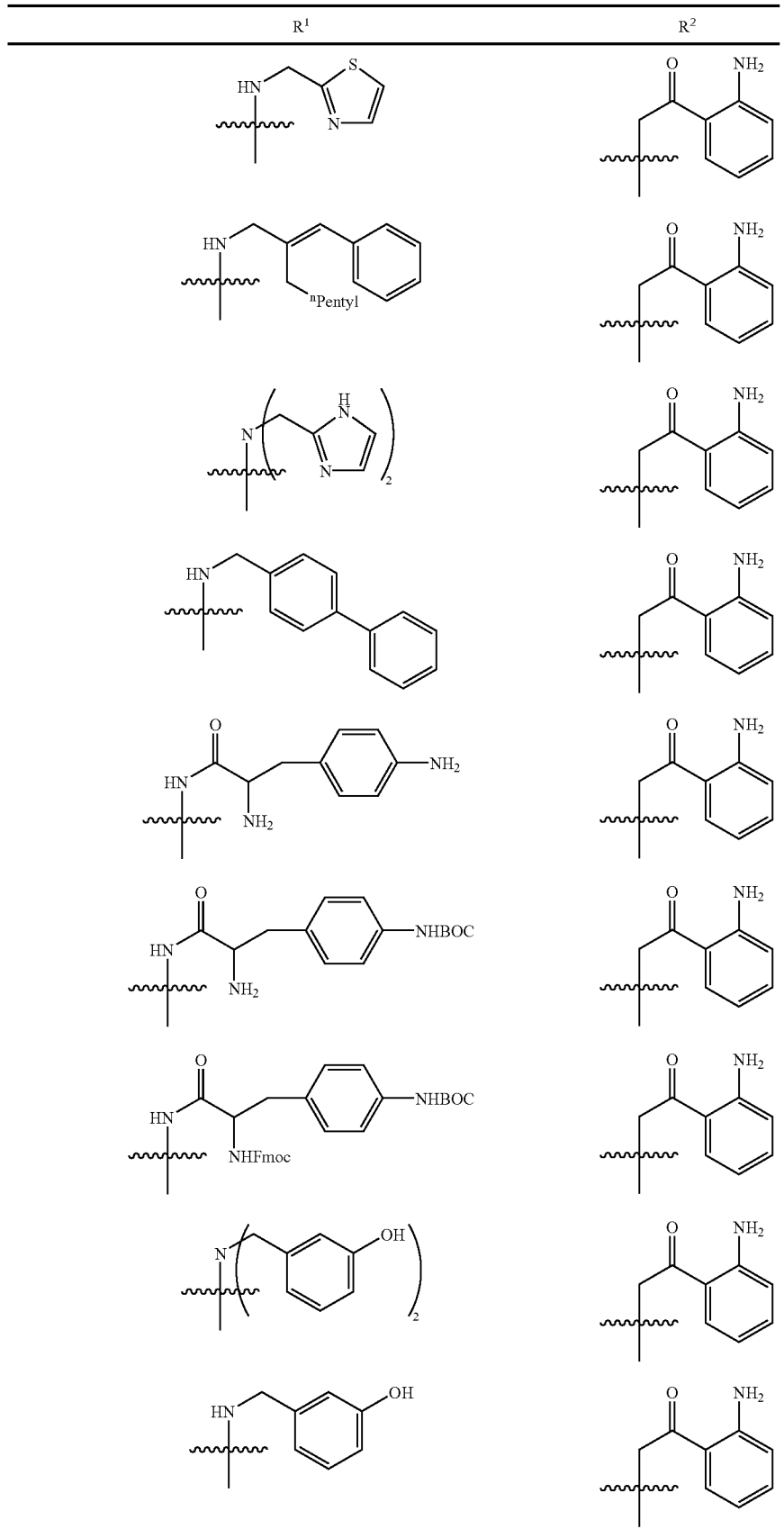

-continued
| R¹ | R² |
|---|---|
| 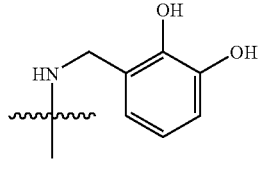 | 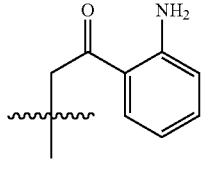 |
| 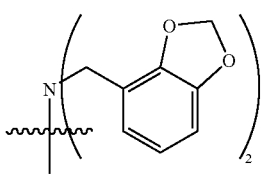 | 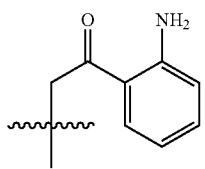 |
| 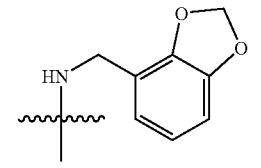 | 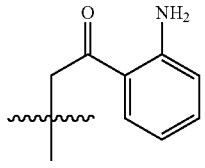 |
| 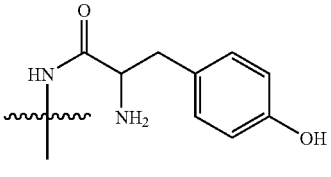 | 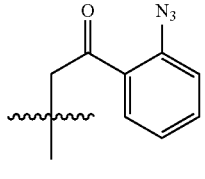 |
| 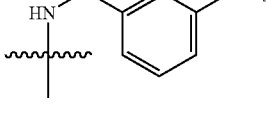 | 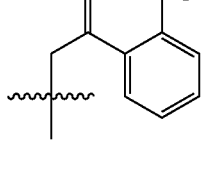 |
| 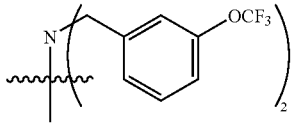 | 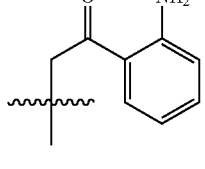 |
| 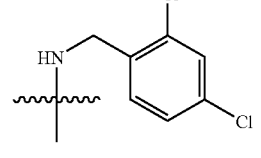 | 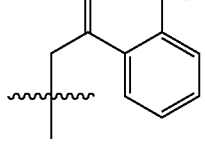 |
| 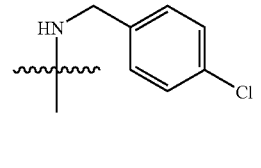 | 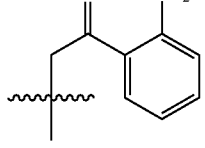 |

-continued
| R¹ | R² |
|---|---|
| 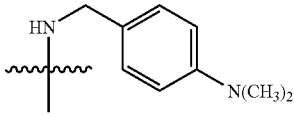 | 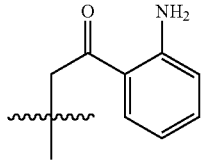 |
| 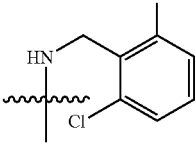 | 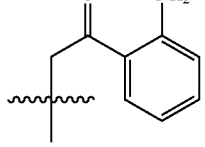 |
| 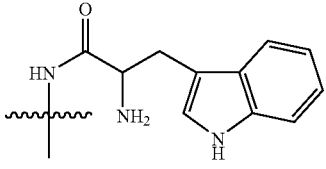 | 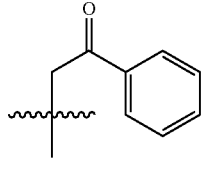 |
| 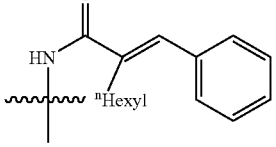 | 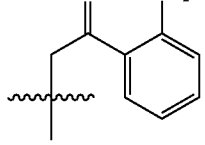 |
| 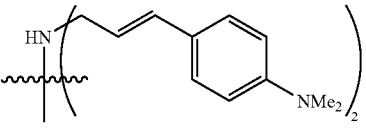 | 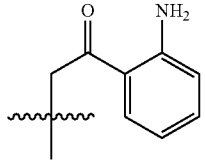 |
| 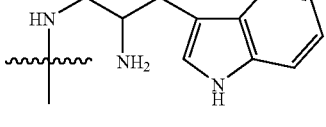 | 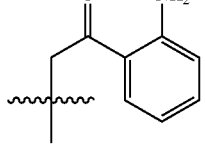 |
| 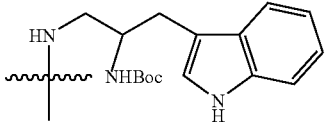 | 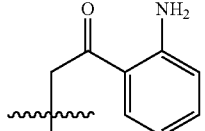 |
| 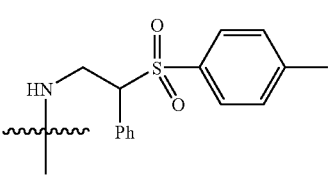 | 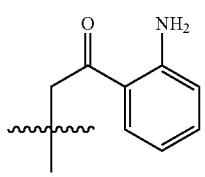 |
| 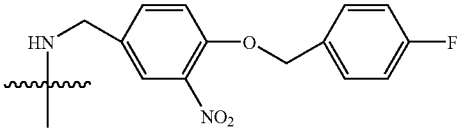 | 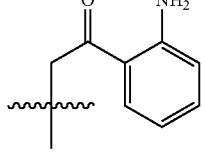 |

-continued

| R¹ | R² |
|---|---|

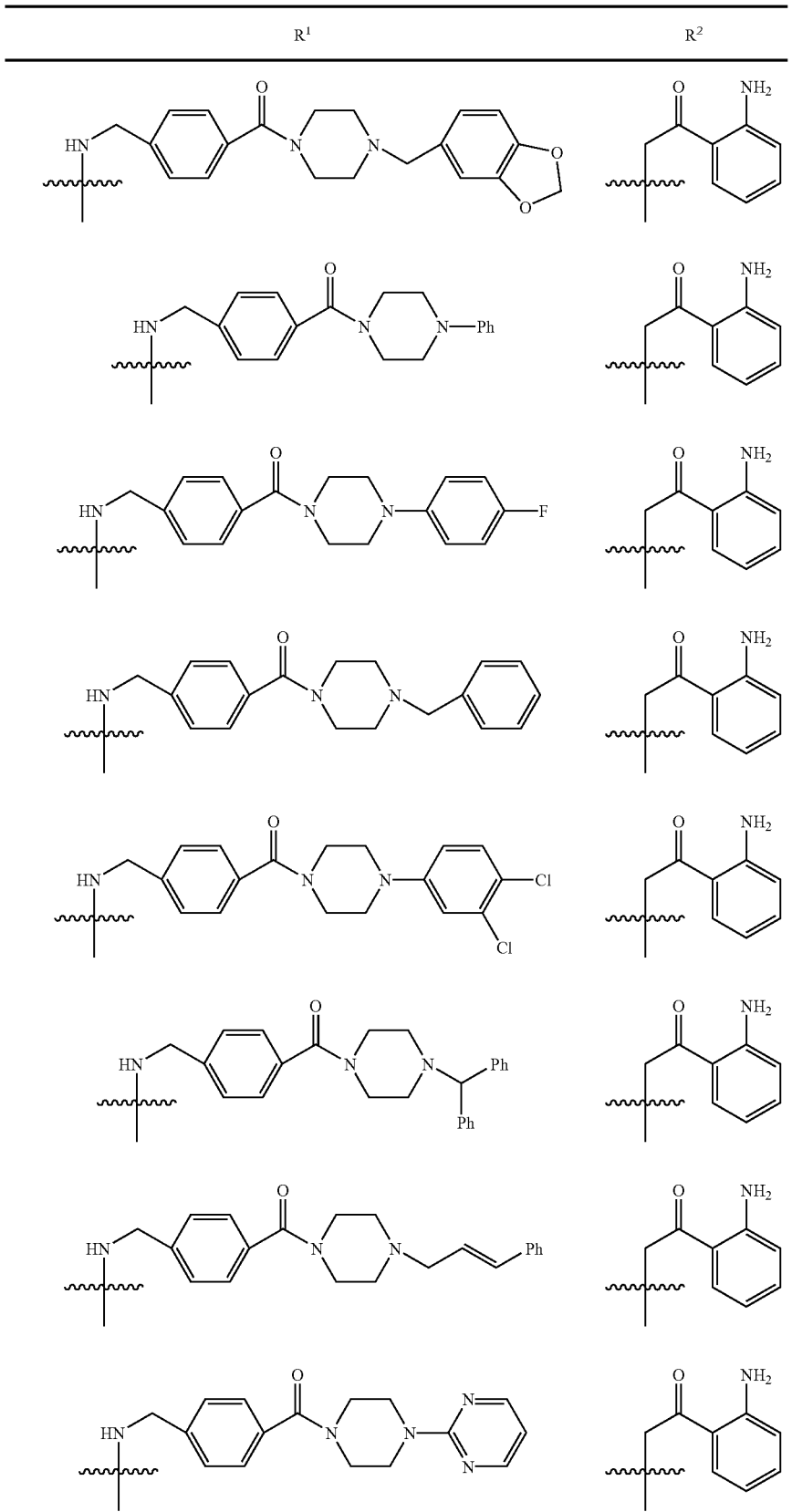

-continued
| R[1] | R[2] |
|---|---|
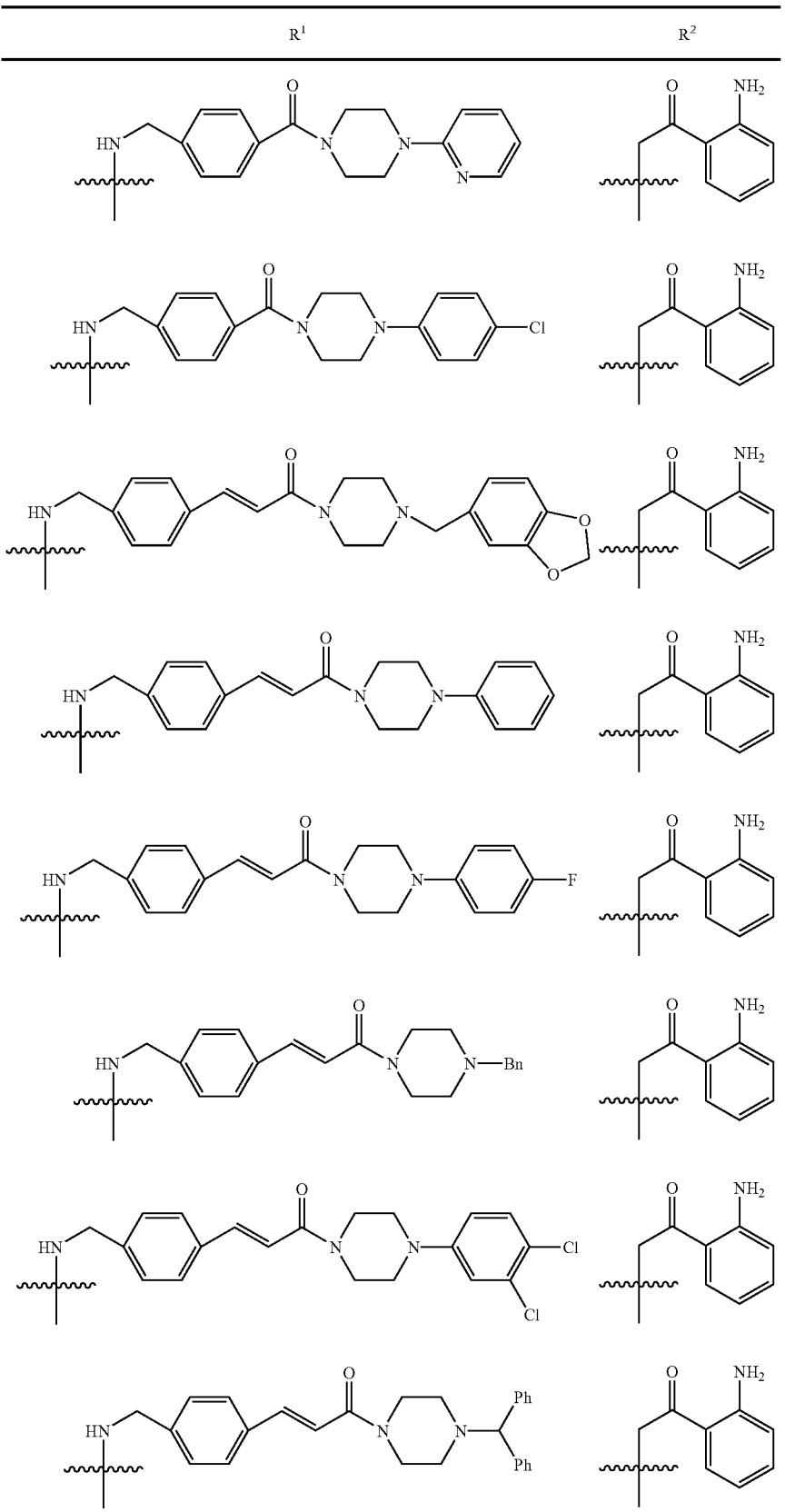

-continued
| R¹ | R² |
|---|---|
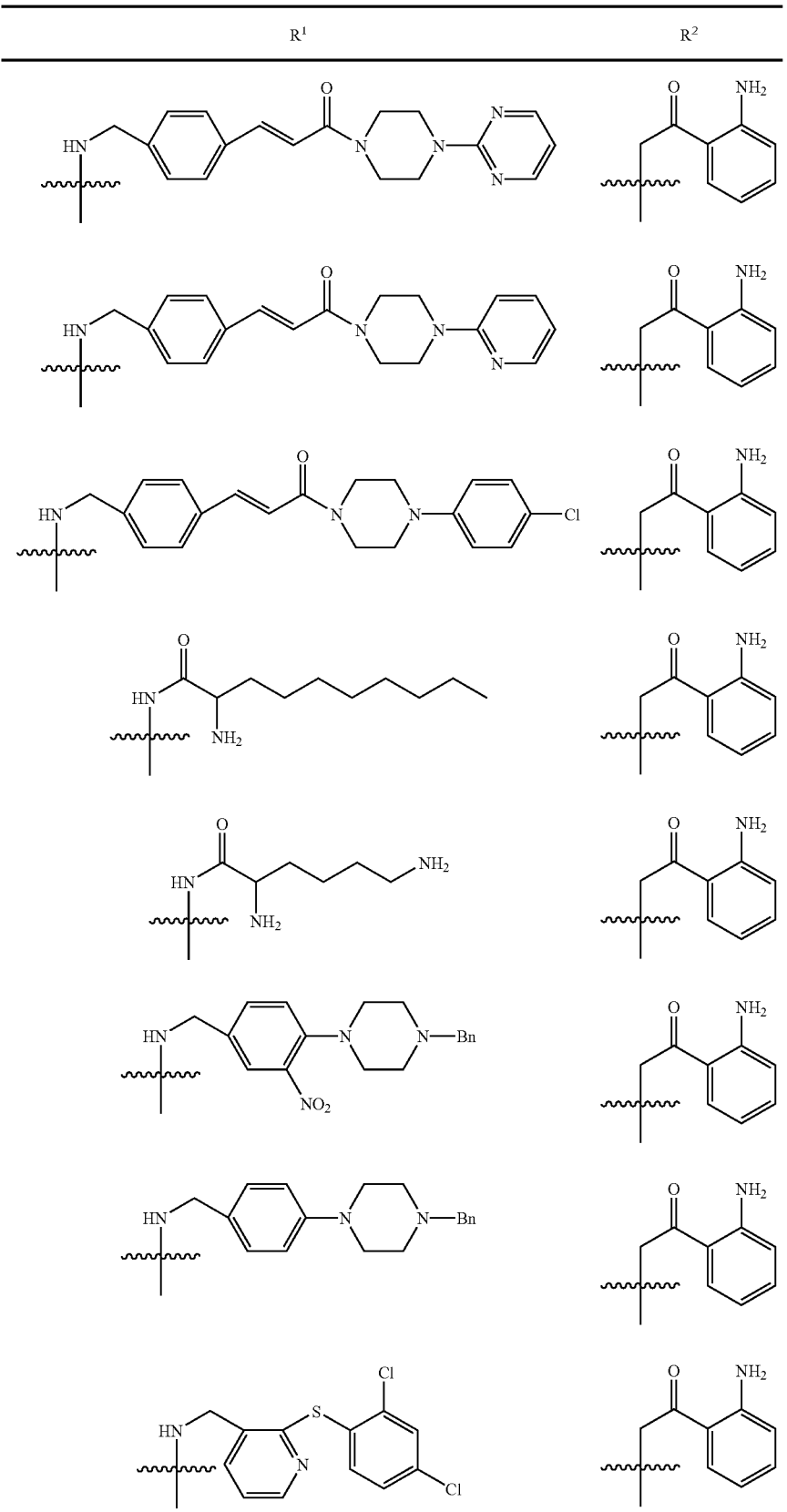

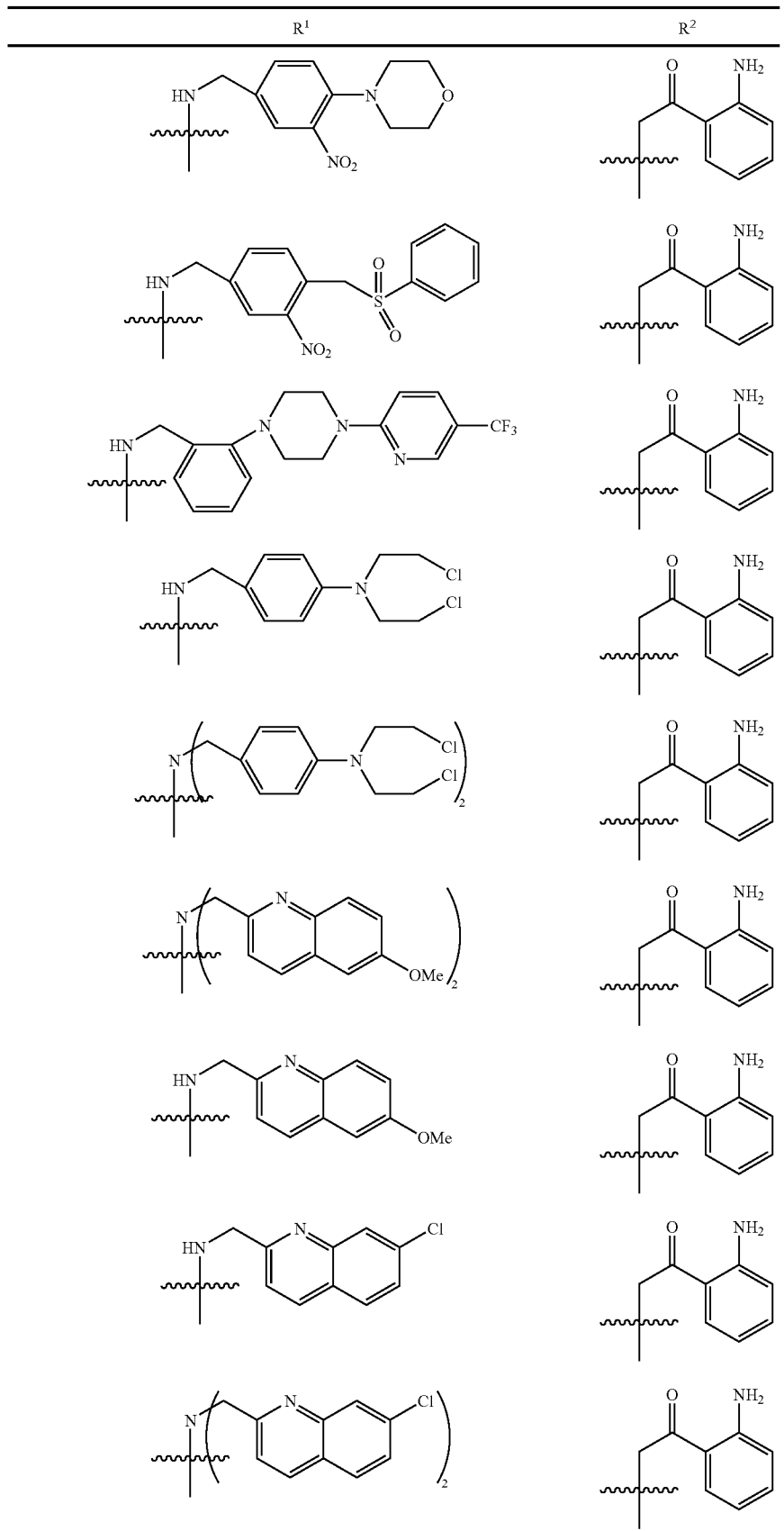

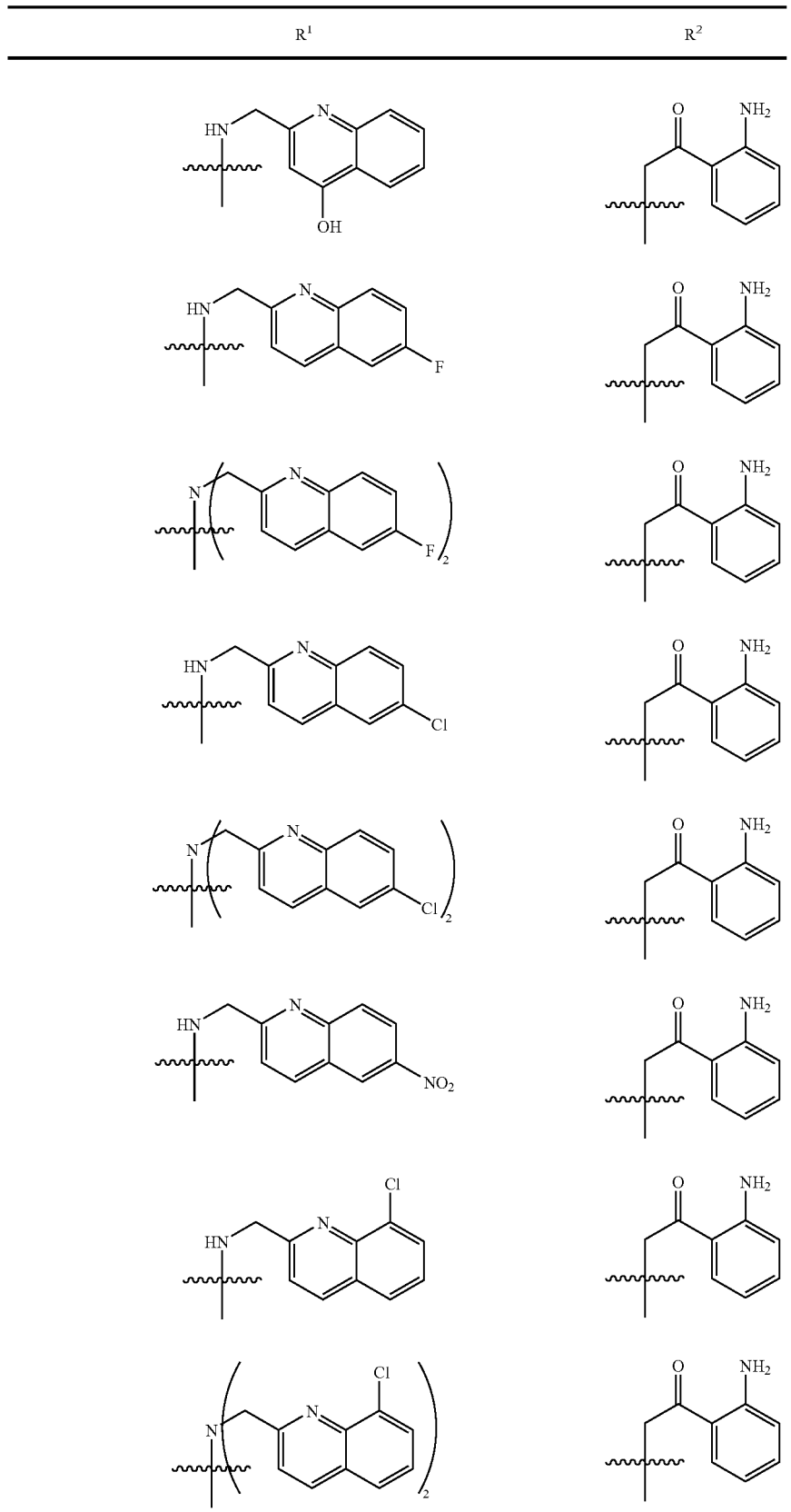

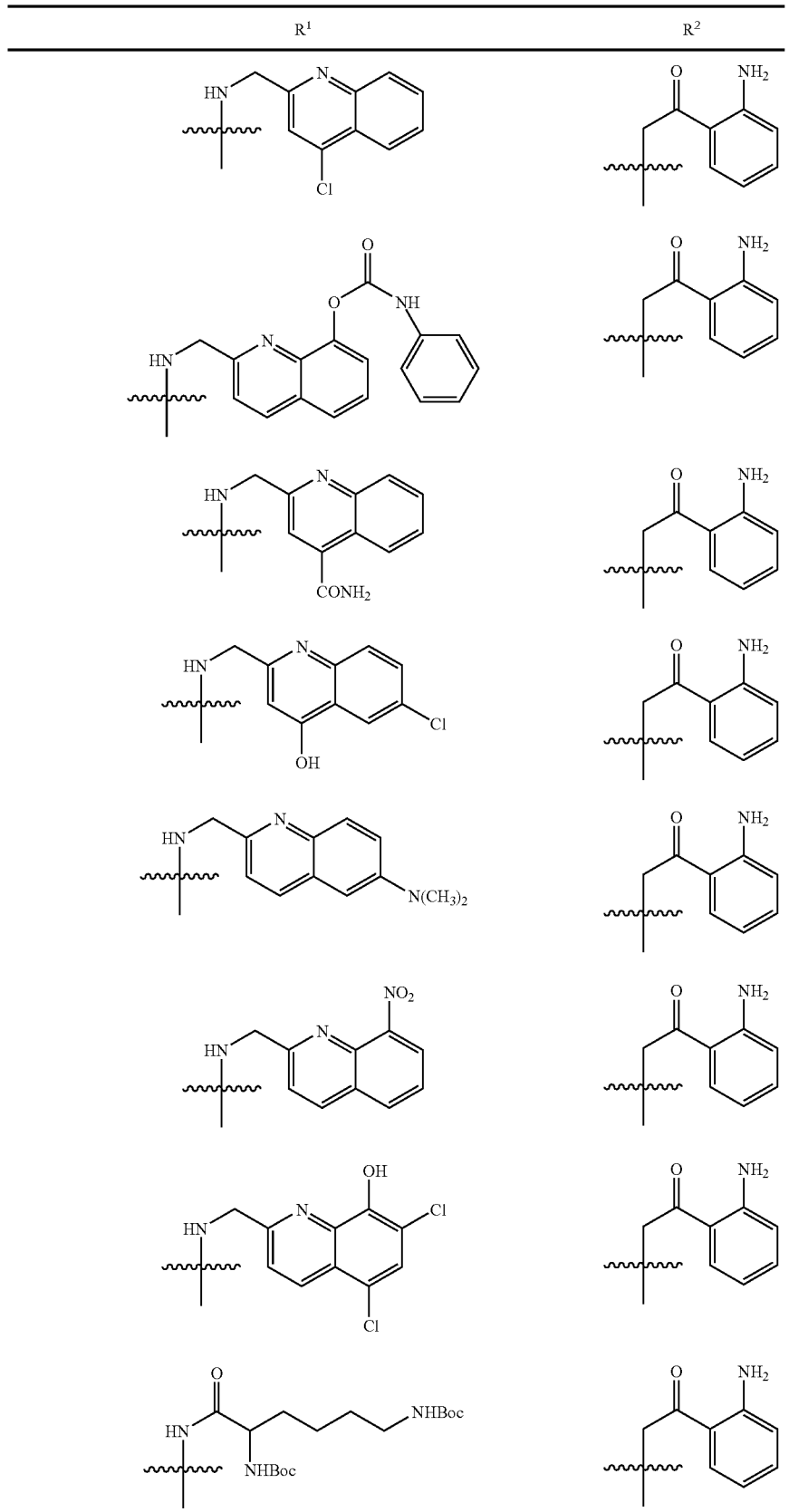

-continued

| R¹ | R² |
|---|---|

-continued
| R¹ | R² |
|---|---|
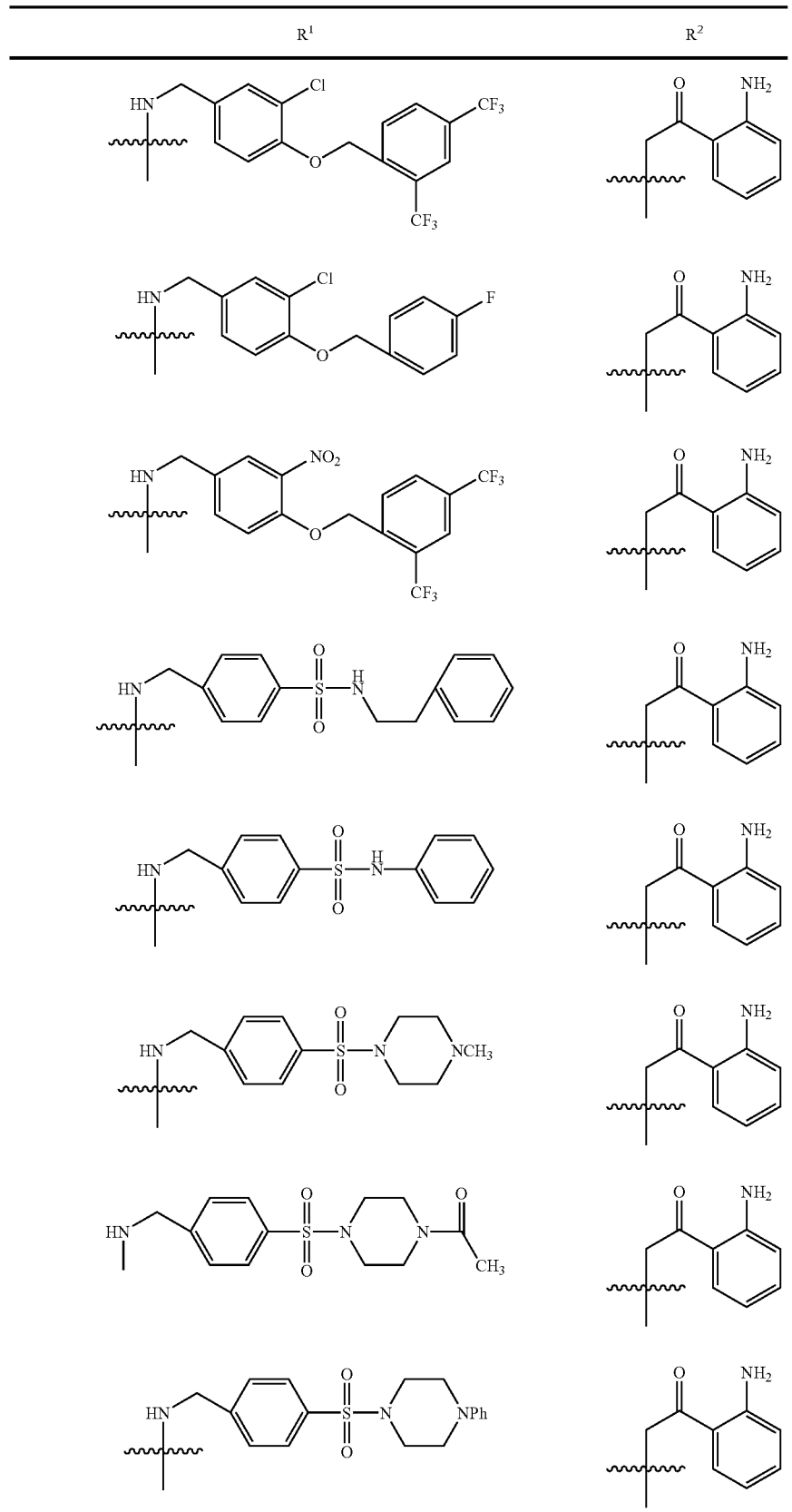

-continued
| R¹ | R² |
|---|---|
| 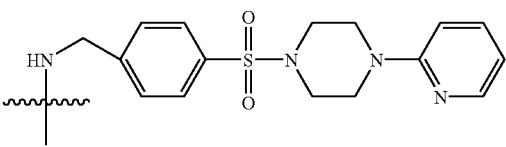 | 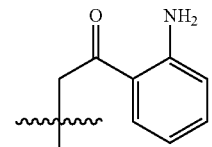 |
| 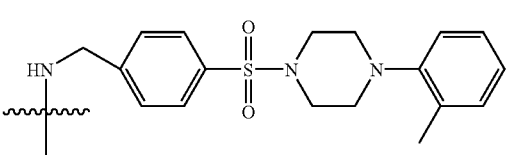 | 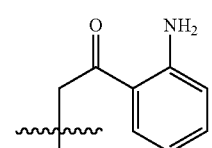 |
| 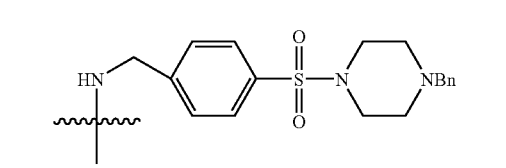 | 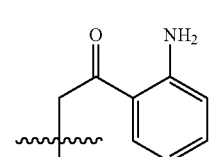 |
| 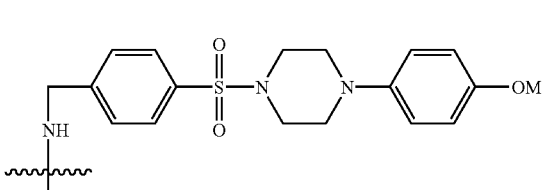 | 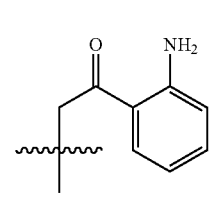 |
| 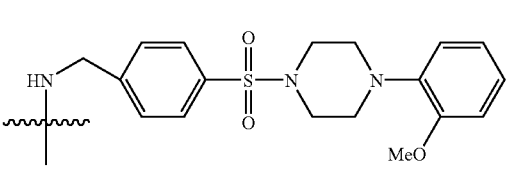 | 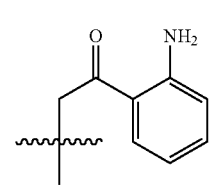 |
| 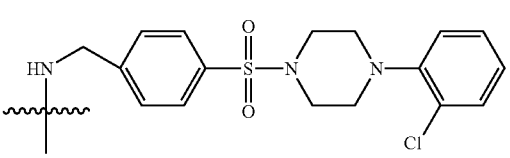 | 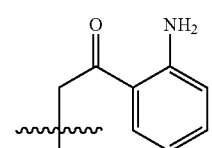 |
| 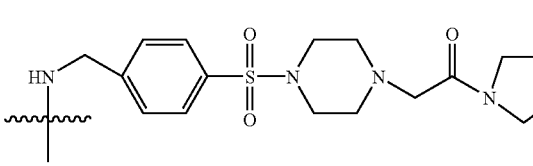 | 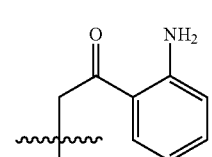 |
| 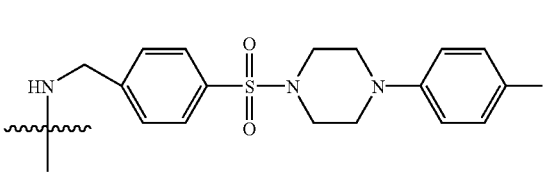 | 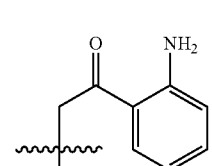 |

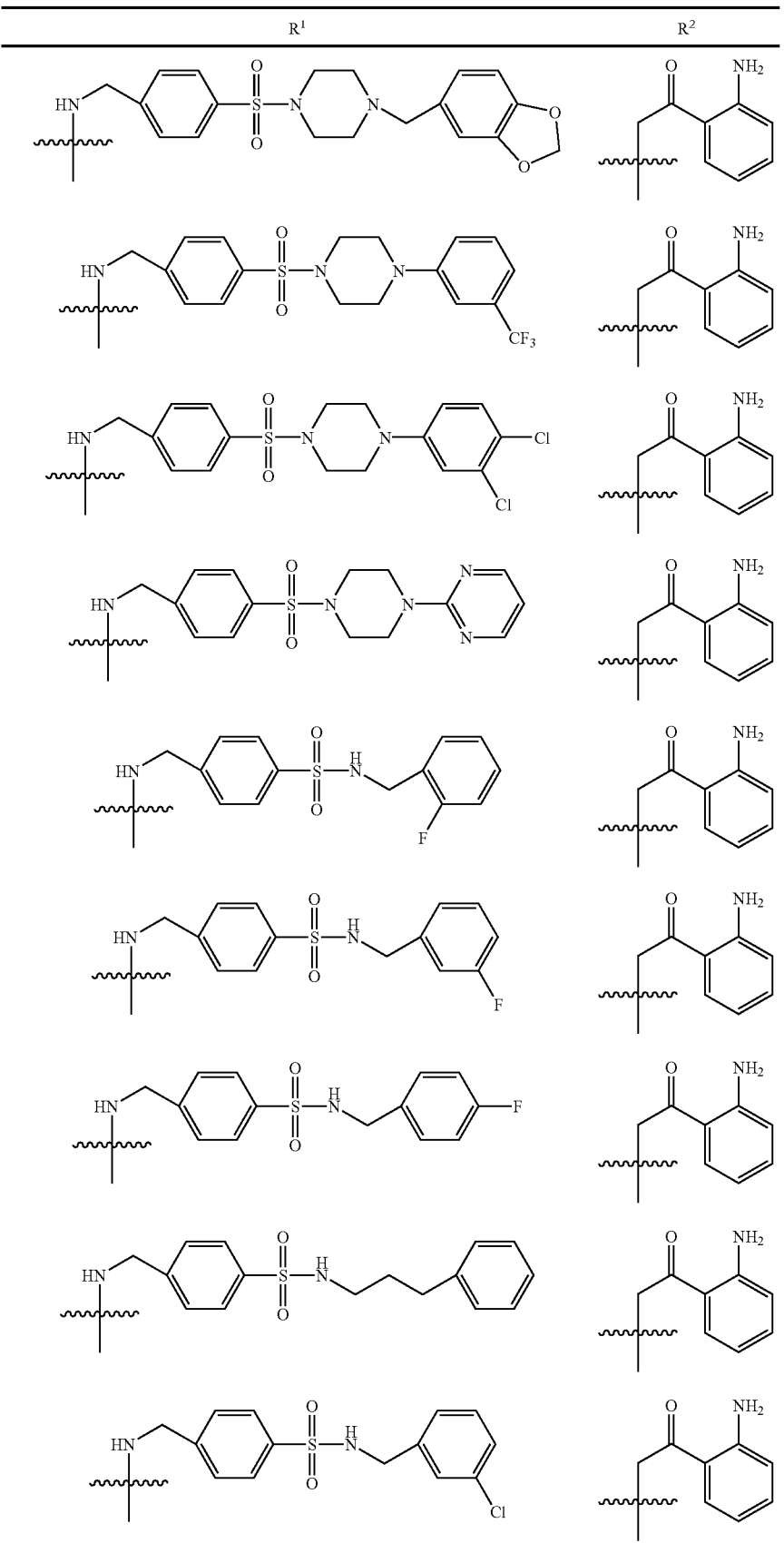

-continued

| R¹ | R² |
|---|---|

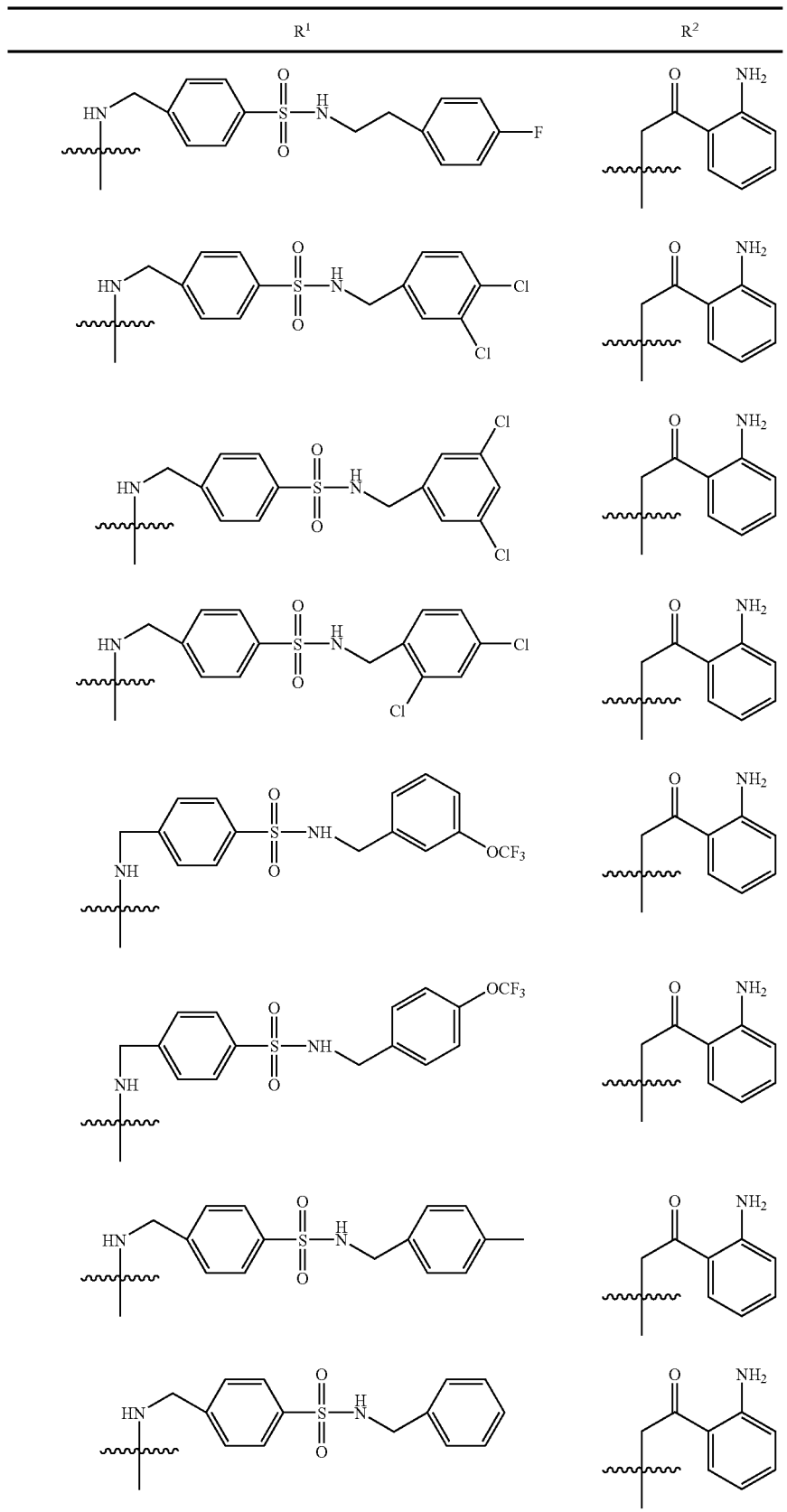

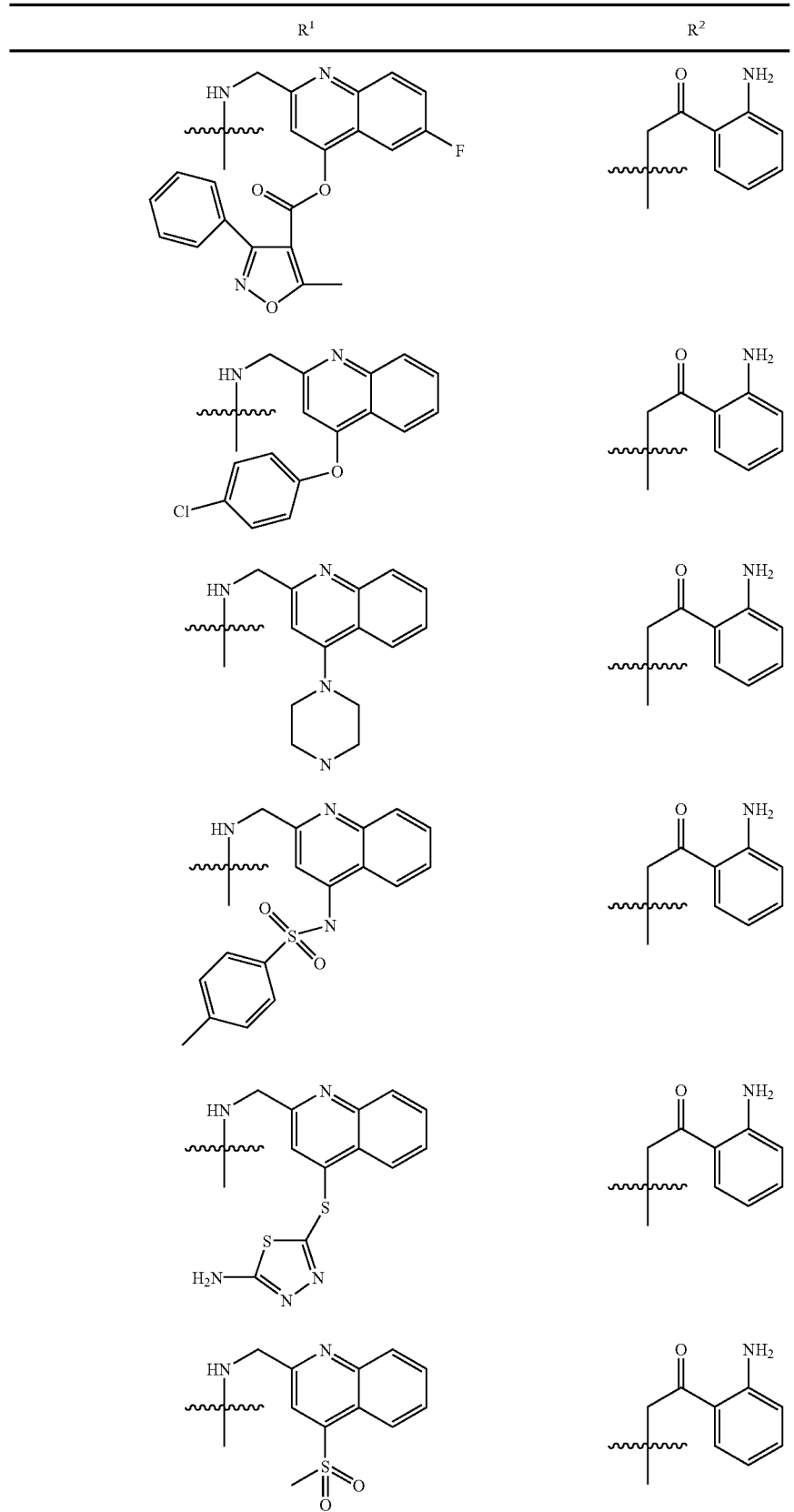

-continued
| R¹ | R² |
|---|---|
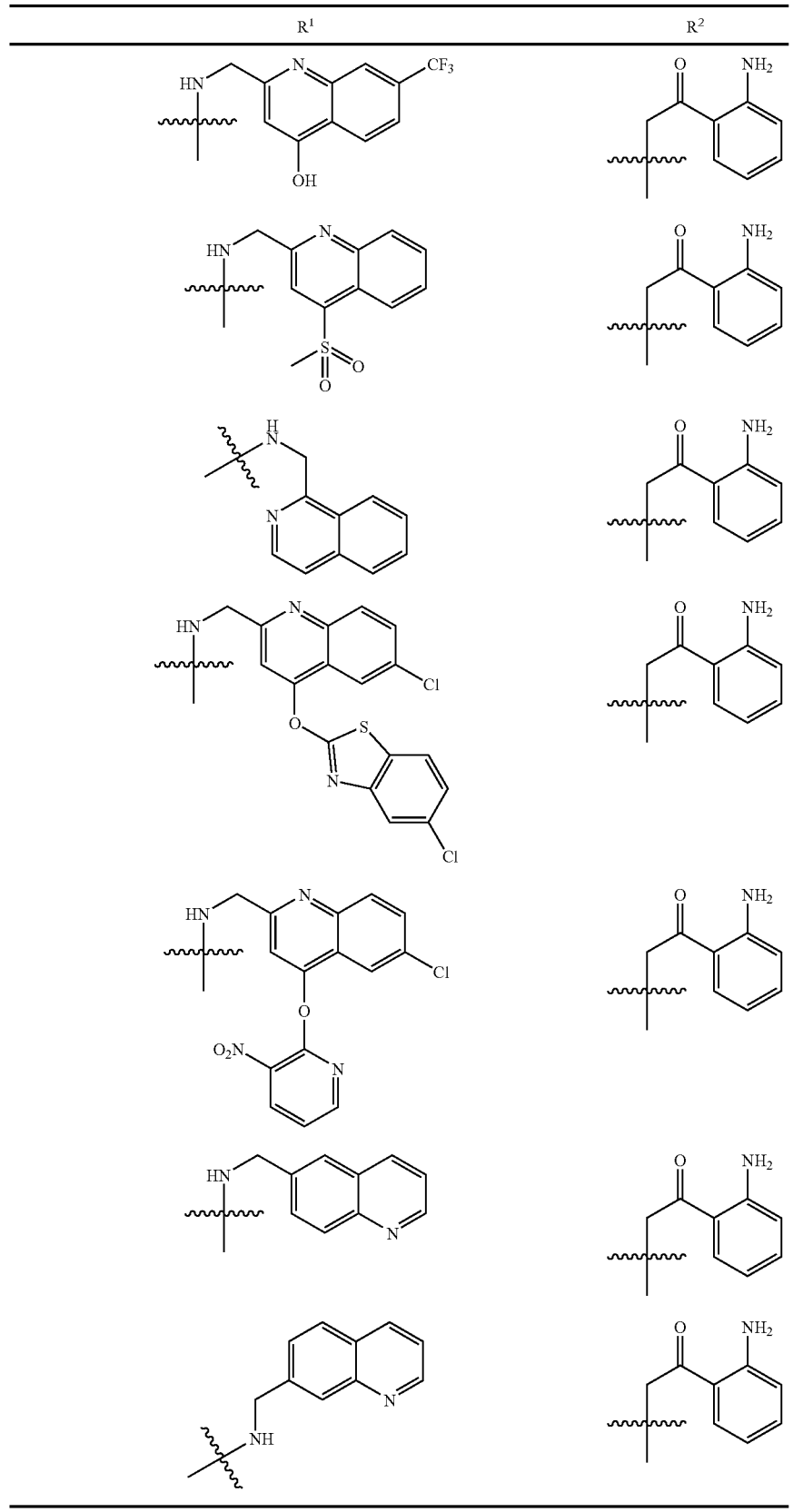

14. The compound according to claim 13, wherein R is NHCO-[(CH$_2$)$_{6-14}$]-CH$_3$.

15. A pharmaceutical composition comprising the compound according to either-one of claims 1 or 2 and a pharmaceutically acceptable carrier.

16. A method of treating a bacterial infection in a subject, comprising the step of administering the pharmaceutical composition according to claim 15 to a subject in need thereof for a time and under conditions effective to ameliorate said bacterial infection.

17. The method according to claim 16, wherein said subject is a human, an animal, a cell culture or a plant.

18. The method according to claim 16, wherein said bacterial infection is caused by a gram-positive bacteria.

19. The method according to claim 18, wherein said bacterial is an antibiotic-resistant bacteria that is resistant to an antibiotic that is not included within the scope of Formula (I).

20. The method according to claim 19, wherein said antibiotic-resistant bacteria are resistant to vancomycin, methicillin, glycopeptide antibiotics, penicillin or daptomycin.

21. The method according to claim 16, further comprising the step of co-administering more than one compound of Formula (I) according to either of claims 3 or 4 to a subject in need thereof.

22. The method according to claim 16, further comprising the step of co-administering a second antimicrobial agent wherein said second antimicrobial agent is not included within the scope of Formula (I).

23. The method according to claim 22, wherein said antimicrobial agent is penicillins, carbapenems, cephalosporins, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, trimethoprim, pyrimethamine, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, everninomicin, glycopeptide, glycylcycline, ketolides, -oxazolidinones, imipenen, amikacin, netilmicin, fosfonycin, gentamicin, ceftriaxone, ZIRACIN (56-deacetyl-57-demethyl-45-O-de(2-methyl-1-oxopropyl)-12-O-(2,3,6-trideoxy-3-C-methyl-4-O-methyl-3-nitro-alpha-L-arabino-hexopyranosyl) flambamycin), LY333328 (oritavancin), linezolid (N-[[(5S)-3-[3-fluoro-4-(4-morpholinyl) phenyl]-2-oxo-5-oxazolidinyl]methyl]acetamide), SYNERCID (dalfopristin-quinupristin), aztreonam (2-[[(Z)-[1-(2-amino-4-thiazolyl)-2-[[(2S,3S)-2-methyl-4-oxo-1-sulfo-3-azetidinyl]amino]-2-oxoethylidene]amino]oxy]-2-methyl-propanoic acid), metonidazole (2-methyl-5-nitro-1H-imidazole-1-ethanol), epiroprim (5-[[3,5-diethoxy-4-(1H-pyrrol-1-yl)phenyl]methyl]-2,4-pyrimidinediamine), OCA-983 (1-[[(2S)-2-amino-3-methyl-1-oxobutyl]amino]-2,5-anhydro-3-S-[(4R,5S,6S)-2-carboxy-6-[(1R)-1-hydroxyethyl]-4-methyl-7-oxo-1-azabicyclo[3,2.0]hept-2-en-3-yl]-1,4-dideoxy-3-thio-D-threo-pentitol), GV-143253 (trinem), sanfetrinem ((1S, 5S,8aS, 8bR)-1, 2, 5, 6, 7, 8, 8a, 8b-octahydro-1-[(1R)-1-hydroxyethyl]-5-methoxy-2-oxo-azeto[2,1-a]isoindole-4-carboxylic acid), CS-83 ((4R,5S, 6S)-6S)-6-[(1R)-1-hydroxyethyl]-4-methyl-7-oxo-3-[[(3R)-5-oxo-3-pyrrolidinyl] thio]-1-azabicyclo [3.2.0]hept-2-ene-2-carboxylic acid (2,2-dimethyl-1-oxopropoxy)methyl ester), biapenem (6[[(4R, 5S,6S)-2-carboxy-6-[(1R)-1-hydroxyethyl]-4-methyl-7-oxo-1-azabicyclo[3.2.0]hept-2-en-3-yl]thio]-6, 7-dihydro-5H-pyrazolo[1,2-a][1,2,4]triazol-4-ium inner salt), KA 159 (stipiamide), dynemicin A ((1S,4R,4aR, 14S,14aS,18Z)-1,4, 7,12,13 14-hexahydro-6,8,11-trihydroxy-3-methoxy-1-methyl-7,12-dioxo-4a,14a-epoxy-4,14-[3]hexene[1,5]diynonaphtho[2,3-c]phenanthridine-2-carboxylic acid), DX8739 ((4R,5S,6S)-3-[[(3S,5S)-5-[[4-[(2S)-5-amino-2-hydroxy-1-oxopentyl]-1-piperazinyl]carbonyl]-3-pyrrolidinyl]thio]-6-[(1R)1-hydroxyethyl]-4-methyl-7-oxo-1-azabicyclo[3.2.0] hept-2-ene-2-carboxylic acid), DU 6681 ((4R,5S,6S)-3-[[(6S)-6,7-dihydro-5H-pyrrolo[1,2-a]imidazol-6-yl]thio]-6-(1R)-1-hydroxyethyl]-4-methyl-7-oxo-1-azabicyclo[3.2.0] hept-2-ene-2-carboxylic acid), cefluprenam ((2E)-N-(2-amino-2-oxoethyl)-3-[[(6R,7R)-7-[[(2Z)-(5-amino-1,2,4-thiadiazol-3-yl)][(fluoro methoxy)imino]acetyl] amino]-2-carboxy-8-oxo-5-thia-1-azabicyclo[4.2.0]oct-2-en-3-yl]-N-ethyl-N-methyl-2-propen-1-aminium inner salt), ER 35786 ((4R, 5S,6S)-6[(1R)-1-hydroxyethyl]-3-[[(3S,5S)-5-[(R)-hydroxy(3R)-3-pyrrolidinylmethy]-3-pyrrolidinyl]thio]-4-methyl-7-oxo-1-azabicyclo[3.2.0]hept-2-ene-2-carboxylic acid monohydrochloride), cefoselis ((6R,7R)-7-[[(2Z)-(2-amino-4-thiazolyl)(methoxy imino)acetyl]amino]-3-[[2,3-dihydro-2-(2-hydroxyethyl)-3-imino-1H-pyrazol-1-yl]methyl]-8-oxo-5-thia-1-azabicyclo[4.2.0]oct-2-ene-2-carboxylic acid), sanfetrinem celexetil ((1S5S,8aS,8bR)-1,2, 5,6,7,8,8a,8b-octahydro-1-[(1R)-1-hydroxyethyl]-5-methoxy-2-oxo-azeto[2,1-a]isoindole-4-carboxylic acid 1-[(cyclohexyloxy)carbonyl] oxy]ethyl ester), cefpirome (1-[[[(6R,7R)-7-[[(2Z)-(2-amino-4-thiazolyl)(methoxyimino) acetyl]amino]-2-carboxy-8-oxo-5-thia-1-azabicyclo[4.2.0] oct-2-en-3-yl]methyl]-6,7-dihydro-5H-cyclopenta[b] pyridinium inner salt), HMR-3647 (3-de[(2,6-dideoxy-3-C-methyl-3-O-methyl-alpha-L-ribo-hexopyranosyl)oxy]-11, 12-dideoxy-6-O-methyl-3-oxo-12,11-[oxycarbonyl[[4-[4-(3-pyridinyl)-1H-imidazol-1-yl]butyl]imino]]-erythromycin), RU-59863 (C-7 catechol substituted cephalosporin), KP 736 ((6R,7R)-7-[[2Z)-(2-amino-4-thiazolyl][[(1,4-dihydro-1,5-dihyroxy-4-oxo-2-pyridinyl)methoxy] imino]acetyl]amino]-8-oxo-3[(1,2,3-thiadiazol-5-ylthio)methyl]-5-this-1-azabicyclo[4.2.0]oct-2-ene-2-carboxylic acid disodium slat), Rifalazil (1',4-didehydro-1-deoxy-1,4-dihydro-3'-hydroxy-5'-[4-(2-methylpropyl)-1-piperazinyl]-1-oxo-rifamycin VII, MEN 10700 ((5R,6S)-3-[[2-amino-2-oxoethyl)methylamino]methyl]-6-[(1R)-1-hydroxyethyl]-7-oxo-4-thia-1-azabicyclo[3.2.0]hept-2-ene-2-carboxylic acid), lenapenem ((4R,5S,6S)-6-[(1R)-1-hydroxyethyl]-3-[[3S,5S)-5-[(1R)-1-hydroxy-3-(methylamino)propyl]-3-pyrrolidinyl]thio]-4-methyl-7-oxo-1-azabicyclo[3.2.0]hept-2-ene-2-carboxylic acid), BO 2502A ((4R,5S,6S)-3-[(2S,3'S,4S)-[2,3'-bipyrrolidin[-4-ylthio]-6-[(1R)-1-hydroxyethyl]-4-methyl-7-oxo-1-azabicyclo[3.2.0]hept-2-ene-2-carboxylic acid), NE-1530 (3+-sialyl]acto-N-neotetraose), K130 (5-[[4-[3-[[4-[(4-aminophenyl)sulfonyl]phenyl]amino]propoxy]-3,5-dimethoxyphenyl] methyl]-2,4-pyrimidinediarnine), PD 138312 ((R)-7-[3-(1-amino-1-methylethyl)-1-pyrrolidinyl-1-cyclopropyl-6-fluoro-1,4-dihydro-4-oxo-1,8-naphthyridine-3-carboxylic acid), PD 140248 (7-[(3R)-3-[(1S)-1-aminoethyl]-1-pyrrolidinyl]-1-(2,4-difluorophenyl)-6-fluoro-1, 4-dihydro-4-oxo-1,8-naphthyridine-3-carboxylic acid), CP 111905 (5-deoxy-5-[[(2E)-3-[3-hydroxy-4-(2-propenyloxy) phenyl]-2-methyl-1-oxo-2-propenyl]amino]-1,2-O-methylene-D-neo-inositol), sulopenem ((5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid), ritipenam acoxyl ((5R,6R)-3-[] aminocarbonyl)oxy]methyl]-6-[(1R)-1-hydroxyethyl]-7-oxo-4-thia-1-azabicyclo[3.2.0]hept-2-ene-2-carboxylic acid (acetyloxy)methyl ester), RO-65-5788 ((6R,7R)-7-[[(2Z)-(5-amino-1,2,4-thiadianol-3-yl)(hydroxyimino)acetyl]amino]-

3-[(E)-[(3'R)-1'-[[(5-methyl-2-oxo-1,3-dioxol-4-yl)methoxy)carbonyl]-2-oxo[1,3'-bipyrrolidinyl]-3-ylidene]methyl]-8-oxo-5-thia-1-azabicyclo[4.2.0]oct-2-ene-2-carboxylic acid monosoidum salt), Sch-40832 (N-[[48-[1-[[2,6-dideoxy-3-O-(2,6-dideoxy-D-arabino-hexopyranosyl)-D-arabino-hexopyranosyl]oxy]ethyl]-15-ethylidene-1,3a,4,510,11,12, 13,14,15,19,20,21,22,28,29, 41,42-octadecahydro-41-hydroxy-12,45-bis(1-hydroxyethyl)-1-(hydroxymethyl)-22-(1-hydroxy-1-methylpropyl)-36-methyl-51,54,57-tris(methylene)-3-(methylthio)-10,13,20,27,38,49,52,55,58-nonaoxo-18H,27H-5a,29-(iminoethaniminoethanimino ethaniminoethanimino[7,2]quinolinomethanoxy methano)-9,6:19,16:26,23:33,30-tetranitrilo-16H,33aH-imidazo(1',5':1,6 pyrido [3,2-m][1,11,17,24,4,7,20,27]tetrathiatetraazacyclotriacontin-1-yl]carbonyl]-2,3-didehydroalanyl]-2,3-didehydro-alanine methyl ester stereoisomer), micacocidin A((OC-6-26-A)-[(4S)-2-[(2S)-2-[(2R,4R)-2-[(4R)-4,5-dihydro-2-[2-(hydroxy-.kappa.O)-6-pentylphenyl]-4-thiazolyl-.kappa.N3]-3-methyl-4-thiaolidinyl-.kappa.N3]-2-(hydroxy-.kappa.N3, .kappa.O4]-Zinc), SR-15402 ((1S,5S,8aS, 8bR)-1,2,5,6,7,8,8a,8b-octahydro-1-[(1R)-1-hydroxyethyl]-2-oxo-5-[(3S)-3-pyrrolidinylthio]-azeto[2,1-a]isoindole-4-carboxylic acid), TOC 39 (1-(2-amino-2-oxoethyl)-4-[[(1E)-2-[(6R,7R)-7-[[(2Z)-(2-amino-4-thiazolyl) (hydroxyimino)acetyl]amino]-2-carboxy-8-oxo-5-thia-1-azabicyclo[4.2.0] oct-2-en-3-yl]ethenyl]thio]-pyridinium inner salt), carurnonam ([[(Z)-[2-[[(2S,3S)-2-[[(aminocarbonyl)oxy] methyl]-4-oxo-1-sulfo-3-azetidinyl]amino]-1-(2-amino-4-thiazolyl)-2-oxoethylidene]amino]oxy]-acetic acid), cefozopran (1-[[(6R,7R)-7-[[(2Z)-(5-amino-1,2,4-thiadiazol-3-yl) (methoxy imino)acetyl]amino]-2-carboxy-8-oxo-5-thia-1-azabicyclo[4.2.0]oct-2-en-3-yl]methyl]-imidazo[1,2-b] pyridazinium inner salt), cefetamet pivoxil ((6R,7R)-7-[[(2Z)-(2-amino-4-thiazolyl)(methoxy imino)acetyl]amino]-3-methyl-8-oxo-5-thia-1-azabicyclo[4.2.0]oct-2-ene-2-carboxylic acid (2,2-dimethyl-1-oxopropoxy)methyl ester), and T 3811 (des-F(6)-quinolone).

24. The method according to claim 22, wherein said antimicrobial agent is selected from the group consisting of imipenen, amikacin, netilmicin, fosfomycin, gentamicin, ceftriaxone, teicoplanin, ZIRACIN, LY333348, CL331022, HMR3647, linezolid, SYNERCID, aztreonam and metronidazole.

25. The method according to claim 17, wherein said subject is selected from a human or an animal.

26. The method according to claim 25, wherein said subject is a human.

27. The compound of claim 1 having the formula (III):

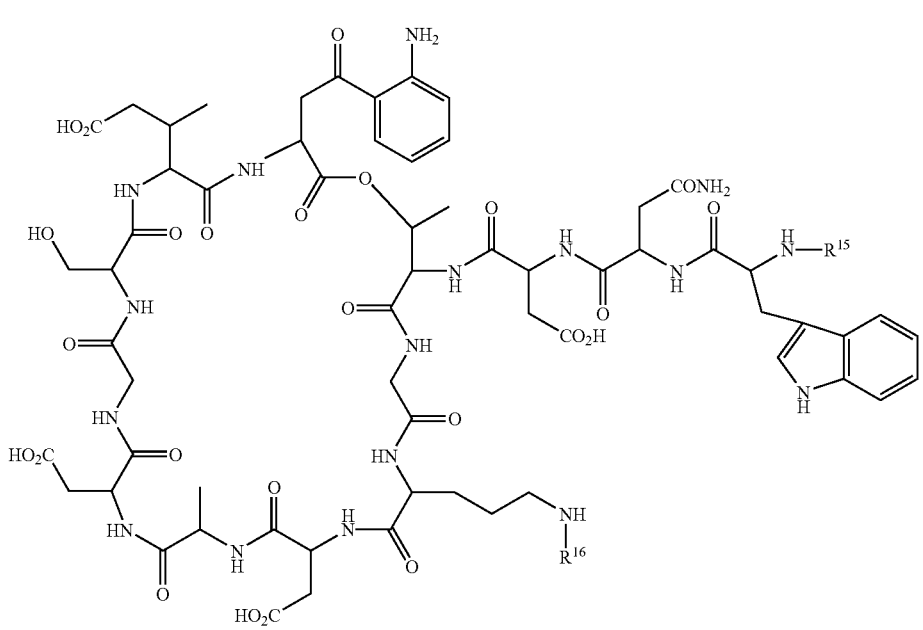

(III)

wherein $R^{15}$ is hydrido or a carbamate amino protecting group; wherein $R^{16}$ is

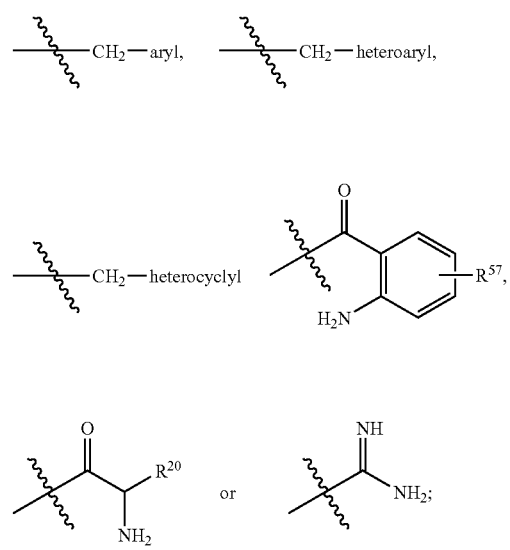

and, wherein, $R^{20}$ is an amino acid side chain.

28. The compound according to claim 27 selected from:

| Compound # | R^16 |
|---|---|
| 45 | (structure: α-amino acid with indole side chain — tryptophan-like acyl group) |
| 54 | (structure: α-amino acid with -(CH$_2$)$_4$-NH$_2$ side chain — lysine-like acyl group) |
| 79 | (structure: CH$_2$-linked indol-3-yl) |
| 80 | (structure: CH$_2$-linked 5-methoxyindol-3-yl) |
| 81 | (structure: CH$_2$-linked 5-fluoroindol-3-yl) |
| 82 | (structure: CH$_2$-linked 1-methylindol-3-yl) |
| 84 | (structure: CH$_2$-linked 1-methylbenzimidazol-2-yl) |
| 139 | (structure: CH$_2$-linked benzofuran-2-yl) |
| 158 | (structure: CH$_2$-linked 3-methylbenzothiophen-2-yl) |
| 146 | (structure: CH$_2$-linked imidazol-4-yl) |
| 212 | (structure: CH$_2$-linked imidazol-2-yl) |
| 85 | (structure: CH$_2$-linked 1-methylimidazol-2-yl) |
| 174 | (structure: CH$_2$-linked thiazol-2-yl) |
| 78 | (structure: CH$_2$-linked triazine with NHPh and NH$_2$ substituents) |
| 150 | (structure: CH$_2$-linked 3-phenyl-1H-pyrazol-4-yl) |
| 130 | (structure: CH$_2$-linked quinolin-2-yl) |
| 138 | (structure: CH$_2$-linked quinolin-4-yl) |
| 168 | (structure: CH$_2$-linked quinolin-3-yl) |
| 274 | (structure: CH$_2$-linked 6-methoxyquinolin-2-yl) |

-continued
| Compound # | R¹⁶ |
|---|---|
| 317 | 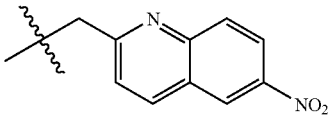 |
| 280 | 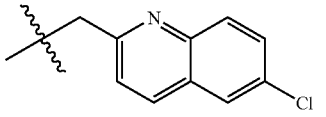 |
| 275 | 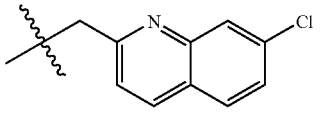 |
| 283 | 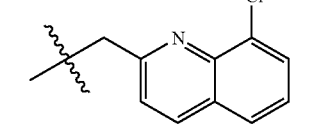 |
| 285 | 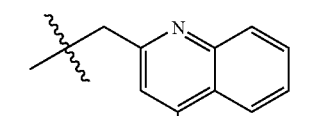 |
| 50 | 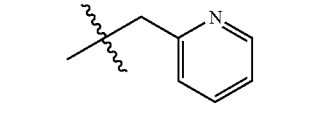 |
| 38 | 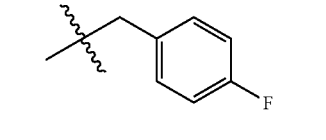 |
| 115 | 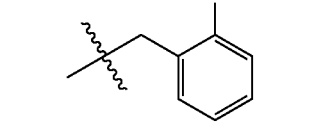 |
| 105 | 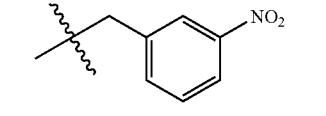 |
| 76 | 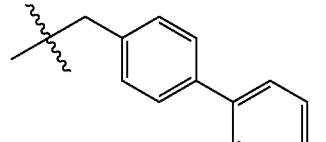 |
-continued
| Compound # | R¹⁶ |
|---|---|
| 147 | 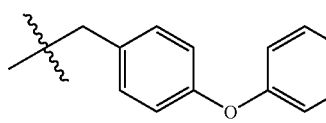 |
| 164 | 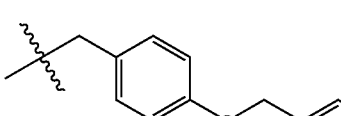 |
| 210 | 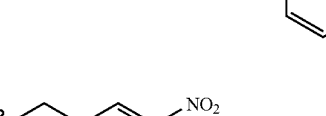 |
| 107 | 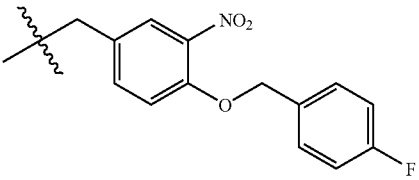 |
| 111 | 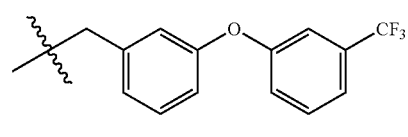 |
| 103 | 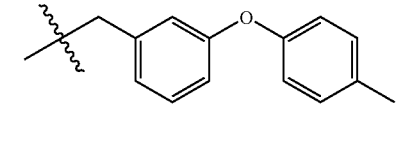 |
| 253 | 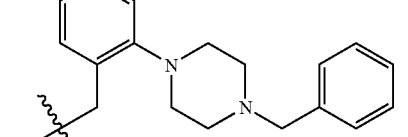 |
| 227 | 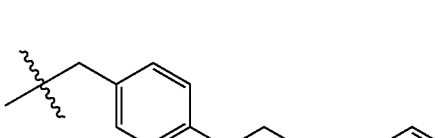 |

-continued
| Compound # | R[16] |
|---|---|
| 372 | 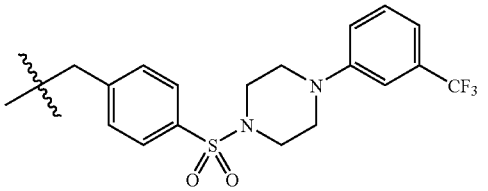 |
| 386 | 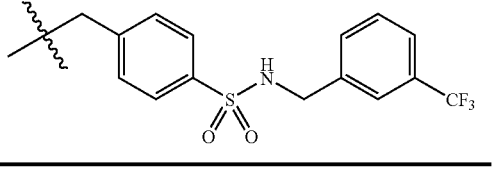 |
29. The compound according to claim 2 wherein said compound is
| Cpd # | R | R[1] | R[2] |
|---|---|---|---|
| 189 | NHCO(CH2)8CH3 | 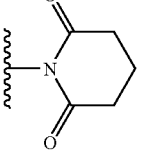 | 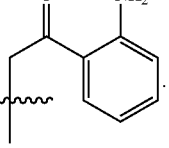 |
30. A compound of formula (I) according to claim 2, wherein R is NHCO-[($C_6$-$C_{14}$)-alkyl]-$CH_3$, and R[1] and R[2] are:
| R[1] | R[2] |
|---|---|
| 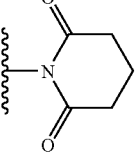 | 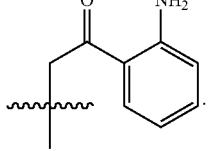 |
* * * * *